US008076324B2

(12) United States Patent
Bohme et al.

(10) Patent No.: US 8,076,324 B2
(45) Date of Patent: Dec. 13, 2011

(54) DI(HETERO)ARYLCYCLOHEXANE DERIVATIVES, THEIR PREPARATION, THEIR USE AND PHARMACEUTICAL COMPOSITIONS COMPRISING THEM

(75) Inventors: Thomas Bohme, Nauheim (DE); Uwe Gerlach, Hattersheim (DE); Dirk Gretzke, Frankfurt (DE); Heinz-Werner Kleemann, Bischofsheim (DE); Stefania Pfeiffer-Marek, Frankfurt (DE); Henning Vollert, Bad Segeberg (DE); Jean-Michel Altenburger, Saint Remy les Chevreuse (FR); Sergio Mallart, Orsay (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/630,537

(22) Filed: Dec. 3, 2009

(65) Prior Publication Data
US 2010/0204206 A1 Aug. 12, 2010

Related U.S. Application Data

(63) Continuation of application No. PCT/EP2008/004112, filed on May 23, 2008.

(30) Foreign Application Priority Data

Jun. 5, 2007 (EP) .................................. 07290698

(51) Int. Cl.
| | |
|---|---|
| A61P 9/00 | (2006.01) |
| A61P 9/06 | (2006.01) |
| A61K 31/55 | (2006.01) |
| A61K 31/444 | (2006.01) |
| A61K 31/506 | (2006.01) |
| A61K 31/404 | (2006.01) |
| A61K 31/19 | (2006.01) |
| A61K 31/415 | (2006.01) |
| A61K 31/426 | (2006.01) |
| A61K 31/4184 | (2006.01) |
| A61K 31/44 | (2006.01) |
| A61K 31/343 | (2006.01) |
| A61K 31/4196 | (2006.01) |
| C07C 62/00 | (2006.01) |
| C07D 213/55 | (2006.01) |
| C07D 317/46 | (2006.01) |
| C07D 215/14 | (2006.01) |
| C07D 487/02 | (2006.01) |
| C07D 231/12 | (2006.01) |
| C07D 277/30 | (2006.01) |
| C07D 239/02 | (2006.01) |
| C07D 209/04 | (2006.01) |
| C07D 235/04 | (2006.01) |

(52) U.S. Cl. ................ 514/214.02; 514/274; 514/277; 514/311; 514/335; 514/345; 514/365; 514/383; 514/394; 514/406; 514/415; 514/464; 514/570; 540/578; 544/315; 546/174; 546/261; 546/301; 546/342; 548/204; 548/269.4; 548/304.4; 548/377.1; 548/469; 549/434; 562/469

(58) Field of Classification Search ........................ None
See application file for complete search history.

(56) References Cited

U.S. PATENT DOCUMENTS

| 5,476,850 | A | 12/1995 | Englert et al. |
| 5,574,069 | A | 11/1996 | Englert et al. |
| 5,652,268 | A | 7/1997 | Englert et al. |
| 5,698,596 | A | 12/1997 | Englert et al. |
| 6,410,573 | B1 | 6/2002 | Heitsch et al. |
| 6,414,030 | B1 | 7/2002 | Wirth et al. |

FOREIGN PATENT DOCUMENTS

| EP | 1 264 829 A1 | 12/2002 |
| EP | 1 679 069 A1 | 7/2006 |
| EP | 1736467 | 12/2006 |
| WO | WO 93/19749 | 10/1993 |
| WO | WO 99/34797 | 7/1999 |
| WO | WO 99/34798 | 7/1999 |
| WO | WO 01/27107 A2 | 4/2001 |
| WO | WO 01/87866 A1 | 11/2001 |
| WO | WO 2004/014370 A2 | 2/2004 |

OTHER PUBLICATIONS

Rubin et al., caplus an 1946:20687.*

(Continued)

*Primary Examiner* — Sun Jae Loewe
(74) *Attorney, Agent, or Firm* — Serena Farquharson-Torres; Scully, Scott, Murphy & Presser, P.C.

(57) ABSTRACT

The present invention relates to di(hetero)arylcyclohexane derivatives of the formula I,

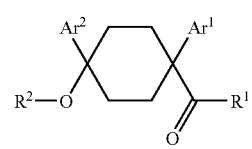

in which $Ar^1$, $Ar^2$, $R^1$ and $R^2$ have the meanings indicated in the claims. The compounds of the formula I are valuable pharmaceutical active compounds which inhibit ATP-sensitive potassium channels in the heart muscle and are suitable, for example, for the treatment of disorders of the cardiovascular system such as arrhythmias or a decreased contractility of the heart, such as can occur, for example, in coronary heart disease, cardiac insufficiency or cardiomyopathies. In particular, they are suitable for the prevention of sudden cardiac death. The invention furthermore relates to processes and intermediates for the preparation of the compounds of the formula I, their use and pharmaceutical compositions comprising them.

12 Claims, No Drawings

OTHER PUBLICATIONS

Agabiti-Rosei et al., The European Cardiologist, 2000.*
Bauer A. et al., "Role of $K_{ATP}$ Channels in Repetitive Induction of Ventricular Fibrillation", *Europace* 9:154-161 (2007).
Sakurai N. et al., "Cooper (II)-Catalyzed O-Phenylation of Alcohols with or Ganobismuth (V) Reagents", *Arkivoc* pp. 254-264 (2007).
Billman G.E. et al., "Effects of a Novel Cardioselective ATP-Sensitive Potassium Channel Antagonist, 1-[[5-[2-(5- Chloro-o-Anisamido)Ethyl]-β-Methoxyethoxyphenyl]Sulfonyl]-3-Methylthiourea, Sodium Salt (HMR 1402), on Susceptibility to Ventricular Fibrillation Induced by Myocardial Ischemia: In Vitro and In Vivo Studies", *The Journal of Pharmacology and Experimental Therapeutics* 309(1):182-192 (2004).
Weyermann A. et al., "Inhibitors of ATP-Sensitive Potassium Channels in Guinea Pig Isolated Ischemic Hearts", *Naunyn-Schmiedeberg's Arch Pharmacol* 369:374-381 (2004).
Kotha S. et al., "Recent Applications of the Suzuki-Miyaura Cross-Coupling Reaction in Organic Synthesis", *Tetrahedron* 58:9633-9695 (2002).
Böhme T.M. et al., "Synthesis and Pharmacology of Benzoxazines as Highly Selective Antagonists at $M_4$ Muscarinic Receptors", *Journal of Medicinal Chemistry* 45(14):3094-3102 (2002).
Kanoh S. et al., "Unusual Cyclodimerization of Small Cyclic Ethers Via Neighboring Carbonyl-Group Participation and Cation Transfer", *Tetrahedron* 58:7065-7074 (2002).
Dendorfer A. et al., "HMR 1372, A Putative Inhibitor of ATP-Sensitive $K^+$-Channels, Reduces Infarct Size by a Cholinergic Mechanism", *Naunyn-Schmiedeberg's Arch Pharmacol.* 363:R74 (2001), Abstract.
Giblin J.P. et al., "The Molecular Assembly of ATP-Sensitive Potassium Channels", *The Journal of Biological Chemistry* 274(32):22652-22659 (1999).
Wirth K.J. et al., "HMR 1883, A CardioSelective $K_{ATP}$ Channel Blocker, Inhibits Ischaemia- and Reperfusion-Induced Ventricular Fibrillation in Rats", *Naunyn-Schmiedeberg's Arch Pharmacol.* 360:295-300 (1999).
Billman G.E. et al., "HMR 1883, A Novel Cardioselective Inhibitor of the ATP-Sensitive Potassium Channel. Part II: Effects on Susceptibility to Ventricular Fibrillation Induced by Myocardial Ischemia in Conscious Dogs", *The Journal of Pharmacology and Experimental Therapeutics* 289(3):1465-1473 (1998).
Gögelein H. et al., "HMR 1883, A Novel Cardioselective Inhibitor of the ATP-Sensitive Potassium Channel. Part I: Effects on Cardiomyocytes, Coronary Flow and Pancreatic β—Cells", *The Journal of Pharmacology and Experimental Therapeutics* 286(3):1453-1464 (1998).
Katritzky A.R. et al., "Selective Reactivity of $sp_3$ and $sp_2$ Carbanions of 1-Substituted 1,2,4-Triazoles. A Comparative Approach", *J. Org. Chem.* 63(13):4323-4331 (1998).
Combes S. et al., "A Convenient Synthesis of Triarylbismuth Diacetates", *Synthetic Communications* 26(24):4569-4575 (1996).
Ghaffar T. et al., "A New Homogeneous Platinum Containing Catalyst for the Hydrolysis of Nitriles", *Tetrahedron Letters* 36(47):8657-8660 (1995).
Krause E. et al., "Adenosine Triphosphate-Dependent K Currents Activated by Metabolic Inhibition in Rat Ventricular Myocytes Differ from Those Elicited by the Channel Opener Rilmakalim", *Pflügers Arch.-Eur J. Physiol.* 429:625-635 (1995).
Barton D.H.R. et al., "Bismuth(V) Reagents in Organic Synthesis", *Pure & Appl. Chem.* 59(8):937-946 (1987).
Chorvat R.J. et al., "22-Hydroxycholesterol Derivatives as HMG CoA Reductase Suppressors and Serum Cholesterol Lowering Agents", *J. Med. Chem.* 28:194-200 (1985).
Comins D.L. et al., "Regiospecific α—Alkylation of 4-Chloro(Bromo)Pyridine", *J. Org. Chem.* 50(22):4410-4411 (1985).
Mitsunobu O., "The Use of Diethyl Azodicarboxylate and Triphenylphospine in Synthesis and Transformation of Natural Products", *Synthesis* pp. 1-28 (1981).
Lednicer D. et al., "Butyrophenones as Hypotensive Agents. Derivatives of 4-Aryl-4-(Hydroxymethyl)Cyclohexylamine", *Journal of Medicinal Chemistry* 18(6):593-599 (1975).
Petersen S. et al., "Reactions of Cyclic Lactim Ethers with Acylhydrazine Derivatives", *Chemische Berichte* 90:909-921 (1957), together with an English-language abstract.
Martin Rubin et al., 1-Arylcyclohexanecarboxylic Acids, Journal of the American Chemical Society, (1946, pp. 628-832, vol. 68).

* cited by examiner

DI(HETERO)ARYLCYCLOHEXANE DERIVATIVES, THEIR PREPARATION, THEIR USE AND PHARMACEUTICAL COMPOSITIONS COMPRISING THEM

The present invention relates to di(hetero)arylcyclohexane derivatives of the formula I,

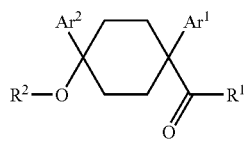

I in which $Ar^1$, $Ar^2$, $R^1$ and $R^2$ have the meanings indicated below. The compounds of the formula I are valuable pharmaceutical active compounds which inhibit ATP-sensitive potassium channels in the heart muscle and are suitable, for example, for the treatment of disorders of the cardiovascular system such as arrhythmias or a decreased contractility of the heart, such as can occur, for example, in coronary heart disease, cardiac insufficiency or cardiomyopathies. In particular, they are suitable for the prevention of sudden cardiac death. The invention furthermore relates to processes and intermediates for the preparation of the compounds of the formula I, their use and pharmaceutical compositions comprising them.

A blood sugar-lowering action, or hypoglycemic action, is described for certain benzenesulfonylureas. Glibenclamide, which is used therapeutically as an agent for the treatment of diabetes mellitus, is regarded as a prototype of such hypoglycemic sulfonylureas. Glibenclamide blocks ATP-sensitive potassium channels (KATP channels) and serves in research as a tool for investigations of such potassium channels. In addition to its hypoglycemic action, glibenclamide additionally exhibits other actions which hitherto, however, cannot be utilized therapeutically, among them an antifibrillatory action on the heart. In the treatment of arrhythmias or of ventricular fibrillation or its pre-stages with glibenclamide, in many cases the pronounced blood sugar-lowering action simultaneously produced by this substance would be undesirable or even hazardous, since it can further worsen the condition of the patient, so that clinically glibenclamide is not generally suitable as an antiarrhythmic.

From various publications, for example U.S. Pat. No. 5,574,069, U.S. Pat. No. 5,698,596, U.S. Pat. No. 5,476,850, U.S. Pat. No. 5,652,268, U.S. Pat. No. 6,410,573, Goegelein et al., J. Pharmacol. Exp. Ther. 286, 1453-1464 (1998), Billman et al., J. Pharmacol. Exp. Ther. 286, 1465-1473 (1998), or Billman et al., J. Pharmacol. Exp. Ther. 309, 182-192 (2004), antifibrillatory benzenesulfonylureas and -thioureas are known which selectively block myocardial KATP channels (isoform SUR2A/Kir6.2) and act only slightly on KATP channels in other organs such as blood vessels and the pancreas and exhibit only a slight blood sugar-lowering action. In U.S. Pat. No. 6,414,030, the action of some of these compounds on the autonomous nervous system is described. There is, however, a need for further compounds which block myocardial KATP channels and have a favorable pharmacodynamic and pharmacokinetic property profile and which are suitable in particular for the treatment of a disturbed cardiac rhythm and its sequelae such as of sudden cardiac death or of a weakened heart power, especially in ischemic conditions.

Surprisingly, it has been found that the 1,4-di(hetero)arylcyclohexane derivatives of the formula I of the present invention have the desired properties.

The specific compound of the formula I, in which $Ar^1$ and $Ar^2$ simultaneously are unsubstituted phenyl, $R^1$ is hydroxy, i.e. in the definition of the compounds further below $R^1$ is $R^4$—O— and therein $R^4$ is hydrogen, and $R^2$ is hydrogen, i.e. the compound 4-hydroxy-1,4-diphenylcyclohexanecarboxylic acid, is already described in Rubin et al., J. Am. Chem. Soc. 68, 828-832 (1946). It was prepared in the course of investigations of 1-arylcyclohexanecarboxylic acids having spasmolytic or analgesic action, but a pharmacological action of this compound is not described.

In WO 93/19749, phenylcyclohexane derivatives are described which are inhibitors of the tumor necrosis factor or of phosphodiesterase IV and are suitable for the treatment of allergic and inflammatory diseases, and whose broad generic definition comprises certain compounds of the formula I of the present invention in which one of the groups $Ar^1$ and $Ar^2$ is a specific heteroaromatic group from the series consisting of pyrazolyl, imidazolyl, triazolyl, oxazolyl, isoxazolyl, oxadiazolyl, thiazolyl and thiadiazolyl, the other of the groups $Ar^1$ and $Ar^2$ is a specifically substituted phenyl group, and $R^2$ is hydrogen or $(C_1-C_4)$-alkyl which is optionally mono- to trisubstituted by fluorine. The specifically substituted phenyl group in the compounds which are defined generically in WO 93/19749, compulsorily carries a substituent in the 3-position which, inter alia, can be an optionally fluoro-substituted alkyl-O— group or HO-alkyl-O— group, and in the 4-position compulsorily carries a substituent which, inter alia, can be a halogen atom or an optionally fluoro-substituted group from the series consisting of $(C_1-C_2)$-alkyl-O—, $(C_1-C_2)$-alkyl-S—, $(C_1-C_2)$-alkyl-S(O)— and $(C_1-C_2)$-alkyl-S$(O)_2$—, and can optionally carry a further substituent. In WO 99/34797 and WO 99/34798, the use of compounds described in WO 93/19749 for the treatment of multiple sclerosis and of COPD (chronic obstructive pulmonary disease) is described. Specific compounds of the formula I of the present invention are not described in the documents.

In EP 1264829, oxygen-containing heterocycles are described which are inhibitors of phosphodiesterase IV and are suitable, for example, for the treatment of inflammatory allergic diseases such as bronchial asthma, and whose very broad generic definition comprises certain compounds of the formula I of the present invention in which one of the groups $Ar^1$ and $Ar^2$ is a heteroaryl group, and the other of the groups $Ar^1$ and $Ar^2$ is a specifically substituted phenyl group which in positions 2 and 3 compulsorily carries a divalent substituent —O-alkyl-O— and which in position 4 compulsorily carries a substituent which, inter alia, can be an optionally substituted alkoxy group, and which can optionally carry a halogen atom in the 6-position as a further substituent. Specific compounds of the formula I of the present invention are not described in EP 1264829.

In WO 01/87866, cyclohexane derivatives are described which are tachykinin antagonists and are suitable, for example, for the treatment of CNS disorders such as depression or anxiety, of pain or of inflammatory disorders, and whose broad generic definition comprises compounds which are related to compounds of the formula I of the present invention in which $Ar^1$ is phenyl or pyridyl, $Ar^2$ is a heteroaryl group and $R^2$ is hydrogen. The pharmacologically active compounds described in WO 01/87866 comprise, in addition to a phenyl group or pyridyl group directly bonded to the cyclohexane ring, a further phenyl group in the same position on the cyclohexane ring which is bonded to the cyclohexane ring via a linker group. Starting compounds for the synthesis of the pharmacologically active compounds described in WO 01/87866 can be 1-phenylcyclohexanecarboxylic acids, for which no pharmacological action is described. Specific 1-phenylcyclohexanecarboxylic acids which carry a heteroaryl group and a hydroxy group in the 4-position of the cyclohexane ring and carry only hydrogen atoms in the 3-positions, are not described in WO 01/87866.

The broad generic definition of the compounds in EP 1736467, which are characterized by a sulfonamide group or other amide group the nitrogen atom of which is linked to a ring, comprises among others compounds in which the said ring is a cyclohexane ring. The said ring can be substituted by various substituents and in particular carries a nitrogen substituent in a position opposite to the linking position. The characteristic structural features of the compounds of the present invention, which do not contain such a sulfonamide group, are not anticipated by EP 1736467. The compounds of EP 1736467 potentiate the expression of a low density lipoprotein receptor and therefore are useful for the treatment of hyperlipidemia or arteriosclerosis which can lead to diseases such as cardiac angina or myocardial infarction. An inhibitory action on ATP-sensitive potassium channels and an anti-arrhythmic activity of the compounds of EP 1736467 or any other compounds is neither disclosed nor suggested in EP 1736467.

Certain compounds of the formula I are also comprised by broad generic definitions of compounds in other patent documents such as WO 01/27107, WO 2004/014370 or EP 1679069 which, however, do not anticipate the structural characteristics of the compounds of the present invention and in which no specific compounds of the formula I are described.

A subject of the present invention is a compound of the formula I,

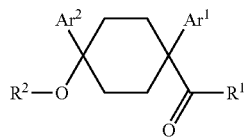

in which $Ar^1$ and $Ar^2$, which are independent of one another and can be identical or different, are phenyl, naphthyl or heteroaryl, which are all optionally substituted by 1, 2, 3 or 4 identical or different substituents from the series consisting of halogen, cyano, $(C_1-C_5)$-alkyl, $(C_2-C_5)$-alkenyl, $(C_3-C_8)$-cycloalkyl-$C_vH_{2v}$—, $Ar^3$, $(C_1-C_5)$-alkyl-O—, HO—$(C_1-C_5)$-alkyl-O—, —O—$(C_1-C_3)$-alkyl-O—, $(C_3-C_8)$-cycloalkyl-S(O)$_f$—, $(C_1-C_5)$-alkyl-S(O)$_k$— and $R^{11}R^{12}N$—S(O)$_2$—, wherein all alkyl groups, alkenyl groups and cycloalkyl groups in $Ar^1$ and $Ar^2$ are optionally substituted by one or more fluorine substituents;

$Ar^3$ and $Ar^5$, which are independent of one another and can be identical or different, are phenyl or monocyclic heteroaryl, which are all optionally substituted by 1, 2 or 3 identical or different substituents from the series consisting of halogen, cyano, $(C_1-C_5)$-alkyl, $(C_1-C_5)$-alkyl-O—, —O—$(C_1-C_3)$-alkyl-O—, $(C_1-C_5)$-alkyl-S(O)$_m$— and $R^{13}R^{14}N$—S(O)$_2$—, wherein all alkyl groups in $Ar^3$ and $Ar^5$ are optionally substituted by one or more fluorine substituents;

$Ar^4$ is phenyl or heteroaryl, which are all optionally substituted by 1, 2, 3 or 4 identical or different substituents from the series consisting of halogen, cyano, $(C_1-C_5)$-alkyl, $(C_2-C_5)$-alkenyl, $(C_3-C_8)$-cycloalkyl-$C_wH_{2w}$—, $Ar^5$, $(C_1-C_5)$-alkyl-O—, HO—$(C_1-C_5)$-alkyl-O—, —O—$(C_1-C_3)$-alkyl-O—, $(C_1-C_5)$-alkyl-S(O)$_n$— and $R^{15}R^{16}N$—S(O)$_2$—, wherein all alkyl groups, alkenyl groups and cycloalkyl groups in $Ar^4$ are optionally substituted by one or more fluorine substituents;

$R^1$ is $R^3$—, $R^4$—O— or $R^5R^6N$—;

$R^2$ is hydrogen, $(C_1-C_8)$-alkyl, $(C_2-C_8)$-alkenyl, $(C_3-C_8)$-alkynyl, phenyl-$(C_2-C_8)$-alkenyl-, $Ar^4$, $R^{17}$—O—$(C_1-C_8)$-alkyl-, $R^{18}R^{19}N$—$(C_1-C_8)$-alkyl-, Het-$C_uH_{2u}$— or $(C_3-C_8)$-cycloalkyl-$C_uH_{2u}$—, wherein the phenyl group in phenyl-$(C_2-C_8)$-alkenyl- is optionally substituted by 1, 2 or 3 identical or different substituents from the series consisting of halogen, cyano, $(C_1-C_5)$-alkyl, $(C_1-C_5)$-alkyl-O— and $(C_1-C_5)$-alkyl-S(O)$_g$—, and wherein all alkyl groups, alkenyl groups, alkynyl groups and cycloalkyl groups in $R^2$ are optionally substituted by one or more fluorine substituents;

$R^3$, $R^4$, $R^5$ and $R^6$, which are all independent of one another and can be identical or different, are hydrogen, $(C_1-C_8)$-alkyl or $(C_3-C_8)$-cycloalkyl-$C_pH_{2p}$—, wherein all alkyl groups and cycloalkyl groups in $R^3$, $R^4$, $R^5$ and $R^6$ are optionally substituted by one or more fluorine substituents;

$R^{11}$, $R^{12}$, $R^{13}$, $R^{14}$, $R^{15}$, $R^{16}$, $R^{17}$, $R^{18}$ and $R^{19}$, which are all independent of one another and can be identical or different, are hydrogen, $(C_1-C_8)$-alkyl or $(C_3-C_8)$-cycloalkyl-$C_qH_{2q}$—, wherein all alkyl groups and cycloalkyl groups in $R^{11}$, $R^{12}$, $R^{13}$, $R^{14}$, $R^{15}$, $R^{16}$, $R^{17}$, $R^{18}$ and $R^{19}$ are optionally substituted by one or more fluorine substituents;

Het is a residue of a monocyclic 4-membered to 7-membered saturated ring which contains 1 or 2 identical or different ring heteroatoms from the series consisting of nitrogen, oxygen and sulfur, which is bonded via a ring carbon atom and which is optionally substituted by 1, 2, 3 or 4 identical or different substituents from the series consisting of phenyl and $(C_1-C_5)$-alkyl, wherein phenyl groups in Het are optionally substituted by 1, 2 or 3 identical or different substituents from the series consisting of halogen, cyano, $(C_1-C_5)$-alkyl, $(C_1-C_5)$-alkyl-O— and $(C_1-C_5)$-alkyl-S(O)$_h$—, and wherein Het and all alkyl groups in Het are optionally substituted by one or more fluorine substituents;

heteroaryl is a residue of a monocyclic 5-membered or 6-membered or of a bicyclic 8-membered, 9-membered or 10-membered aromatic ring system which contains 1, 2 or 3 identical or different ring heteroatoms from the series consisting of nitrogen, oxygen and sulfur;

f, g, h, k, m and n, which are all independent of one another and can be identical or different, are 0, 1 or 2;

p, q, v and w, which are all independent of one another and can be identical or different, are 0, 1, 2, 3 or 4;

u is 0, 1, 2, 3, 4, 5 or 6;

wherein all cycloalkyl groups, independently of any other substituents, are optionally substituted by one or more identical or different $(C_1-C_4)$-alkyl substituents;

in any of its stereoisomeric forms or a mixture of stereoisomeric forms in any ratio, or a physiologically acceptable salt thereof;

provided that $Ar^1$ and $Ar^2$ cannot both be unsubstituted phenyl if simultaneously $R^1$ is hydroxy and $R^2$ is hydrogen.

If structural elements such as groups, substituents or numbers can occur several times in the compounds of the formula I or are defined conjointly, they are all independent of one another and can in each case have any desired meanings of the indicated meanings, and can in each case be identical to or different from any other group, substituent or number.

Alkyl groups, i.e. saturated hydrocarbon residues, and alkenyl groups and alkynyl groups, i.e. unsaturated hydrocarbon residues, can be straight-chain (=linear) or branched. This also applies if these groups are substituted or are part of another group, for example of an alkyl-O— group (=alkyloxy group=alkoxy group), of a sulfur-containing group such as $(C_1-C_5)$-alkyl-S(O)$_k$—, of an alkenyl-O— group or of an alkynyl-O— group. Corresponding to their respective definition, alkyl, alkenyl and alkynyl groups can contain 1, 2, 3, 4, 5, 6, 7 or 8 carbon atoms. In one embodiment of the invention, corresponding to the respective definition, an alkyl group, alkenyl group or alkynyl group in the compounds of the formula I, independently of any other alkyl, alkenyl or alkynyl group, contains up to 6 carbon atoms, in another embodiment up to 5 carbon atoms, in another embodiment up to 4 carbon atoms, in another embodiment up to 3 carbon atoms. Examples of alkyl are methyl, ethyl, propyl, butyl, pentyl, hexyl, heptyl, octyl, the n-isomers of these groups, isopropyl, sec-butyl, isobutyl, tert-butyl, 1-methylbutyl, isopentyl, neopentyl, tert-pentyl, 3-methylbutyl, 3,3-dimethylbutyl and isohexyl. Examples of alkyl-O— are methoxy, ethoxy, n-propoxy, isopropoxy, n-butoxy, isobutoxy, tert-butoxy, n-pentoxy. Examples of sulfur-containing groups such as $(C_1-C_5)$-alkyl-S(O)$_k$— or $(C_1-C_8)$-alkyl-S(O)$_m$— are methylsulfanyl (=methanesulfanyl=methylthio=$CH_3$—S—), methanesulfinyl (=$CH_3$—S(O)—), methanesulfonyl (=$CH_3$—S(O)$_2$—), ethylsulfanyl (=ethanesulfanyl=$CH_3$—$CH_2$—S—), ethanesulfinyl (=$CH_3$—$CH_2$—S(O)—), ethanesulfonyl (=$CH_3$—$CH_2$—S(O)$_2$—), isopropylsulfanyl (=1-methylethylsulfanyl=1-methylethanesulfanyl=$(CH_3)_2$CH—S—), propane-2-sulfinyl (=1-methylethanesulfinyl=$(CH_3)_2$CH—S(O)—), propane-2-sulfonyl (=1-methylethanesulfonyl=$(CH_3)_2$CH—S(O)$_2$—). In one embodiment of the invention, a $(C_2-C_8)$-alkenyl group is a $(C_3-C_8)$-alkenyl group. In one embodiment of the invention, an alkenyl group contains one double bond. In one embodiment of the invention, an alkynyl group contains one triple bond. The double bonds in an alkenyl group and the triple bonds in an alkynyl group can be present in any desired positions. In one embodiment of the invention, an alkynyl group is bonded via a carbon atom which is not part of a triple bond. In another embodiment of the invention, an alkenyl group is bonded via a carbon atom which is not part of a double bond. Examples of alkenyl groups and alkynyl groups are ethenyl (=vinyl), prop-1-enyl, prop-2-enyl (=allyl), but-2-enyl, 2-methylprop-2-enyl, 3-methylbut-2-enyl, hex-3-enyl, hex-4-enyl, 4-methylhex-4-enyl, prop-1-ynyl, prop-2-ynyl (=propargyl), but-2-ynyl, but-3-ynyl, 4-methylpent-2-ynyl, hex-4-ynyl and hex-5-ynyl.

Substituted alkyl groups, alkenyl groups and alkynyl groups can be substituted in any desired positions, provided that the resulting group is stable and is suitable as a subgroup in a pharmaceutical active compound. The prerequisite that a subgroup in the compounds of the formula I and the molecule as a whole are stable and suitable as a pharmaceutical active compound applies in general and with respect to all definitions of groups, substituents and numbers. An alkyl group, alkenyl group or alkynyl group in the compounds of the formula I which is optionally substituted by one or more fluorine substituents, i.e. which can be mono- or polysubstituted by fluorine, can be unsubstituted, i.e. not carry fluorine substituents, or substituted, for example by 1, 2, 3, 4, 5, 6, 7, 8, 9, 10 or 11 fluorine substituents which can be present in any desired positions. In one embodiment of the invention, an alkyl group, alkenyl group or alkynyl group which is optionally substituted by fluorine substituents, can be unsubstituted or substituted by 1, 2, 3, 4, 5 or 6 fluorine substituents, in another embodiment it can be unsubstituted or substituted by 1, 2, 3, 4 or 5 fluorine substituents, in another embodiment it can be unsubstituted or substituted by 1, 2 or 3 fluorine substituents. For example, one or more methyl groups in such an alkyl group, alkenyl group or alkynyl group can carry three fluorine substituents and be present as trifluoromethyl groups, and/or one or more methylene groups (=$CH_2$) can carry two fluorine substituents and be present as difluoromethylene groups. These details for substitution by fluorine also apply if the groups additionally carry other substituents and/or are part of another group, for example of an alkyl-O— group. Examples of fluoro-substituted alkyl groups are trifluoromethyl, 2-fluoroethyl, 1,1-difluoroethyl, 2,2,2-trifluoroethyl, pentafluoroethyl, 3,3,3-trifluoropropyl, 2,2,3,3,3-pentafluoropropyl, 4,4,4-trifluorobutyl and heptafluoroisopropyl. Examples of fluoro-substituted alkyl-O— groups are trifluoromethoxy, 2,2,2-trifluoroethoxy, pentafluoroethoxy and 3,3,3-trifluoropropoxy. Examples of fluoro-substituted sulfur-containing group such as $(C_1-C_5)$-alkyl-S(O)$_k$—, $(C_1-C_5)$-alkyl-S(O)$_m$— and $(C_1-C_5)$-alkyl-S(O)$_n$— are trifluoromethylsulfanyl (=trifluoromethanesulfanyl=$CF_3$—S—), trifluoromethanesulfinyl (=$CF_3$—S(O)—) and trifluoromethanesulfonyl (=$CF_3$—S(O)$_2$—). In a phenyl-alkenyl- group the phenyl group can be present in any position. In one embodiment of the invention, the phenyl group is present on a carbon atom which is part of a double bond, in another embodiment the phenyl group is not present on the carbon atom via which the phenyl-alkenyl- group is bonded. Examples of phenyl-alkenyl groups are 2-phenylprop-2-enyl (=2-phenylallyl), 3-phenylprop-2-enyl (=3-phenylallyl), 2-phenyl-but-2-enyl, 2-phenylbut-3-enyl and 4-phenylbut-3-enyl, wherein in these groups the phenyl moiety is optionally substituted as indicated.

If applicable, the above explanations on alkyl groups apply correspondingly to divalent alkyl groups such as alkanediyl groups and alkylene groups, for example the groups $C_pH_{2p}$, $C_qH_{2q}$, $C_uH_{2u}$, $C_vH_{2v}$ and $C_wH_{2w}$, which can also be regarded as an alkyl moiety of a substituted alkyl group, just as the alkyl moiety of substituted alkyl groups can also be regarded as a divalent alkyl group. For example, the alkyl moiety of the divalent substituent —O—$(C_1-C_3)$-alkyl-O— can be regarded as a divalent alkyl group. Divalent alkyl groups can also be straight-chain or branched. The bonds to the adjacent groups can be present in any desired positions and can start from the same carbon atom or from different carbon atoms. If alkyl groups which are contained in a group in the compounds of the formula I are optionally substituted by fluorine, this also applies to the divalent alkyl groups which can be contained in the respective group, for example to the divalent alkyl groups $C_vH_{2v}$ and $C_uH_{2u}$ which can be present in the groups $Ar^1$, $Ar^2$ and $R^2$. Examples of divalent alkyl groups are —$CH_2$—, —$CH_2$—$CH_2$—, —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH_2$—$CH_2$—$CH_2$—$CH_2$—$CH_2$—$CH_2$—, —CH($CH_3$)—, —C($CH_3$)$_2$—, —CH($CH_3$)—$CH_2$—, —$CH_2$—CH($CH_3$)—, —C($CH_3$)$_2$—$CH_2$—, —$CH_2$—C($CH_3$)$_2$—. Examples of fluoro-substituted divalent alkyl groups which, for example, can contain 1, 2, 3, 4, 5 or 6 fluorine atoms, are —$CF_2$—, —$CF_2$—$CH_2$—, —$CH_2$—$CF_2$—, —$CF_2$—$CF_2$—, —CF($CH_3$)—, —C($CF_3$)$_2$—, —C($CH_3$)$_2$—$CF_2$—, —$CF_2$—C($CH_3$)$_2$—. Examples of the divalent substituent —O—$(C_1-C_3)$-alkyl-O—, which is optionally substituted by fluorine substituents, are —O—$CH_2$—O—, —O—$CH_2$—$CH_2$—O—, —O—C($CH_3$)$_2$—O— and —O—$CF_2$—O—. If the number p, q, u, v and w in the divalent alkyl groups $C_pH_{2p}$, $C_qH_{2q}$, $C_uH_{2u}$, $C_vH_{2v}$ and $C_wH_{2w}$ is 0 (=zero), the two adjacent groups which are bonded to these groups are directly bonded to one another via a single bond. If, for example, $R^2$ is the group $(C_3-C_8)$-cycloalkyl-$C_uH_{2u}$— or the group Het-$C_uH_{2u}$—, which are bonded to the remainder of the molecule via the group $C_uH_{2u}$ as is symbolized by the terminal hyphen next to the group $C_uH_{2u}$, which hyphen in general represents the free bond via which a group is bonded, and the number u is 0, the ($C_3$-$C_8$)-cycloalkyl group or the group Het is bonded directly to the oxygen atom which carries the group $R^2$ via a single bond.

Examples of cycloalkyl are cyclopropyl, cyclobutyl, cyclopentyl, cyclohexyl, cycloheptyl and cyclooctyl. In one embodiment of the invention, a cycloalkyl group, such as ($C_3$-$C_8$)-cycloalkyl or ($C_3$-$C_6$)-alkyl, in the definition of any group is independently of any other group chosen from a subgroup of any two or more of the listed specific cycloalkyl groups, for example from cyclopropyl and cyclobutyl, i.e. it is a ($C_3$-$C_4$)-cycloalkyl group, or from cyclopropyl, cyclobutyl and cyclopentyl, i.e. it is a ($C_3$-$C_5$)-cycloalkyl group, or from cyclopropyl, cyclopentyl and cyclohexyl, i.e. it is a $C_3$— or ($C_5$-$C_6$)-cycloalkyl group, or from cyclopentyl and cyclohexyl, i.e. it is a ($C_5$-$C_6$)-cycloalkyl group, or from cyclopentyl, cyclohexyl and cycloheptyl, i.e. it is a ($C_5$-$C_7$)-cycloalkyl group, or from cyclopropyl, cyclobutyl, cyclopentyl, cyclohexyl and cycloheptyl, i.e. it is a ($C_3$-$C_7$)-cycloalkyl group, or from cyclopropyl, cyclobutyl, cyclopentyl and cyclohexyl, i.e. it is a ($C_3$-$C_6$)-cycloalkyl group. Generally, cycloalkyl groups in the compounds of the formula I are optionally substituted by one or more identical or different ($C_1$-$C_4$)-alkyl substituents, i.e., they are unsubstituted by ($C_1$-$C_4$)-alkyl or carry one or more, for example, 1, 2, 3 or 4, identical or different ($C_1$-$C_4$)-alkyl substituents, for example methyl groups and/or ethyl groups and/or isopropyl groups and/or tert-butyl groups, in particular methyl groups, which alkyl substituents can be present in any desired positions. Examples of alkyl-substituted cycloalkyl groups are 1-methylcyclopropyl, 2,2-dimethylcyclopropyl, 1-methylcyclopentyl, 2,3-dimethylcyclopentyl, 4-methylcyclohexyl, 4-isopropylcyclohexyl, 4-tert-butylcyclohexyl and 3,3,5,5-tetramethylcyclohexyl. Generally, cycloalkyl groups also are optionally substituted by one ore more flourine substituents, i.e. they are unsubstituted by fluorine substituents or mono- or polysubstituted by fluorine substituents, for example by 1, 2, 3, 4, 5, 6, 7, 8, 9, 10 or 11 fluorine substituents. In one embodiment of the invention, a cycloalkyl group which is optionally substituted by one ore more fluorine substituents, is unsubstituted by fluorine substituents or substituted by 1, 2, 3, 4, 5 or 6 fluorine substituents, in another embodiment it is unsubstituted or substituted by 1, 2, 3 or 4 fluorine substituents, in another embodiment it is unsubstituted by fluorine substituents. A cycloalkyl group can also be substituted simultaneously by fluorine and alkyl. The fluorine substituents can be present in any desired positions of the cycloalkyl group and can also be present in an alkyl substituent on the cycloalkyl group. Examples of fluoro-substituted cycloalkyl groups are 1-fluoro-cyclopropyl, 2,2-difluorocyclopropyl, 3,3-difluorocyclobutyl, 1-fluorocyclohexyl, 4,4-difluorocyclohexyl and 3,3,4,4,5,5-hexafluorocyclohexyl. Examples of the group cycloalkylalkyl, which is bonded to the remainder of the molecule via the acyclic alkyl group and which, for example, can be the group ($C_3$-$C_8$)-cycloalkyl-$C_uH_{2u}$— in the definition of $R^2$ or can occur as a substituent ($C_3$-$C_8$)-cycloalkyl-$C_vH_{2v}$— in $Ar^1$ and $Ar^2$, are cyclopropylmethyl, cyclobutylmethyl, cyclopentylmethyl, cyclohexylmethyl, cycloheptylmethyl, cyclooctylmethyl, cyclopropyldifluoromethyl, cyclobutyldifluoromethyl, cyclopentyldifluoromethyl, cyclohexyldifluoromethyl, cycloheptyldifluoromethyl, cyclooctyldifluoromethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl, 2-cyclohexylethyl, 1-cycloheptylethyl, 2-cycloheptylethyl, 1-cyclooctylethyl, 2-cyclooctylethyl, 3-cyclopropylpropyl, 3-cyclobutylpropyl, 3-cyclopentylpropyl, 3-cyclohexylpropyl, 3-cycloheptylpropyl, 3-cyclooctylpropyl, 2-cyclopropylpropyl, 2-cyclobutylpropyl, 2-cyclopentylpropyl, 2-cyclohexylpropyl, 2-cycloheptylpropyl, 2-cyclooctylpropyl, which can also be substituted by fluorine substituents in the cycloalkyl moiety and the alkyl moiety and/or by alkyl substituents in the cycloalkyl moiety as indicated in the respective definitions.

Halogen is fluorine, chlorine, bromine or iodine. In one embodiment of the invention, halogen in any occurrence in the compounds of the formula I, independently of any other halogen, is fluorine, chlorine or bromine, in another embodiment fluorine or chlorine, in another embodiment chlorine or bromine.

In substituted phenyl groups, the substituents can be present in any desired positions. In monosubstituted phenyl groups, the substituent can be present in the 2-position, the 3-position or the 4-position. In disubstituted phenyl groups, the substituents can be present in positions 2 and 3, positions 2 and 4, positions 2 and 5, positions 2 and 6, positions 3 and 4 or positions 3 and 5. In trisubstituted phenyl groups, the substituents can be present in positions 2, 3 and 4, positions 2, 3 and 5, positions 2, 3 and 6, positions 2, 4 and 5, positions 2, 4 and 6 or positions 3, 4 and 5. If a phenyl group carries four substituents, of which, for example, 1, 2, 3 or 4 substituents can be fluorine substituents, the unsubstituted ring carbon atom can be present in the 2-position, the 3-position or the 4-position, i.e., the four substituents can be present in positions 2, 3, 4 and 5, positions 2, 3, 4 and 6 or positions 2, 3, 5 and 6. In one embodiment of the invention, the number of substituents in an optionally substituted phenyl group, i.e. a phenyl group which is unsubstituted or substituted as indicated, is independently of the number of substituents in any other phenyl group 1, 2 or 3, in another embodiment 1 or 2, in another embodiment 1, wherein the substituents can be identical or different. Likewise, in one embodiment of the invention the number of substituents in an optionally substituted naphthyl group or heteroaryl group, independently of the number of substituents in any other such group, is 1, 2 or 3, in another embodiment 1 or 2, in another embodiment 1, wherein the substituents can be identical or different. If a polysubstituted phenyl group, naphthyl group or heteroaryl group carries different substituents, each of the substituents can be present in any suitable position, and all such positional isomers are subject of the invention. If a phenyl group, a naphthyl group or a heteroaryl group is substituted by the group —O—($C_1$-$C_3$)-alkyl-O—, in which the alkyl group is optionally substituted by one or more fluorine substituents, in one embodiment of the invention it carries only one such substituent. Examples of such substituted phenyl groups are methylenedioxyphenyl and ethylenedioxyphenyl, for example 2,3-methylenedioxyphenyl, 3,4-methylenedioxyphenyl, 2,3-(difluoromethylene)dioxyphenyl, 3,4-(difluoromethylene)dioxyphenyl, 2,3-ethylenedioxyphenyl and 3,4-ethylenedioxyphenyl. If a phenyl group, a naphthyl group or a heteroaryl group is substituted by substituents $Ar^3$ or substituents $Ar^5$, in one embodiment of the invention it carries only one such substituent $Ar^3$ or $Ar^5$, respectively. Naphthyl (=naphthalenyl) can be 1-naphthyl (=naphthalen-1-yl) or 2-naphthyl (=naphthalen-2-yl). In monosubstituted 1-naphthyl groups, the substituent can be present in the 2-position, the 3-position, the 4-position, the 5-position, the 6-position, the 7-position or the 8-position, in monosubstituted 2-naphthyl groups in the 1-position, the 3-position, the 4-position, the 5-position, the 6-position, the 7-position or the 8-position. Also in polysubstituted naphthyl groups, for example disubstituted or trisubstituted naphthyl groups, the substituents can be present in all suitable positions.

Heteroaryl is a residue of a monocyclic or fused bicyclic aromatic ring system. In the case of a bicyclic aromatic ring system, at least one of the two rings is aromatic, i.e. it has a conjugated pi electron sextet, and the ring system is bonded to the remainder of the molecule via an atom in an aromatic ring. The second ring in a bicyclic aromatic ring system in a heteroaryl group contains a double bond by means of the condensation to the aromatic ring and can additionally contain one or two further double bonds or can contain no further double bond, and it can be aromatic or non-aromatic. In one embodiment of the invention, an 8-membered bicyclic ring system contains two fused 5-membered rings, a 9-membered bicyclic ring system contains a 5-membered ring and a 6-membered ring which are fused, and a 10-membered bicyclic ring system contains two fused 6-membered rings or a 5-membered ring and a 7-membered ring which are fused. In a bicyclic ring system, both rings can contain ring heteroatoms, or only one of the rings can contain one or more ring heteroatoms and the second ring contain no ring heteroatoms. Nitrogen ring heteroatoms can be common to both rings. In a bicyclic ring system in a heteroaryl group, a ring which contains one or more ring heteroatoms, as well as a ring which contains no ring heteroatoms, can be aromatic or non-aromatic.

The ring heteroatoms indicated in the definition of the group heteroaryl can be present in any combination and can be present in any suitable position, provided that the resulting group and the molecule as a whole are stable and suitable as a pharmaceutical active compound and at least one of the rings in the ring system is aromatic. In one embodiment of the invention, two ring heteroatoms from the series consisting of oxygen and sulfur cannot be present in adjacent ring positions. Examples of ring systems from which a heteroaryl residue can be derived are pyrrole, furan, thiophene, imidazole, pyrazole, triazoles such as [1,2,3]triazole and [1,2,4] triazole, oxazole (=[1,3]oxazole), isoxazole (=[1,2]oxazole), thiazole (=[1,3]thiazole), isothiazole (=[1,2]thiazole), oxadiazoles such as [1,2,4]oxadiazole, [1,3,4]oxadiazole and [1,2,5]oxadiazole, thiadiazoles such as [1,3,4]thiadiazole, pyridine, pyridazine, pyrimidine, pyrazine, triazines such as [1,2,3]triazine, [1,2,4]triazine and [1,3,5]triazine, indole, benzothiophene, benzofuran, benzo[1,3]dioxole (=[1,3]benzodioxole=1,2-methylenedioxybenzene), [1,3]benzoxazole, [1,3]benzothiazole, benzoimidazole, 4,5,6,7-tetrahydrobenzoimidazole, pyrrolopyridines such as pyrrolo[2,3-b]pyridine, pyrrolo[3,2-b]pyridine, pyrrolo[2,3-c]pyridine and pyrrolo[3,2-c]pyridine, imidazopyridines such as imidazo[4,5-b]pyridine and imidazo[4,5-c]pyridine, chromane, isochromane, benzo[1,4]dioxane (=[1,4]benzodioxane=1,2-ethylenedioxybenzene), quinoline, 1,2,3,4-tetrahydroquinoline, 5,6,7,8-tetrahydroquinoline, 1,2,3,4-tetrahydroisoquinoline, 5,6,7,8-tetrahydroisoquinoline, cinnoline, quinazoline, quinoxaline, phthalazine, pyrroloazepines such as 6,7,8,9-tetrahydro-5H-pyrrolo[1,2-a]azepine, imidazoazepines such as 6,7,8,9-tetrahydro-5H-imidazo[1,2-a] azepine and 6,7,8,9-tetrahydro-5H-imidazo[1,5-a]azepine, triazoloazepines such as 6,7,8,9-tetrahydro-5H-[1,2,4]triazolo[4,3-a]azepine, thienothiophenes, thienopyrroles, thienopyridines, naphthyridines etc. In one embodiment of the invention, heteroaryl groups are bonded via a ring carbon atom, and can be bonded via any suitable ring carbon atom in an aromatic ring. A thiophenyl group (=thienyl), for example, can be thiophen-2-yl (=2-thienyl) or thiophen-3-yl (=3-thienyl), furanyl can be furan-2-yl or furan-3-yl, pyridinyl (=pyridyl) can be pyridin-2-yl, pyridin-3-yl or pyridin-4-yl, pyrazolyl can be 1H-pyrazol-3-yl, 1H-pyrazol-4-yl or 2H-pyrazol-3-yl, imidazolyl can be 1H-imidazol-2-yl, 1H-imidazol-4-yl or 3H-imidazol-4-yl, thiazolyl can be thiazol-2-yl, thiazol-4-yl or thiazol-5-yl, [1,2,4]triazolyl can be 1H-[1,2,4]triazol-3-yl, 2H-[1,2,4]triazol-3-yl or 4H-[1,2,4]triazol-3-yl, indolyl can be 1H-indol-2-yl, 1H-indol-3-yl, 1H-indol-4-yl, 1H-indol-5-yl, 1H-indol-6-yl or 1H-indol-7-yl, benzoimidazolyl can be 1H-benzoimidazol-2-yl, 1H-benzoimidazol-4-yl, 1H-benzoimidazol-5-yl, 1H-benzoimidazol-6-yl, 1H-benzoimidazol-7-yl, 3H-benzoimidazol-4-yl or 3H-benzoimidazol-5-yl, 4,5,6,7-tetrahydrobenzoimidazolyl can be 4,5,6,7-tetrahydro-1H-benzoimidazol-2-yl, imidazo[4,5-b]pyridinyl can be 1H-imidazo[4,5-b]pyridin-2-yl, 1H-imidazo[4,5-b]pyridin-5-yl, 1H-imidazo[4,5-b]pyridin-6-yl, 1H-imidazo[4,5-b]pyridin-7-yl, 3H-imidazo[4,5-b]pyridin-2-yl, 3H-imidazo[4,5-b]pyridin-5-yl, 3H-imidazo[4,5-b]pyridin-6-yl or 3H-imidazo[4,5-b]pyridin-7-yl, quinolinyl (=quinolyl) can be quinolin-2-yl, quinolin-3-yl, quinolin-4-yl, quinolin-5-yl, quinolin-6-yl, quinolin-7-yl or quinolin-8-yl, isoquinolinyl (=isoquinolyl) can be isoquinolin-1-yl, isoquinolin-3-yl, isoquinolin-4-yl, isoquinolin-5-yl, isoquinolin-6-yl, isoquinolin-7-yl or isoquinolin-8-yl, 6,7,8,9-tetrahydro-5H-imidazo[1,2-a]azepinyl can be 6,7,8,9-tetrahydro-5H-imidazo[1,2-a]azepin-2-yl or 6,7,8,9-tetrahydro-5H-imidazo[1,2-a]azepin-3-yl, 6,7,8,9-tetrahydro-5H-imidazo[1,5-a]azepinyl can be 6,7,8,9-tetrahydro-5H-imidazo[1,5-a]azepin-1-yl or 6,7,8,9-tetrahydro-5H-imidazo[1,5-a]azepin-3-yl, 6,7,8,9-tetrahydro-5H-[1,2,4]triazolo[4,3-a]azepinyl can be 6,7,8,9-tetrahydro-5H-[1,2,4]triazolo[4,3-a]azepin-3-yl, for example. In one embodiment of the invention, a heteroaryl group in the compounds of the formula I, for example a heteroaryl group representing $Ar^1$ or a heteroaryl group representing $Ar^2$ or a heteroaryl group representing $Ar^3$ or a heteroaryl group representing $Ar^4$ or a heteroaryl group representing $Ar^5$, independently of any other heteroaryl group, contains 1 or 2 identical or different ring heteroatoms, in another embodiment 1 ring heteroatom. In one embodiment of the invention, the ring heteroatoms in a heteroaryl group in the compounds of the formula I, for example a heteroaryl group representing $Ar^1$ or a heteroaryl group representing $Ar^2$ or a heteroaryl group representing $Ar^3$ or a heteroaryl group representing $Ar^4$ or a heteroaryl group representing $Ar^5$, independently of any other heteroaryl group, are chosen from the series consisting of nitrogen and sulfur, in another embodiment the ring heteroatoms are nitrogen atoms. In one embodiment of the invention, a heteroaryl group in the compounds of the formula I, for example a heteroaryl group representing $Ar^1$ or a heteroaryl group representing $Ar^2$ or a heteroaryl group representing $Ar^3$ or a heteroaryl group representing $Ar^4$ or a heteroaryl group representing $Ar^5$, independently of any other heteroaryl group, is chosen from the series consisting of thienyl, pyrazolyl, imidazolyl, [1,2,4]triazolyl, thiazolyl, pyridinyl, pyrimidinyl, indolyl, benzodioxolyl, benzoimidazolyl, 4,5,6,7-tetrahydrobenzoimidazolyl, imidazo[4,5-b]pyridinyl, quinolinyl, isoquinolinyl and 6,7,8,9-tetrahydro-5H-imidazo[1,5-a] azepinyl, or from any subgroup thereof, for example from thienyl, pyrazolyl, imidazolyl, [1,2,4]triazolyl, thiazolyl, pyridinyl, indolyl, benzoimidazolyl, quinolinyl and isoquinolinyl, or from thienyl, pyrazolyl, imidazolyl, [1,2,4]triazolyl, thiazolyl, pyridinyl, pyrimidinyl, benzoimidazolyl, quinolinyl and isoquinolinyl, or from thienyl, pyrazolyl, imidazolyl, [1,2,4]triazolyl, thiazolyl, pyridinyl, pyrimidinyl, quinolinyl and isoquinolinyl, or from thienyl, pyrazolyl, imidazolyl, [1,2,4]triazolyl, thiazolyl, pyridinyl, pyrimidinyl and benzoimidazolyl, or from thienyl, pyrazolyl, imidazolyl, [1,2,4] triazolyl, thiazolyl, pyridinyl and pyrimidinyl, or from thienyl, thiazolyl and pyridinyl, or from thienyl and pyridinyl, or from pyridinyl and pyrimidinyl, or from pyrazolyl, imidazolyl, [1,2,4]triazolyl and pyridinyl, or from pyrazolyl, imidazolyl and [1,2,4]triazolyl, or is pyridinyl, or example, wherein all groups are optionally substituted as indicated.

In substituted heteroaryl groups, the substituents can be present on ring carbon atoms and ring nitrogen atoms in any desired positions, for example in a thiophen-2-yl group or a furan-2-yl group in the 3-position and/or in the 4-position and/or in the 5-position, in a thiophen-3-yl group or a furan-3-yl group in the 2-position and/or in the 4-position and/or in the 5-position, in a pyrazol-3-yl group in the 1-position and/or the 2-position and/or the 4-position and/or the 5-position, in a pyrazol-4-yl group in the 1-position and/or the 2-position and/or the 3-position and/or the 5-position, in an imidazol-2-yl group in the 1-position and/or the 3-position and/or the 4-position and/or the 5-position, in an imidazol-4-yl group in the 1-position and/or the 2-position and/or the 3-position and/or the 5-position, in an imidazol-5-yl group in the 1-position and/or the 2-position and/or the 3-position and/or the 4-position, in a [1,2,4]triazol-3-yl group in the 1-position and/or the 2-position and/or the 4-position and/or the 5-position, in a [1,2,4]triazol-5-yl group in the 1-position and/or the 2-position and/or the 3-position and/or the 4-position, in a pyridin-2-yl group in the 3-position and/or in the 4-position and/or in the 5-position and/or in the 6-position, in a pyridin-3-yl group in the 2-position and/or in the 4-position and/or in the 5-position and/or in the 6-position, in a pyridin-4-yl group in the 2-position and/or in the 3-position and/or in the 5-position and/or in the 6-position, in a benzoimidazol-2-yl group in the 1-position and/or the 3-position and/or the 4-position and/or the 5-position and/or the 6-position and/or the 7-position, for example. In one embodiment of the invention, the number of substituents in an optionally substituted heteroaryl group, i.e. a heteroaryl group which is unsubstituted or substituted as indicated, is independently of the number of substituents in any other heteroaryl group 1, 2 or 3, in another embodiment 1 or 2, in another embodiment 1, wherein the substituents can be identical or different. If a ring nitrogen atom in a heteroaryl group which can carry a hydrogen atom or a substituent, for example a nitrogen atom in a pyrrolyl group, pyrazolyl group, imidazolyl group, triazolyl group, indolyl group, benzoimidazolyl group or imidazopyridinyl group, is substituted, in one embodiment of the invention the substituent on a ring nitrogen atom is selected from $(C_1-C_5)$-alkyl, $(C_3-C_8)$-cycloalkyl-$C_vH_{2v}$—, $(C_3-C_8)$-cycloalkyl-$C_wH_{2w}$—, $(C_3-C_8)$-cycloalkyl-S(O)$_f$—, $(C_1-C_5)$-alkyl-S(O)$_k$—, $(C_1-C_5)$-alkyl-S(O)$_m$—, $(C_1-C_5)$-alkyl-S(O)$_n$—, Ar$^3$ and Ar$^5$, depending on the definition of the respective group, in another embodiment from the series consisting of $(C_1-C_5)$-alkyl, $(C_3-C_8)$-cycloalkyl-$C_vH_{2v}$—, $(C_3-C_8)$-cycloalkyl-$C_wH_{2w}$—, Ar$^3$ and Ar$^5$, depending on the definition of the respective group, in another embodiment from the series consisting of $(C_1-C_5)$-alkyl and $(C_3-C_8)$-cycloalkyl-$C_vH_{2v}$— and $(C_3-C_8)$-cycloalkyl-$C_wH_{2w}$—, depending on the definition of the respective group, and in another embodiment it is selected from any of such groups as methyl, n-propyl, isopropyl, isobutyl and cyclopropylmethyl, for example, wherein all alkyl groups and cycloalkyl groups are optionally substituted by one or more fluorine substituents and all cycloalkyl groups are optionally substituted by one or more identical or different $(C_1-C_4)$-alkyl substituents. Generally, suitable ring nitrogen atoms in an aromatic ring of a heteroaryl group, for example the nitrogen atom in a pyridinyl group, quinolinyl group or isoquinolinyl group or a nitrogen atom in a [1,2,5]oxadiazolylgroup, can also carry an oxido substituent —O$^-$ and be present as an N-oxide.

The ring of the group Het can be 4-membered, 5-membered, 6-membered or 7-membered. In one embodiment of the invention, Het is 4-membered, 5-membered or 6-membered, in another embodiment 4-membered or 5-membered, in another embodiment 4-membered. In one embodiment of the invention, the ring heteroatoms in the group Het are selected from the series consisting of nitrogen and oxygen, in another embodiment from the series consisting of oxygen and sulfur, in another embodiment the ring heteroatoms are oxygen atoms. The ring heteroatoms in the group Het can be present in any combination and can be present in any suitable position, provided that the resulting group and the molecule as a whole are stable and suitable as a pharmaceutical active compound. In one embodiment of the invention, two oxygen atoms cannot be present as ring heteroatoms in adjacent ring positions, in another embodiment two ring heteroatoms from the series consisting of oxygen and sulfur cannot be present in adjacent ring positions. Examples of ring systems from which a residue Het can be derived, are azetidine, oxetane, thietane, pyrrolidine, tetrahydrofuran, tetrahydrothiophene, imidazolidine, pyrazolidine, [1,3]dioxolane, oxazolidine (=[1,3]oxazolidine), isoxazolidine (=[1,2]oxazolidine), thiazolidine (=[1,3]thiazolidine), isothiazolidine (=[1,2]thiazolidine), piperidine, tetrahydropyran, tetrahydrothiopyran, [1,4]dioxane, hexahydropyrimidine, piperazine, morpholine, thiomorpholine, azepane, oxepane. The group Het can be bonded via any suitable ring carbon atom. An azetidinyl group, for example, can be azetidin-2-yl or azetidin-3-yl, oxetanyl can be oxetan-2-yl or oxetan-3-yl, thietanyl can be thietan-2-yl or thietan-3-yl, pyrrolidinyl can be pyrrolidin-2-yl or pyrrolidin-3-yl, tetrahydrofuranyl can be tetrahydrofuran-2-yl or tetrahydrofuran-3-yl, tetrahydrothiophenyl can be tetrahydrothiophen-2-yl or tetrahydrothiophen-3-yl, thiazolidinyl can be thiazolidin-2-yl, thiazolidin-4-yl or thiazolidin-5-yl, piperidinyl can be piperidin-2-yl, piperidin-3-yl or piperidin-4-yl, tetrahydropyranyl can be tetrahydropyran-2-yl, tetrahydropyran-3-yl or tetrahydropyran-4-yl, [1,4]dioxanyl can be [1,4]dioxan-2-yl, morpholinyl can be morpholin-2-yl or morpholin-3-yl. In one embodiment of the invention, the group Het is bonded via a carbon atom which is not adjacent to a ring heteroatom. In one embodiment of the invention, Het contains 1 ring heteroatom. In another embodiment, Het is chosen from the series consisting of oxetanyl, thietanyl, tetrahydrofuranyl, tetrahydrothiophenyl, tetrahydropyranyl, tetrahydrothiopyranyl and [1,4]dioxanyl, or from any subgroup thereof, for example from oxetanyl, tetrahydrofuranyl, tetrahydropyranyl and [1,4]dioxanyl, or from oxetanyl, tetrahydrofuranyl and tetrahydropyranyl, or from oxetanyl and tetrahydrofuranyl, or from oxetanyl, thietanyl, tetrahydrofuranyl, tetrahydrothiophenyl and tetrahydropyranyl, or from oxetanyl and thietanyl, or from oxetanyl, thietanyl, tetrahydrofuranyl and tetrahydrothiophenyl, or is oxetanyl, for example, wherein all groups are optionally substituted as indicated.

In substituted groups Het, the substituents can be present on ring carbon atoms and/or ring nitrogen atoms in any desired positions, for example in an azetidinyl group in the 1-position and/or in the 2-position and/or in the 3-position and/or in the 4-position, in an oxetanyl group or a thietanyl group in the 2-position and/or in the 3-position and/or in the 4-position, in a pyrrolidinyl group in the 1-position and/or in the 2-position and/or in the 3-position and/or in the 4-position and/or in the 5-position, in a tetrahydrofuranyl group or a tetrahydrothiophenyl group in the 2-position and/or in the 3-position and/or in the 4-position and/or in the 5-position, in a piperidinyl group in the 1-position and/or in the 2-position and/or in the 3-position and/or in the 4-position and/or in the 5-position and or in the 6-position, in a tetrahydropyranyl group or a tetrahydrothiopyranyl group in the 2-position and/or in the 3-position and/or in the 4-position and/or in the 5-position and or in the 6-position. Ring nitrogen atoms in a group Het which do not carry a substituent from the series consisting of phenyl and $(C_1$-$C_5)$-alkyl, carry a hydrogen atom. In one embodiment of the invention, the number of phenyl and $(C_1$-$C_5)$-alkyl substituents in an optionally substituted group Het , i.e. a group Het which is unsubstituted or substituted as indicated, is 1, 2 or 3, in another embodiment 1 or 2, in another embodiment 1, wherein the substituents can be identical or different. If a group Het is substituted by phenyl groups, in one embodiment of the invention it carries not more than two such phenyl substituents, and in another embodiment it carries not more than one such phenyl substituent, wherein the phenyl substituents are optionally substituted as indicated. If a group Het is substituted by fluorine, in one embodiment of the invention the number of fluorine substituents which are optionally present in the group Het is 1, 2, 3, 4 or 5, in another embodiment the number of such fluorine substituents is 1, 2, 3 or 4, in another embodiment it is 1, 2 or 3, in another embodiment it is 1 or 2, in another embodiment it is 1, and in another embodiment the group Het is not substituted by fluorine substituents, it being possible for alkyl and phenyl substituents on the group Het to be optionally substituted by fluorine substituents as indicated independently of the substitution of Het itself by fluorine substituents.

The present invention comprises all stereoisomeric forms of the compounds of the formula I, for example all possible enantiomers and diastereomers including cis/trans isomers. The invention likewise comprises mixtures of two or more stereoisomeric forms, for example mixtures of enantiomers and/or diastereomers including cis/trans isomers, in all ratios. Asymmetric centers contained in the compounds of the formula I, for example in unsubstituted or substituted alkyl groups, can all independently of one another have the S configuration or the R configuration. The invention relates to enantiomers, both the levorotatory and the dextrorotatory antipode, in enantiomerically pure form and essentially enantiomerically pure form and in the form of racemates and in the form of mixtures of the two enantiomers in all ratios. The invention likewise relates to diastereomers including, for example, meso compounds, in the form of pure and essentially pure diastereomers and in the form of mixtures of two or more diastereomers in all ratios. The invention also comprises all possible cis/trans isomers and E/Z isomers in pure form and essentially pure form and in the form of mixtures of the cis isomer and the trans isomer or of the E isomer and the Z isomer in all ratios. Cis/trans isomerism or E/Z isomerism can occur in substituted rings and on double bonds, for example in the cyclohexane ring shown in the formula I in which two groups such as $Ar^1$ and $Ar^2$, for example, can be present in the cis position or in the trans position with respect to each other, or in a substituted cycloalkyl group or in an alkenyl group. In one embodiment of the present invention, the 1,1,4,4-tetrasubstituted cyclohexane ring shown in the formula I is cis-configured, and in another embodiment of the present invention it is trans-configured, the assignment of cis or trans configuration being dependent on the relative positions of the groups $Ar^1$, $Ar^2$, —CO—$R^1$ and $R^2$—O— and their order of priority. When considering two specific groups on the cyclohexane ring, for example the groups $Ar^1$ and $Ar^2$, in one embodiment of the present invention these groups are in the cis position with respect to each other, and in another embodiment of the invention these groups are in trans position with respect to each other. The preparation of individual stereoisomers, if desired, can be carried out by resolution of a mixture according to customary methods, for example by chromatography or crystallization, or by use of stereochemically uniform starting substances in the synthesis or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. The invention also comprises all tautomeric forms of the compounds of the formula I.

Physiologically acceptable salts of the compounds of the formula I are in particular salts with a nontoxic salt component and include pharmaceutically utilizable salts. They can contain inorganic or organic salt components. Such salts can, for example, be formed from compounds of the formula I which contain an acidic group, for example compounds of the formula I in which $R^1$ is a hydroxy group, and nontoxic inorganic or organic bases. Examples of such bases are suitable alkali metal compounds or alkaline earth metal compounds, such as sodium hydroxide, potassium hydroxide, sodium carbonate or sodium hydrogencarbonate, or ammonia or organic amino compounds or quaternary ammonium hydroxides. Reactions of compounds of the formula I with bases for the preparation of the salts are in general carried out according to customary procedures in a solvent or diluent. On account of the physiological and chemical stability, advantageous salts of acidic groups are in many cases sodium, potassium, magnesium or calcium salts or ammonium salts, which can also carry one or more organic groups on the nitrogen atom. Compounds of the formula I which contain a basic, i.e. protonatable, group, for example an amino group or a basic heterocycle, can be present in the form of their acid addition salts with physiologically acceptable acids, for example as salts with hydrogen chloride, hydrogen bromide, phosphoric acid, sulfuric acid, acetic acid, benzoic acid, methanesulfonic acid, p-toluenesulfonic acid, which salts can in general be prepared from the compounds of the formula I by reaction with an acid in a solvent or diluent according to customary procedures. If the compounds of the formula I simultaneously contain an acidic group and a basic group in the molecule, the invention also includes, in addition to the salt forms mentioned, internal salts (=betaines=zwitterions). The present invention also comprises all salts of the compounds of the formula I which, because of low physiological tolerability, are not directly suitable for use in pharmaceuticals, but are suitable, for example, as intermediates for chemical reactions or for the preparation of physiologically acceptable salts, for example by anion exchange or cation exchange. The present invention furthermore comprises all solvates of compounds of the formula I, for example hydrates or adducts with alcohols such as $(C_1$-$C_4)$-alkanols, and derivatives of the compounds of the formula I and prodrugs and active metabolites of compounds of the formula I.

In one embodiment of the invention, the groups $Ar^1$ and $Ar^2$ are, independently of one another, phenyl or heteroaryl, in another embodiment phenyl or monocyclic heteroaryl, in another embodiment phenyl, which are all optionally substituted as indicated. In one embodiment of the invention, $Ar^1$ is phenyl or heteroaryl, in another embodiment phenyl or monocyclic heteroaryl, in another embodiment phenyl or pyridinyl, in another embodiment phenyl, in another embodiment heteroaryl, in another embodiment monocyclic heteroaryl, in another embodiment pyridinyl, in a another embodiment heteroaryl which is not pyridinyl, in another embodiment monocyclic heteroaryl which is not pyridinyl, wherein all groups are optionally substituted as indicated. In one embodiment of the invention, $Ar^2$ is phenyl or naphthyl, in another embodiment phenyl, in another embodiment phenyl or heteroaryl, in another embodiment phenyl or monocyclic heteroaryl, in another embodiment heteroaryl, in another embodiment monocyclic heteroaryl, wherein all groups are optionally substituted as indicated. In further embodiments of the invention, one or both of the groups $Ar^1$ and $Ar^2$ are any specific group, or chosen from any two or more specific groups, which are mentioned in the definitions of $Ar^1$ and $Ar^2$, such as phenyl, or which are mentioned as examples of generic meanings mentioned in the definitions of $Ar^1$ and $Ar^2$. For example, in one embodiment of the invention one or both of the groups $Ar^1$ and $Ar^2$ are independently of one another chosen from the series consisting of phenyl, thienyl, imidazolyl, pyrazolyl, [1,2,4]triazolyl, thiazolyl, pyridinyl, indolyl, benzoimidazolyl, imidazo[4,5-b]pyridinyl, quinolinyl and isoquinolinyl, in another embodiment from the series consisting of phenyl, thienyl, imidazolyl, pyrazolyl, [1,2,4]triazolyl, thiazolyl, pyridinyl, quinolinyl and isoquinolinyl, in another embodiment from the series consisting of phenyl, thienyl, imidazolyl, pyrazolyl, [1,2,4]triazolyl, thiazolyl, pyridinyl, indolyl, benzoimidazolyl and imidazo[4,5-b]pyridinyl, in another embodiment from the series consisting of phenyl, thienyl, imidazolyl, pyrazolyl, [1,2,4]triazolyl, thiazolyl, pyridinyl and benzoimidazolyl, in another embodiment from the series consisting of phenyl, thienyl, imidazolyl, pyrazolyl, [1,2,4] triazolyl, thiazolyl and pyridinyl, which are all optionally substituted as indicated. In one embodiment of the invention, phenyl groups representing $Ar^1$ or $Ar^2$ are unsubstituted. In another embodiment of the invention, phenyl groups representing $Ar^1$ or $Ar^2$ are substituted.

In one embodiment of the invention, substituted phenyl groups, naphthyl groups and heteroaryl groups representing $Ar^1$ or $Ar^2$ are substituted by 1, 2 or 3, in another embodiment by 1 or 2, identical or different substituents. In one embodiment of the invention, substituents in substituted groups $Ar^1$ and $Ar^2$ are independently of one another selected from the series consisting of halogen, cyano, $(C_1-C_5)$-alkyl, $(C_3-C_6)$-cycloalkyl-$C_vH_{2v}$—, $Ar^3$, $(C_1-C_5)$-alkyl-O—, —O—$(C_1-C_3)$-alkyl-O—, $(C_3-C_6)$-cycloalkyl-S(O)$_f$— and $(C_1-C_5)$-alkyl-S(O)$_k$—, in another embodiment from the series consisting of halogen, $(C_1-C_5)$-alkyl, $(C_3-C_6)$-cycloalkyl-$C_vH_{2v}$—, $Ar^3$, $(C_1-C_5)$-alkyl-O—, —O—$(C_1-C_3)$-alkyl-O—, $(C_3-C_6)$-cycloalkyl-S(O)$_f$— and $(C_1-C_5)$-alkyl-S(O)$_k$—, in another embodiment from the series consisting of halogen, cyano, $(C_1-C_5)$-alkyl, $(C_3-C_6)$-cycloalkyl-$C_vH_{2v}$—, $Ar^3$, $(C_1-C_5)$-alkyl-O—, —O—$(C_1-C_3)$-alkyl-O— and $(C_1-C_5)$-alkyl-S(O)$_k$—, in another embodiment from the series consisting of halogen, $(C_1-C_5)$-alkyl, $(C_3-C_6)$-cycloalkyl-$C_vH_{2v}$—, $Ar^3$, $(C_1-C_5)$-alkyl-O—, —O—$(C_1-C_3)$-alkyl-O— and $(C_1-C_5)$-alkyl-S(O)$_k$—, in another embodiment from the series consisting of halogen, cyano, $(C_1-C_5)$-alkyl, $(C_3-C_6)$-cycloalkyl-$C_vH_{2v}$—, $Ar^3$, $(C_1-C_5)$-alkyl-O—, $(C_3-C_6)$-cycloalkyl-S(O)$_f$— and $(C_1-C_5)$-alkyl-S(O)$_k$—, in another embodiment from the series consisting of halogen, $(C_1-C_5)$-alkyl, $(C_3-C_6)$-cycloalkyl-$C_vH_{2v}$—, $Ar^3$, $(C_1-C_5)$-alkyl-O—, $(C_3-C_6)$-cycloalkyl-S(O)$_f$— and $(C_1-C_5)$-alkyl-S(O)$_k$—, in another embodiment from the series consisting of halogen, cyano, $(C_1-C_5)$-alkyl, $(C_3-C_6)$-cycloalkyl-$C_vH_{2v}$—, $Ar^3$, $(C_1-C_5)$-alkyl-O— and $(C_1-C_5)$-alkyl-S(O)$_k$—, in another embodiment from the series consisting of halogen, $(C_1-C_5)$-alkyl, $(C_3-C_6)$-cycloalkyl-$C_vH_{2v}$—, $Ar^3$, $(C_1-C_5)$-alkyl-O— and $(C_1-C_5)$-alkyl-S(O)$_k$—, wherein in all cases all alkyl groups and cycloalkyl groups are optionally substituted by one or more fluorine substituents and all cycloalkyl groups are optionally substituted by one or more identical or different $(C_1-C_4)$-alkyl substituents. In one embodiment of the invention, the substituents in substituted groups $Ar^1$ and $Ar^2$ are independently of one another selected from the series consisting of halogen, $(C_1-C_5)$-alkyl, $(C_3-C_6)$-cycloalkyl-$C_vH_{2v}$— and $Ar^3$, in another embodiment from the series consisting of halogen, $(C_1-C_5)$-alkyl-O—, —O—$(C_1-C_3)$-alkyl-O—, $(C_3-C_6)$-cycloalkyl-S(O)$_f$— and $(C_1-C_5)$-alkyl-S(O)$_k$—, in another embodiment from the series consisting of halogen, cyano, $(C_1-C_5)$-alkyl-O—, —O—$(C_1-C_3)$-alkyl-O— and $(C_1-C_5)$-alkyl-S(O)$_k$—, in another embodiment from the series consisting of halogen, $(C_1-C_5)$-alkyl-O—, —O—$(C_1-C_3)$-alkyl-O— and $(C_1-C_5)$-alkyl-S(O)$_k$—, in another embodiment from the series consisting of halogen, cyano, $(C_1-C_5)$-alkyl-O—, $(C_3-C_6)$-cycloalkyl-S(O)$_f$— and $(C_1-C_5)$-alkyl-S(O)$_k$—, in another embodiment from the series consisting of halogen, $(C_1-C_5)$-alkyl-O—, $(C_3-C_6)$-cycloalkyl-S(O)$_f$— and $(C_1-C_5)$-alkyl-S(O)$_k$—, in another embodiment from the series consisting of halogen, cyano, $(C_1-C_5)$-alkyl-O— and $(C_1-C_5)$-alkyl-S(O)$_k$—, in another embodiment from the series consisting of halogen, $(C_1-C_5)$-alkyl-O— and $(C_1-C_5)$-alkyl-S(O)$_k$—, wherein in all cases all alkyl groups and cycloalkyl groups are optionally substituted by one or more fluorine substituents and all cycloalkyl groups are optionally substituted by one or more identical or different $(C_1-C_4)$-alkyl substituents. In further embodiments of the invention, one or more substituents in the general series of substituents in $Ar^1$ and $Ar^2$ or in any specified embodiment can have one or more specific meanings which are mentioned as examples of the generic meanings of substituents. For example, all series of substituents which comprise fluoro-substituted alkyl groups or alkyl-O— groups, can as specific substituents contain the groups trifluoromethyl or trifluoromethoxy, respectively, which are mentioned as examples of fluoro-substituted alkyl groups and alkyl-O— groups.

In one embodiment of the invention, the groups $Ar^3$ and $Ar^5$ are, independently of one another, phenyl or one or more specific monocyclic heteroaryl groups which are mentioned as examples of the generic meaning heteroaryl, for example are phenyl, thienyl or pyridinyl, or are phenyl or pyridinyl, or are phenyl, which are all optionally substituted as indicated. In one embodiment of the invention, substituted phenyl groups and heteroaryl groups representing $Ar^3$ or $Ar^5$ are substituted by 1 or 2 identical or different substituents, in another embodiment by 1 substituent. In one embodiment of the invention, substituents in substituted groups $Ar^3$ and $Ar^5$ are, independently of one another, selected from the series consisting of halogen, $(C_1-C_5)$-alkyl, $(C_1-C_5)$-alkyl-O—, —O—$(C_1-C_3)$-alkyl-O— and $(C_1-C_5)$-alkyl-S(O)$_m$—, in another embodiment from the series consisting of halogen, $(C_1-C_5)$-alkyl, $(C_1-C_5)$-alkyl-O— and —O—$(C_1-C_3)$-alkyl-O—, in another embodiment from the series consisting of halogen, $(C_1-C_5)$-alkyl, $(C_1-C_5)$-alkyl-O— and $(C_1-C_5)$-alkyl-S(O)$_m$—, in another embodiment from the series consisting of halogen, $(C_1-C_5)$-alkyl and $(C_1-C_5)$-alkyl-O—, in another embodiment from the series consisting of halogen and $(C_1-C_5)$-alkyl, wherein in all cases all alkyl groups are optionally substituted by one or more fluorine substituents. In further embodiments of the invention, one or more substituents in the general series of substituents in $Ar^3$ and $Ar^5$ or in any specified embodiment can have one or more specific meanings which are mentioned as examples of the generic meanings. For example, all series of substituents which comprise fluoro-substituted alkyl groups or alkyl-O— groups, can as specific substituents contain the groups trifluoromethyl or trifluoromethoxy, respectively, which are mentioned as examples of fluoro-substituted alkyl groups and alkyl-O— groups.

In one embodiment of the invention, the group $Ar^4$ is phenyl or monocyclic heteroaryl which are all optionally substituted as indicated. In one embodiment of the invention, $Ar^4$ is phenyl, in another embodiment $Ar^4$ is heteroaryl, another embodiment monocyclic heteroaryl, wherein all groups are optionally substituted as indicated. In further embodiments of the invention, $Ar^4$ is any specific group, or chosen from any two or more specific groups, which are mentioned in the definitions of $Ar^4$ or which are mentioned as examples of generic meanings mentioned in the definitions. For example, in one embodiment of the invention the group $Ar^4$ is any one or more groups from the series consisting of phenyl, thienyl, pyridinyl and pyrimidinyl, in another embodiment from the series consisting of phenyl, pyridinyl and pyrimidinyl, in another embodiment from phenyl and pyridinyl, which are all optionally substituted as indicated. In one embodiment of the invention, substituted phenyl groups and heteroaryl groups representing $Ar^4$ are substituted by 1, 2 or 3, in another embodiment by 1 or 2, in another embodiment by 1, identical or different substituents. In one embodiment of the invention, substituents in substituted groups $Ar^4$ are selected from the series consisting of halogen, cyano, $(C_1-C_5)$-alkyl, $Ar^5$, $(C_1-C_5)$-alkyl-O—, HO—$(C_1-C_5)$-alkyl-O—, —O—$(C_1-C_3)$-alkyl-O— and $(C_1-C_5)$-alkyl-S(O)$_n$—, in another embodiment from the series consisting of halogen, cyano, $(C_1-C_5)$-alkyl, $Ar^5$, $(C_1-C_5)$-alkyl-O—, HO—$(C_1-C_5)$-alkyl-O— and $(C_1-C_5)$-alkyl-S(O)$_n$—, in another embodiment from the series consisting of halogen, cyano, $(C_1-C_5)$-alkyl, $Ar^5$, $(C_1-C_5)$-alkyl-O— and $(C_1-C_5)$-alkyl-S(O)$_n$—, in another embodiment from the series consisting of halogen, $(C_1-C_5)$-alkyl, $(C_1-C_5)$-alkyl-O— and $(C_1-C_5)$-alkyl-S(O)$_n$—, in another embodiment from the series consisting of halogen, $(C_1-C_5)$-alkyl and $(C_1-C_5)$-alkyl-O—, in another embodiment from the series consisting of halogen, $(C_1-C_5)$-alkyl and $(C_1-C_5)$-alkyl-S(O)$_n$—, in another embodiment from the series consisting of halogen and $(C_1-C_5)$-alkyl, wherein in all cases all alkyl groups are optionally substituted by one or more fluorine substituents. In further embodiments of the invention, one or more substituents in the general series of substituents in $Ar^4$ or in any specified embodiment can have one or more specific meanings which are mentioned as examples of the generic meanings. For example, all series of substituents which comprise fluoro-substituted alkyl groups or alkyl-O— groups can as specific substituents contain the groups trifluoromethyl or trifluoromethoxy, respectively, which are mentioned as examples of fluoro-substituted alkyl groups and alkyl-O— groups. In one embodiment of the invention, the group $Ar^4$ is unsubstituted. In another embodiment of the invention, the group $Ar^4$ is substituted.

In one embodiment of the invention, $R^1$ is $R^3$—, in another embodiment $R^1$ is $R^4$—O— or $R^5R^6N$—, in another embodiment $R^1$ is $R^4$—O—.

In one embodiment of the invention, $R^2$ is hydrogen, $(C_1-C_8)$-alkyl, $(C_2-C_8)$-alkenyl, $(C_3-C_8)$-alkynyl, $Ar^4$, $R^{17}$—O—$(C_1-C_8)$-alkyl-, $R^{18}R^{19}N$—$(C_1-C_8)$-alkyl-, Het-$C_uH_{2u}$— or $(C_3-C_8)$-cycloalkyl-$C_uH_{2u}$—, in another embodiment hydrogen, $(C_1-C_8)$-alkyl, $(C_2-C_8)$-alkenyl, $Ar^4$, $R^{17}$—O—$(C_1-C_8)$-alkyl-, $R^{18}R^{19}N$—$(C_1-C_8)$-alkyl-, Het-$C_uH_{2u}$— or $(C_3-C_8)$-cycloalkyl-$C_uH_{2u}$—, in another embodiment hydrogen, $(C_1-C_8)$-alkyl, $(C_2-C_8)$-alkenyl, $Ar^4$, $R^{17}$—O—$(C_1-C_8)$-alkyl-, $R^{18}R^{19}N$—$(C_1-C_8)$-alkyl- or $(C_3-C_8)$-cycloalkyl-$C_uH_{2u}$—, in another embodiment hydrogen, $(C_1-C_8)$-alkyl, $Ar^4$, $R^{17}$—O—$(C_1-C_8)$-alkyl-, $R^{18}R^{19}N$—$(C_1-C_8)$-alkyl-, Het-$C_uH_{2u}$— or $(C_3-C_8)$-cycloalkyl-$C_uH_{2u}$—, in another embodiment hydrogen, $(C_1-C_8)$-alkyl, $Ar^4$, $R^{17}$—O—$(C_1-C_8)$-alkyl-, Het-$C_uH_{2u}$— or $(C_3-C_8)$-cycloalkyl-$C_uH_{2u}$—, in another embodiment hydrogen, $(C_1-C_8)$-alkyl, $Ar^4$, $R^{17}$—O—$(C_1-C_8)$-alkyl-, $R^{18}R^{19}N$—$(C_1-C_8)$-alkyl- or $(C_3-C_8)$-cycloalkyl-$C_uH_{2u}$—, in another embodiment hydrogen, $(C_1-C_8)$-alkyl, $Ar^4$, Het-$C_uH_{2u}$— or $(C_3-C_8)$-cycloalkyl-$C_uH_{2u}$—, in another embodiment hydrogen, $(C_1-C_8)$-alkyl, $Ar^4$ or $(C_3-C_8)$-cycloalkyl-$C_uH_{2u}$—, wherein in all cases all alkyl groups, alkenyl groups and cycloalkyl groups in $R^2$ are optionally substituted by one or more fluorine substituents and all cycloalkyl groups are optionally substituted by one or more identical or different $(C_1-C_4)$-alkyl substituents. In another embodiment of the invention, $R^2$ is not hydrogen, and in this embodiment $R^2$ thus is $(C_1-C_8)$-alkyl, $(C_2-C_8)$-alkenyl, $(C_3-C_8)$-alkynyl, phenyl-$(C_2-C_8)$-alkenyl-, $Ar^4$, $R^{17}$—O—$(C_1-C_8)$-alkyl-, $R^{18}R^{19}N$—$(C_1-C_8)$-alkyl-, Het-$C_uH_{2u}$— or $(C_3-C_8)$-cycloalkyl-$C_uH_{2u}$—, wherein the phenyl group in phenyl-$(C_2-C_8)$-alkenyl- is optionally substituted by 1, 2 or 3 identical or different substituents from the series consisting of halogen, cyano, $(C_1-C_5)$-alkyl, $(C_1-C_5)$-alkyl-O— and $(C_1-C_5)$-alkyl-S(O)$_g$—, and wherein all alkyl groups, alkenyl groups, alkynyl groups and cycloalkyl groups in $R^2$ are optionally substituted by one or more fluorine substituents and all cycloalkyl groups are optionally substituted by one or more identical or different $(C_1-C_4)$-alkyl substituents. In another embodiment of the invention, $R^2$ is $(C_1-C_8)$-alkyl, $(C_2-C_8)$-alkenyl, $Ar^4$, $R^{17}$—O—$(C_1-C_8)$-alkyl-, $R^{18}R^{19}N$—$(C_1-C_8)$-alkyl-, Het-$C_uH_{2u}$— or $(C_3-C_8)$-cycloalkyl-$C_uH_{2u}$—, in another embodiment $(C_1-C_8)$-alkyl, $(C_2-C_8)$-alkenyl, $Ar^4$, $R^{17}$—O—$(C_1-C_8)$-alkyl-, $R^{18}R^{19}N$—$(C_1-C_8)$-alkyl- or $(C_3-C_8)$-cycloalkyl-$C_uH_{2u}$—, in another embodiment $(C_1-C_8)$-alkyl, $Ar^4$, $R^{17}$—O—$(C_1-C_8)$-alkyl-, $R^{18}R^{19}N$—$(C_1-C_8)$-alkyl-, Het-$C_uH_{2u}$— or $(C_3-C_8)$-cycloalkyl-$C_uH_{2u}$—, in another embodiment $(C_1-C_8)$-alkyl, $Ar^4$, $R^{17}$—O—$(C_1-C_8)$-alkyl-, Het-$C_uH_{2u}$— or $(C_3-C_8)$-cycloalkyl-$C_uH_{2u}$—, in another embodiment $(C_1-C_8)$-alkyl, $Ar^4$, $R^{17}$—O—$(C_1-C_8)$-alkyl-, $R^{18}R^{19}N$—$(C_1-C_8)$-alkyl- or $(C_3-C_8)$-cycloalkyl-$C_uH_{2u}$—, in another embodiment $(C_1-C_8)$-alkyl, $Ar^4$, Het-$C_uH_{2u}$— or $(C_3-C_8)$-cycloalkyl-$C_uH_{2u}$—, in another embodiment $(C_1-C_8)$-alkyl, $Ar^4$ or $(C_3-C_8)$-cycloalkyl-$C_uH_{2u}$—, in another embodiment $(C_1-C_8)$-alkyl, Het-$C_uH_{2u}$— or $(C_3-C_8)$-cycloalkyl-$C_uH_{2u}$—, in another embodiment $(C_1-C_8)$-alkyl or $(C_3-C_8)$-cycloalkyl-$C_uH_{2u}$—, in another embodiment $(C_1-C_8)$-alkyl, in another embodiment $(C_3-C_8)$-cycloalkyl-$C_uH_{2u}$—, in another embodiment Het-$C_uH_{2u}$—, in another embodiment $Ar^4$, wherein in all cases all alkyl groups, alkenyl groups and cycloalkyl groups in $R^2$ are optionally substituted by one or more fluorine substituents and all cycloalkyl groups are optionally substituted by one or more identical or different $(C_1-C_4)$-alkyl substituents. In one embodiment of the invention, unsubstituted and substituted alkyl groups, alkenyl groups and alkynyl groups in $R^2$, independently of one another, contain up to 6 carbon atoms, in another embodiment up to 5 carbon atoms. In one embodiment of the invention, an alkenyl group representing $R^2$ contains at least 3 carbon atoms. In another embodiment, an alkenyl group representing $R^2$ is bonded via a carbon atom which is not part of the double bond. In one embodiment of the invention a cycloalkyl group contained in $R^2$ is a $(C_3-C_7)$-cycloalkyl group, in another embodiment a $(C_3-C_6)$-cycloalkyl group, in another embodiment any one or more groups selected from the series consisting of cyclopropyl, cyclobutyl, cyclopentyl and cyclohexyl, for example from the series consisting of cyclopropyl and cyclobutyl, in another embodiment is a cyclopropyl group, which are all optionally substituted by one or more fluorine substituents and/or one or more identical or different $(C_1-C_4)$-alkyl substituents. In one embodiment of the invention, the $(C_1-C_8)$-alkyl group in the groups $R^{17}$—O—$(C_1-C_8)$-alkyl- and $R^{18}R^{19}N$—$(C_1-C_8)$-alkyl- representing $R^2$ contains at least 2 carbon atoms. In another embodiment, a chain of at least 2 carbon atoms is present between the group $R^{17}$—O— or the group $R^{18}R^{19}N$— and the oxygen atom which carries the group $R^2$. In one embodiment of the invention, the number of substituents which are optionally present in the phenyl group in the group phenyl-($C_2$-$C_8$)-alkenyl-representing $R^2$, is 1 or 2, in another embodiment 1, and in another embodiment this phenyl group is unsubstituted. In one embodiment of the invention, the substituents which are optionally present in the phenyl group in the group phenyl-($C_2$-$C_8$)-alkenyl-representing $R^2$, are selected from the series consisting of halogen, ($C_1$-$C_5$)-alkyl, ($C_1$-$C_6$)-alkyl-O— and ($C_1$-$C_5$)-alkyl-S(O)$_g$—, in another embodiment from halogen, ($C_1$-$C_5$)-alkyl and ($C_1$-$C_5$)-alkyl-O—, in another embodiment from halogen and ($C_1$-$C_5$)-alkyl, wherein all alkyl groups are optionally substituted by one or more fluorine substituents.

In one embodiment of the invention, alkyl groups in $R^3$, $R^4$, $R^5$, $R^6$, $R^{11}$, $R^{12}$, $R^{13}$, $R^{14}$, $R^{15}$, $R^{16}$, $R^{17}$, $R^{18}$ and $R^{19}$ are independently of one another ($C_1$-$C_5$)-alkyl groups, in another embodiment ($C_1$-$C_4$)-alkyl groups, in another embodiment groups selected from the series consisting of methyl, ethyl, isopropyl and isobutyl. In one embodiment of the invention cycloalkyl groups in $R^3$, $R^4$, $R^5$, $R^6$, $R^{11}$, $R^{12}$, $R^{13}$, $R^{14}$, $R^{15}$, $R^{16}$, $R^{17}$, $R^{18}$ and $R^{19}$ are independently of one another ($C_3$-$C_7$)-cycloalkyl groups, in another embodiment ($C_3$-$C_6$)-cycloalkyl groups, in another embodiment groups selected from the series consisting of cyclopropyl, cyclopentyl and cyclohexyl. In all cases all alkyl groups and cycloalkyl groups in $R^3$, $R^4$, $R^5$, $R^6$, $R^{11}$, $R^{12}$, $R^{13}$, $R^{14}$, $R^{15}$, $R^{16}$, $R^{17}$, $R^{18}$ and $R^{19}$ are optionally substituted by one or more fluorine substituents and all cycloalkyl groups are optionally substituted by one or more identical or different ($C_1$-$C_4$)-alkyl substituents.

In one embodiment of the invention, $R^3$ is hydrogen, i.e. the group —CO—$R^1$, or the group —CO—$R^3$, respectively, is the aldehyde group —CO—H (=—CHO). In another embodiment, $R^3$ is an alkyl group or a cycloalkyl-$C_pH_{2p}$— group, in another embodiment an alkyl group, i.e. the group —CO—$R^1$, or the group —CO—$R^3$, respectively, in the compounds of the formula I is a ketone group, wherein all alkyl and cycloalkyl groups are optionally substituted by one or more fluorine substituents and cycloalkyl groups are optionally substituted by one or more identical or different ($C_1$-$C_4$)-alkyl substituents. In one embodiment of the invention, $R^4$ is hydrogen, i.e. the group —CO—$R^1$, or the group —CO—O$R^4$, respectively, is the carboxylic acid group —CO—OH (=—COOH=—C(=O)—OH=hydroxycarbonyl group). In another embodiment of the invention, $R^4$ is a ($C_1$-$C_8$)-alkyl group or a ($C_3$-$C_8$)-cycloalkyl-$C_pH_{2p}$— group, in another embodiment a ($C_1$-$C_8$)-alkyl group, i.e. the group —CO—$R^1$, or the group —CO—O$R^4$, respectively, is an ester group, wherein all alkyl and cycloalkyl groups are optionally substituted by one or more fluorine substituents and cycloalkyl groups are optionally substituted by one or more identical or different ($C_1$-$C_4$)-alkyl substituents. In another embodiment of the invention, $R^4$ is hydrogen or ($C_1$-$C_8$)-alkyl, in another embodiment hydrogen or ($C_1$-$C_4$)-alkyl, wherein the alkyl groups are optionally substituted by one or more fluorine substituents. In one embodiment of the invention, an alkyl group or cycloalkyl group in $R^4$ is not substituted by fluorine. In one embodiment of the invention, $R^5$ and $R^6$ are both hydrogen, i.e. the group —CO—$R^1$, or the group —CO—N$R^5R^6$, respectively, is an unsubstituted amide group. In another embodiment of the invention, one of the groups $R^5$ and $R^6$ is hydrogen and the other of the groups $R^5$ and $R^6$ is an alkyl group or a cycloalkyl-$C_pH_{2p}$— group, i.e. the group —CO—$R^1$, or the group —CO—N$R^5R^6$, respectively, is a monosubstituted amide group, and in another embodiment both groups $R^5$ and $R^6$ are identical or different alkyl groups or cycloalkyl-$C_pH_{2p}$— groups, wherein all alkyl and cycloalkyl groups are optionally substituted by one or more fluorine substituents and cycloalkyl groups are optionally substituted by one or more identical or different ($C_1$-$C_4$)-alkyl substituents.

In one embodiment of the invention, $R^{11}$ and $R^{12}$ are both hydrogen, in another embodiment one of the groups $R^{11}$ and $R^{12}$ is hydrogen and the other of the groups $R^{11}$ and $R^{12}$ is an alkyl group or a cycloalkyl-$C_qH_{2q}$— group, and in another embodiment both groups $R^{11}$ and $R^{12}$ are identical or different alkyl groups or cycloalkyl-$C_qH_{2q}$-groups, wherein all alkyl and cycloalkyl groups are optionally substituted by one or more fluorine substituents and cycloalkyl groups are optionally substituted by one or more identical or different ($C_1$-$C_4$)-alkyl substituents.

In one embodiment of the invention, $R^{13}$ and $R^{14}$ are both hydrogen, in another embodiment one of the groups $R^{13}$ and $R^{14}$ is hydrogen and the other of the groups $R^{13}$ and $R^{14}$ is an alkyl group or a cycloalkyl-$C_qH_{2q}$— group, and in another embodiment both groups $R^{13}$ and $R^{14}$ are identical or different alkyl groups or cycloalkyl-$C_qH_{2q}$-groups, wherein all alkyl and cycloalkyl groups are optionally substituted by one or more fluorine substituents and cycloalkyl groups are optionally substituted by one or more identical or different ($C_1$-$C_4$)-alkyl substituents.

In one embodiment of the invention, $R^{15}$ and $R^{16}$ are both hydrogen, in another embodiment one of the groups $R^{15}$ and $R^{16}$ is hydrogen and the other of the groups $R^{15}$ and $R^{16}$ is an alkyl group or a cycloalkyl-$C_qH_{2q}$— group, and in another embodiment both groups $R^{15}$ and $R^{16}$ are identical or different alkyl groups or cycloalkyl-$C_qH_{2q}$-groups, wherein all alkyl and cycloalkyl groups are optionally substituted by one or more fluorine substituents and cycloalkyl groups are optionally substituted by one or more identical or different ($C_1$-$C_4$)-alkyl substituents.

In one embodiment of the invention, $R^{17}$ is hydrogen, ($C_1$-$C_5$)-alkyl or ($C_3$-$C_6$)-cycloalkyl-$C_qH_{2q}$—, in another embodiment hydrogen or ($C_1$-$C_5$)-alkyl, in another embodiment hydrogen, in another embodiment ($C_1$-$C_5$)-alkyl or ($C_3$-$C_6$)-cycloalkyl-$C_qH_{2q}$—, in another embodiment ($C_1$-$C_5$)-alkyl, wherein all alkyl and cycloalkyl groups in $R^{17}$ are optionally substituted by one or more fluorine substituents and cycloalkyl groups are optionally substituted by one or more identical or different ($C_1$-$C_4$)-alkyl substituents.

In one embodiment of the invention, $R^{18}$ and $R^{19}$ are both hydrogen, in another embodiment one of the groups $R^{18}$ and $R^{19}$ is hydrogen and the other of the groups $R^{18}$ and $R^{19}$ is an alkyl group or a cycloalkyl-$C_qH_{2q}$— group, and in another embodiment both groups $R^{18}$ and $R^{19}$ are identical or different alkyl groups or cycloalkyl-$C_qH_{2q}$-groups, wherein all alkyl and cycloalkyl groups are optionally substituted by one or more fluorine substituents and cycloalkyl groups are optionally substituted by one or more identical or different ($C_1$-$C_4$)-alkyl substituents.

In one embodiment of the invention, the group Het is a residue of a monocyclic 4-membered to 6-membered saturated ring, in another embodiment a residue of a 4-membered or 5-membered saturated ring, in another embodiment a residue of a 4-membered saturated ring. In one embodiment of the invention, the ring heteroatoms in the group Het are selected from the series consisting of nitrogen and oxygen, in another embodiment from the series consisting of oxygen and sulfur, in another embodiment the ring heteroatoms are oxygen atoms. In one embodiment of the invention, Het contains 1 ring heteroatom. In one embodiment of the invention, a phenyl group which is optionally present as a substituent in Het, is optionally substituted by 1 or 2 identical or different substituents from the series consisting of halogen, cyano, $(C_1-C_5)$-alkyl, $(C_1-C_5)$-alkyl-O— and $(C_1-C_5)$-alkyl-S$(O)_h$—, in another embodiment from the series consisting of halogen, $(C_1-C_5)$-alkyl and $(C_1-C_5)$-alkyl-O—, in another embodiment from the series consisting of halogen and $(C_1-C_5)$-alkyl, and in another embodiment is optionally substituted by 1 substituent from any of these series.

In one embodiment of the invention, heteroaryl is a residue of a monocyclic 5-membered or 6-membered or of a bicyclic 9-membered or 10-membered aromatic ring system which contains 1, 2 or 3 identical or different ring heteroatoms from the series consisting of nitrogen, oxygen and sulfur, in another embodiment a residue of a monocyclic 5-membered or 6-membered aromatic ring system which contains 1, 2 or 3 identical or different ring heteroatoms from the series consisting of nitrogen, oxygen and sulfur. In one embodiment of the invention, a bicyclic ring system is 9-membered, in another embodiment it is 10-membered. If a group in the compounds of the formula I can have the meaning heteroaryl, it applies to this meaning, as it applies generally to all generic meanings in all definitions of groups, that the group can also have any one or more of the specific meanings which are mentioned as examples in the explanations of the generic meaning.

In one embodiment of the invention, the numbers f, g, k, m and n, which are all independent of one another and can be identical or different, are 0 or 2.

In one embodiment of the invention, the numbers p and q, which are all independent of one another and can be identical or different, are 0, 1 or 2, in another embodiment 0 or 1.

In one embodiment of the invention, the number u is 0, 1, 2 or 3, in another embodiment 0, 1 or 2, in another embodiment 0 or 1. In one embodiment of the invention u is 0. In another embodiment u has a meaning other than 0 and is 1, 2, 3, 4, 5 or 6, in another embodiment 1, 2 and 3, in another embodiment 1 and 2, in another embodiment 1.

In one embodiment of the invention, the number v is 0, 1 or 2, in another embodiment 0 or 1. In one embodiment of the invention, the number v is 0, in another embodiment v has a meaning other than 0 and is 1, 2, 3 or 4, in another embodiment 1, 2 and 3, in another embodiment 1 and 2, in another embodiment 1.

In one embodiment of the invention, the number w is 0, 1 or 2, in another embodiment 0 or 1. In one embodiment of the invention, the number w is 0, in another embodiment w has a meaning other than 0 and is 1, 2, 3 or 4, in another embodiment 1, 2 and 3, in another embodiment 1 and 2, in another embodiment 1.

A subject of the invention are all compounds of the formula I wherein any one or more structural elements such as groups, substituents and numbers in the general definition of the compounds of the invention are defined as in any of the specified embodiments of the invention or in definitions of the structural elements and explanations thereon or have one or more of the more specific meanings which are mentioned herein as examples of structural elements, wherein all combinations of one or more specified embodiments and/or definitions and/or specific meanings of the structural elements are a subject of the present invention. Also with respect to all such compounds of the formula I, all their stereoisomeric forms and mixtures of stereoisomeric forms in any ratios, and their physiologically acceptable salts, are a subject of the present invention. Likewise, also with respect to all specific compounds described herein, such as the example compounds which represent embodiments of the invention wherein the various groups and numbers in the general definition of the compounds of the formula I have the specific meanings present in the respective specific compound, it applies that they are a subject of the invention in any of their stereoisomeric forms or a mixture of stereoisomeric forms in any ratio, as well in the form of a physiologically acceptable thereof. All specific compounds described herein, irrespective thereof whether they are described as a free compound and/or as a specific salt, are a subject of the invention both in the form of the free compound and in the form of all its physiologically acceptable salts, and if a specific salt is described, additionally in the form of this specific salt. For example, in the case of the compound 4-(4-fluorophenyl)-4-methoxy-1-phenylcyclohexanecarboxylic acid which is described in the form of the free compound, a subject of the invention is 4-(4-fluorophenyl)-4-methoxy-1-phenylcyclohexanecarboxylic acid, in any of its stereoisomeric forms or a mixture of stereoisomeric forms in any ratio, or a physiologically acceptable salt thereof. In the case of the compound 4-cyclopropylmethoxy-4-(4-fluorophenyl)-1-phenylcyclohexanecarboxylic acid which is described in the form of the free compound and in form of its sodium salt, subjects of the invention are 4-cyclopropylmethoxy-4-(4-fluorophenyl)-1-phenylcyclohexanecarboxylic acid, in any of its stereoisomeric forms or a mixture of stereoisomeric forms in any ratio, or a physiologically acceptable salt thereof, as well as 4-cyclopropylmethoxy-4-(4-fluorophenyl)-1-phenylcyclohexanecarboxylic acid sodium salt.

In one embodiment of the invention, which is an example of compounds which with respect to structural elements are defined as in specified embodiments of the invention or definitions and explanations of such elements, a subject of the invention is a compound of the formula I in which $Ar^1$ and $Ar^2$, which are independent of one another and can be identical or different, are phenyl, naphthyl or heteroaryl, which are all optionally substituted by 1, 2 or 3 identical or different substituents from the series consisting of halogen, cyano, $(C_1-C_5)$-alkyl, $(C_2-C_5)$-alkenyl, $(C_3-C_7)$-cycloalkyl-$C_vH_{2v}$—, $Ar^3$, $(C_1-C_5)$-alkyl-O—, HO—$(C_1-C_5)$-alkyl-O—, —O—$(C_1-C_3)$-alkyl-O—, $(C_3-C_7)$-cycloalkyl-S(O)$_f$—, $(C_1-C_5)$-alkyl-S(O)$_k$— and $R^{11}R^{12}N$—S(O)$_2$—, wherein all alkyl groups, alkenyl groups and cycloalkyl groups in $Ar^1$ and $Ar^2$ are optionally substituted by one or more fluorine substituents;

$Ar^3$ and $Ar^5$, which are independent of one another and can be identical or different, are phenyl or monocyclic heteroaryl, which are all optionally substituted by 1 or 2 identical or different substituents from the series consisting of halogen, $(C_1-C_5)$-alkyl, $(C_1-C_5)$-alkyl-O— and —O—$(C_1-C_3)$-alkyl-O—, wherein all alkyl groups in $Ar^3$ and $Ar^5$ are optionally substituted by one or more fluorine substituents;

$Ar^4$ is phenyl or monocyclic heteroaryl, which are all optionally substituted by 1, 2 or 3 identical or different substituents from the series consisting of halogen, cyano, $(C_1-C_5)$-alkyl, $(C_2-C_5)$-alkenyl, $(C_3-C_7)$-cycloalkyl-$C_wH_{2w}$—, $Ar^5$, $(C_1-C_5)$-alkyl-O—, HO—$(C_1-C_5)$-alkyl-O—, —O—$(C_1-C_3)$-alkyl-O—, $(C_1-C_5)$-alkyl-S(O)$_n$— and $R^{15}R^{16}N$—S(O)$_2$—, wherein all alkyl groups, alkenyl groups and cycloalkyl groups in $Ar^4$ are optionally substituted by one or more fluorine substituents;

$R^1$ is $R^4$—O— or $R^5R^6N$—;

$R^2$ is hydrogen, $(C_1-C_6)$-alkyl, $(C_3-C_5)$-alkenyl, $(C_3-C_5)$-alkynyl, $Ar^4$, $R^{17}$—O—$(C_1-C_6)$-alkyl-, $R^{18}R^{19}N$—$(C_1-C_6)$-alkyl-, Het-$C_uH_{2u}$— or $(C_3-C_7)$-cycloalkyl-$C_uH_{2u}$—, wherein all alkyl groups, alkenyl groups, alkynyl groups and cycloalkyl groups in $R^2$ are optionally substituted by one or more fluorine substituents;

$R^4$, $R^5$ and $R^6$, which are all independent of one another and can be identical or different, are hydrogen, $(C_1-C_5)$-alkyl or $(C_3-C_7)$-cycloalkyl-$C_pH_{2p}$—, wherein all alkyl groups and cycloalkyl groups in $R^4$, $R^5$ and $R^6$ are optionally substituted by one or more fluorine substituents;

$R^{11}$, $R^{12}$, $R^{15}$, $R^{16}$, $R^{17}$, $R^{18}$ and $R^{19}$, which are all independent of one another and can be identical or different, are hydrogen, $(C_1-C_5)$-alkyl or $(C_3-C_7)$-cycloalkyl-$C_qH_{2q}$—, wherein all alkyl groups and cycloalkyl groups in $R^{11}$, $R^{12}$, $R^{15}$, $R^{16}$, $R^{17}$, $R^{18}$ and $R^{19}$ are optionally substituted by one or more fluorine substituents;

Het is a residue of a monocyclic 4-membered to 7-membered saturated ring which contains 1 or 2 identical or different ring heteroatoms from the series consisting of nitrogen, oxygen and sulfur, which is bonded via a ring carbon atom and which is optionally substituted by 1, 2 or 3 identical or different substituents from the series consisting of phenyl and $(C_1-C_5)$-alkyl, wherein phenyl groups in Het are optionally substituted by 1 or 2 identical or different substituents from the series consisting of halogen, cyano, $(C_1-C_5)$-alkyl, $(C_1-C_5)$-alkyl-O— and $(C_1-C_5)$-alkyl-S(O)$_h$—, and wherein Het and all alkyl groups in Het are optionally substituted by one or more fluorine substituents;

heteroaryl is a residue of a monocyclic 5-membered or 6-membered or of a bicyclic 8-membered, 9-membered or 10-membered aromatic ring system which contains 1, 2 or 3 identical or different ring heteroatoms from the series consisting of nitrogen, oxygen and sulfur;

f, h, k and n, which are all independent of one another and can be identical or different, are 0, 1 or 2;

p, q, v and w, which are all independent of one another and can be identical or different, are 0, 1 or 2;

u is 0, 1, 2 or 3;

wherein all cycloalkyl groups, independently of any other substituents, are optionally substituted by one or more identical or different $(C_1-C_4)$-alkyl substituents;

in any of its stereoisomeric forms or a mixture of stereoisomeric forms in any ratio, or a physiologically acceptable salt thereof;

provided that $Ar^1$ and $Ar^2$ cannot both be unsubstituted phenyl if simultaneously $R^1$ is hydroxy and $R^2$ is hydrogen.

In another such embodiment of the invention, a subject of the invention is a compound of the formula I in which $Ar^1$ and $Ar^2$, which are independent of one another and can be identical or different, are phenyl, naphthyl or heteroaryl, which are all optionally substituted by 1, 2 or 3 identical or different substituents from the series consisting of halogen, cyano, $(C_1-C_5)$-alkyl, $(C_3-C_6)$-cycloalkyl-$C_vH_{2v}$—, $Ar^3$, $(C_1-C_5)$-alkyl-O—, —O—$(C_1-C_3)$-alkyl-O—, $(C_3-C_6)$-cycloalkyl-S(O)$_f$— and $(C_1-C_5)$-alkyl-S(O)$_k$—, wherein all alkyl groups and cycloalkyl groups in $Ar^1$ and $Ar^2$ are optionally substituted by one or more fluorine substituents;

$Ar^3$ and $Ar^5$, which are independent of one another and can be identical or different, are phenyl or monocyclic heteroaryl, which are all optionally substituted by 1 or 2 identical or different substituents from the series consisting of halogen, $(C_1-C_5)$-alkyl and $(C_1-C_5)$-alkyl-O—, wherein all alkyl groups in $Ar^3$ and $Ar^5$ are optionally substituted by one or more fluorine substituents;

$Ar^4$ is phenyl or monocyclic heteroaryl, which are all optionally substituted by 1, 2 or 3 identical or different substituents from the series consisting of halogen, cyano, $(C_1-C_5)$-alkyl, $Ar^5$, $(C_1-C_5)$-alkyl-O—, HO—$(C_1-C_5)$-alkyl-O—, —O—$(C_1-C_3)$-alkyl-O— and $(C_1-C_5)$-alkyl-S(O)$_n$—, wherein all alkyl groups in $Ar^4$ are optionally substituted by one or more fluorine substituents;

$R^1$ is $R^4$—O— or $R^5R^6N$—;

$R^2$ is hydrogen, $(C_1-C_6)$-alkyl, $Ar^4$, $R^{17}$—O—$(C_1-C_6)$-alkyl-, $R^{18}R^{19}N$—$(C_1-C_6)$-alkyl-, Het-$C_uH_{2u}$— or $(C_3-C_7)$-cycloalkyl-$C_uH_{2u}$—, wherein all alkyl groups and cycloalkyl groups in $R^2$ are optionally substituted by one or more fluorine substituents;

$R^4$, $R^5$ and $R^6$, which are all independent of one another and can be identical or different, are hydrogen, $(C_1-C_5)$-alkyl or $(C_3-C_7)$-cycloalkyl-$C_pH_{2p}$—, wherein all alkyl groups and cycloalkyl groups in $R^4$, $R^5$ and $R^6$ are optionally substituted by one or more fluorine substituents;

$R^{17}$, $R^{18}$ and $R^{19}$, which are all independent of one another and can be identical or different, are hydrogen, $(C_1-C_5)$-alkyl or $(C_3-C_7)$-cycloalkyl-$C_qH_{2q}$—, wherein all alkyl groups and cycloalkyl groups in $R^{17}$, $R^{18}$ and $R^{19}$ are optionally substituted by one or more fluorine substituents;

Het is a residue of a monocyclic 4-membered to 7-membered saturated ring which contains 1 ring heteroatom from the series consisting of nitrogen, oxygen and sulfur, which is bonded via a ring carbon atom and which is optionally substituted by 1, 2 or 3 identical or different substituents from the series consisting of phenyl and $(C_1-C_5)$-alkyl, wherein phenyl groups in Het are optionally substituted by 1 or 2 identical or different substituents from the series consisting of halogen, $(C_1-C_5)$-alkyl and $(C_1-C_5)$-alkyl-O—, and wherein Het and all alkyl groups in Het are optionally substituted by one or more fluorine substituents;

heteroaryl is a residue of a monocyclic 5-membered or 6-membered or of a bicyclic 9-membered or 10-membered aromatic ring system which contains 1, 2 or 3 identical or different ring heteroatoms from the series consisting of nitrogen, oxygen and sulfur;

f, k and n, which are all independent of one another and can be identical or different, are 0, 1 or 2;

p, q and v, which are all independent of one another and can be identical or different, are 0, 1 or 2;

u is 0, 1, 2 or 3;

wherein all cycloalkyl groups, independently of any other substituents, are optionally substituted by one or more identical or different $(C_1-C_4)$-alkyl substituents;

in any of its stereoisomeric forms or a mixture of stereoisomeric forms in any ratio, or a physiologically acceptable salt thereof;

provided that $Ar^1$ and $Ar^2$ cannot both be unsubstituted phenyl if simultaneously $R^1$ is hydroxy and $R^2$ is hydrogen.

In another embodiment of the invention, a subject of the invention is a compound of the formula I in which $Ar^1$ and $Ar^2$, which are independent of one another and can be identical or different, are phenyl, naphthyl or heteroaryl, which can all be unsubstituted or substituted by 1, 2, 3 or 4 identical or different substituents from the series consisting of halogen, cyano, $(C_1-C_5)$-alkyl, $(C_2-C_5)$-alkenyl, $(C_3-C_8)$-cycloalkyl-$C_vH_{2v}$—, $Ar^3$, $(C_1-C_5)$-alkyl-O—, HO—$(C_1-C_5)$-alkyl-O—, —O—$(C_1-C_3)$-alkyl-O—, $(C_1-C_5)$-alkyl-S(O)$_k$— and $R^{11}R^{12}N$—SO$_2$—, where all alkyl groups, alkenyl groups and cycloalkyl groups in $Ar^1$ and $Ar^2$ can be mono- or polysubstituted by fluorine;

$Ar^3$ and $Ar^5$, which are independent of one another and can be identical or different, are phenyl or monocyclic heteroaryl, which can all be unsubstituted or substituted by 1, 2 or 3 identical or different substituents from the series consisting of halogen, cyano, $(C_1-C_5)$-alkyl, $(C_1-C_5)$-alkyl-O—, —O—$(C_1-C_3)$-alkyl-O—, $(C_1-C_5)$-alkyl-S(O)$_m$— and $R^{13}R^{14}N$—SO$_2$—, where all alkyl groups in $Ar^3$ and $Ar^5$ can be mono- or polysubstituted by fluorine;

$Ar^4$ is phenyl or heteroaryl, which can all be unsubstituted or substituted by 1, 2, 3 or 4 identical or different substituents from the series consisting of halogen, cyano, $(C_1-C_5)$-alkyl, $(C_2-C_5)$-alkenyl, $(C_3-C_8)$-cycloalkyl-$C_wH_{2w}$—, $Ar^5$, $(C_1-C_5)$-alkyl-O—, HO—$(C_1-C_5)$-alkyl-O—, —O—$(C_1-C_3)$-alkyl-O—, $(C_1-C_5)$-alkyl-S(O)$_n$— and $R^{15}R^{16}N$—$SO_2$—, where all alkyl groups, alkenyl groups and cycloalkyl groups in $Ar^4$ can be mono- or polysubstituted by fluorine;

$R^1$ is $R^3$—, $R^4$—O— or $R^5R^6N$—;

$R^2$ is hydrogen, $(C_1-C_8)$-alkyl, $(C_2-C_8)$-alkenyl, $(C_3-C_8)$-alkynyl, $Ar^4$, $R^{17}$—O—$(C_1-C_8)$-alkyl-, $R^{18}R^{19}N$—$(C_1-C_8)$-alkyl- or $(C_3-C_8)$-cycloalkyl-$C_uH_{2u}$—, where all alkyl groups, alkenyl groups, alkynyl groups and cycloalkyl groups in $R^2$ can be mono- or polysubstituted by fluorine;

$R^3$, $R^4$, $R^5$ and $R^6$, which are all independent of one another and can be identical or different, are hydrogen, $(C_1-C_8)$-alkyl or $(C_3-C_8)$-cycloalkyl-$C_pH_{2p}$—, where all alkyl groups and cycloalkyl groups in $R^3$, $R^4$, $R^5$ and $R^6$ can be mono- or polysubstituted by fluorine;

$R^{11}$, $R^{12}$, $R^{13}$, $R^{14}$, $R^{15}$, $R^{16}$, $R^{17}$, $R^{18}$ and $R^{19}$, which are all independent of one another and can be identical or different, are hydrogen, $(C_1-C_8)$-alkyl or $(C_3-C_8)$-cycloalkyl-$C_qH_{2q}$—, where all alkyl groups and cycloalkyl groups in $R^{11}$, $R^{12}$, $R^{13}$, $R^{14}$, $R^{15}$, $R^{16}$, $R^{17}$, $R^{18}$ and $R^{19}$ can be mono- or polysubstituted by fluorine;

heteroaryl is a residue of a monocyclic 5-membered or 6-membered or of a bicyclic 8-membered, 9-membered or 10-membered aromatic ring system, which contains 1, 2 or 3 identical or different ring heteroatoms from the series consisting of nitrogen, oxygen and sulfur;

k, m and n, which are all independent of one another and can be identical or different, are 0, 1 or 2;

p, q, v and w, which are all independent of one another and can be identical or different, are 0, 1, 2, 3 or 4;

u is 0, 1, 2, 3, 4, 5 or 6;

in all their stereoisomeric forms and mixtures of stereoisomeric forms in all ratios, and their physiologically acceptable salts;

where $Ar^1$ and $Ar^2$ cannot both be unsubstituted phenyl if simultaneously $R^1$ is hydroxy and $R^2$ is hydrogen.

In one embodiment of the invention, from the compounds which are a subject of the invention, such compounds are excluded in which simultaneously one of the groups $Ar^1$ and $Ar^2$ is an optionally substituted group from the series consisting of pyrazolyl, imidazolyl, triazolyl, oxazolyl, isoxazolyl, oxadiazolyl, thiazolyl and thiadiazolyl, the other of the groups $Ar^1$ and $Ar^2$ is substituted phenyl, and $R^2$ is hydrogen or $(C_1-C_4)$-alkyl which is optionally substituted by one to three fluorine substituents, wherein in these compounds the substituted phenyl group representing one of the groups $Ar^1$ and $Ar^2$ carries in its 3-position a substituent from the series consisting of $(C_1-C_5)$-alkyl-O— and HO—$(C_1-C_5)$-alkyl-O—, which are both optionally substituted by one or more fluorine substituents, and carries in its 4-position a substituent from the series consisting of $(C_1-C_2)$-alkyl-O—, $(C_1-C_2)$-alkyl-S—, $(C_1-C_2)$-alkyl-S(O)—, $(C_1-C_2)$-alkyl-S(O)$_2$—, which are all optionally substituted by one or more fluorine substituents, and halogen, and optionally carries an additional substituent from the series consisting of $(C_1-C_2)$-alkyl-O—, $(C_1-C_2)$-alkyl-S—, $(C_1-C_2)$-alkyl-S(O)—, $(C_1-C_2)$-alkyl-S(O)$_2$—, which are all optionally substituted by one or more fluorine substituents, and halogen.

In another embodiment of the invention, from the compounds which are a subject of the invention, such compounds are excluded in which simultaneously one of the groups $Ar^1$ and $Ar^2$ is optionally substituted heteroaryl and the other of the groups $Ar^1$ and $Ar^2$ is substituted phenyl which carries in its positions 2 and 3 a substituent —O—$(C_1-C_3)$-alkyl-O—, in which the alkyl group is optionally substituted by one or more fluorine substituents, and carries in its 4-position a substituent from the series consisting of $(C_1-C_5)$-alkyl-O— and HO—$(C_1-C_5)$-alkyl-O—, which are both optionally substituted by one or more fluorine substituents, and is unsubstituted in its 5-position, and is optionally substituted by halogen in its 6-position, but wherein those compounds are not excluded in which the substituted phenyl group carries in its positions 2 and 3 the group —O—$CF_2$—O—. The phenyl group substituted in its positions 2 and 3 by —O—$(C_1-C_3)$-alkyl-O— in the compounds which are excluded in this embodiment, can also be regarded as a heteroaryl group and designated as benzo[1,3]dioxol-4-yl group (=[1,3]benzodioxol-4-yl group), which carries in its 7-position a substituent from the series consisting of $(C_1-C_5)$-alkyl-O— and HO—$(C_1-C_5)$-alkyl-O— which are both optionally substituted by one or more fluorine substituents, which is unsubstituted in its 6-position, which is optionally substituted by halogen in its 5-position, and which is optionally substituted in its 2-position by one or two alkyl groups which are optionally substituted by one or more fluorine substituents, or as benzo[1,4]dioxan-5-yl group (=[1,4]benzodioxan-5-yl group), respectively, which carries in its 8-position a substituent from the series consisting of $(C_1-C_5)$-alkyl-O— and HO—$(C_1-C_5)$-alkyl-O—, which are both optionally substituted by one or more fluorine substituents, which is unsubstituted in its 7-position, which is optionally substituted by halogen in its 6-position, and which is optionally substituted in its 2-position or its 3-position by methyl which is optionally substituted by one or more fluorine substituents.

A subject of the present invention also are processes for the preparation of the compounds of the formula I which are illustrated below and by which the compounds according to the invention are obtainable. The preparation of the compounds of the formula I can be carried out by first reacting, in a manner known per se, a (hetero)arylacetonitrile of the formula II with an acrylic acid ester of the formula III in a Michael addition and cyclizing the resulting 4-cyano-4-(hetero)arylpimelic acid ester of the formula IV in a Dieckmann condensation to give the 3-cyano-3-(hetero)arylcyclohexanecarboxylic acid ester of the formula V, which is then converted by hydrolysis of the ester group and decarboxylation into the 4-oxo-1-(hetero)arylcyclohexanecarbonitrile of the formula VI.

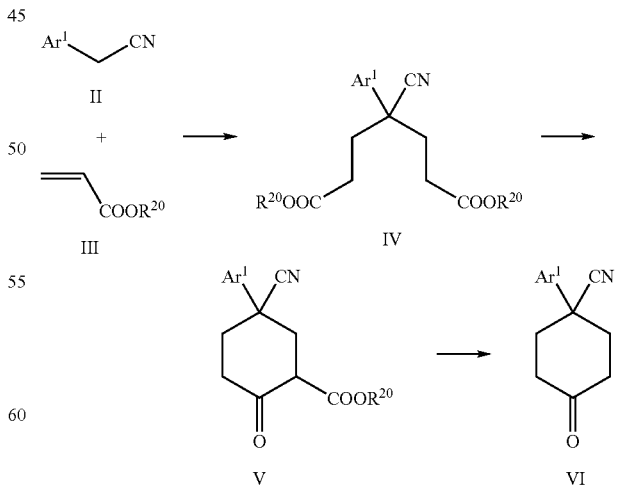

The group $R^{20}$ in the compounds of the formulae III, IV and V is, for example, $(C_1-C_4)$-alkyl, in particular methyl or ethyl. The group $Ar^1$ in the compounds of the formulae II, IV, V and VI is as defined in the compounds of the formula I, and additionally functional groups can be present in Ar¹ in protected form or in the form of precursors which are later converted into the desired groups. The compounds of the formulae II and III are commercially obtainable or can be prepared by or analogously to processes which are described in the literature. Likewise, the reactions in the preparation of the compounds of the formula VI can be carried out by or analogously to processes which are described in the literature and are familiar to the person skilled in the art.

The Michael addition of the compound of the formula II to the compound of the formula III is in general carried out in an organic solvent in the presence of a base. As a base, for example, alkali metal alcoholates (alkali metal alkoxides), for example sodium and potassium salts of $(C_1-C_4)$-alkanols such as sodium methylate, potassium methylate, sodium ethylate, potassium ethylate, sodium tert-butylate or potassium tert-butylate, alkali metal hydroxides such as sodium hydroxide or potassium hydroxide, alkali metal hydrides such as sodium hydride, or quaternary ammonium hydroxides such as benzyltrimethylammonium hydroxide can be used. Examples of solvents which can be used, are alcohols, for example $(C_1-C_4)$-alkanols such as methanol, ethanol or tert-butanol, or ethers such as tetrahydrofuran (THF), dioxane, ethylene glycol dimethyl ether (DME). Depending on the circumstances of the individual case such as the reactivity of the compounds and the manner of carrying out the reaction, the Michael addition can be carried out, for example, at temperatures of about 10° C. to about 80° C., for example at about room temperature or at elevated temperature. Also the subsequent cyclization of the Michael adduct of the formula IV to the compound of the formula V is in general carried out in an organic solvent, in particular in an aprotic solvent, in the presence of a base. The bases and solvents mentioned, in particular ethers such as tetrahydrofuran, but also other aprotic solvents, for example amides such as dimethylformamide (DMF) or hydrocarbons such as benzene or toluene, can also be used in the cyclization, which can likewise be carried out, depending on the circumstances of the individual case, for example at about room temperature or at elevated temperature for example, at temperatures of about 10° C. to about 110° C. Frequently, the Michael addition and the cyclization can also be carried out in an advantageous manner in a one-pot reaction, without isolation of the compound of the formula IV, for example in tetrahydrofuran at reflux temperature in the presence of an alkali metal alcoholate such as sodium methylate.

The hydrolysis of the ester group in the compound of the formula V and the decarboxylation to give the compound of the formula VI can be carried out, for example, by heating the compound of the formula V in a solvent, for example water or a water-containing organic solvent, for example acetic acid, in the presence of an acid, for example hydrochloric acid or sulfuric acid, for example at temperatures of about 80° C. to about 130° C. The hydrolysis of the ester group in the compound of the formula V can, however, also be carried out under basic conditions, for example in the presence of lithium hydroxide, and then after acidification of the reaction mixture the decarboxylation can be carried out. The conversion of a compound of the formula V into the compound of the formula VI can also be carried out, for example, by heating with sodium chloride in dimethyl sulfoxide in the presence of water, for example at temperatures of about 150° C. to about 180° C. Further details of the preparation of compounds of the formula VI from compounds of the formula II are described, for example, in Lednicer et al., J. Med. Chem. 18, 593-599 (1975).

The intermediates of the formula VI can be converted by reaction of the keto function with a (hetero)aryl-organometallic compound of the formula VII into the intermediates of the formula VIII.

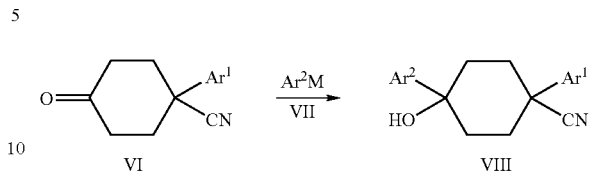

The groups Ar¹ and Ar² in the compounds of the formulae VII and VIII are as defined in the compounds of the formula I, and functional groups in Ar¹ and Ar² can additionally be present in protected form or in the form of precursors which are later converted into the desired groups. The group M in the compounds of the formula VII is a suitable metal, in particular a suitable alkali metal or alkaline earth metal. In particular, the compounds of the formula VII can, for example, be organolithium compounds and M can be lithium, or Grignard compounds and M can be a magnesium halide group MgHal¹, in which Hal¹ can be chlorine, bromine or iodine. The compounds of the formula VII are commercially obtainable or can be prepared by or analogously to processes which are described in the literature. Likewise, the reaction of the compounds of the formulae VI and VII can be carried out by or analogously to processes which are described in the literature and are familiar to the person skilled in the art.

The preparation of compounds of the formula VII can, for example, be carried out from halo(hetero)aromatics of the formula Ar²-Hal¹, in which Ar² and Hal¹ is as defined in the compounds of the formula VII, by reaction with a metal, for example lithium or magnesium, or reaction with another organometallic compound, for example an alkyllithium compound such as methyllithium, n-butyllithium or tert-butyllithium, under standard conditions. The metalation of compounds of the formula Ar²-Hal¹, in which Hal¹ can in particular be bromine, with n-butyllithium, which is employed in the form of a solution in a hydrocarbon such as hexane or an ether such as tetrahydrofuran, is particularly advantageous. The metalation is in general carried out at low temperatures, for example at temperatures from about −100° C. to about 0° C., in particular from about −80° C. to about −50° C. The preparation of Grignard compounds by reaction of compounds of the formula Ar²-Hal¹ withmetallic magnesium, which can optionally be activated, can in many cases be carried out, for example, at room temperature. As a solvent for such preparations of the compounds of the formula VII, which in general are generated in situ and directly reacted further, and for their reaction with compounds of the formula VI, especially ethers and hydrocarbons, for example dialkyl ether such as diethyl ether or dibutyl ether, cyclic ethers such as tetrahydrofuran or dioxane, ethylene glycol dimethyl ether, pentane, hexane, heptane or benzene and mixtures thereof, are suitable. The temperature in the reaction of the compounds of the formulae VI and VII depends on the circumstances of the individual case, for example the reactivity of the compound of the formula VII, and can lie in the range of lower temperatures, for example in the range from about −80° C. to about 30° C., and/or in the range of higher temperatures, for example in the range from about 0° C. to about 80° C. For example, the compounds of the formulae VI and VII can first be reacted at lower temperature and the reaction mixture subsequently be heated to a higher temperature for completion of the reaction.

In the compounds of the formula VIII, the hydroxy group can be etherified with compounds of the formula IX by standard processes to give compounds of the formula X. In the compounds of the forms IX and X, $Ar^1$, $Ar^2$ and $R^2$ are defined as in the compounds of the formula I, and functional groups in $Ar^1$, $Ar^2$ and $R^2$ can additionally be present in protected form or in the form of precursors which are later converted into the desired groups, provided that $R^2$ is not hydrogen. A subject of the present invention also are the novel compounds of the formulae VIII and X, in any of their stereoisomeric forms or a mixture of stereoisomeric forms in any ratio, or a salt thereof, including a physiologically acceptable salt thereof, in which $Ar^1$, $Ar^2$ and $R^2$ are defined as in the compounds of the formula I, i.e. $R^2$ can also be hydrogen, and additionally functional groups in $Ar^1$, $Ar^2$ and $R^2$ can be present in protected form or in the form of precursors which are later converted into the desired groups, and all other novel intermediates for the preparation of the compounds of the formula I described herein, and the use of these compounds as intermediates. All above statements relating to the compounds of the formula I, for example explanations on the contained groups, examples of the groups and specified embodiments of the invention, apply accordingly to the nitriles of the formulae VIII and X which, for example, are valuable intermediates for the preparation of compounds of the formula I, and all other intermediates.

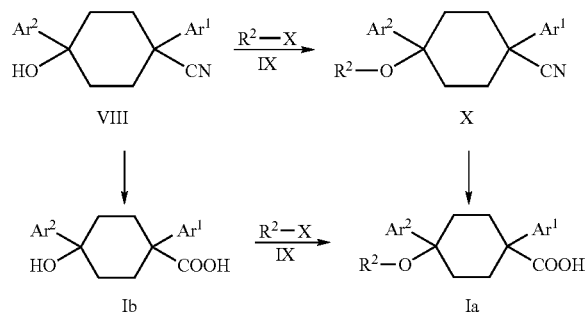

The group X in the compounds of the formula IX can be a nucleophilically substitutable leaving group, for example fluorine, chlorine, bromine, iodine or an arylsulfonyloxy group or alkylsulfonyloxy group such as benzenesulfonyloxy, toluenesulfonyloxy, nitrobenzenesulfonyloxy, methanesulfonyloxy or trifluoromethanesulfonyloxy, for example in the case of compounds of the formula IX in which $R^2$ is an optionally substituted alkyl, alkenyl or alkynyl group, for example a $(C_3-C_8)$-cycloalkyl-$C_uH_{2u}$— group or a group Het-$C_uH_{2u}$—, or in which $R^2$ is an aromatic group $Ar^4$ which is susceptible to a nucleophilic substitution reaction or a reaction of another mechanistic type, including transition metal-catalyzed reactions, which results in the replacement of such a nucleophilically substitutable group by the hydroxy group present in the compound of the formula VIII or the formula Ib, including a phenyl or heteroaryl group which is substituted with a suitable electron-accepting group or a suitable electron-deficient heteroaryl group such as pyridinyl or pyrimidinyl. The group X in the compounds of the formula IX can also be an organometallic residue which is capable of transferring the group $R^2$ onto the hydroxy group in the compound of the formula VIII or the formula Ib, in particular in the case of compounds in which $R^2$ is an aromatic group $Ar^4$ such as optionally substituted phenyl or heteroaryl, i.e. in the case of an O-arylation or O-heteroarylation of the alcohol function. An example of such organometallic compounds are organobismuth(V) compounds, for example triarylbismuth (V) derivatives such as triarylbismuth diacetates (=bis(acetato)tris(aryl)bismuth) and triarylbismuth bis(trifluoroacetates) or tetraarylbismuth(V) derivatives such as tetraarylbismuth trifluoroacetates and tetraarylbismuthonium tetrafluoroborates, which can be regarded as compounds of the formula IX in which the group X is a bis(acetato)bis(aryl)bismuth residue or a positively charged tris(aryl)bismuth residue having a tetrafluoroborate anion as counterion, for example. The group X in the compounds of the formula IX can also be a hydroxy group and the reaction of the compound of the formula VIII or the formula Ib with the compound of the formula IX can be carried out, for example, under the conditions of the Mitsunobu reaction.

The etherification of a compound of the formula VIII with a compound of the formula IX, in which the group X is a nucleophilically substitutable leaving group, is in general carried out in a protic or aprotic organic solvent with addition of a base. For example, first the base can act on the compound of the formula VIII and then the compound of the formula IX added. As a base, for example, alkali metal alcoholates, for example sodium and potassium salts of $(C_1-C_4)$-alkanols such as sodium methylate, potassium methylate, sodium ethylate, potassium ethylate, sodium tert-butylate or potassium tert-butylate, alkali metal hydroxides such as sodium hydroxide or potassium hydroxide, alkali metal carbonates such as sodium carbonate, potassium carbonate or cesium carbonate, alkali metal hydrides such as lithium hydride or sodium hydride, organometallic compounds such as n-butyllithium, or amides such as sodium amide or lithium diisopropylamide can be used. As a solvent, for example, alcohols, for example $(C_1-C_4)$-alkanols such as methanol, ethanol or tert-butanol, ethers such as tetrahydrofuran, dioxane or ethylene glycol dimethyl ether, amides such as dimethylformamide, N-methylpyrrolidone (NMP) or hexamethylphosphoric acid triamide (HMPA), hydrocarbons such as benzene or toluene, ketones such as acetone or methyl ethyl ketone, acetonitrile or dimethyl sulfoxide (DMSO) can be used. Mixtures of bases and/or mixtures of solvents can also be used. Depending on the circumstances of the individual case such as the reactivity of the compounds and the manner of carrying out the reaction, the etherification can be carried out at temperatures from about 0° C. to about 100° C., for example at about room temperature. O-arylations and O-heteroarylations by means of the above-mentioned organobismuth(V) compounds are favorably carried out in the presence of a copper compound, such as copper(II) acetate or another copper(II) salt, in a solvent, for example a hydrocarbon such as toluene, chlorobenzene, benzene or dichloromethane, an ether such as tetrahydrofuran or dioxane, a ketone such as methyl ethyl ketone, or acetonitrile, or a mixture of solvents, at temperatures from about 20° C. to about 120° C. Details of such O-arylations of alcohols and the preparation of suitable bismuth(V) compounds are described in Barton et al., Pure Appl. Chem. 59, 937-946 (1987); Sakurai et al., Arkivoc, 254-264 (2007); or Combes et al., Synth. Commun. 26, 4569-4575 (1996), for example. In the case of an etherification under Mitsunobu conditions, a hydroxy group is activated by reaction with an azodicarboxylic acid ester such as diethyl azodicarboxylate or diisopropyl azodicarboxylate and a phosphane such as tributylphosphane or triphenylphosphane and then replaced in a nucleophilic substitution by a hydroxy group in the reaction partner. Details on the Mitsunobu reaction can be found, for example, in Mitsunobu, Synthesis, 1-28 (1981).

In the compounds of the formulae VIII and X, the nitrile group can be hydrolyzed to the carboxylic acid group by standard processes. In the resulting carboxylic acids of the formulae Ia and Ib, which are compounds of the formula I in which $R^1$ is $R^4$—O— and $R^4$ is hydrogen, $Ar^1$, $Ar^2$ and $R^2$ are as defined in the compounds of the formula I, and functional groups in $Ar^1$, $Ar^2$ and $R^2$ can additionally be present in protected form or in the form of precursors which for the preparation of the final compounds of the formula I are later converted into the desired groups. Advantageously, the hydrolysis of the nitrile group takes place under basic conditions in a solvent at elevated temperature, for example, at temperatures of about 80° C. to about 200° C., in particular at temperatures of about 160° C. to about 200° C. As a solvent, for example, water, alcohols, ethers or mixtures of solvents can be used, in particular high-boiling solvents such as ethylene glycols or ethers of ethylene glycols, for example ethylene glycol. As bases, in particular alkali metal hydroxides such as potassium hydroxide, sodium hydroxide or lithium hydroxide can be used. The hydrolysis of the nitrile group in the compounds of the formulae VIII and X can also be performed stepwise, for example by hydrolysis of the nitrile to the carboxamide, i.e. the respective compound of the formula I in which $R^1$ is $R^5R^6N$— and $R^5$ and $R^6$ are both hydrogen, in the first step and hydrolysis of the said carboxamide to the carboxylic acid of the formula Ia or Ib in the second step. For example, the hydrolysis of the nitrile to the carboxamide can advantageously be performed by treatment with hydrogen peroxide in the presence of an alkali metal hydroxide such as sodium hydroxide or potassium hydroxide at temperatures of about 40° C. to about 70° C. The hydrolysis of the said carboxamide to the carboxylic acid can be performed under basic or acidic conditions under standard conditions or, for example, in an advantageous manner by treatment with a diazotizing agent, for example a nitrite such as sodium nitrite or a nitrosyl compound such as nitrosylsulfuric acid or nitrosonium tetrafluoroborate, at temperatures of about 0° C. to about 20° C. The workup of the reaction mixture and the purification of the product of the hydrolysis of the nitrile takes place, just as in all other steps of the synthesis of the compounds of the formula I, according to customary methods which, for example, comprise the adjustment of a certain pH, precipitation, extraction, drying, concentration, crystallization, distillation and chromatography.

Like the hydroxy group in a nitrile of the formula VIII, the hydroxy group in a carboxylic acid of the formula Ib can also be etherified by reaction with a compound of the formula IX with formation of a compound of the formula Ia, in which $Ar^1$, $Ar^2$ and $R^2$ are as defined above for the compounds of the formula X. In the reaction of the compounds of the formulae Ib and IX, on account of the different reactivities of the hydroxy group and of the carboxylic acid group and/or by the choice of the reaction conditions, a reaction can be carried out selectively on the hydroxy group with formation of the compound of the formula Ia, or both the hydroxy group can be etherified and the carboxylic acid group esterified. The compound obtained in the latter case can be a compound of the formula I according to the invention, in which $R^1$ is $R^4$—O— and $R^4$ is an alkyl group or a group cycloalkyl-$C_pH_{2p}$—, or the compound obtained can be converted by hydrolysis of the ester group under standard conditions into the carboxylic acid of the formula Ia. As is outlined below, in a compound of the formula Ib the carboxylic acid group can also be esterified selectively with formation of a compound of the formula I in which $R^2$ is hydrogen, $R^1$ is $R^4$—O— and $R^4$ is an alkyl group or a group cycloalkyl-$C_pH_{2p}$—.

In another synthesis route, compounds of the formula I, in particular compounds of the formula I in which $R^1$ is $R^4$—O— or $R^5R^6N$—, and especially is $R^4$—O—, for example compounds in which the group $R^4$ therein is hydrogen, can also be prepared by initially reacting not a (hetero)arylacetonitrile of the formula II, but a (hetero)arylacetic acid ester of the formula XI with an acrylic acid ester of the formula III in a Michael addition. The reactions steps carried out in this route largely correspond to those in the route illustrated above.

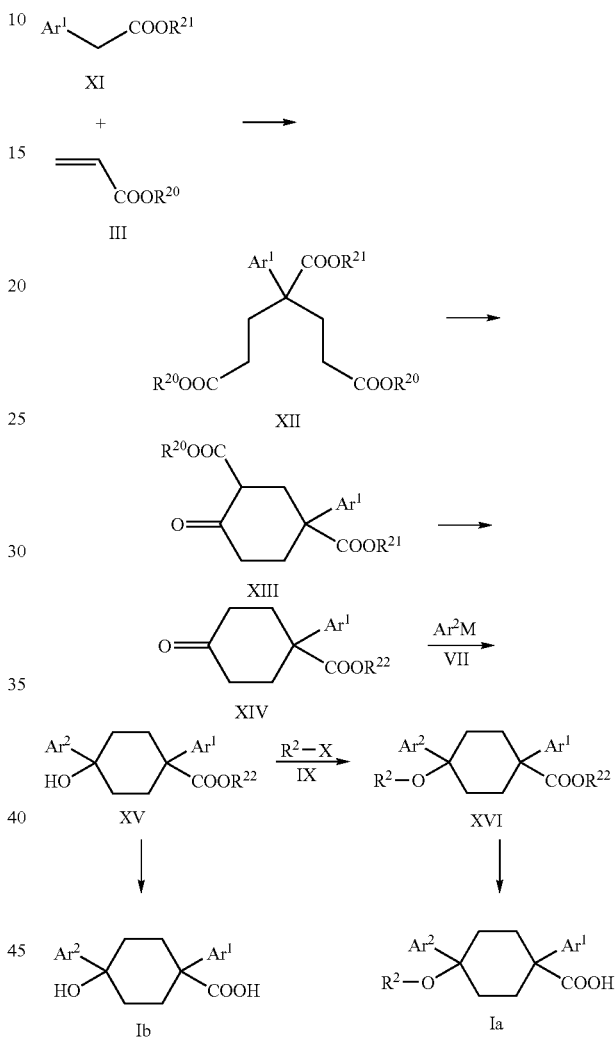

The groups $Ar^1$, $Ar^2$ and $R^2$ in the compounds of the formulae XI, XII, XIII, XIV, XV and XVI are as defined in the compounds of the formula I, and functional groups in $Ar^1$, $Ar^2$ and $R^2$ can additionally be present in protected form or in the form of precursors which are later converted into the desired groups. The group $R^{20}$ in the compounds of the formulae III, XII and XIII is as defined above for the formula III. The group $R^{21}$ in the compounds of the formulae XI, XII and XIII is, for example, $(C_1$-$C_6)$-alkyl, in particular methyl or ethyl or a bulky alkyl group such as tert-butyl, or is benzyl, for example.

The Michael addition of a compound of the formula XI to an acrylic ester of the formula III yields a triester of the formula XII, which is cyclized in a Dieckmann condensation to the cyclohexanedicarboxylic acid diester of the formula XIII.

Depending on the reactivity of the two ester groups $COOR^{20}$ and $COOR^{21}$ and the reaction conditions used, the subsequent hydrolysis and decarboxylation of the compound of the formula XIII yields a compound of the formula XIV in which $R^{22}$ is hydrogen, i.e. a carboxylic acid, or a compound of the formula XIV in which $R^{22}$ has the same meaning as in the compound of the formula XIII employed and is a ($C_1$-$C_6$)-alkyl group or benzyl, for example. The reaction of the compound of the formula XIV, in which $R^{22}$ is hydrogen or a suitable alkyl group or benzyl, with an organolithium compound or Grignard compound of the formula VII, in which $Ar^2$ and M are as defined above, then yields a compound of the formula XV in which $R^{22}$ is hydrogen or a ($C_1$-$C_6$)-alkyl group or benzyl, as in the compound of the formula XIV. In the reaction with a compound of the formula XIV in which $R^{22}$ is hydrogen, an additional equivalent of the compound of the formula VII is employed or the compound of the formula XIV is employed in the form of a salt of the carboxylic acid. In the compounds of the formula XV, the hydroxy group can subsequently be etherified with a compound of the formula IX, in which $R^2$ and X are as defined above, to give a compound of the formula XVI. For all reaction steps mentioned in this route, all the above explanations apply correspondingly. Further explanations regarding this route are also found in Rubin et al., J. Am. Chem. Soc. 68, 828-832 (1946). Compounds of the formulae XV and XVI in which $R^{22}$ is hydrogen or alkyl and $Ar^1$, $Ar^2$ and $R^2$ are as defined in the compounds of the formula I, are compounds according to the invention. Compounds of the formulae XV and XVI in which $R^{22}$ is not hydrogen, can be converted by hydrolysis of the ester group $COOR^{22}$ into the carboxylic acids of the formulae Ia and Ib. The hydrolysis can be carried out under standard conditions, for example in the presence of an acid such as hydrochloric acid or of a base such as lithium hydroxide, sodium hydroxide or potassium hydroxide, for example at temperatures of about 20° C. to about 100° C., or in the case of a tert-butyl ester by treatment with trifluoroacetic acid, or in the case of a benzyl ester by catalytic hydrogenation in the presence of a noble metal catalyst, for example palladium on carbon. Optionally, for the preparation of the final compounds of the formula I, any protected groups and/or precursor groups in the compounds of the formulae XV, XVI, Ib and Ia are converted into the desired groups.

Compounds of the formula I in which $R^1$ is $R^4$—O— and $R^4$ is an alkyl group or a group cycloalkyl-$C_pH_{2p}$—, or $R^1$ is $R^5R^6N$—, can be obtained from the corresponding compounds of the formula I in which $R^1$ is $R^4$—O— and $R^4$ is hydrogen, including the compounds of the formulae Ia and Ib, by conversion of the carboxylic acid group into an ester group or carboxamide group by standard processes. Advantageously, for this the carboxylic acid is converted into a reactive derivative, which can be isolated or prepared in situ, for example into the acid chloride by treatment with thionyl chloride or oxalyl chloride or into a mixed anhydride by treatment with a chloroformic acid ester such as ethyl chloroformate or isobutyl chloroformate, or the acid is activated, for example with a customary coupling reagent such as propanephosphonic anhydride, N,N'-carbonyldiimidazole (CU), a carbodiimide such as N,N'-diisopropylcarbodiimide, N,N'-dicyclohexylcarbodiimide (DCC) or N-ethyl-N'-(3-dimethylaminopropyl)carbodiimide hydrochloride, O-(cyano(ethoxycarbonyl)methyleneamino)-N,N,N',N'-tetramethyluronium tetrafluoroborate (TOTU) or ethyl 1,2-dihydro-2-ethoxy-quinoline-1-carboxylate, and then reacted with an alcohol of the formula $R^4$—OH or an amine of the formula $R^5R^6NH$ in which $R^4$, $R^5$ and $R^6$ are as defined for the compounds of the formula I, but $R^4$ is not hydrogen. The esterification and amidation of the carboxylic acid customarily takes place in the presence of a suitable base, for example a tertiary amine such as triethylamine, ethyldiisopropylamine or pyridine, or a basic alkali metal compound, for example sodium hydroxide or an alkali metal carbonate such as sodium carbonate, in a solvent, for example an ether such as tetrahydrofuran, dioxane or ethylene glycol dimethyl ether, a hydrocarbon such as toluene, an amide such as dimethylformamide or N-methylpyrrolidone, at temperatures of about 0° C. to about 60° C. Compounds of the formula I in which $R^1$ is $R^5R^6N$— and $R^5$ and $R^6$ are both hydrogen, i.e.

unsubstituted carboxylic acid amides, can also be obtained from the corresponding nitriles of the formulae VIII and X by partial hydrolysis of the nitrile group under standard conditions, for example with hydrogen peroxide in the presence of an alkali metal hydroxide such as sodium hydroxide or potassium hydroxide at temperatures of about 40° C. to about 70° C.

Compounds of the formula I, in which $R^1$ is $R^3$ and $R^3$ is hydrogen, i.e. compounds in which the group —CO—$R^1$ is the aldehyde group —CHO, can be prepared, for example, by reduction of the nitrile group in the compounds of the formulae VIII and X. Advantageous reductants for the conversion of a nitrile group into an aldehyde group are in particular metal hydrides and complex metal hydrides of suitable reactivity, for example aluminum hydrides such as diisobutylaluminum hydride or complex aluminum hydrides such as lithium tri(tert-butoxy)aluminum hydride, under suitable reaction conditions. The reduction to the aldehyde is in general carried out in an ether or hydrocarbon, for example diethyl ether, tetrahydrofuran, dioxane, ethylene glycol dimethyl ether, diethylene glycol dimethyl ether or toluene, or a mixture of solvents, at lower temperatures, for example at temperatures from about −80° C. to about 0° C. Compounds of the formula I in which $R^1$ is $R^3$ and $R^3$ is an alkyl group or a group cycloalkyl-$C_pH_{2p}$—, i.e. compounds in which the group —CO—$R^1$ is an acyl group and the compound of the formula I is a ketone, can be prepared, for example, by reaction of compounds of the formulae VIII and X with Grignard compounds of the formula $R^3MgHal^1$, in which $R^3$ is as defined for the compounds of the formula I, but is not hydrogen, and $Hal^1$ is chlorine, bromine or iodine. The Grignard compounds can be prepared in situ from the corresponding halides of the formula $R^3$-$Hal^1$ under standard conditions. The conversion of nitriles which do not contain more reactive groups in the molecule, for example no carbonyl groups, with Grignard compounds into ketones is in general carried out in an ether, for example a dialkyl ether such as diethyl ether or a cyclic ether such as tetrahydrofuran, at temperatures of about 0° C. to about 80° C. If a nitrile of the formula VIII is employed, an additional equivalent of the Grignard compound is needed for the deprotonation of the hydroxy group. The imines primarily resulting in the reduction of the nitriles and in the reaction with a Grignard compound can be converted under standard conditions, for example by acidic hydrolysis, into the aldehydes and ketones. Compounds of the formula I in which the group —CO—$R^1$ is the aldehyde group —CHO can also be prepared by converting compounds of the formula I in which the group —CO—$R^1$ is a carboxylic acid group or a carboxylic acid ester group, by reduction, for example with a complex metal hydride such as lithium aluminum hydride, in an ether such as, for example, diethyl ether, dibutyl ether or tetrahydrofuran, into the corresponding compounds which instead of the group —CO—$R^1$ contain the alcohol group —$CH_2$—OH, and converting the group —$CH_2$—OH in the obtained compound by standard processes for the selective oxidation of alcohols to aldehydes, for example with sodium hypochlorite in the presence of 4-acetamido-2,2,6,6-tetramethylpiperidin-1-oxyl (4-acetamido-TEMPO), into the aldehyde group —CHO. For the preparation of compounds of the formula I in which the group —CO—$R^1$ is —CO—$R^3$ and $R^3$ has a meaning other than hydrogen, also compounds of the formula I in which the group —CO—$R^1$ is the aldehyde group —CHO can be reacted with Grignard compounds of the formula $R^3MgHal^1$ in which $R^3$ and $Hal^1$ are as defined above, and the compounds obtained, which instead of the group —CO—$R^1$ contain the group —CH(OH)—$R^3$, then oxidized to the ketones.

Compounds of the formula I according to the invention, which have been prepared by the processes described above, can be converted by functionalization or by modification of functional groups into further compounds of the formula I. This also applies correspondingly to the intermediates in the synthesis of the compounds of the formula I. In addition to the possibilities already described above, for example for modifying the groups $R^2$—O— and —CO—$R^1$, the groups $Ar^1$ and $Ar^2$ can also be modified. For example, compounds in which $Ar^1$ or $Ar^2$ carries a halogen substituent such as, for example, bromine, can be converted in a Suzuki-Miyaura coupling reaction with (hetero)arylboronic acids or cycloalkylboronic acids into compounds in which $Ar^1$ or $Ar^2$ carries a substituent $Ar^3$ or cycloalkyl. The Suzuki-Miyaura reaction can be carried out, for example, in the presence of a palladium catalyst, for example a palladium complex such as tetrakis(triphenylphosphine)palladium or a palladium salt such as palladium acetate, and a base, for example an alkali metal carbonate such as sodium carbonate, in a solvent, for example an ether such as ethylene glycol dimethyl ether or tetrahydrofuran or a hydrocarbon such as toluene, or a mixture of solvents. Further details with respect to such reactions are found, for example, in Kotha et al., Tetrahedron 58, 9633-9695 (2002). Furthermore, for example, reactive halogen substituents in the groups $Ar^1$ or $Ar^2$ can be converted in a nucleophilic substitution under standard conditions into another substituent, for example by reaction with an alcohol into an alkoxy substituent or a hydroxyalkoxy substituent or an alkylsulfanyl substituent. Another example of modifications of groups, which can be performed in compounds of the formula I and in synthesis intermediates, is the oxidation of alkylsulfanyl groups (=alkylthio groups) to alkanesulfinyl groups and alkanesulfonyl groups, which can be carried out with hydrogen peroxide or another peroxy compound, for example with a peracid such as m-chloroperbenzoic acid or monoperoxyphthalic acid, in a solvent, for example a chlorinated hydrocarbon such as dichloromethane or an ester such as ethyl acetate, or a mixture of solvents, for example a mixture of an organic solvent with water, at temperatures of about 0° C. to about 30° C., for example.

All reactions carried out in the preparation of the compounds of the formula I are known per se and can be carried out in manner familiar to the person skilled in the art by or analogously to procedures which are described in the standard literature, for example in Houben-Weyl, Methoden der Organischen Chemie [Methods of Organic Chemistry], Thieme-Verlag, Stuttgart, or Organic Reactions, John Wiley & Sons, New York, or Larock, Comprehensive Organic Transformations: A Guide to Functional Group Preparations, VCH Publishers, New York, Weinheim, and the references cited therein. As already mentioned, it can be advantageous or necessary in all reactions which are carried out in the course of the preparation of the compounds of the formula Ito temporarily protect functional groups or have them initially present in the form of precursor groups, and later deprotect them or convert them into the desired groups. Appropriate synthesis strategies and protective groups and precursor groups which are suitable for the respective case, are known to the person skilled in the art. Examples of protective groups which may be mentioned, are benzyl protective groups, for example benzyl ethers of hydroxy compounds and benzyl esters of carboxylic acids, from which the benzyl group can be removed by catalytic hydrogenation in the presence of a palladium catalyst, tert-butyl protective groups, for example tert-butyl esters of carboxylic acids, from which the tert-butyl group can be removed by treatment with trifluoroacetic acid, acyl protective groups, for example ester and amides of hydroxy compounds and amino compounds, which can be cleaved again by acidic or basic hydrolysis, or alkoxycarbonyl protective groups, for example tert-butoxycarbonyl derivatives of amino compounds, which can be cleaved again by treatment with trifluoroacetic acid. Examples of precursors which may be mentioned are halogen atoms which, as already mentioned, can be replaced by many other groups, or nitro groups which can be converted, for example by catalytic hydrogenation, into amino groups which can be diazotized and converted into a large number of groups.

The compounds of the formula I inhibit ATP-sensitive potassium channels and influence the action potential of cells, in particular of heart muscle cells. They have, in particular, a normalizing action on a disturbed action potential, as is present, for example, in ischemias, and are suitable, for example, for the treatment of disorders of the cardiovascular system or of heart diseases. In particular, the compounds of the formula I are suitable, for example, for the treatment of arrhythmias and their sequelae, for example ventricular fibrillation or sudden cardiac death, especially sudden cardiac death as a result of a ventricular arrhythmia, and for the treatment of a decreased contractility of the heart, such as can occur as a result of coronary heart disease, cardiac insufficiency or cardiomyopathy. The compounds of the formula I are also suitable for the treatment of cardiovascular disorders which can occur as concomitant symptoms of other syndromes, for example in different forms of states of shock. The treatment of diseases is to be understood as meaning both the therapy of existing pathological changes or malfunctions of the organism or of existing symptoms with the aims of relief, alleviation or cure, and the prophylaxis or prevention of pathological changes or malfunctions of the organism or of symptoms in humans or animals which are susceptible thereto and are in need of such a prophylaxis or prevention, with the aim of a prevention or suppression of their occurrence or of an attenuation in the case of their occurrence. For example, in patients who on account of their disease history are susceptible to myocardial reinfarctions or to arrhythmically caused sudden cardiac death, by means of the prophylactic or preventive medicinal treatment sudden cardiac death or a fresh myocardial infarction can be prevented, or if a myocardial infarction occurs, its extent and sequelae can be decreased. The treatment of diseases can occur both in acute cases and in chronic cases.

The efficacy of the compounds of the formula I can be demonstrated, for example, in the pharmacological models described below, in which the rubidium efflux via the SUR2A/Kir6.2 potassium channel is determined in transfected cells, or the action potential duration is determined in the papillary muscle of the guinea pig. The selectivity of the compounds can be demonstrated in the pharmacological models described below, in which the rubidium efflux or the action on the membrane potential and the hypoglycemic or vasoconstrictory action connected therewith is determined in cells which are transfected with the components of the SUR1/Kir6.2 potassium channel or the SUR2B/Kir6.2 potassium channel, or the action on the coronary flow is determined in the guinea pig heart.

Preferred compounds of the formula I selectively inhibit the cardiac ATP-sensitive potassium channel (isoform SUR2A/Kir6.2). On account of only a slight action on the pancreatic and the vascular ATP-sensitive potassium channel (isoforms SUR1/Kir6.2 and SUR2B/Kir6.2), such substances do not lead to a significant lowering of the blood sugar level, as is in general not desired in non-diabetic patients, and do not lead to a constriction of blood vessels, in particular coronary vessels, which constriction would lead to an insufficient blood supply which is in general undesirable. In diabetic patients, on the other hand, for the treatment of cardiac arrhythmias or of a decreased contractility of the heart in coronary heart disease, for example, or for the prevention of sudden cardiac death, an action on the pancreatic ATP-sensitive potassium channel and the lowering of the blood sugar level associated therewith can be advantageous, and a corresponding property profile of the compound of the formula I be desirable. Furthermore, the compounds of the formula I can also exert an action on the peripheral and/or the central autonomous nervous system and in particular influence ATP-sensitive potassium channels of the vagal or parasympathetic nervous system. They can thereby have a stimulating action on the vagal nervous system, in particular a stimulating action on the vagal nervous system of the heart by inhibition of ATP-sensitive potassium channels in the cardiac nerve, and be suitable for the treatment of a vagal dysfunction or a sympathovagal imbalance, in particular a vagal dysfunction of the heart. A dysfunction of the vagal nervous system of the heart can, for example, temporarily occur in case of an oxygen deficiency of the heart, which can lead to a lower release of vagal neurotransmitters, for example of acetylcholine.

The compounds of the formula I and their physiologically acceptable salts can therefore be used in animals, in particular in mammals including humans, as a pharmaceutical or medicament on their own, in mixtures with one another or in the form of pharmaceutical compositions. Besides humans, mammals in which the compounds of the formula I and their physiologically acceptable salts can be used or tested include, for example, monkeys, dogs, mice, rats, rabbits, guinea pigs, cats and larger farm animals such as, for example, horses, cattle and pigs. A subject of the present invention also are the compounds of the formula I and their physiologically acceptable salts for use as a pharmaceutical and pharmaceutical compositions, or pharmaceutical preparations, and medicaments which contain an efficacious dose of at least one compound of the formula I and/or of a physiologically acceptable salt thereof as an active constituent, and a pharmaceutically acceptable carrier, i.e. one or more pharmaceutically innocuous vehicles and/or excipients. A subject of the present invention furthermore are the compounds of the formula I, in all their stereoisomeric forms and mixtures of stereoisomeric forms in all ratios, and their physiologically acceptable salts, for use in the treatment of the diseases mentioned above and below, for example of disorders of the cardiovascular system, heart diseases, arrhythmias, ventricular fibrillation, sudden cardiac death, a decreased contractility of the heart, ischemias of the heart, coronary heart disease, angina pectoris, cardiac insufficiency, cardiomyopathy, cardiac hypertrophy or of a vagal dysfunction of the heart, wherein the treatment of diseases, as mentioned, comprises their therapy and prophylaxis, the use of the compounds of the formula I, in all their stereoisomeric forms and mixtures of stereoisomeric forms in all ratios, and their physiologically acceptable salts for the manufacture of a medicament for the treatment of the diseases mentioned above or below, as well as their use for the manufacture of a medicament for the inhibition of ATP-sensitive potassium channels, in particular ATP-sensitive potassium channels in the heart, especially in the heart muscle. A subject of the invention also are methods for the treatment of the diseases mentioned above and below, which comprise administering an efficacious amount of at least one compound according to the invention, in any of its stereoisomeric forms or a mixture of stereoisomeric forms in any ratio, to a human or an animal which is in need thereof. The compounds of the formula I and pharmaceutical compositions and medicaments comprising them can be administered, for example, by enteral, for example oral or rectal, administration, by parenteral administration, for example by intravenous, intramuscular or subcutaneous injection or infusion, or by another type of administration, for example topical, percutaneous or transcutaneous administration.

A subject of the invention also is the use of the compound of the formula I already described as such, in which simultaneously $Ar^1$ and $Ar^2$ are unsubstituted phenyl, $R^1$ is hydroxy and $R^2$ is hydrogen, in any of its stereoisomeric forms or a mixture of stereoisomeric forms in any ratio, or a physiologically acceptable salt thereof, as a pharmaceutical, the use of this compound for the manufacture of a medicament for the treatment of the diseases mentioned above and below or for the inhibition of ATP-sensitive potassium channels, and a pharmaceutical composition which contains an efficacious dose of this compound, in any of its stereoisomeric forms or a mixture of stereoisomeric forms in any ratio, and/or a physiologically acceptable salt thereof, as an active constituent, and a pharmaceutically acceptable carrier. All explanations above and below with respect to the use of the compounds of the formula I according to the invention and to pharmaceutical compositions comprising a compound of the formula I correspondingly apply to this part of the invention.

The pharmaceutical compositions and medicaments according to the invention normally contain about 0.5 to about 90 percent by weight of compounds of the formula I and/or their physiologically acceptable salts. The amount of active ingredient of the formula I and/or its physiologically acceptable salts in the pharmaceutical compositions and medicaments is in general about 0.2 mg to about 1000 mg, in particular about 0.2 mg to about 500 mg, for example about 1 mg to about 300 mg, per unit dose. The production of the pharmaceutical compositions and medicaments can be carried out in a manner known per se. For this, the compounds of the formula I and/or their physiologically acceptable salts are mixed together with one or more solid or liquid vehicles and/or excipients, if desired also in combination with other active ingredients, for example cardiovascular-active agents such as, for example, calcium antagonists, ACE inhibitors or β-blockers, and brought into a suitable form for dosage and administration, which can then be used in human medicine or veterinary medicine.

As vehicles and excipients, suitable organic and inorganic substances can be used which do not react in an undesired manner with the compounds of the formula I. As examples of types of excipients, or additives, which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants, flavorings and aromatic substances may be mentioned. Examples of vehicles and excipients are water, vegetable oils, waxes, alcohols such as ethanol, isopropanol, 1,2-propanediol, benzyl alcohols or glycerol, polyols, polyethylene glycols, polypropylene glycols, glycerol triacetate, polyvinylpyrrolidone, gelatin, carbohydrates such as lactose or starch like corn starch, cellulose, stearic acid and its salts such as magnesium stearate, talc, lanolin, petroleum jelly, or mixtures thereof, for example mixtures of water with one or more organic solvents such as mixtures of water with alcohols. For oral and rectal use, in particular pharmaceutical forms such as, for example, tablets, film-coated tablets, sugar-coated tablets, granules, hard and soft gelatin capsules, suppositories, solutions, including oily, alcoholic or aqueous solutions, syrups, juices or drops, furthermore suspensions or emulsions, can be used. For parenteral use, for example by injection or infusion, in particular pharmaceutical forms such as solutions, for example aqueous solutions, can be used. For topical use, in particular pharmaceutical forms such as ointments, creams, pastes, lotions, gels, sprays, foams, aerosols, solutions or powders can be used. Further suitable pharmaceutical forms are, for example, implants and patches. The compounds of the formula I and their physiologically acceptable salts can also be lyophilized and the obtained lyophilizates used, for example, for the production of injectable compositions. In particular for topical application, also liposomal compositions are suitable. If desired, the pharmaceutical compositions and medicaments can also contain one or more further active ingredients and/or, for example, one or more vitamins.

The compounds of the formula I and the pharmaceutical compositions and medicaments comprising them are in particular used as antiarrhythmics for the treatment of cardiac arrhythmias having a wide range of origins, and especially for the prevention of arrhythmically caused sudden cardiac death. Examples of arrhythmic disorders of the heart are supraventricular arrhythmias such as, for example, atrial tachycardia, atrial flutters or paroxysomal supraventricular arrhythmias, or ventricular arrhythmias such as ventricular extrasystoles, and in particular life-threatening ventricular tachycardia or the particularly hazardous fatal ventricular fibrillation. They are suitable in particular for those cases in which arrhythmias are a result of a constriction of a coronary vessel, such as occur, for example, in angina pectoris or during acute cardiac infarction or as a chronic sequela of a cardiac infarction. They are therefore suitable in particular in postinfarction patients for the prevention of sudden cardiac death. Further syndromes in which such arrhythmias and/or sudden, arrhythmically caused cardiac death play a role are, for example, cardiac insufficiency or cardiac hypertrophy as a result of chronically raised blood pressure.

Moreover, the compounds of the formula I and the pharmaceutical compositions and medicaments comprising them are able to positively influence decreased contractility of the heart and weakened heart power. This can be a chronic disease-related decline in cardiac contractility such as, for example, in cardiac insufficiency, and also an acute case such as heart failure under the action of shock, for example in septic shock, hemorrhagic shock or cardiac shock. In particular, the compounds according to the invention are suitable for the treatment of the pathological blood pressure changes occurring in septic shock. Generally, the compounds according to the invention and their physiologically acceptable salts are suitable for improving the cardiac function. Especially, in a heart transplantation the heart can resume its functionality more rapidly and more reliably after operation has taken place under the influence of the compounds of the formula I. The same applies to operations on the heart which necessitate a temporary stoppage of cardiac activity by means of cardioplegic solutions.

Furthermore, the compounds of the formula I and pharmaceutical compositions and medicaments comprising them can in general be employed in the treatment of diseases which are associated with a dysfunction of the autonomous nervous system or of a subfunction or dysfunction of the vagal nervous system, in particular in the heart, or which are caused by such a dysfunction or subfunction, or in whose treatment an increase or normalization of the activity of the vagal nervous system is desired, for example a vagal dysfunction of the heart which occurs as a result of a metabolic disorder such as, for example, diabetes mellitus. The compounds of the formula I and pharmaceutical compositions and medicaments comprising them can generally be employed also in diseases which are characterized by oxygen deficiency states, and in cerebral vascular disorders.

The dosage of the compounds of the formula I or their physiologically acceptable salts depends, as usual, on the circumstances of the respective individual case and is adjusted by the person skilled in the art according to the customary rules and procedures. It depends, for example, on the compound of the formula I administered, its potency and duration of action, on the nature and severity of the individual syndrome, on the sex, age, weight and the individual responsiveness of the human or animal to be treated, on whether the treatment is acute or chronic or prophylactic or on whether further pharmaceutical active compounds are administered in addition to compounds of the formula I. Normally, in the case of administration to an adult weighing about 75 kg, it is possible to manage with a dose which is about 0.1 mg to about 100 mg per kg per day, in particular about 1 mg to about 10 mg per kg per day (in each case in mg per kg of body weight). The daily dose can be administered, for example, in the form of a single dose, for example a single oral or parenteral dose, or divided into a number of individual doses, for example two, three or four individual doses. The administration can also be carried out continuously. In particular in the treatment of acute cases of cardiac arrhythmias, for example in an intensive care unit, parenteral administration, for example by injection or by intravenous continuous infusion, can be advantageous. In particular in critical situations, the dose can then be in a range from about 1 mg to about 100 mg per kg of body weight per day. Depending on the individual behavior in a specific case, it may be necessary to deviate upward or downward from the indicated dosages.

Besides as a pharmaceutical active compound in human medicine and veterinary medicine, the compounds of the formula I can also be employed, for example, as an aid in biochemical investigations or as a scientific tool if a respective influencing of ion channels is intended, and for the isolation or characterization of potassium channels. Furthermore, they can be used for diagnostic purposes, for example in in vitro diagnoses of cell samples or tissue samples. In addition, the compounds of the formula I and their salts can be used as intermediates for the preparation of further pharmaceutical active substances.

The following examples illustrate the invention.

| Abbreviations | |
|---|---|
| DCI | desorption chemical ionization |
| DCM | dichloromethane |
| DIP | diisopropyl ether |
| DMF | dimethylformamide |
| EA | ethyl acetate |
| EI | electron impact |
| ESI | electrospray ionization |
| HEP | n-heptane |
| MP | melting point |
| MOH | methanol |
| MTB | methyl tert-butyl ether |
| TFA | trifluoroacetic acid |
| THF | tetrahydrofuran |

When compounds containing a basic group were purified by preparative high pressure liquid chromatography (HPLC) on reversed phase (RP) column material and, as customary, the eluent was a gradient mixture of water and acetonitrile containing trifluoroacetic acid, they were in part obtained in the form of their acid addition salts with trifluoroacetic acid, depending on the workup such as freeze-drying conditions. In the structural formulae and names of the respective example compounds, any such contained trifluoroacetic acid is not specified.

Characterization of the Compounds

The prepared compounds were in general characterized by spectroscopic data from mass spectra (MS) and/or NMR spectra and/or by chromatographic data from high pressure liquid chromatograms (HPLC), gas chromatograms (GC) and/or thin layer chromatograms (TLC). In many cases, combined HPLC/MS or GC/MS characterizations were carried out. If not stated otherwise, in the MS characterization in general the mass number (m/e, m/z) of the peak of the observed molecular ion (M) or of a related ion such as the protonated molecular ion (M+H=M+1) or deprotonated molecular ion (M−H=M−1), which was formed depending on the ionization method used, and the ionization method (DCI, EI+, ESI+, ESI−) is indicated. In the NMR characterization, the chemical shift δ (in ppm) of the signals, their multiplicity (s: singlet, d: doublet, t: triplet, m: multiplet, b: broad signal) and the number of hydrogen atoms (H) is indicated. In the HPLC characterization, the HPLC method used and the retention time Rt (in min) is indicated. The detection in the HPLC characterization was carried out by means of the UV absorption at 220 nm and 254 nm. In the TLC characterization, which was carried out on silica gel plates, the mobile phase used and the Rf value is indicated.

HPLC Methods

Method LC1
Column: YMC JSphere 33×2 mm, 4 μm
Eluent: eluent A: water+0.05% TFA, eluent B: acetonitrile+0.05% TFA; gradient: from 95% A+5% B to 5% A+95% B in 2.5 min, then 5% A+95% B for 1.0 min; flow: 1 ml/min Method LC2
Column: YMC JSphere 33×2 mm, 4 μm
Eluent: eluent A: water+0.05% TFA, eluent B: acetonitrile+0.05% TFA; gradient: from 95% A+5% B to 5% A+95% B in 3.7 min; flow: 1 ml/min Method LC3
Column: Interchrom 33×2 mm
Eluent: eluent A: water+0.08 TFA, eluent B: acetonitrile+0.1 TFA; gradient: from 95% A+5% B to 5% A+95% B in 2.5 min; flow: 1 ml/min Method LC4
Column: Uptisphere ODB 33×2 mm, 4 μm
Eluent: eluent A: water+0.05% TFA, eluent B: acetonitrile+0.05% TFA; gradient: from 95% A+5% B to 5% A+95% B in 2.5 min; flow: 1 ml/min Method LC5
Column: Uptisphere ODB 33×2 mm, 4 μm
Eluent: eluent A: water+0.1% TFA, eluent B: acetonitrile+0.08% TFA; gradient: from 95% A+5% B to 5% A+95% B in 2.5 min, then to 95% A+5% B in 0.5 min; flow: 1 ml/min Method LC6
Column: YMC JSphere 33×2 mm, 4 μm
Eluent: eluent A: water+0.1% formic acid, eluent B: acetonitrile+0.08% formic acid; gradient: from 95% A+5% B to 5% A+95% B in 2.5 min; flow: 1 ml/min Method LC7
Column: Merck Purospher 55×2 mm
Eluent: eluent A: water+0.1% TFA, eluent B: acetonitrile+0.08% TFA; gradient: from 95% A+5% B to 5% A+95% B in 5.0 min, then 5% A+95% B for 2.0 min; flow: 1 ml/min Method LC8
Column: YMC JSphere 33×2 mm, 4 μm
Eluent: eluent A: water+0.1% TFA, eluent B: acetonitrile+0.08% TFA; gradient: from 95% A+5% B to 5% A+95% B in 2.5 min; then 5% A+95% B for 0.5 min; flow: 1 ml/min Method LC9
Column: YMC JSphere 33×2.1 mm
Eluent: eluent A: water+0.1% TFA, eluent B: acetonitrile+0.08% TFA; gradient: from 95% A+5% B to 5% A+95% B in 2.5 min, then 5% A+95% B for 0.5 min; flow: 1 ml/min Method LC10
Column: YMC JSphere 33×2 mm, 4 μm
Eluent: eluent A: water+0.05 TFA, eluent B: acetonitrile+0.05% TFA; gradient: from 95% A+5% B to 5% A+95% B in 2.5 min, then 5% A+95% B for 0.5 min; flow: 1 ml/min Method LC11
Column: Merck Purospher 55×2 mm
Eluent: eluent A: water+0.1% TFA, eluent B: acetonitrile+0.08% TFA; gradient: from 95% A+5% B to 5% A+95% B in 7.0 min; flow: 1 ml/min Method LC12
Column: YMC JSphere 33×2 mm, 4 μm
Eluent: eluent A: water+0.1% TFA, eluent B: acetonitrile+0.1% TFA; gradient: from 95% A+5% B to 5% A+95% B in 2.5 min; then 5% A+95% B for 0.5 min; flow: 1 ml/min Method LC13
Column: YMC JSphere 33×2 mm, 4 μm
Eluent: eluent A: water+0.05% TFA, eluent B: acetonitrile+0.05% TFA; gradient: from 95% A+5% B to 5% A+95% B in 2.5 min; then 5% A+95% B for 1.9 min; flow: 1 ml/min Method LC14
Column: YMC JSphere 33×2 mm, 4 μm
Eluent: eluent A: water+0.1% TFA, eluent B: acetonitrile+0.08% TFA; gradient: from 95% A+5% B to 5% A+95% B in 2.0 min; then 5% A+95% B for 1.0 min; flow: 1 ml/min Method LC15
Column: YMC JSphere 33×2 mm, 4 μm
Eluent: eluent A: water+0.05% TFA, eluent B: acetonitrile+0.05% TFA; gradient: from 95% A+5% B to 5% A+95% B in 3.4 min; then 5% A+95% B for 1.0 min; flow: 1 ml/min Method LC16
Column: YMC JSphere ODS H80 20×2 mm, 4 μm
Eluent: eluent A: water+0.05% TFA, eluent B: acetonitrile; gradient: from 96% A+4% B to 5% A+95% B in 2.0 min; then 5% A+95% B for 0.4 min; flow: 1 ml/min; temperature: 30° C.

Method LC17
Column: YMC JSphere 33×2.1 mm, 4 μm
Eluent: eluent A: water+0.05% TFA, eluent B: acetonitrile+0.05% TFA; gradient: from 95% A+5% B to 5% A+95% B in 2.5 min, then 5% A+95% B for 1.0 min; flow: 1 ml/min Method LC18
Column: XBridge MSC18 30×4.6 mm, 3.5 μm
Eluent: eluent A: water+0.1% formic acid, eluent B: acetonitrile+0.1% formic acid; gradient: 95% A+5% B for 1 min, then from to 95% A+5% B to 100% B in 8 min, then 100% B for 3 min; flow: 1 ml/min Method LC19
Column: Kromasil C18 50×2.1 mm, 3.5 μm
Eluent: eluent A: water+0.1% TFA, eluent B: acetonitrile+0.1% TFA; gradient: 95% A+5% B for 1 min, then from 95% A+5% B to 100% B in 19 min, then 100% B for 3 min; flow: 1 ml/min Method LC20
Column: Acquity BEH C18 50×2.1 mm, 1.7 μm
Eluent: eluent A: water+0.1% TFA, eluent B: acetonitrile+ 0.1% TFA; gradient: from 95% A+5% B to 100% B in 3 min; flow: 1 ml/min
Method LC21
Column: Kromasil C18 50×2.1 mm, 3.5 μm
Eluent: eluent A: water+ammonium acetate (5 mM)+3% acetonitrile, eluent B: acetonitrile; gradient: 100% A for 5.5 min, then from 100% A to 100% B in 1.5 min, then 100% B for 3 min; flow 0.8 ml/min; temperature: 40° C.

EXAMPLE 1

4-(4-Fluorophenyl)-4-hydroxy-1-phenylcyclohexanecarbonitrile

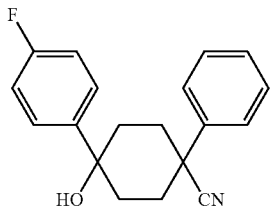

8.8 g of 1-bromo-4-fluorobenzene were dissolved in 50 ml of dry THF in a dried two-necked flask under an argon atmosphere, cooled to −70° C., and 32.2 ml of n-butyllithium solution (1.55 M in n-hexane) were slowly added dropwise so that the internal temperature did not exceed −65° C. The reaction mixture was stirred for 1 h at −70° C. Subsequently, 10.0 g of 4-oxo-1-phenylcyclohexanecarbonitrile in the form of a suspension in 50 ml of THF were slowly added dropwise so that the internal temperature did not exceed −65° C. The reaction solution was stirred further for 1 h at −70° C. and subsequently warmed to room temperature. It was stirred for 3 h at room temperature, the reaction mixture was added to ice water, cautiously acidified with 1 N hydrochloric acid and extracted three times with EA. The combined organic phases were dried over magnesium sulfate and the solvent was removed in vacuo. The crude product, a brown oil, was crystallized from toluene. 13.8 g of the title compound were obtained as a white solid.

MS (ESI+): 296
HPLC (Method LC1): Rt 2.21 min

EXAMPLE 2

4-(3-Fluoro-4-methoxyphenyl)-4-hydroxy-1-phenylcyclohexanecarbonitrile

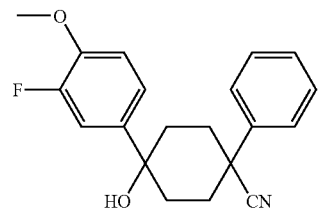

Under an argon atmosphere, 15 ml of 3-fluoro-4-methoxyphenylmagnesium bromide solution (0.5 M in THF) were dissolved in 15 ml of dry THF in a dried two-necked flask equipped with a reflux condenser, and subsequently 1.5 g of 4-oxo-1-phenylcyclohexanecarbonitrile in the form of a suspension in 10 ml of THF were slowly added dropwise at room temperature. A precipitate was formed in the course of this. The reaction solution was heated under reflux for 2 h, subsequently added to ice water, treated with saturated ammonium chloride solution and extracted three times with EA. The combined organic phases were dried over magnesium sulfate and the solvent was removed in vacuo. The residue was purified chromatographically (HEP/EA 2:1) on silica gel. 950 mg of the title compound were obtained as a white solid.

MS (ESI+): 326
HPLC (Method LC1): Rt 2.13 min

According to the preparation processes described in Examples 1 and 2, the 4-(hetero)aryl-4-hydroxy-1-phenylcyclohexanecarbonitriles of the formula VIIIa listed in Table 1 were prepared by reaction of the corresponding bromo(hetero)aromatics with n-butyllithium and 4-oxo-1-phenylcyclohexanecarbonitrile or by reaction of the corresponding (hetero)arylmagnesium halide with 4-oxo-1-phenylcyclohexanecarbonitrile.

TABLE 1

Example compounds of the formula VIIIa

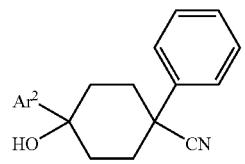

VIIIa

| Example | Ar$^2$ | Preparation (1) | MS | HPLC (Rt [min], Method) |
|---|---|---|---|---|
| 3 | 3-fluorophenyl | a | 296 ESI+ | |
| 4 | 2,3-difluorophenyl | a | 313 EI+ | |
| 5 | 2,4-difluorophenyl | a | 313 EI+ | |
| 6 | 3,4-difluorophenyl | a | 313 EI+ | |
| 7 | 3,5-difluorophenyl | a | 313 ESI+ | 2.34 LC2 |
| 8 | 2,4,6-trifluorophenyl | a | 332 ESI+ | 1.84 LC1 |
| 9 | 2,3,4-trifluorophenyl | a | 332 ESI+ | 1.89 LC1 |
| 10 | 3-fluoro-4-methylphenyl | a | 310 ESI+ | 2.38 LC1 |
| 11 | 4-trifluoromethylphenyl | a | 346 ESI+ | 2.59 LC1 |

TABLE 1-continued

Example compounds of the formula VIIIa

VIIIa

| Example | Ar² | Preparation (1) | MS | HPLC (Rt [min], Method) |
|---|---|---|---|---|
| 12 | 3-trifluoromethylphenyl | a | 346 DCI | |
| 13 | 2-fluoro-4-trifluoromethylphenyl | a | 364 ESI+ | 2.38 LC1 |
| 14 | 4-chloro-3-trifluoromethylphenyl | a | 378 ESI− | 2.32 LC3 |
| 15 | 4-fluoronaphthalen-1-yl | a | 346 ESI+ | 2.90 LC1 |
| 16 | 2,2-difluorobenzo[1,3]dioxol-4-yl | a | 356 EI+ | |
| 17 | 4-bromophenyl | a | 356 EI+ | |
| 18 | 4-chlorophenyl | a | 311 ESI− | 2.16 LC4 |
| 19 | 3-chlorophenyl | a | 312 ESI+ | |
| 20 | 3,4-dichlorophenyl | a | 345 ESI− | 2.29 LC3 |
| 21 | 4-methoxyphenyl | a | 308 ESI+ | |
| 22 | 3-methoxyphenyl | a | 308 ESI− | 2.04 LC3 |
| 23 | 2-methoxyphenyl | a | 308 ESI− | 2.10 LC3 |
| 24 | phenyl | a | 276 ESI− | 2.02 LC3 |
| 25 | 2-vinylphenyl | a | 304 EI+ | |
| 26 | naphthalen-2-yl | a | 328 ESI+ | 2.58 LC1 |
| 27 | quinolin-6-yl | a | 329 ESI+ | 1.10 LC1 |
| 28 | isoquinolin-4-yl | a | 329 ESI+ | 1.19 LC1 |
| 29 | isoquinolin-5-yl | a | 329 ESI+ | 1.18 LC1 |
| 30 | quinolin-3-yl | a | 329 ESI+ | 1.33 LC1 |
| 31 | 6-fluoropyridin-3-yl | a | 296 ESI+ | 1.78 LC1 |
| 32 | 2-bromo-5-fluoropyridin-4-yl | a (2) | 376 ESI+ | 2.10 LC1 |
| 33 | 3-fluoropyridin-4-yl | a | 297 ESI+ | 1.31 LC1 |
| 34 | 5-chloropyridin-2-yl | a | 312 ESI+ | 1.82 LC1 |
| 35 | 6-methoxypyridin-3-yl | a | 309 ESI+ | 1.82 LC1 |
| 36 | thiophen-2-yl | b | 284 ESI+ | 2.13 LC1 |
| 37 | thiophen-3-yl | b | 284 ESI+ | 2.14 LC1 |
| 38 | benzo[1,3]dioxol-5-yl | b | 322 ESI+ | 2.09 LC1 |
| 39 | 2,4-dimethoxyphenyl | b | 338 ESI+ | 2.25 LC1 |

(1) a = preparation according to Example 1
b = preparation according to Example 2; in Example 36 using 2-thienyl-magnesium chloride; in Example 37 using 3-thienylmagnesium iodide; in Example 38 using benzo[1,3]dioxol-5-ylmagnesium chloride; in Example 39 using 2,4-dimethoxyphenylmagnesium bromide
(2) starting material was not 2,4-dibromo-5-fluoropyridine, but 2-bromo-5-fluoropyridine

EXAMPLE 40

4-(4-Fluorophenyl)-4-methoxy-1-phenylcyclohexanecarbonitrile

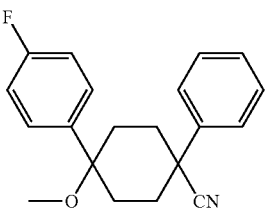

300 mg of 4-(4-fluorophenyl)-4-hydroxy-1-phenylcyclohexanecarbonitrile were dissolved in 2.5 ml of dry DMF in a flask which had been dried and flushed with argon, treated under argon with 73 mg of sodium hydride (80% strength in mineral oil) and stirred for 30 min at room temperature. Subsequently, 0.14 ml of iodomethane was slowly added dropwise under argon. The reaction mixture was stirred for 3 h, then treated with water and extracted with EA. The combined organic phases were dried over magnesium sulfate and the solvent was removed in vacuo. The crude product, a brown oil, was purified by chromatography on silica gel using HEP/EA (2:1). 290 mg of the title compound were obtained as a white amorphous solid.
MS (ESI+): 310
HPLC (Method LC1): Rt 2.04 min

EXAMPLE 41

4-Cyclopropylmethoxy-4-(4-fluorophenyl)-1-phenylcyclohexanecarbonitrile

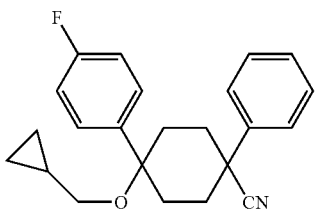

500 mg of 4-(4-fluorophenyl)-4-hydroxy-1-phenylcyclohexanecarbonitrile were dissolved in 10 ml of dry dimethyl sulfoxide, treated with 190 mg of potassium hydroxide and stirred for 30 min at room temperature. Subsequently, 0.17 ml of bromomethylcyclopropane were slowly added dropwise. The reaction mixture was stirred for 24 h, treated with water and extracted with EA. The combined organic phases were dried over magnesium sulfate and the solvent was removed in vacuo. The crude product, a clear oil, was purified by chromatography on silica gel using HEP/EA (2:1). 510 mg of the title compound were obtained as a white solid.

MS (ESI+): 350

According to the preparation processes described in Examples 40 and 41, the 4-(hetero)aryl-4-(optionally substituted alkoxy)-1-phenylcyclohexanecarbonitriles of the formula Xa listed in Table 2 were prepared by reaction of the corresponding 4-(hetero)aryl-4-hydroxy-1-phenylcyclohexanecarbonitriles with the corresponding optionally substituted alkyl halide in the presence of sodium hydride or of potassium hydroxide.

TABLE 2

Example compounds of the formula Xa

| Example | Ar² | R² | Preparation (1) | MS | HPLC (Rt [min], Method) |
|---|---|---|---|---|---|
| 42 | 3-fluorophenyl | methyl | a | 310 DCI | |
| 43 | 2,3-difluorophenyl | methyl | a | 328 ESI+ | 2.46 LC1 |
| 44 | 2,4-difluorophenyl | methyl | a | 328 ESI+ | |
| 45 | 3,4-difluorophenyl | methyl | a | 328 EI+ | |
| 46 | 3,5-difluorophenyl | methyl | a | 328 ESI+ | 2.54 LC1 |
| 47 | 2,4,6-trifluorophenyl | methyl | a | 346 ESI+ | |
| 48 | 2,3,4-trifluorophenyl | methyl | a | 346 ESI+ | 2.54 LC1 |
| 49 | 4-trifluoromethylphenyl | methyl | a | 360 ESI+ | 2.60 LC1 |
| 50 | 3-trifluoromethylphenyl | methyl | a | 360 EI+ | |
| 51 | 4-fluoronaphthalen-1-yl | methyl | a | 360 ESI+ | 2.43 LC1 |
| 52 | 2,2-difluorobenzo[1,3]dioxol-4-yl | methyl | a | 372 ESI+ | 2.03 LC1 |
| 53 | 4-methoxyphenyl | methyl | a | 321 ESI– | 2.27 LC5 |
| 54 | 3-methoxyphenyl | methyl | a | 321 ESI– | 2.28 LC6 |
| 55 | 2-methoxyphenyl | methyl | a | 321 ESI– | 2.29 LC3 |
| 56 | 3-fluoro-4-methoxyphenyl | methyl | a | 340 ESI+ | |
| 57 | 2,4-dimethoxyphenyl | methyl | a | 352 ESI+ | 2.48 LC1 |
| 58 | benzo[1,3]dioxol-5-yl | methyl | a | 336 ESI+ | 2.13 LC1 |
| 59 | phenyl | methyl | a | 290 ESI– | 2.31 LC3 |
| 60 | 2-vinylphenyl | methyl | a | 318 ESI+ | 2.33 LC1 |
| 61 | 6-fluoropyridin-3-yl | methyl | a | 311 ESI+ | 2.33 LC1 |
| 62 | 2-bromo-5-fluoropyridin-4-yl | methyl | a | 389 ESI+ | 1.97 LC1 |
| 63 | 3-fluoropyridin-4-yl | methyl | a | 311 ESI+ | 1.60 LC1 |
| 64 | 6-methoxypyridin-3-yl | methyl | a | 323 ESI+ | 2.22 LC1 |
| 65 | thiophen-2-yl | methyl | a | 298 EI+ | |
| 66 | 4-fluorophenyl | ethyl | a | 324 ESI+ | 2.62 LC1 |
| 67 | 2-bromo-5-fluoropyridin-4-yl | ethyl | a | 403 ESI+ | 2.12 LC1 |
| 68 | 3-fluoropyridin-4-yl | ethyl | a | 325 ESI+ | 1.86 LC1 |
| 69 | 6-fluoropyridin-3-yl | ethyl | a | 325 ESI+ | 1.86 LC1 |
| 70 | 6-methoxypyridin-3-yl | ethyl | a | 337 ESI+ | |
| 71 | 4-fluorophenyl | allyl | a | 336 DCI | |
| 72 | 4-fluorophenyl | n-butyl | b | 352 ESI+ | 2.92 LC1 |
| 73 | 4-fluorophenyl | 3-methyl-butyl | b | 366 ESI+ | 3.08 LC1 |
| 74 | 4-fluorophenyl | but-2-ynyl | b | 348 ESI+ | 2.25 LC1 |
| 75 | 4-fluorophenyl | 4,4,4-tri-fluorobutyl | b | 406 ESI+ | 2.56 LC1 |
| 76 | 4-fluorophenyl | 2,2,2-tri-fluoroethyl | b | 378 ESI+ | |
| 77 | 4-fluorophenyl | n-propyl | b | 338 EI+ | |
| 78 | 4-bromophenyl | n-propyl | b | 399 ESI+ | 2.58 LC1 |
| 79 | 2,3,4-trifluorophenyl | n-propyl | b | 374 ESI+ | 2.41 LC1 |
| 80 | 2,4,6-trifluorophenyl | n-propyl | b | 374 EI+ | |
| 81 | 4-bromophenyl | cyclopropylmethyl | b | 410 ESI+ | 1.97 LC1 |
| 82 | 2,3,4-trifluorophenyl | cyclopropylmethyl | b | 386 ESI+ | 2.72 LC1 |
| 83 | quinolin-3-yl | cyclopropylmethyl | b | 383 ESI+ | 1.56 LC1 |
| 84 | isoquinolin-4-yl | cyclopropylmethyl | b | 383 ESI+ | 1.49 LC1 |

TABLE 2-continued

Example compounds of the formula Xa

Xa

| Example | Ar² | R² | Preparation (1) | MS | HPLC (Rt [min], Method) |
|---|---|---|---|---|---|
| 85 | isoquinolin-5-yl | cyclopropylmethyl | b | 383 ESI+ | 1.46 LC1 |
| 86 | quinolin-6-yl | cyclopropylmethyl | b | 383 ESI+ | 2.05 LC1 |
| 87 | 6-methoxypyridin-3-yl | cyclopropylmethyl | b | 363 ESI+ | 2.01 LC1 |
| 88 | 5-chloropyridin-2-yl | cyclopropylmethyl | b | 366 ESI+ | 2.39 LC1 |
| 89 | 2-bromo-5-fluoropyridin-4-yl | cyclopropylmethyl | b | 429 ESI+ | 2.19 LC1 |
| 90 | 3-fluoropyridin-4-yl | cyclopropylmethyl | b | 351 ESI+ | 1.84 LC1 |
| 91 | 6-fluoropyridin-3-yl | cyclopropylmethyl | b | 351 ESI+ | 1.97 LC1 |

(1) a = preparation according to Example 40
b = preparation according to Example 41
The following alkyl halides were employed as alkylating agents:
R² = methyl: iodomethane
R² = ethyl: bromoethane
R² = allyl: 1-bromoprop-2-ene
R² = n-butyl: 1-bromobutane
R² = 3-methylbutyl: 1-bromo-3-methylbutane
R² = but-2-ynyl: 1-bromobut-2-yne
R² = 4,4,4-trifluorobutyl: 1-bromo-4,4,4-trifluorobutane
R² = 2,2,2-trifluoroethyl: 1-bromo-2,2,2-trifluoroethane
R² = n-propyl: 1-bromopropane
R² = cyclopropylmethyl: bromomethylcyclopropane

EXAMPLE 92

4-(4-Fluorophenyl)-4-methoxy-1-phenylcyclohexanecarboxylic Acid

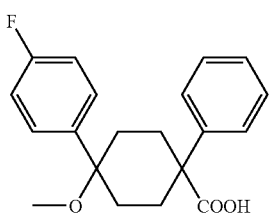

500 mg of 4-(4-fluorophenyl)-4-methoxy-1-phenylcyclohexanecarbonitrile were dissolved in 30 ml of ethylene glycol and 272 mg of potassium hydroxide were added. The reaction mixture was subsequently stirred for 5 h at 200° C. After cooling, the reaction mixture was poured onto an ice/water mixture and extracted three times with MTB. The aqueous phase was acidified to pH=1 with 2 N hydrochloric acid. The precipitated crude product was filtered off with suction and dissolved in a little hot toluene. The crystals deposited during cooling were filtered off with suction and dried. 450 mg of the title compound were obtained as a white solid.
MS (ESI−): 327
HPLC (Method LC9): Rt 2.22 min According to the preparation process described in Example 92, the 4-(hetero)aryl-4-hydroxy-1-phenylcyclohexanecarboxylic acids of the formula Ic listed in Table 3 were prepared from the corresponding 4-(hetero)aryl-4-hydroxy-1-phenyl-cyclohexanecarbonitrile by reaction with potassium hydroxide.

TABLE 3

Example compounds of the formula Ic

Ic

| Example | Ar² | MS | HPLC (Rt [min], Method) |
|---|---|---|---|
| 93 | 4-fluorophenyl | 313 ESI− | 1.70 LC3 |
| 94 | 2,3-difluorophenyl | 331 ESI− | 1.96 LC6 |
| 95 | 2,4-difluorophenyl | 331 ESI− | 1.97 LC6 |
| 96 | 3,4-difluorophenyl | 331 ESI− | 1.94 LC6 |
| 97 | 3,5-difluorophenyl | 331 ESI− | 1.97 LC6 |
| 98 | 2,4,6-trifluorophenyl | 349 ESI− | 2.32 LC6 |
| 99 | 2,3,4-trifluorophenyl | 351 ESI+ | 2.06 LC1 |

TABLE 3-continued

Example compounds of the formula Ic

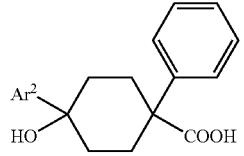

| Example | Ar² | MS | HPLC (Rt [min], Method) |
|---|---|---|---|
| 100 | 3-fluoro-4-methylphenyl | 329 ESI+ | 2.42 LC1 |
| 101 | 4-trifluoromethylphenyl | 363 ESI− | 2.14 LC6 |
| 102 | 3-trifluoromethylphenyl | 363 ESI− | 2.17 LC6 |
| 103 | 2-fluoro-4-trifluoromethylphenyl | 383 ESI+ | 2.34 LC1 |
| 104 | 4-chloro-3-trifluoromethylphenyl | 397 ESI− | 2.29 LC6 |
| 105 | 4-bromophenyl | 373 ESI− | 2.12 LC6 |
| 106 | 4-chlorophenyl | 329 ESI− | 2.11 LC3 |
| 107 | 3,4-dichlorophenyl | 364 ESI− | 1.92 LC3 |
| 108 | 2,2-difluorobenzo[1,3]dioxol-4-yl | 375 ESI− | 2.11 LC6 |
| 109 | benzo[1,3]dioxol-5-yl | 339 ESI− | 1.84 LC6 |
| 110 | 4-methoxyphenyl | 325 ESI− | 1.81 LC6 |
| 111 | 3-methoxyphenyl | 325 ESI− | 1.89 LC6 |
| 112 | 2-methoxyphenyl | 327 ESI+ | 3.50 LC7 |
| 113 | 2,4-dimethoxyphenyl | 355 ESI− | 2.16 LC6 |

TABLE 3-continued

Example compounds of the formula Ic

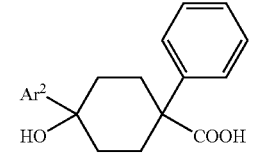

| Example | Ar² | MS | HPLC (Rt [min], Method) |
|---|---|---|---|
| 114 | 3-fluoro-4-methoxyphenyl | 379 DCI, M + Cl | |
| 115 | phenyl | 295 ESI− | 1.92 LC6 |
| 116 | naphthalen-1-yl | 345 ESI− | 2.26 LC3 |
| 117 | thiophen-3-yl | 303 ESI+ | 2.42 LC1 |
| 118 | 6-methoxypyridin-3-yl | 328 ESI+ | 1.34 LC1 |

According to the preparation process described in Example 92, the 4-(hetero)aryl-4-(optionally substituted alkoxy)-1-phenylcyclohexanecarboxylic acids of the formula Id listed in Table 4 were prepared from the corresponding 4-(hetero)aryl-4-(optionally substituted alkoxy)-1-phenylcyclohexanecarbonitrile by reaction with potassium hydroxide.

TABLE 4

Example compounds of the formula Id

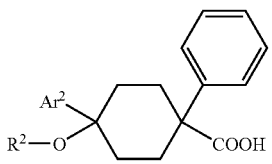

| Example | Ar² | R² | MS | HPLC (Rt [min], Method) |
|---|---|---|---|---|
| 119 | 3-fluorophenyl | methyl | 327 ESI− | 2.22 LC6 |
| 120 | 2,3-difluorophenyl | methyl | 345 ESI− | 2.29 LC6 |
| 121 | 3,4-difluorophenyl | methyl | 345 ESI− | 2.26 LC9 |
| 122 | 3,5-difluorophenyl | methyl | 345 ESI− | 2.27 LC9 |
| 123 | 3-fluoro-4-methylphenyl | methyl | 341 ESI− | 2.38 LC6 |
| 124 | 4-trifluoromethylphenyl | methyl | 377 ESI− | 2.41 LC9 |
| 125 | 3-trifluoromethylphenyl | methyl | 377 ESI− | 2.40 LC9 |
| 126 | 2,2-difluorobenzo[1,3]dioxol-4-yl | methyl | 389 ESI− | 2.38 LC6 |
| 127 | 3-chlorophenyl | methyl | 345 ESI+ | 4.31 LC11 |
| 128 | 4-methoxyphenyl | methyl | 339 ESI− | 2.14 LC6 |
| 129 | 3-methoxyphenyl | methyl | 341 ESI+ | 4.11 LC11 |
| 130 | 2-methoxyphenyl | methyl | 341 ESI+ | |
| 131 | 3-fluoro-4-methoxyphenyl | methyl | 357 ESI− | 2.12 LC9 |
| 132 | 2,4-dimethoxyphenyl | methyl | 369 ESI− | 1.95 LC9 |
| 133 | benzo[1,3]dioxol-5-yl | methyl | 353 ESI− | 1.84 LC9 |
| 134 | phenyl | methyl | 309 ESI− | 2.45 LC9 |
| 135 | 2-vinylphenyl | methyl | 335 ESI− | 2.45 LC9 |
| 136 | quinolin-3-yl | methyl | 360 ESI− | 1.19 LC9 |
| 137 | 5-chloropyridin-2-yl | methyl | 346 ESI+ | 1.79 LC9 |
| 138 | 3-fluoropyridin-4-yl | methyl | 330 ESI+ | 1.33 LC1 |
| 139 | 6-methoxypyridin-3-yl | methyl | 342 ESI+ | 1.63 LC9 |
| 140 | thiophen-2-yl | methyl | 315 ESI− | 1.92 LC9 |
| 141 | 4-fluorophenyl | ethyl | 341 ESI− | 2.37 LC9 |
| 142 | 3-fluoropyridin-4-yl | ethyl | 344 ESI+ | 3.01 LC1 |
| 143 | 6-methoxypyridin-3-yl | ethyl | 356 ESI+ | 1.56 LC1 |
| 144 | 4-fluorophenyl | allyl | 355 DCI | |
| 145 | 4-fluorophenyl | n-butyl | 369 ESI− | 2.64 LC9 |
| 146 | 4-fluorophenyl | 3-methyl-butyl | 385 EI+ | |
| 147 | 4-fluorophenyl | 4,4,4-tri-fluorobutyl | 423 ESI− | 2.59 LC9 |
| 148 | 4-fluorophenyl | n-propyl | 355 ESI− | 2.57 LC9 |

TABLE 4-continued

Example compounds of the formula Id

Id

| Example | Ar² | R² | MS | HPLC (Rt [min], Method) |
|---------|-----|-----|-----|------------------------|
| 149 | 4-bromophenyl | n-propyl | 418 ESI+ | 2.14 LC6 |
| 150 | 4-fluorophenyl | cyclopropylmethyl- | 367 ESI– | 2.50 LC9 |
| 151 | 4-bromophenyl | cyclopropylmethyl | 430 ESI+ | 2.69 LC9 |
| 152 | quinolin-3-yl | cyclopropylmethyl | 402 ESI+ | 1.13 LC1 |
| 153 | isoquinolin-4-yl | cyclopropylmethyl | 402 ESI+ | 1.33 LC1 |
| 154 | isoquinolin-5-yl | cyclopropylmethyl | 402 ESI+ | 1.33 LC1 |
| 155 | quinolin-6-yl | cyclopropylmethyl | 402 ESI+ | 1.26 LC1 |
| 156 | 6-methoxypyridin-3-yl | cyclopropylmethyl | 382 ESI+ | 1.69 LC1 |
| 157 | 6-chloropyridin-3-yl | cyclopropylmethyl | 386 ESI+ | 2.01 LC1 |
| 158 | 3-fluoropyridin-4-yl | cyclopropylmethyl | 370 ESI+ | 1.53 LC1 |

EXAMPLE 159

4-(6-(2-Hydroxyethoxy)pyridin-3-yl)-4-methoxy-1-phenylcyclohexanecarboxylic Acid

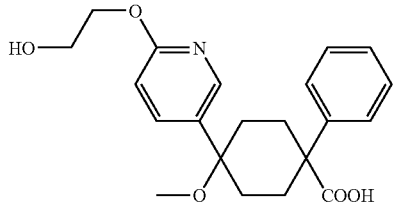

The title compound was obtained according to the process described in Example 92 in the reaction of 4-(6-fluoropyridin-3-yl)-4-methoxy-1-phenylcyclohexanecarbonitrile with potassium hydroxide in ethylene glycol.

MS (ESI+): 372

HPLC (Method LC15): Rt 1.30 min

EXAMPLE 160

4-Hydroxy-4-(4-methylsulfanylphenyl)-1-phenylcyclohexanecarbonitrile

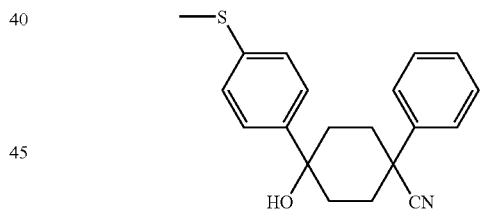

5.10 g of 4-bromothioanisole were dissolved in 50 ml of dry THF and 9.29 ml of an n-butyllithium solution (2.7 M in HEP) were added dropwise at a temperature between −65° C. and −70° C. The reaction mixture was stirred for 3 h at −70° C. Subsequently a solution of 5.00 g of 4-oxo-1-phenylcyclohexanecarbonitrile in 30 ml of THF was added dropwise at this temperature and the mixture was stirred for 10 min at −70° C. and 26 h at room temperature. The reaction mixture was then poured onto 400 g of ice, 100 ml of a 1 N hydrochloric acid were added and the mixture was extracted three times with 200 ml each of DCM. The combined extracts were dried over magnesium sulfate and the solvent was removed in vacuo. Chromatography of the residue on silica gel with EA/HEP (1:2) yielded 5.96 g of the title compound as a colorless oil.

MS (DCI): 324

TLC (EA/HEP 1:2): Rf 0.24

EXAMPLE 161

4-Hydroxy-4-(4-methylsulfanylphenyl)-1-phenylcyclohexanecarboxylic Acid

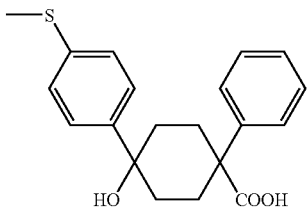

262 mg of 4-hydroxy-4-(4-methylsulfanylphenyl)-1-phenylcyclohexanecarbonitrile were reacted with potassium hydroxide according to the process described in Example 92. 99 mg of the title compound were obtained as an amorphous white solid.

MS (ESI−): 342
TLC (DIP/2% acetic acid): Rf 0.12

EXAMPLE 162

4-Methoxy-4-(4-methylsulfanylphenyl)-1-phenylcyclohexanecarbonitrile

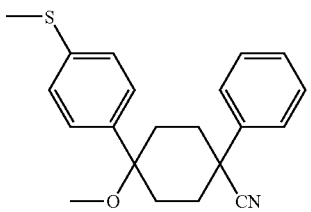

1.50 g of 4-hydroxy-4-(4-methylsulfanylphenyl)-1-phenylcyclohexanecarbonitrile were reacted with iodomethane according to the process described in Example 40. 1.19 g of the title compound were obtained as a colorless oil.

MS (DCI): 338
TLC (EA/HEP 1:2): Rf 0.47

EXAMPLE 163

4-Methoxy-4-(4-methylsulfanylphenyl)-1-phenylcyclohexanecarboxylic Acid

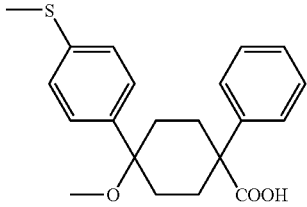

1.19 g of 4-methoxy-4-(4-methylsulfanylphenyl)-1-phenylcyclohexanecarbonitrile were dissolved in 30 ml of ethylene glycol and 1.98 g of potassium hydroxide were added. The reaction mixture was heated for 5 h to 200° C. After cooling, it was diluted at 0° C. with 150 ml of a 5% strength aqueous sodium hydrogensulfate solution and extracted three times with 100 ml each of EA. The combined extracts were dried over magnesium sulfate and the solvent was removed in vacuo. Chromatography of the residue on silica gel with EA/HEP (1:2) yielded 720 mg of the title compound as an amorphous white solid.

MS (DCI): 356
TLC (EA/HEP 1:1): Rf 0.31

EXAMPLE 164

4-Methoxy-4-(4-methanesulfonylphenyl)-1-phenylcyclohexanecarboxylic Acid

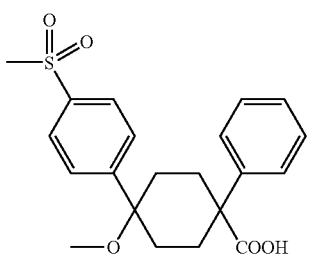

690 mg of 4-methoxy-4-(4-methylsulfanylphenyl)-1-phenylcyclohexanecarboxylic acid were dissolved in 30 ml of DCM and 865 mg of 3-chloroperbenzoic acid were added at room temperature. The reaction mixture was stirred at room temperature was for 5 h and 40 min. 60 ml of a saturated aqueous sodium sulfite solution were then added, the mixture was stirred for 15 min at room temperature, adjusted to pH=3 with a saturated aqueous sodium hydrogensulfate solution and extracted three times with 100 ml each of DCM. The combined extracts were dried over magnesium sulfate and the solvent was removed in vacuo. Chromatography of the residue on silica gel with MTB yielded 464 mg of the title compound as an amorphous solid.

MS (ESI−): 388
TLC (MTB/HEP 1:1): Rf 0.12

The 4-(substituted phenyl)-4-hydroxy-1-phenylcyclohexanecarboxylic acids and 4-(substituted phenyl)-4-(optionally substituted alkoxy)-1-phenylcyclohexanecarboxylic acids of the formula Id listed in Table 5 were prepared according to the preparation processes described in Examples 160 to 164. In the preparation of the compounds in which $R^2$ is an optionally substituted alkyl group, the alkylation was carried out as described in Example 40, using ethylene glycol dimethyl ether as the solvent instead of DMF and employing the following alkylating agents: $R^2$=methyl: iodomethane; $R^2$=ethyl: bromoethane; $R^2$=n-propyl: 1-bromopropane; $R^2$=cyclopropylmethyl-: bromomethylcyclopropane.

TABLE 5

Example compounds of the formula Id

Id

R²—O—[cyclohexane with Ar² and COOH]

| Example | Ar² | R² | MS | TLC (Rf) (1) |
|---|---|---|---|---|
| 165 | 3-methylsulfanylphenyl | hydrogen | 342 ESI– | 0.40 a |
| 166 | 2-methylsulfanylphenyl | hydrogen | 342 ESI– | 0.60 a |
| 167 | 3-methanesulfonylphenyl | ethyl | 402 ESI– | 0.26 b |
| 168 | 3-methanesulfonylphenyl | n-propyl | 416 ESI– | 0.36 b |
| 169 | 3-methanesulfonylphenyl | cyclopropyl-methyl | 428 ESI– | 0.30 b |
| 170 | 4-methanesulfonylphenyl | n-propyl | 416 ESI– | 0.33 b |
| 171 | 4-methanesulfonylphenyl | cyclopropyl-methyl | 428 ESI– | 0.27 b |
| 172 | 2-methanesulfonylphenyl | methyl | 388 ESI– | 0.21 b |
| 173 | 2-methanesulfonylphenyl | ethyl | 402 ESI– | 0.37 b |
| 174 | 2-methanesulfonylphenyl | n-propyl | 416 ESI– | 0.43 b |
| 175 | 2-methanesulfonylphenyl | cyclopropyl-methyl | 428 ESI– | 0.47 b |
| 176 | 4-methanesulfonylphenyl | hydrogen | 374 ESI– | 0.56 c |
| 177 | 3-methanesulfonylphenyl | hydrogen | 374 ESI– | 0.53 c |
| 178 | 2-methanesulfonylphenyl | hydrogen | 374 ESI– | 0.26 c |

(1) mobile phase of the TLC characterization: a = EA; b = DIP/2% acetic acid; c = EA/2% acetic acid

EXAMPLE 179

4-(3-Bromophenyl)-4-hydroxy-1-phenylcyclohexanecarbonitrile

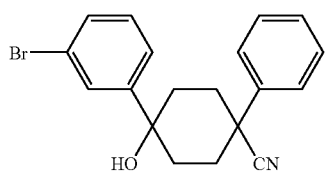

8.00 g of 1,3-dibromobenzene were dissolved in 200 ml of dry diethyl ether and 22.61 ml of an n-butyllithium solution (1.5 M in n-hexane) were added dropwise between 0° C. and 5° C. The reaction mixture was stirred for 5 min at 0° C. Subsequently a solution of 6.76 g of 4-oxo-1-phenylcyclohexanecarbonitrile in 70 ml of dry THF was injected at −70° C. The reaction mixture was allowed to warm to room temperature and was stirred for 30 min at room temperature. The reaction mixture was then poured onto 200 ml of a saturated aqueous sodium hydrogensulfate solution, and the phases were separated and the aqueous phase extracted with 200 ml of EA. The combined organic phases were dried over magnesium sulfate and the solvent was removed in vacuo. The residue was stirred with 70 ml of HEP. 7.50 g of the title compound were obtained as a resinous, partially crystallizing solid.

TLC (EA/HEP 1:2): Rf 0.36

EXAMPLE 180

4-(3-Bromophenyl)-4-cyclopropylmethoxy-1-phenylcyclohexanecarbonitrile

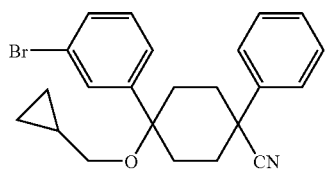

The title compound was prepared from 4-(3-bromophenyl)-4-hydroxy-1-phenylcyclohexanecarbonitrile and bromomethylcyclopropane according to the process described in Example 41.

EXAMPLE 181

4-(3-Bromophenyl)-4-cyclopropylmethoxy-1-phenylcyclohexanecarboxylic Acid

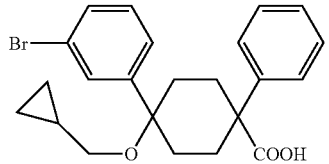

2.3 g of 4-(3-bromophenyl)-4-cyclopropylmethoxy-1-phenylcyclohexanecarbonitrile were suspended in 10 ml of ethylene glycol, 0.94 g of potassium hydroxide was added and the mixture was heated for 4 h at 195° C. The reaction mixture was then allowed to stand for 16 h at room temperature, poured onto 100 ml of water and adjusted to pH=3 with saturated aqueous sodium hydrogensulfate solution. The precipitated product was filtered off with suction and purified by preparative HPLC (column: Waters X-Terra MS $C_{18}$ prep, 200×50 mm, 10 μm; eluent A: water+0.2% TFA, eluent B: acetonitrile; gradient and flow: 90% A+10% B and 50 ml/min for 2.2 min, then to 90% A+10% B and 150 ml/min in 1.3 min, then 90% A+10% B and 150 ml/min for 0.5 min, then to 80% A+20% B and 150 ml/min in 0.5 min, then to 5% A+95% B and 150 ml/min in 19.5 min, then 5% A+95% B and 150 ml/min for 6 min, then to 90% A+10% B and 150 ml/min in 1 min, then 90% A+10% B and 150 ml/min for 4 min). 215 mg of the title compound were obtained as a colorless oil.

MS (ESI-): 429

TLC (MTB): Rf 0.67

EXAMPLE 182

4-Cyclopropylmethoxy-4-(3-cyclopropylphenyl)-1-phenylcyclohexanecarboxylic Acid

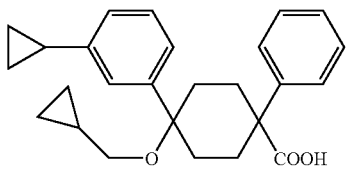

190 mg of 4-(3-bromophenyl)-4-cyclopropylmethoxy-1-phenylcyclohexanecarboxylic acid, 57 mg of cyclopropylboronic acid, 12.4 mg of tricyclohexylphosphine, 4.97 mg of palladium(II) acetate and 376 mg of potassium phosphate ($K_3PO_4$) were heated for 4 h at 100° C. in 10 ml of toluene and 1 ml of water. The reaction mixture was allowed to stand for 15 h at room temperature and subsequently heated for a further 3 h at 100° C. It was then diluted with 50 ml of EA and washed twice with 20 ml each of a saturated aqueous sodium hydrogensulfate solution. The organic phase was dried over magnesium sulfate and the solvent was removed in vacuo. The residue was purified by preparative HPLC (column: Waters X-Terra MS $C_{18}$, 100×30 mm, 5 μm; eluent A: water+ 0.1% TFA, eluent B: acetonitrile; flow: 30 ml/min; gradient: 90% A+10% B for 2.5 min, then to 75% A+25% B in 0.5 min, then to 25% A+75% B in 11 min, then to 5% A+95% B in 1 min, then to 90% A+10% B in 2.5 min). 25 mg of the title compound were obtained as an amorphous solid.

MS (ESI–): 390
TLC (DIP): Rf 0.22

EXAMPLE 183

1-(2-Methylsulfanylphenyl)-4-oxocyclohexanecarbonitrile

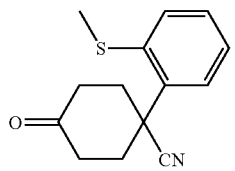

a) (2-Methylsulfanylphenyl)methanol

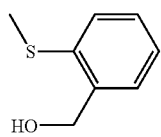

5 g of 2-methylsulfanylbenzoic acid were dissolved in 50 ml of toluene, treated in portions at 20° C. with 14.5 ml of a solution of sodium dihydridobis(2-methoxy-ethoxy)aluminate (Red-Al®; 65% strength in toluene) and stirred for 5 h. The reaction mixture was added to 200 ml of water and extracted three times with 100 ml each of EA. The combined organic phases were dried with magnesium sulfate and the solvent was removed in vacuo. 4.6 g of the crude title compound were obtained as a brown oil.

MS (ESI+): 155 b) (2-Methylsulfanylphenyl)acetonitrile

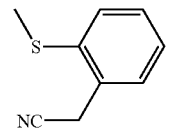

4.6 g of (2-methylsulfanylphenyl)methanol were dissolved in 50 ml of toluene, treated at 10° C. in portions with 3.2 ml of thionyl chloride and heated for 3 h under reflux.

After cooling to 20° C., the reaction mixture was concentrated in vacuo. The brown oil obtained (4.68 g) was taken up in 20 ml of dry acetonitrile and the solution was treated with 0.45 ml of 18-crown-6-ether and 2.25 g of potassium cyanide (cf. Böhme et al., J. Med. Chem. 45, 3094-3102 (2002)). The reaction mixture was stirred for 48 h at 20° C. and then treated with 150 ml of DCM. The white precipitate which deposited was filtered off. The filtrate was washed twice with 50 ml each of water, dried with magnesium sulfate and concentrated in vacuo. The residue was purified by vacuum distillation (105° C., 1 mm Hg). 3.1 g of the title compound were obtained as a pale yellow oil.

MS (ESI+): 164 c) 1-(2-Methylsulfanylphenyl)-4-oxocyclohexanecarbonitrile 3.05 g of (2-methylsulfanylphenyl)acetonitrile were added dropwise to a mixture of 3.3 ml of 30% strength sodium methylate solution in MOH and 10 ml of dry THF and stirred for 1 h at 20° C. 1.69 ml of methyl acrylate were then added at 20° C. and the reaction mixture was heated for 4 h under reflux. After cooling, the reaction mixture was poured onto cold 2 N hydrochloric acid and extracted three times with 100 ml each of DCM. The combined organic phases were washed with 100 ml of water and 100 ml of sodium chloride solution, dried with magnesium sulfate and concentrated in vacuo. The residue (4.7 g) was dissolved in 10 ml of dimethyl sulfoxide, 1.5 g of sodium chloride were added and the mixture was heated for 5 h at 180° C. After cooling, 150 ml of EA were added and the mixture was washed three times with 100 ml each of water. The organic phase was dried with magnesium sulfate and concentrated in vacuo. The residue was purified by preparative HPLC (acetonitrile/water). 1.2 g of the title compound were obtained.

MS (ESI+): 245.09
HPLC (Method LC1): Rt 1.53 min

EXAMPLE 184

1-(3-Methylsulfanylphenyl)-4-oxocyclohexanecarbonitrile

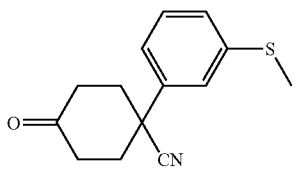

The title compound was prepared according to the process described in Example 183 via the intermediates (3-methylsulfanylphenyl)methanol (MS (ESI+): 155) and (3-methylsulfanylphenyl)acetonitrile (MS (ESI+): 164). In step c), the reaction mixture was not heated under reflux after the addition of the methyl acrylate, but stirred for 16 h at room temperature. From 2.9 g of (3-methylsulfanylphenyl)acetonitrile, 0.85 g of the title compound was obtained.

MS (ESI+): 246.05
HPLC (Method LC16): Rt 1.38 min

According to the process described in Examples 183 and 184, the corresponding substituted phenylacetonitrile was reacted with methyl acrylate to give the 4-oxo-1-(substituted phenyl)cyclohexanecarbonitriles of the formula VI listed in Table 6.

TABLE 6

Example compounds of the formula VI

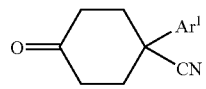

VI

| Example | Ar$^1$ | MS | HPLC (Rt [min], Method) |
|---|---|---|---|
| 185 | 4-fluorophenyl | 218.3 DCI | |
| 186 | 3-fluorophenyl | 218.05 ESI+ | 1.29 LC16 |
| 187 | 2-fluorophenyl | 218.15 ESI+ | 1.23 LC16 |
| 188 | 4-chlorophenyl | | |
| 189 | 3-chlorophenyl | | |
| 190 | 4-methoxyphenyl | (1) | |
| 191 | 3,4-dimethoxyphenyl | | |
| 192 | 4-trifluoromethoxyphenyl | 284.10 ESI+ | 1.53 LC16 |
| 193 | 3-trifluoromethoxyphenyl | 284.05 ESI+ | 1.52 LC16 |
| 194 | 2-trifluoromethoxyphenyl | 284.05 ESI+ | 1.44 LC16 |
| 195 | 4-methylphenyl | 214.15 ESI+ | 1.38 LC16 |
| 196 | 4-methylsulfanylphenyl | 246.05 ESI+ | 1.40 LC16 |

(1) $^1$H-NMR (d$_6$-DMSO; 500 MHz): 2.38 (m, 6H), 2.68 (m, 2H), 3.78 (s, 3H), 7.00 (AB system, 2H), 7.48 (AB system, 2H)

According to the preparation process described in Example 1, the 1-(substituted phenyl)-4-hydroxy-4-(substituted phenyl)cyclohexanecarbonitriles of the formula VIII listed in Table 7 were prepared by reaction of the corresponding substituted bromobenzene with n-butyllithium and the corresponding 4-oxo-1-(substituted phenyl)cyclohexanecarbonitrile.

TABLE 7

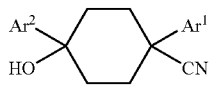

VIII

Example compounds of the formula VIII

| Example | Ar$^1$ | Ar$^2$ | MS | HPLC (Rt [min], Method) |
|---|---|---|---|---|
| 197 | 4-methoxyphenyl | 4-fluorophenyl | 308.15 ESI+ | 1.55 LC16 |
| 198 | 3-fluorophenyl | 4-fluorophenyl | 313.13 ESI+ | 2.23 LC15 |
| 199 | 2-fluorophenyl | 4-fluorophenyl | 313.13 ESI+ | 2.24 LC15 |
| 200 | 4-fluorophenyl | 4-fluorophenyl | 313.13 ESI+ | 1.81 LC8 |
| 201 | 4-methylphenyl | 4-fluorophenyl | 310.10 ESI+ | 1.64 LC16 |
| 202 | 4-methylsulfanylphenyl | 4-fluorophenyl | 324.10 ESI+, M − 17 | 1.63 LC16 |
| 203 | 3-methylsulfanylphenyl | 4-fluorophenyl | 342.47 ESI+ | 2.31 LC9 |
| 204 | 2-methylsulfanylphenyl | 4-fluorophenyl | 324.05 ESI+, M − 17 | 2.03 LC16 |
| 205 | 4-trifluoromethoxyphenyl | 4-fluorophenyl | 362.10 ESI+, M − 17 | 1.73 LC16 |
| 206 | 3-trifluoromethoxyphenyl | 4-fluorophenyl | 362.10 ESI+, M − 17 | 1.17 LC16 |
| 207 | 2-trifluoromethoxyphenyl | 4-fluorophenyl | 362.10 ESI+, M − 17 | 1.67 LC16 |
| 208 | 4-fluorophenyl | 2-methylsulfanylphenyl | 341.13 ESI+ | 1.94 LC10 |
| 209 | 4-fluorophenyl | 4-fluoro-2-methylsulfanylphenyl | | |
| 210 | 4-fluorophenyl | 5-fluoro-2-methylsulfanylphenyl | 359.12 ESI+ | 2.41 LC15 |

EXAMPLE 211

1-Bromo-4-fluoro-2-methylsulfanylbenzene

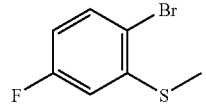

a) O-(2-Bromo-5-fluorophenyl)dimethylthiocarbamate 97.79 g of 2-bromo-5-fluorophenol, 106.10 g of potassium carbonate and 77.34 g of dimethylthiocarbamoyl chloride were stirred in 580 ml of DMF for 17 h at room temperature. Subsequently, the reaction mixture was slowly poured onto 300 g of ice in 1.9 l of water with stirring and stirred for 2 h at room temperature. The product was filtered off with suction and dried in vacuo. 120.63 g of the title compound were obtained as a pale yellow solid.

MP: 83° C.
MS (ESI+): 279
TLC (EA/HEP 1:4): Rf 0.44 b) S-(2-Bromo-5-fluorophenyl)dimethylthiocarbamate 120.63 g of O-(2-bromo-5-fluorophenyl)dimethylthiocarbamate were dissolved in 480 ml of N,N-diethylaniline and heated for 5 h under reflux. The reaction solution was slowly poured onto 1 kg of ice in 1.4 l of a 4 N hydrochloric acid with stirring and the mixture was allowed to stand overnight. It was then stirred for 15 min, and the product was filtered off with suction and dried in vacuo. 104.33 g of the title compound were obtained as a pale yellow solid.

MP: 97° C.
MS (ESI+): 279
TLC (EA/HEP 1:2): Rf 0.48 c) 2-Bromo-5-fluorothiophenol 51.30 g of S-(2-bromo-5-fluorophenyl) dimethylthiocarbamate were dissolved in 700 ml of MOH, 494 ml of a 1 N aqueous sodium hydroxide solution were added and the reaction mixture was heated for 2 h under reflux. After cooling, the MOH was removed in vacuo, 200 ml of water were added and the mixture was extracted three times with 150 ml each of DCM. Subsequently, the mixture was acidified to pH=1 with concentrated hydrochloric acid and extracted four times with 200 ml each of EA. The combined organic phases were dried over sodium sulfate and the solvent was removed in vacuo. 37.80 g of the title compound were obtained as a pale yellow oil.

MS (ESI+): 208
TLC (EA/HEP 1:4): Rf 0.70 d) 1-Bromo-4-fluoro-2-methylsulfanylbenzene 76.61 g of 2-bromo-5-fluorothiophenol were dissolved in 740 ml of DMF and 62.23 g of potassium carbonate were added. A solution of 26.07 ml of iodomethane in 130 ml of DMF was then added dropwise at a temperature between 3° C. and 11° C. The reaction mixture was stirred for 3 h at room temperature, then diluted with 3 l of water and extracted four times with 500 ml each of MTB. The combined extracts were dried over sodium sulfate and the solvent was removed in vacuo. 72.71 g of the title compound were obtained as a pale brown oil.

MS (ESI+): 222
TLC (HEP): Rf 0.47

According to the preparation process described in Example 41, the 1-(substituted phenyl)-4-(optionally substituted alkoxy)-4-(substituted phenyl)cyclohexane-carbonitriles of the formula X listed in Table 8 were prepared by reaction of the corresponding 1-(substituted phenyl)-4-hydroxy-4-(substituted phenyl)-cyclohexanecarbonitrile with potassium hydroxide and bromomethylcyclopropane or 1-bromopropane as alkylating agents.

TABLE 8

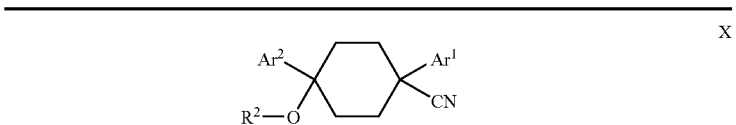

Example compounds of the formula X

| Example | Ar¹ | Ar² | R² | MS | HPLC (Rt [min], Method) |
|---|---|---|---|---|---|
| 212 | 3-fluorophenyl | 4-fluorophenyl | methyl | 296.15 ESI+, M − 31 | 1.81 LC16 |
| 213 | 2-fluorophenyl | 4-fluorophenyl | methyl | 296.15 ESI+, M − 31 | 1.79 LC16 |
| 214 | 4-fluorophenyl | 4-fluorophenyl | cyclopropylmethyl | 367.17 ESI+ | 2.29 LC10 |
| 215 | 4-methylphenyl | 4-fluorophenyl | cyclopropylmethyl | 292.10 ESI+, M − 31 | 1.90 LC16 |
| 216 | 4-methylsulfanylphenyl | 4-fluorophenyl | methyl | 324.15 ESI+, M − 31 | 1.89 LC16 |
| 217 | 4-methylsulfanylphenyl | 4-fluorophenyl | cyclopropylmethyl | 324.10 ESI+, M − 71 | 2.05 LC16 |
| 218 | 3-methylsulfanylphenyl | 4-fluorophenyl | cyclopropylmethyl | 324.10 ESI+, M − 71 | 2.03 LC16 |
| 219 | 2-methylsulfanylphenyl | 4-fluorophenyl | cyclopropylmethyl | 324.10 ESI+, M − 71 | 2.04 LC16 |
| 220 | 4-trifluoromethoxyphenyl | 4-fluorophenyl | methyl | 362.10 ESI+, M − 31 | 1.95 LC16 |
| 221 | 3-trifluoromethoxyphenyl | 4-fluorophenyl | methyl | 362.10 ESI+, M − 31 | 1.95 LC16 |
| 222 | 2-trifluoromethoxyphenyl | 4-fluorophenyl | methyl | 362.10 ESI+, M − 31 | 1.91 LC16 |

TABLE 8-continued

Example compounds of the formula X

| Example | Ar¹ | Ar² | R² | MS | HPLC (Rt [min], Method) |
|---|---|---|---|---|---|
| 223 | 4-fluorophenyl | 4-fluoro-2-methyl-sulfanylphenyl | cyclopropylmethyl | 342.05 ESI+ | 1.69 LC16 |
| 224 | 4-fluorophenyl | 4-fluoro-2-methyl-sulfanylphenyl | n-propyl | | |
| 225 | 4-fluorophenyl | 2-methylsulfanyl-phenyl | n-propyl | 383.17 ESI+ | 2.87 LC9 |
| 226 | 4-fluorophenyl | 2-methylsulfanyl-phenyl | cyclopropylmethyl | 395.17 ESI+ | 244 LC10 |
| 227 | 4-fluorophenyl | 5-fluoro-2-methyl-sulfanylphenyl | cyclopropylmethyl | 413.16 ESI+ | 2.46 LC10 |

According to the preparation process described in Example 92, the 1-(substituted phenyl)-4-hydroxy-4-(optionally substituted phenyl)cyclohexanecarboxylic acids of the formula Ib listed in Table 9 were prepared from the corresponding 1-(substituted phenyl)-4-hydroxy-4-(optionally substituted phenyl)cyclohexanecarbonitrile by reaction with potassium hydroxide.

TABLE 9

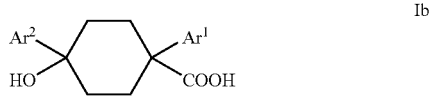

Example compounds of the formula Ib

| Example | Ar¹ | Ar² | MS | HPLC (Rt [min], Method) |
|---|---|---|---|---|
| 228 | 4-chlorophenyl | 4-chlorophenyl | 364.06 ESI+ | 2.20 LC9 |
| 229 | 4-methoxyphenyl | 4-chlorophenyl | 360.11 ESI+ | 2.04 LC9 |
| 230 | 4-methoxyphenyl | 4-fluorophenyl | 344.14 ESI+ | 1.91 LC9 |
| 231 | 3-chlorophenyl | 4-chlorophenyl | 364.06 ESI+ | 2.19 LC9 |
| 232 | 3,4-dimethoxyphenyl | 4-chlorophenyl | 390.12 ESI+ | 1.91 LC9 |

According to the preparation process described in Example 92, the 1-(substituted phenyl)-4-(optionally substituted alkoxy)-4-(substituted phenyl)cyclohexanecarboxylic acids of the formula Ia listed in Table 10 were prepared from the corresponding 1-(substituted phenyl)-4-(optionally substituted alkoxy)-4-(substituted phenyl)cyclohexanecarbonitrile by reaction with potassium hydroxide.

TABLE 10

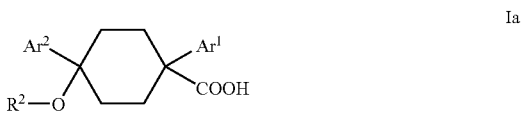

Example compounds of the formula Ia

| Example | Ar¹ | Ar² | R² | MS | HPLC (Rt [min], Method) |
|---|---|---|---|---|---|
| 233 | 4-methoxy-phenyl | 4-fluorophenyl | methyl | 281.21 ESI+, M − 77 | 2.71 LC1 |
| 234 | 3-fluorophenyl | 4-fluorophenyl | methyl | 315.3 DCI | |
| 235 | 2-fluorophenyl | 4-fluorophenyl | methyl | 346.14 ESI− | 2.22 LC17 |
| 236 | 4-trifluoro-methoxyphenyl | 4-fluorophenyl | methyl | 412.13 ESI− | 2.45 LC1 |
| 237 | 3-trifluoro-methoxyphenyl | 4-fluorophenyl | methyl | 335.23 ESI+, M − 77 | 2.00 LC1 |
| 238 | 2-trifluoro-methoxyphenyl | 4-fluorophenyl | methyl | 381.4 DCI, M − 31 | |
| 239 | 4-methylphenyl | 4-fluorophenyl | methyl | 342.16 ESI− | 2.30 LC17 |

TABLE 10-continued

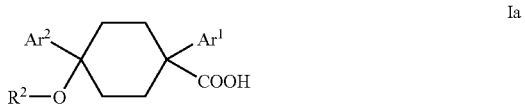

Example compounds of the formula Ia

| Example | Ar¹ | Ar² | R² | MS | HPLC (Rt [min], Method) |
|---|---|---|---|---|---|
| 240 | 4-methyl-sulfanylphenyl | 4-fluorophenyl | methyl | 373.14 ESI– | 2.38 LC17 |
| 241 | 4-methyl-sulfanylphenyl | 4-fluorophenyl | cyclopropyl-methyl | 414.20 ESI– | 2.58 LC17 |
| 242 | 4-fluorophenyl | 4-fluoro-2-methyl-sulfanylphenyl | n-propyl | 420.16 ESI– | 2.64 LC17 |
| 243 | 4-fluorophenyl | 4-fluoro-2-methyl-sulfanylphenyl | cyclopropyl-methyl | | |
| 244 | 4-fluorophenyl | 2-methylsulfanyl-phenyl | cyclopropyl-methyl | 414.20 ESI– | 2.60 LC17 |
| 245 | 3-methyl-sulfanylphenyl | 4-fluorophenyl | cyclopropyl-methyl | | |
| 246 | 2-methyl-sulfanylphenyl | 4-fluorophenyl | cyclopropyl-methyl | 343.16 ESI+, M − 71 | 2.58 LC1 |
| 247 | 4-fluorophenyl | 5-fluoro-2-methyl-sulfanylphenyl | cyclopropyl-methyl | 432.16 ESI– | 2.62 LC17 |
| 248 | 4-fluorophenyl | 5-fluoro-2-methyl-sulfanylphenyl | n-propyl | 419.45 ESI– | 2.66 LC1 |
| 249 | 4-fluorophenyl | 4-fluorophenyl | cyclopropyl-methyl | 386.17 ESI– | 2.49 LC17 |
| 250 | 2-methyl-sulfanylphenyl | 4-fluorophenyl | ethyl | 297.15 ESI+, M − 90 | 2.47 LC1 |

According to the preparation process described in Example 164, the 1-(substituted phenyl)-4-(optionally substituted alkoxy)-4-(substituted phenyl)cyclohexanecarboxylic acids of the formula Ia comprising a methanesulfonyl substituent which are listed in Table 11 were prepared from the corresponding 1-(substituted phenyl)-4-(optionally substituted alkoxy)-4-(substituted phenyl)cyclohexanecarboxylic acid comprising a methylsulfanyl substituent by oxidation with 3-chloroperbenzoic acid.

TABLE 11

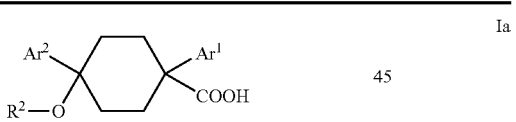

Example compounds of the formula Ia

| Example | Ar¹ | Ar² | R² | MS | HPLC (Rt [min], Method) |
|---|---|---|---|---|---|
| 251 | 4-methane-sulfonylphenyl | 4-fluorophenyl | methyl | 407.50 ESI– | 2.03 LC17 |
| 252 | 4-methane-sulfonylphenyl | 4-fluorophenyl | cyclopropyl-methyl | 447.14 ESI– | 2.11 LC1 |
| 253 | 4-fluorophenyl | 4-fluoro-2-methane-sulfonylphenyl | cyclopropyl-methyl | 347.06 ESI+, M − 117 | 1.87 LC1 |
| 254 | 4-fluorophenyl | 2-methanesulfonyl-phenyl | cyclopropyl-methyl | 446.16 ESI– | 2.14 LC17 |
| 255 | 4-fluorophenyl | 2-methanesulfonyl-phenyl | n-propyl | 434.10 ESI– | 2.16 LC17 |
| 256 | 2-methane-sulfonylphenyl | 4-fluorophenyl | cyclopropyl-methyl | 401.65 ESI–, M − 45 | 2.16 LC17 |
| 257 | 3-methane-sulfonylphenyl | 4-fluorophenyl | cyclopropyl-methyl | 447.62 ESI– | 2.19 LC1 |
| 258 | 4-fluorophenyl | 5-fluoro-2-methane-sulfonylphenyl | cyclopropyl-methyl | 464.15 ESI– | 2.21 LC17 |
| 259 | 2-methane-sulfonylphenyl | 4-fluorophenyl | ethyl | 375.67 ESI–, M − 45 | 2.07 LC17 |

EXAMPLE 260

Cis-1-(4-Fluorophenyl)-4-(5-fluoropyridin-2-yl)-4-hydroxycyclohexanecarbonitrile and Trans-(4-fluorophenyl)-4-(5-fluoropyridin-2-yl)-4-hydroxycyclohexanecarbonitrile

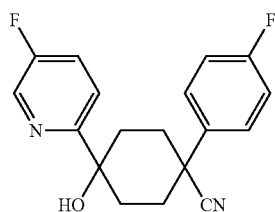

In a three-necked flask equipped with a septum, stirrer and reflux condenser, which had been dried and flushed with argon, 25 mmol of 2-bromo-5-fluoropyridine were added with stirring at −15° C. to 25 ml of a solution of isopropylmagnesium chloride×lithium chloride (1 M in THF; 25 mmol) cooled to −15° C. The mixture was stirred for 30 min at −5° C. 25 mmol of 1-(4-fluorophenyl)-4-oxocyclohexanecarbonitrile (dissolved in 50 ml of THF) were then added dropwise to the pale-yellow, clear solution of the Grignard reagent obtained. After addition was complete, the reaction mixture was allowed to slowly warm to room temperature and was stirred for 12 h at room temperature. It was then added to ice water, acidified with saturated ammonium chloride solution and extracted three times with EA. The combined organic phases were dried over magnesium sulfate and the solvent was removed in vacuo. By means of chromatographic separation (silica gel flash column; HEP/EA 3:1) of the crude product (cis/trans mixture), 1.8 g of the trans title compound and 2.2 g of the cis title compound were obtained.

EXAMPLE 260-1

Trans-(4-Fluorophenyl)-4-(5-fluoropyridin-2-yl)-4-hydroxycyclohexanecarbonitrile

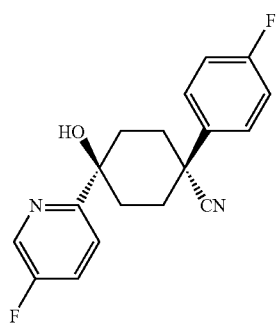

TLC (HEP/EA 1:1): Rf 0.59
MS (ESI+): 314
HPLC (Method LC1): Rt 1.71 min

EXAMPLE 260-2

Cis-1-(4-Fluorophenyl)-4-(5-fluoropyridin-2-yl)-4-hydroxycyclohexanecarbonitrile

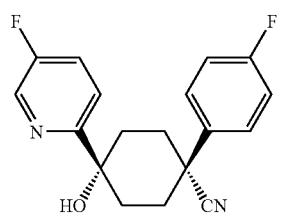

TLC (HEP/EA 1:1): Rf 0.50
MS (ESI+): 314
HPLC (Method LC1): Rt 1.66 min

EXAMPLE 261

Cis-4-Cyclopropylmethoxy-1-(4-fluorophenyl)-4-(5-fluoropyridin-2-yl)cyclohexanecarbonitrile

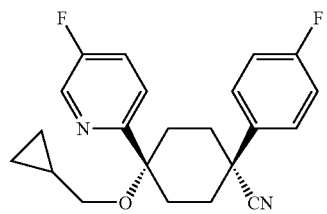

2.1 g of cis-1-(4-fluorophenyl)-4-(5-fluoropyridin-2-yl)-4-hydroxycyclohexanecarbonitrile were dissolved in 20 ml of DMF, 0.4 g of sodium hydride (80% strength in mineral oil) and 4.51 g of bromomethylcyclopropane were added and the reaction mixture was stirred for 24 h at room temperature. One equivalent of sodium hydride and bromomethylcyclopropane each were then added, the reaction mixture was stirred for 24 h at room temperature, subsequently treated with water and extracted with EA. The combined organic phases were dried over magnesium sulfate and the solvent was removed in vacuo. By means of chromatography (silica gel; HEP/EA 2:1) of the residue, 2.1 g of the title compound were obtained as a viscous yellow oil.

MS (ESI+): 368
HPLC (Method LC1): Rt 2.22 min

EXAMPLE 262

Cis-4-Cyclopropylmethoxy-1-(4-fluorophenyl)-4-(5-fluoropyridin-2-yl)cyclohexanecarboxamide

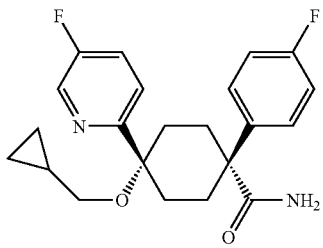

2 g of cis-4-cyclopropylmethoxy-1-(4-fluorophenyl)-4-(5-fluoropyridin-2-yl)cyclohexanecarbonitrile were taken up in 60 ml of MOH, treated with 20 ml of hydrogen peroxide solution (30% strength) and 2 ml of an aqueous potassium hydroxide solution (25% strength) and the reaction mixture was stirred for 12 h at 55° C. It was then treated with water and extracted with EA. The combined extracts were dried over magnesium sulfate and the solvent was removed. The main quantity of the yellowish crude product obtained (2 g) was hydrolyzed without further purification to give the carboxylic acid. The pure title compound was prepared from a part of the crude product by preparative HPLC.

MS (ESI+): 387

HPLC (Method LC1): Rt 1.68 min

EXAMPLE 263

Cis-4-Cyclopropylmethoxy-1-(4-fluorophenyl)-4-(5-fluoropyridin-2-yl)cyclohexanecarboxylic Acid

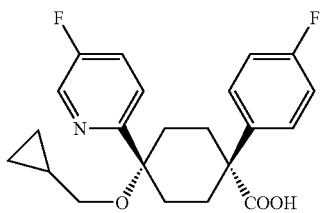

1.3 g of cis-4-cyclopropylmethoxy-1-(4-fluorophenyl)-4-(5-fluoropyridin-2-yl)cyclohexanecarboxamide were taken up in 20 ml of MOH, treated with 10 ml of an aqueous sodium hydroxide solution (10% strength) and the reaction mixture was heated to reflux for 48 h with stirring. For workup, water was added, the mixture was extracted twice with 10 ml each of EA, and the aqueous phase was acidified to pH=4 with 1 N hydrochloric acid and likewise extracted with EA. The combined organic phases from the basic and the acidic extraction were concentrated and the residue was purified by chromatography (silica gel; HEP/EA 1:1). The product obtained (500 mg) was purified by preparative HPLC. 250 mg of the title compound were obtained as a white powder.

MS (ESI+): 388

HPLC (Method LC2): Rt 2.36 min

EXAMPLE 264

4-(5-Fluoropyridin-2-yl)-4-hydroxy-1-phenylcyclohexanecarbonitrile

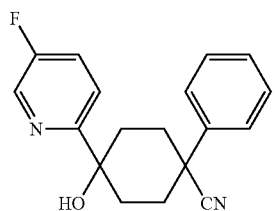

According to the process described in Example 260, 25 mmol of 2-bromo-5-fluoropyridine were converted into the Grignard reagent and reacted with 25 mmol of 4-oxo-1-phenylcyclohexanecarbonitrile (dissolved in 100 ml of THF). The chromatographic separation of the crude product (silica gel flash column; HEP/EA 3:1) afforded two main fractions (TLC (HEP/EA 1:1): Rf 0.58 and 0.49), which were combined. 6.6 g of the title compound (cis/trans mixture) were obtained as a viscous yellow oil.

MS (ESI+): 296

HPLC (Method LC9): Rt 1.99 min and 2.08 min

EXAMPLE 265

Cis-4-Cyclopropylmethoxy-4-(5-fluoropyridin-2-yl)-1-phenylcyclohexanecarbonitrile

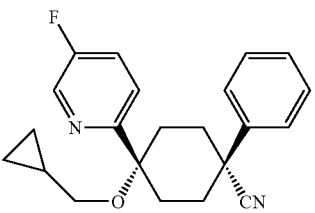

6.6 g of 4-(5-fluoropyridin-2-yl)-4-hydroxy-1-phenylcyclohexanecarbonitrile were dissolved in 50 ml of DMF, 1.7 g of sodium hydride (80% strength in mineral oil) and 11 ml of bromomethylcyclopropane were added and the reaction was carried out as described in Example 261. By means of chromatographic purification (silica gel; HEP/EA 3:1) of the residue, 3.1 g of the title compound (cis isomer) were obtained as a viscous yellow oil.

MS (ESI+): 351

HPLC (Method LC16): Rt 1.91 min

EXAMPLE 266

Cis-4-Cyclopropylmethoxy-4-(5-fluoropyridin-2-yl)-1-phenylcyclohexanecarboxamide

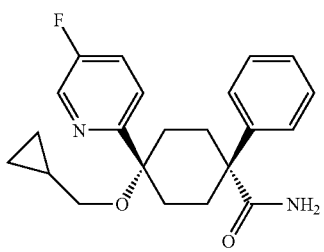

550 mg of cis-4-cyclopropylmethoxy-4-(5-fluoropyridin-2-yl)-1-phenylcyclohexanecarbonitrile were taken up in 10 ml of MOH, treated with 10 ml of hydrogen peroxide solution (30% strength) and 1 ml of an aqueous potassium hydroxide solution (25% strength) and the reaction was carried out as described in Example 262. The main quantity of the crude product obtained in the form of a white solid (520 mg) was hydrolyzed to the carboxylic acid without further purification. The pure title compound was prepared from a part of the crude product by preparative HPLC.

MS (ESI+): 369

HPLC (Method LC1): Rt 1.72 min

The structure of the compound was confirmed by X-ray structural analysis.

EXAMPLE 267

Cis-4-Cyclopropylmethoxy-4-(5-fluoropyridin-2-yl)-1-phenylcyclohexanecarboxylic Acid

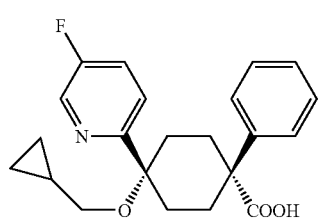

500 mg of cis-4-cyclopropylmethoxy-4-(5-fluoropyridin-2-yl)-1-phenylcyclohexanecarboxamide were taken up in 10 ml of MOH, treated with 2 ml of an aqueous sodium hydroxide solution (10% strength) and the reaction was carried out as described in Example 264. By means of chromatographic purification (silica gel; HEP/EA 1:1) of the crude product obtained from the basic and from the acidic extraction, 220 mg of the title compound were obtained as a white solid.

TLC (HEP/EA 1:1): Rf 0.4

MS (ESI+): 370

HPLC (Method LC1): Rt 1.90 min

EXAMPLE 268

Cis-4-Hydroxy-1-phenyl-4-(5-phenyl-1H-[1,2,4]triazol-3-yl)cyclohexanecarbonitrile and Trans-4-hydroxy-1-phenyl-4-(5-phenyl-1H-[1,2,4]triazol-3-yl)cyclohexanecarbonitrile

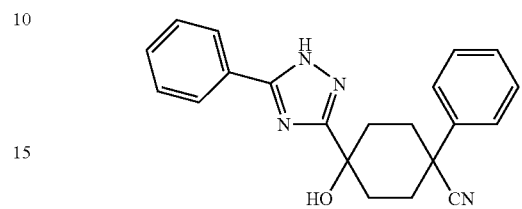

Under an argon atmosphere, 4.5 g of 5-bromo-3-phenyl-1H-[1,2,4]triazole were dissolved in 40 ml of dry THF in a dried two-necked flask, cooled to −70° C., and 30.9 ml of n-butyllithium solution (1.55 M in THF) were slowly added dropwise so that the internal temperature did not exceed −65° C. The reaction mixture was stirred for 1 h at −70° C. and subsequently a suspension of 4.0 g of 4-oxo-1-phenylcyclohexanecarbonitrile in 30 ml of THF was added dropwise so slowly that the internal temperature did not exceed −65° C. The reaction mixture was stirred for 1 h at −70° C., subsequently warmed to room temperature and stirred for 12 h at room temperature. For workup, it was added to ice water, acidified with saturated ammonium chloride solution and extracted three times with EA. The combined organic phases were dried over magnesium sulfate and the solvent was removed in vacuo. By means of chromatographic separation (silica gel flash column; from HEP/EA 1:2 to EA) of the crude product (cis/trans mixture), 0.6 g of the trans title compound and 1.1 g of the cis title compound were obtained.

EXAMPLE 268-1

Trans-4-Hydroxy-1-phenyl-4-(5-phenyl-1H-[1,2,4]triazol-3-yl)cyclohexanecarbonitrile

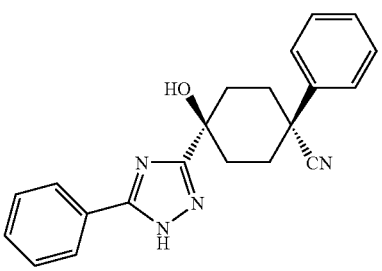

MS (ESI+): 345

HPLC (Method LC16): Rt 1.33 min

EXAMPLE 268-2

Cis-4-Hydroxy-1-phenyl-4-(5-phenyl-1H-[1,2,4]triazol-3-yl)cyclohexanecarbonitrile

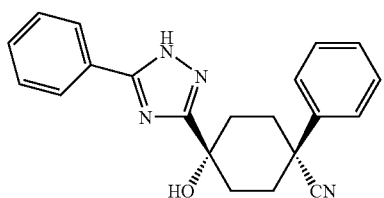

MS (ESI+): 345

HPLC (Method LC16): Rt 1.36 min

EXAMPLE 269

Trans-4-Cyclopropylmethoxy-4-(1-cyclopropylmethyl-5-phenyl-1H-[1,2,4]triazol-3-yl)-1-phenylcyclohexanecarbonitrile

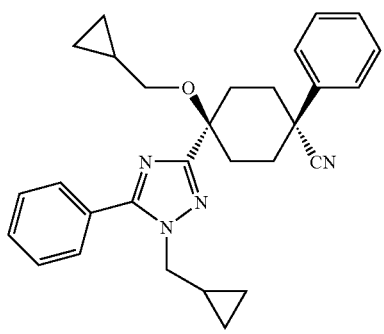

570 mg of trans-4-hydroxy-1-phenyl-4-(5-phenyl-1H-[1,2,4]triazol-3-yl)cyclohexanecarbonitrile were dissolved in 15 ml of dry DMF in a flask which had been dried and flushed with argon, treated with 120 mg of sodium hydride (80% strength in mineral oil) and stirred for 30 min at room temperature. Subsequently, 0.32 ml of bromomethylcyclopropane was slowly added dropwise. The reaction mixture was stirred for 3 h, then treated with water and extracted with EA. The combined organic phases were dried over magnesium sulfate and the solvent was removed in vacuo. The crude product was purified by preparative HPLC. 210 mg of the title compound were obtained.

MS (ESI+): 452

HPLC (Method LC1): Rt 2.32 min

EXAMPLE 270

Trans-4-Cyclopropylmethoxy-4-(1-cyclopropylmethyl-5-phenyl-1H-[1,2,4]triazol-3-yl)-1-phenylcyclohexanecarboxylic Acid

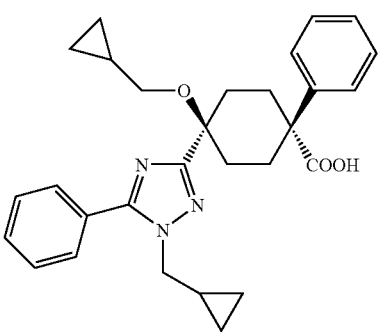

180 mg of trans-4-cyclopropylmethoxy-4-(1-cyclopropyl methyl-5-phenyl-1H-[1,2,4]triazol-3-yl)-1-phenylcyclohexanecarbonitrile were dissolved in 5 ml of ethylene glycol and 66 mg of potassium hydroxide were added. The reaction mixture was subsequently stirred for 12 h at 200° C. After cooling, the reaction mixture was poured onto an ice/water mixture and extracted three times with EA. The aqueous phase was acidified to pH=4 with 1 N hydrochloric acid, extracted twice with EA, and the combined extracts were dried over magnesium sulfate and the solvent was removed. 25 mg of the title compound were obtained as a white solid, which was recrystallized from EA.

MS (ESI+): 471

HPLC (Method LC1): Rt 1.98 min

The structure of the compound was confirmed by X-ray structural analysis.

EXAMPLE 271

Cis-4-Cyclopropylmethoxy-4-(1-cyclopropylmethyl-5-phenyl-1H-[1,2,4]triazol-3-yl)-1-phenylcyclohexanecarbonitrile and Cis-4-cyclopropylmethoxy-4-(2-cyclopropylmethyl-5-phenyl-2H-[1,2,4]triazol-3-yl)-1-phenylcyclohexanecarbonitrile 570 mg of cis-4-hydroxy-1-phenyl-4-(5-phenyl-1H-[1,2,4]triazol-3-yl)cyclohexanecarbonitrile were dissolved in 20 ml of dry DMF in a flask which had been dried and flushed with argon, treated with 250 mg of sodium hydride (80% strength in mineral oil) and stirred for 30 min at room temperature. Subsequently, 0.66 ml of bromomethylcyclopropane was slowly added dropwise. The reaction mixture was stirred for 12 h, then treated with water and extracted with EA. The combined organic phases were dried over magnesium sulfate and the solvent was removed in vacuo. The crude product (mixture of the 1H-[1,2,4]triazole derivative and of the 2H-[1,2,4]triazole derivative) was separated into the two isomeric triazole derivatives by preparative HPLC.

EXAMPLE 271-1

Cis-4-Cyclopropylmethoxy-4-(1-cyclopropylmethyl-5-phenyl-1H-[1,2,4]triazol-3-yl)-1-phenylcyclohexanecarbonitrile

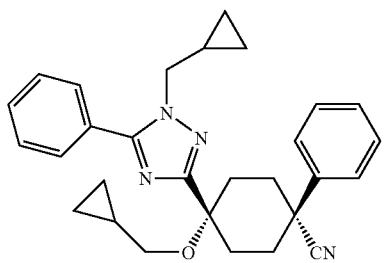

MS (ESI+): 453
HPLC (Method LC1): Rt 2.18 min

EXAMPLE 271-2

Cis-4-Cyclopropylmethoxy-4-(2-cyclopropylmethyl-5-phenyl-2H-[1,2,4]triazol-3-yl)-1-phenylcyclohexanecarbonitrile

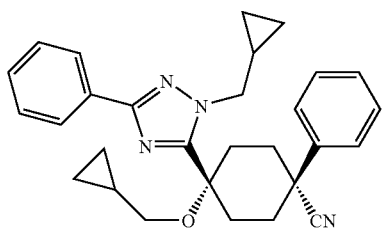

MS (ESI+): 453
HPLC (Method LC1): Rt 2.60 min

EXAMPLE 272

Cis-4-Cyclopropylmethoxy-4-(1-cyclopropylmethyl-5-phenyl-1H-[1,2,4]triazol-3-yl)-1-phenylcyclohexanecarboxylic Acid

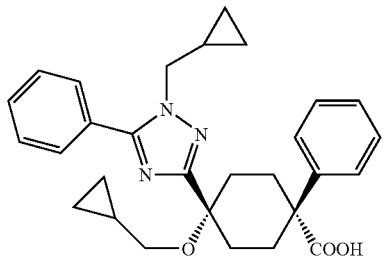

970 mg of cis-4-cyclopropylmethoxy-4-(1-cyclopropylmethyl-5-phenyl-1H-[1,2,4]triazol-3-yl)-1-phenylcyclohexanecarbonitrile were dissolved in 15 ml of ethylene glycol and 600 mg of potassium hydroxide were added. The reaction mixture was subsequently stirred for 24 h at 200° C. After cooling, the reaction mixture was treated with saturated ammonium chloride solution and extracted twice with EA. The combined extracts were dried over magnesium sulfate and the solvent was removed. After chromatographic purification (silica gel; HEP/EA 3:2) 670 mg of the title compound were obtained as a white solid, which was recrystallized from EA.

MS (ESI+): 472
HPLC (Method LC1): Rt 1.88 min

The structure of the compound was confirmed by X-ray structural analysis.

EXAMPLE 273

Cis-4-Cyclopropylmethoxy-4-(2-cyclopropylmethyl-5-phenyl-2H-[1,2,4]triazol-3-yl)-1-phenylcyclohexanecarboxylic Acid

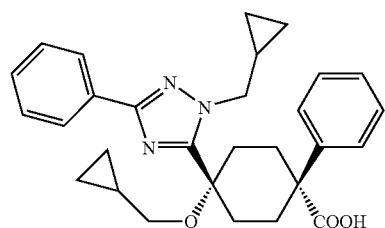

280 mg of cis-4-cyclopropylmethoxy-4-(2-cyclopropylmethyl-5-phenyl-2H-[1,2,4]triazol-3-yl)-1-phenylcyclohexanecarbonitrile were dissolved in 10 ml of ethylene glycol and 104 mg of potassium hydroxide were added. The reaction mixture was subsequently stirred for 12 h at 200° C. After cooling, the reaction mixture was poured onto an ice/water mixture and extracted three times with EA. The aqueous phase was acidified to pH=4 with 1 N hydrochloric acid, extracted twice with EA. The combined extracts were dried over magnesium sulfate and the solvent was removed. After purification by preparative HPLC, 270 mg of the title compound were obtained as a white solid, which was recrystallized from EA.

MS (ESI+): 472
HPLC (Method LC1): Rt 2.31 min

The structure of the compound was confirmed by X-ray structural analysis.

EXAMPLE 274

4-Cyclopropylmethoxy-4-(4'-fluorobiphenyl-4-yl)-1-phenylcyclohexanecarboxylic Acid

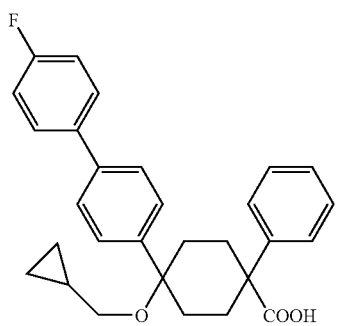

19 mg of tetrakis(triphenylphosphine)palladium(0) were added to a solution of 200 mg of 4-(4-bromophenyl)-4-cyclopropylmethoxy-1-phenylcyclohexanecarboxylic acid in 4 ml of degassed toluene under argon in a two-necked flask and the mixture was stirred for 10 min at room temperature. Subsequently, 65.1 mg of 4-fluorobenzeneboronic acid and 0.341 ml of a 2 M sodium carbonate solution were added and the reaction mixture was heated for 24 h at 100° C. After cooling, water and EA were added, the organic phase was separated and the aqueous phase was extracted twice with EA. The combined organic phases were dried over magnesium sulfate and the solvent was removed in vacuo. After purification of the residue by preparative HPLC, 20 mg of the title compound were obtained as a white lyophilizate.

MS (ESI−): 443

HPLC (Method LC14): Rt 2.65 min

According to the process described in Example 274, the 4-cyclopropylmethoxy-1-phenyl-4-(4-substituted phenyl)cyclohexanecarboxylic acids and 4-cyclopropylmethoxy-1-phenyl-4-(4-substituted phenyl)cyclohexanecarbonitriles of the formula XX listed in Table 12 were prepared from 4-(4-bromophenyl)-4-cyclopropylmethoxy-1-phenylcyclohexanecarboxylic acid or 4-(4-bromophenyl)-4-cyclopropylmethoxy-1-phenylcyclohexanecarbonitrile and the corresponding boronic acid.

TABLE 12

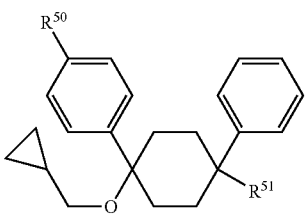

XX

Example compounds of the formula XX

| Example | $R^{50}$ | $R^{51}$ | MS | HPLC (Rt [min], Method) |
|---|---|---|---|---|
| 275 | 3-bromo-4-fluorophenyl | —COOH | 522 ESI− | 3.32 LC9 |
| 276 | 2-fluoropyridin-3-yl | —CN | 427 ESI+ | 2.62 LC15 |
| 277 | pyridin-3-yl | —CN | 409 ESI+ | 1.80 LC15 |

EXAMPLE 278

4-Cyclopropylmethoxy-1-phenyl-4-(4-(pyridin-3-yl)phenyl)cyclohexanecarboxylic Acid

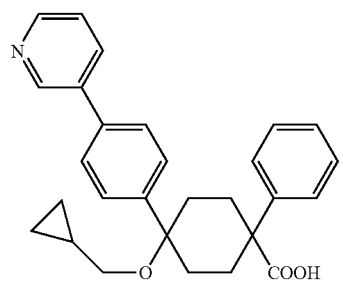

The title compound was prepared from 4-cyclopropylmethoxy-1-phenyl-4-(4-(pyridin-3-yl)phenyl)cyclohexanecarbonitrile with potassium hydroxide according to the process described in Example 92.

MS (ESI+): 428

HPLC (Method LC1): Rt 1.35 min

EXAMPLE 279

Sodium 4-cyclopropylmethoxy-4-(4-fluorophenyl)-1-phenylcyclohexanecarboxylate

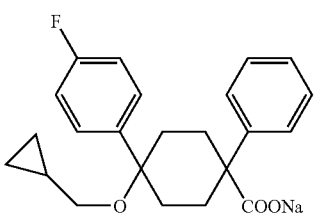

185 mg of 4-cyclopropylmethoxy-4-(4-fluorophenyl)-1-phenylcyclohexanecarboxylic acid were treated with 0.5 ml of a 1 M sodium hydroxide solution and 2 ml of water and cautiously heated to 100° C. The solution became clear. The sodium salt crystallized during cooling. It was filtered off with suction and dried. 155 mg of the title compound were obtained as silvery white flakes.

MS (ESI−): 367 (M-23)

HPLC (Method LC12): Rt 2.40 min

EXAMPLE 280

Sodium 4-ethoxy-4-(4-fluorophenyl)-1-phenylcyclohexanecarboxylate

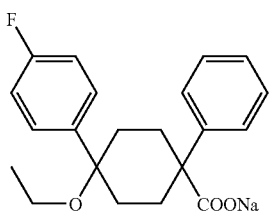

The title compound prepared from 4-ethoxy-4-(4-fluorophenyl)-1-phenylcyclohexanecarboxylic acid according to the process described in Example 279.
MS (ESI−): 341 (M-23)
HPLC (Method LC13): Rt 3.34 min

EXAMPLE 281

Sodium 4-methoxy-4-(6-methoxypyridin-3-yl)-1-phenylcyclohexanecarboxylate

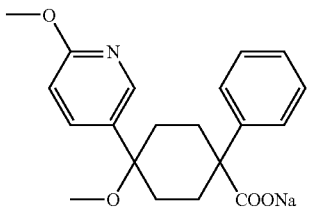

The title compound was prepared from 4-methoxy-4-(6-methoxypyridin-3-yl)-1-phenylcyclohexanecarboxylic acid according to the process described in Example 279.
MS (ESI+): 341 (M-22)
HPLC (Method LC1): Rt 1.48 min

EXAMPLE 282

Cis-4-Hydroxy-1-phenyl-4-(2H-[1,2,4]triazol-3-yl)cyclohexanecarbonitrile and Trans-4-hydroxy-1-phenyl-4-(2H-[1,2,4]triazol-3-yl)cyclohexanecarbonitrile

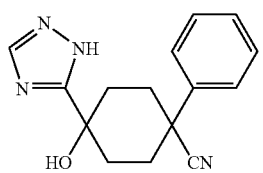

48.2 ml of a 1.6 M solution of n-butyllithium in n-hexane were added dropwise at −70° C. to a solution of 10.0 g of 1-pyrrolidin-1-ylmethyl-1H-[1,2,4]triazole (Katritzky et al., J. Org. Chem. 63, 4323-4331 (1998)) in 250 ml of anhydrous THF. The mixture was stirred at −75° C. for 15 min, subsequently at 25° C. for 30 min, then a solution of 13.1 g of 4-oxo-1-phenylcyclohexanecarbonitrile in 100 ml of anhydrous THF was added dropwise at −70° C. The mixture was stirred at −75° C. for 2 h, then warmed to room temperature and subsequently poured onto 1000 ml of a saturated aqueous ammonium chloride solution. The mixture was extracted three times with 200 ml each of EA, the combined organic phases were dried over magnesium sulfate and the solvent was removed in vacuo. 18 g of a viscous oil were obtained, which was chromatographed on silica gel using EA. 9.5 g of the title compound (cis/trans mixture) were obtained as an amorphous solid.
TLC (EA): Rf 0.18

EXAMPLE 283

Cis-4-Hydroxy-4-(2-methyl-2H-[1,2,4]triazol-3-yl)-1-phenylcyclohexanecarbonitrile and Trans-4-hydroxy-4-(2-methyl-2H-[1,2,4]triazol-3-yl)-1-phenylcyclohexanecarbonitrile; Cis-4-hydroxy-4-(1-methyl-1H-[1,2,4]triazol-3-yl)-1-phenylcyclohexanecarbonitrile and Trans-4-hydroxy-4-(1-methyl-1H-[1,2,4]triazol-3-yl)-1-phenylcyclohexanecarbonitrile 1.0 g of potassium carbonate, 2.0 g of the compound of Example 282 and 1.1 g of iodomethane were stirred at room temperature for 3 h in 20 ml of anhydrous DMF. Subsequently, the mixture was poured onto 100 ml of water and extracted three times with 100 ml each of EA. The combined organic phases were dried over magnesium sulfate and the solvent was removed in vacuo. By chromatography on reversed phase silica gel, 730 mg of 2-methyl derivative (cis/trans mixture) and 1.2 g of 1-methyl derivative (cis/trans mixture) were obtained.

EXAMPLE 283-1

Cis-4-Hydroxy-4-(2-methyl-2H-[1,2,4]triazol-3-yl)-1-phenylcyclohexanecarbonitrile and Trans-4-hydroxy-4-(2-methyl-2H-[1,2,4]triazol-3-yl)-1-phenylcyclohexanecarbonitrile

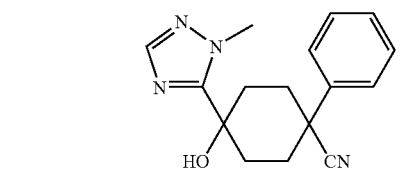

MS (ESI+): 283
TLC (EA): Rf 0.24

EXAMPLE 283-2

Cis-4-Hydroxy-4-(1-methyl-1H-[1,2,4]triazol-3-yl)-1-phenylcyclohexanecarbonitrile and Trans-4-hydroxy-4-(1-methyl-1H-[1,2,4]triazol-3-yl)-1-phenyl-cyclohexanecarbonitrile

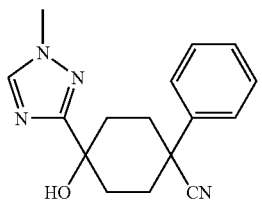

MS (ESI+): 283
TLC (EA): Rf 0.24

EXAMPLE 284

Cis-4-Cyclopropylmethoxy-4-(2-methyl-2H-[1,2,4]triazol-3-yl)-1-phenylcyclohexanecarbonitrile and Trans-4-cyclopropylmethoxy-4-(2-methyl-2H-[1,2,4]triazol-3-yl)-1-phenylcyclohexanecarbonitrile

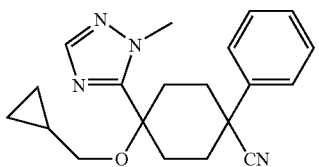

720 mg of the compound of Example 283-1 and 380 mg of bromomethylcyclopropane were dissolved in 20 ml of anhydrous DMF and treated with 67 mg of sodium hydride. The mixture was stirred at room temperature for 20 h, subsequently poured onto 50 ml of water and extracted three times with 50 ml each of EA. The combined organic phases were dried over magnesium sulfate and the solvent was removed in vacuo. 320 mg of the title compound (cis/trans mixture) were obtained as a viscous oil, which was further reacted without purification.

MS (ESI+): 337
TLC (EA): Rf 0.38

EXAMPLE 285

Cis-4-Cyclopropylmethoxy-4-(2-methyl-2H-[1,2,4]triazol-3-yl)-1-phenylcyclohexanecarboxylic Acid and Trans-4-cyclopropylmethoxy-4-(2-methyl-2H-[1,2,4]triazol-3-yl)-1-phenylcyclohexanecarboxylic Acid

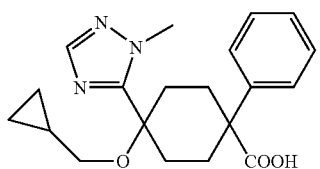

80 mg of the compound of Example 284 and 67 mg of potassium hydroxide in 1 ml of ethylene glycol were stirred at 200° C. for 7 h. The mixture was then allowed to cool to room temperature and poured onto 50 ml of water. It was adjusted to pH=4 using aqueous sodium hydrogensulfate solution and extracted three times with 20 ml each of EA. The combined organic phases were dried over magnesium sulfate and the solvent was removed in vacuo. By chromatography of the residue on reversed phase silica gel, 50 mg of the cis title compound and 10 mg of the trans title compound were obtained.

EXAMPLE 285-1

Cis-4-Cyclopropylmethoxy-4-(2-methyl-2H-[1,2,4]triazol-3-yl)-1-phenylcyclohexanecarboxylic Acid

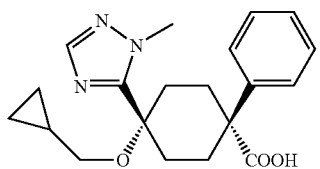

MS (ESI+): 356
TLC (EA): Rf 0.46

EXAMPLE 285-2

Trans-4-Cyclopropylmethoxy-4-(2-methyl-2H-[1,2,4]triazol-3-yl)-1-phenylcyclohexanecarboxylic Acid

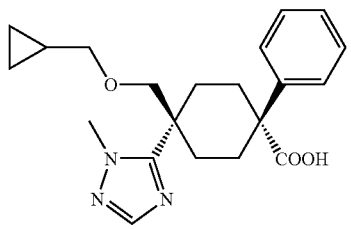

MS (ESI+): 356
TLC (EA): Rf 0.46

EXAMPLE 286

4-Cyclopropylmethoxy-4-(1-methyl-1H-[1,2,4]triazol-3-yl)-1-phenylcyclohexanecarbonitrile

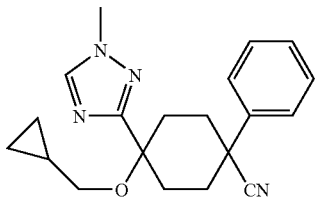

1.1 g of the compound of Example 283-2, 580 mg of bromomethylcyclopropane and 100 mg of sodium hydride in 20 ml of anhydrous DMF were stirred at room temperature for 20 h. Subsequently, a further 580 mg of bromomethylcyclopropane and 100 mg of sodium hydride were added and the mixture was stirred for 48 h at room temperature. It was then poured onto 50 ml of water and extracted three times with 50 ml each of EA. The combined organic phases were dried over magnesium sulfate and the solvent was removed in vacuo. 1.0 g of the title compound (cis/trans mixture) was obtained as a pale yellow oil.

MS (ESI+): 337
TLC (EA): Rf 0.35

EXAMPLE 287

4-Cyclopropylmethoxy-4-(1-methyl-1H-[1,2,4]triazol-3-yl)-1-phenylcyclohexanecarboxylic Acid

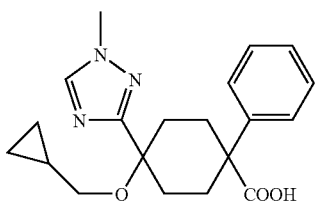

70 mg of the compound of Example 286 and 58 mg of potassium hydroxide in 2 ml of ethylene glycol were stirred at 200° C. for 6 h. The mixture was then poured onto 20 ml of water and extracted three times with 20 ml each of EA. The combined organic phases were dried over magnesium sulfate and the solvent was removed in vacuo. Chromatography on reversed phase silica gel yielded 40 mg of the title compound (mixture of cis-4-cyclopropylmethoxy-4-(1-methyl-1H-[1,2,4]triazol-3-yl)-1-phenylcyclohexanecarboxylic acid and trans-4-cyclopropylmethoxy-4-(1-methyl-1H-[1,2,4]triazol-3-yl)-1-phenylcyclohexanecarboxylic acid) as an amorphous solid.

MS (ESI+): 356

EXAMPLE 288

4-(1-Cyclobutyl-1H-[1,2,4]triazol-3-yl)-4-hydroxy-1-phenylcyclohexanecarbonitrile

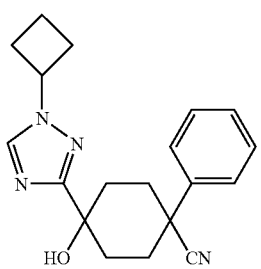

3.0 g of the compound of Example 282, 1.5 g of cyclobutyl bromide and 1.7 g of potassium carbonate in 30 ml of anhydrous DMF were stirred for 2 days at room temperature. Subsequently, the mixture was stirred for 5 h at 80° C., then a further 1.5 g of cyclobutyl bromide and 1.7 g of potassium carbonate were added and the mixture was stirred for 4 h at 80° C. Subsequently, 1.0 g of cyclobutyl bromide was added and the mixture was stirred for 6 h at 110° C. It was then poured onto 50 ml of water and extracted three times with 50 ml each of EA. The combined organic phases were dried over magnesium sulfate and the solvent was removed in vacuo. 3.2 g of the title compound were obtained as a pale yellow oil.

MS (ESI+): 323
TLC (EA): Rf 0.23

EXAMPLE 289

4-(1-Cyclobutyl-1H-[1,2,4]triazol-3-yl)-4-cyclopropylmethoxy-1-phenylcyclohexanecarbonitrile

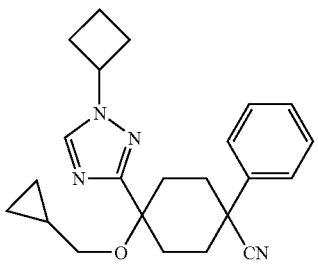

3.2 g of the compound of Example 288, 1.5 g of bromomethylcyclopropane and 260 mg of sodium hydride in 20 ml of anhydrous DMF were stirred at room temperature for 20 h. Subsequently, 1.5 g of bromomethylcyclopropane and 260 mg of sodium hydride were added and the mixture was stirred at room temperature for 48 h. It was then poured onto 100 ml of water and extracted three times with 100 ml each of EA. The combined organic phases were dried over magnesium sulfate and the solvent was removed in vacuo. 2.9 g of the title compound were obtained as a pale yellow oil.

MS (ESI+): 377
TLC (EA): Rf 0.53

EXAMPLE 290

4-(1-Cyclobutyl-1H-[1,2,4]triazol-3-yl)-4-cyclopropylmethoxy-1-phenylcyclohexanecarboxylic Acid

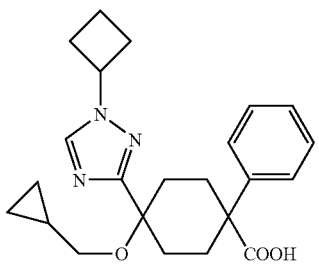

70 mg of the compound of Example 289 and 52 mg of potassium hydroxide in 2 ml of ethylene glycol were stirred at 200° C. for 5 h. The mixture was then poured onto 20 ml of water and extracted three times with 20 ml each of EA. The combined organic phases were dried over magnesium sulfate and the solvent was removed in vacuo. Chromatography on reversed phase silica gel yielded 40 mg of the title compound as an amorphous solid.

MS (ESI+): 396

EXAMPLE 291

4-(1-Cyclobutyl-5-methyl-1H-[1,2,4]triazol-3-yl)-4-cyclopropylmethoxy-1-phenylcyclohexanecarbonitrile

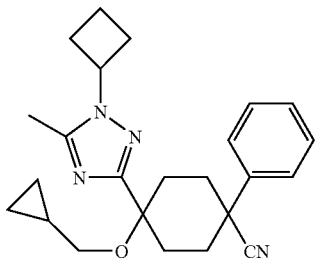

300 mg of the compound of Example 289 were dissolved in 20 ml of anhydrous THF and 0.59 ml of a 1.6 M solution of n-butyllithium in hexane was added dropwise at −75° C. The mixture was stirred at −75° C. for 1 h, and 136 mg of iodomethane were subsequently added at this temperature. The mixture was stirred for a further hour at −75° C., then it was warmed to room temperature and allowed to stand for 15 h. 50 ml of water were added and the mixture was extracted three times with 20 ml each of EA. The combined organic phases were dried over magnesium sulfate and the solvent was removed in vacuo. 250 mg of the title compound were obtained as an amorphous solid, which was reacted further without purification.

MS (ESI+): 391

TLC (EA): Rf 0.48

EXAMPLE 292

4-(1-Cyclobutyl-5-methyl-1H-[1,2,4]triazol-3-yl)-4-cyclopropylmethoxy-1-phenylcyclohexanecarboxylic Acid

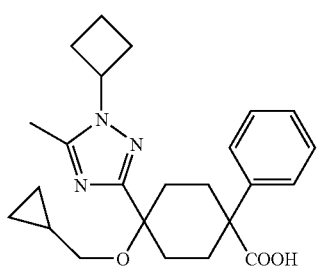

250 mg of the compound of Example 291 and 180 ml of potassium hydroxide in 2 ml of ethylene glycol were stirred at 200° C. for 4 h. The mixture was then poured onto 30 ml of water, adjusted to pH=4 using aqueous sodium hydrogensulfate solution and extracted three times with 30 ml each of EA. The combined organic phases were dried over magnesium sulfate and the solvent was removed in vacuo.

Chromatography on reversed phase silica gel yielded 70 mg of the title compound as an amorphous solid.

MS (ESI+): 410

TLC (EA): Rf 0.40

EXAMPLE 293

3-Bromo-5-cyclopropyl-1H-[1,2,4]triazole

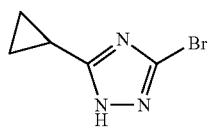

5.0 g of 3-amino-5-cyclopropyl-1H-[1,2,4]triazole were dissolved in 30 ml of acetic acid and 20 ml of a 48% aqueous hydrogen bromide solution were added dropwise. Subsequently, a solution of 3.1 g of sodium nitrite in 10 ml of water was added dropwise at 0° C. in the course of 10 min and the mixture was subsequently stirred at 0° C. for 10 min. The suspension thus obtained was added in portions at 0° C. to a suspension of 11.6 g of copper(I) bromide in 20 ml of a 24% aqueous hydrogen bromide solution. Subsequently, it was stirred at room temperature for 1 h, then the mixture was added to 400 ml of a saturated aqueous sodium carbonate solution and precipitated copper compound was filtered off. The mixture was washed with 100 ml of EA, then the phases were allowed to separate and the aqueous phase was extracted a further two times with 100 ml each of EA. The combined organic phases were dried over magnesium sulfate and the solvent was removed in vacuo. 2.5 g of the title compound were obtained as a light yellow oil.

MS (ESI+): 188

EXAMPLE 294

Cis-4-(5-Cyclopropyl-1H-[1,2,4]triazol-3-yl)-4-hydroxy-1-phenylcyclohexanecarbonitrile and Trans-4-(5-cyclopropyl-1H-[1,2,4]triazol-3-yl)-4-hydroxy-1-phenylcyclohexanecarbonitrile

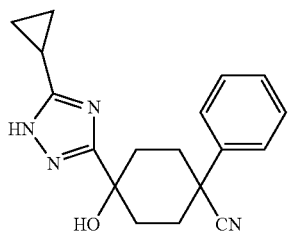

1.0 g of 3-bromo-5-cyclopropyl-1H-[1,2,4]triazole was dissolved in 25 ml of anhydrous THF and 4.7 ml of a 2.7 M solution of n-butyllithium in HEP were added dropwise at −75° C. The mixture was stirred at −65° C. to −75° C. for 2 h, and then a solution of 1.3 g of 4-oxo-1-phenylcyclohexanecarbonitrile in 10 ml of anhydrous THF was added dropwise. The mixture was stirred at −65° C. to −75° C. for 1 h, subsequently warmed to room temperature and added to 100 ml of a saturated aqueous sodium hydrogencarbonate solution. The mixture was extracted three times with 50 ml each of EA. The combined organic phases were dried over magnesium sulfate and the solvent was removed in vacuo. Chromatography on reversed phase silica gel yielded 590 mg of the title compound (cis/trans mixture) as an amorphous solid.

MS (ESI+): 309

EXAMPLE 295

Cis-4-(5-Cyclopropyl-1-cyclopropylmethyl-1H-[1,2,4]triazol-3-yl)-4-cyclopropyl-methoxy-1-phenylcyclohexanecarbonitrile and Trans-4-(5-cyclopropyl-1-cyclopropylmethyl-1H-[1,2,4]triazol-3-yl)-4-cyclopropyl-methoxy-1-phenylcyclohexanecarbonitrile

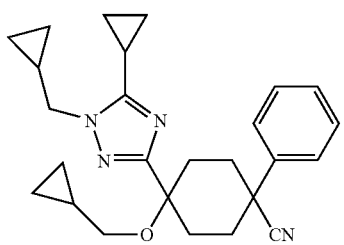

400 mg of the compound of Example 294 were dissolved in 20 ml of anhydrous DMF and first 99 mg of sodium hydride, then 0.3 ml of bromomethylcyclopropane were added at room temperature. The mixture was stirred at room temperature for 3 h, then allowed to stand for 16 h. Subsequently, a further 99 mg of sodium hydride and then 0.3 ml of bromomethylcyclopropane were added. The mixture was stirred at room temperature for 5 h, then allowed to stand for 16 h. Subsequently, it was stirred at room temperature for a further 5 h, then allowed to stand at room temperature for 65 h. Subsequently, a further 99 mg of sodium hydride and then 0.3 ml of bromomethylcyclopropane were added the mixture was stirred at room temperature for 7 h, then allowed to stand for 16 h. Subsequently, it was stirred at room temperature for a further 6 h. Then it was added to 50 ml of a saturated aqueous sodium hydrogencarbonate solution and extracted three times with 25 ml each of EA. The combined organic phases were dried over magnesium sulfate and the solvent was removed in vacuo. Chromatography on reversed phase silica gel yielded 278 mg of the title compound (cis/trans mixture) as an amorphous solid.

MS (ESI+): 417

EXAMPLE 296

Cis-4-(5-Cyclopropyl-1-cyclopropylmethyl-1H-[1,2,4]triazol-3-yl)-4-cyclopropylmethoxy-1-phenylcyclohexanecarboxylic Acid and Trans-4-(5-cyclopropyl-1-cyclopropylmethyl-1H-[1,2,4]triazol-3-yl)-4-cyclopropylmethoxy-1-phenylcyclohexanecarboxylic Acid

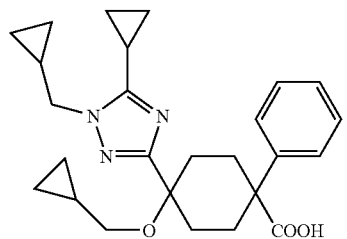

270 mg of the compound of Example 295 and 182 mg of potassium hydroxide in 2 ml of ethylene glycol were stirred at 200° C. for 13 h. After cooling to room temperature, the reaction mixture was added to 20 ml of water, pH=4 was adjusted using aqueous sodium hydrogensulfate solution and the mixture was extracted twice with 15 ml each of EA. The combined organic phases were dried over magnesium sulfate and the solvent was removed in vacuo. By chromatography on a chiral phase (Chiralcel OD-H/56 HPLC column, 250× 4.6 mm; eluent HEP/ethanol/MOH=30:1:1) 25 mg of the cis title compound, 12 mg of the trans title compound and 95 mg of a cis/trans mixture were obtained. The cis/trans configuration was confirmed by X-ray structural analysis.

EXAMPLE 296-1

Cis-4-(5-Cyclopropyl-1-cyclopropylmethyl-1H-[1,2,4]triazol-3-yl)-4-cyclopropyl-methoxy-1-phenylcyclohexanecarboxylic Acid

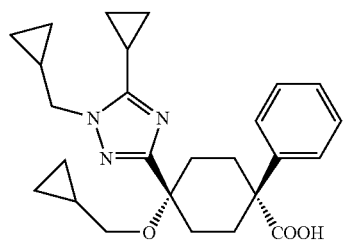

MS (ESI+): 436

EXAMPLE 296-2

Trans-4-(5-Cyclopropyl-1-cyclopropylmethyl-1H-[1,2,4]triazol-3-yl)-4-cyclopropylmethoxy-1-phenylcyclohexanecarboxylic Acid

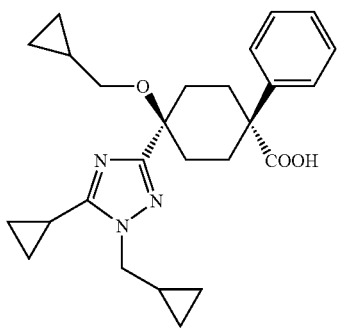

MS (ESI+): 436

EXAMPLE 297

1-Bromo-3-fluoro-5-methylsulfanylbenzene

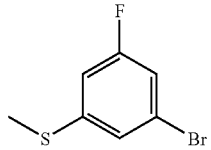

50.0 g of 1-bromo-3,5-difluorobenzene and 18.2 g sodium methanethiolate were stirred at 150° C. for 15 min in 300 ml of anhydrous DMF. Subsequently, the mixture was cooled to room temperature, poured onto 1 l of saturated aqueous ammonium chloride solution and extracted three times with 200 ml each of EA. The combined organic phases were dried over magnesium sulfate and the solvent was removed in vacuo. 48.5 g of the title compound were obtained as a pale yellow oil.

EXAMPLE 298

Cis-4-(3-Fluoro-5-methylsulfanylphenyl)-4-hydroxy-1-(4-fluorophenyl)cyclohexanecarbonitrile

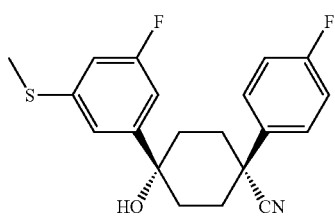

1.0 g of 1-bromo-3-fluoro-5-methylsulfanylbenzene was dissolved in 25 ml of anhydrous diethyl ether and 1.7 ml of a 2.7 M solution of n-butyllithium in HEP was added dropwise at −65° C. to −75° C. The mixture was stirred at −75° C. for 45 min and then a solution of 1.0 g of 4-oxo-1-phenylcyclohexanecarbonitrile in 15 ml of anhydrous THF was added dropwise at −65° C. to −75° C. The mixture was stirred at −75° C. for 1 h, and subsequently allowed to stand at room temperature for 15 h. Then it was poured onto 200 ml of a saturated aqueous sodium hydrogencarbonate solution and extracted twice with 300 ml each of EA. The combined organic phases were dried over magnesium sulfate and the solvent was removed in vacuo. 1.5 g of the title compound were obtained as a viscous oil.

MS (ESI+): 360

EXAMPLE 299

Cis-4-Cyclopropylmethoxy-4-(3-fluoro-5-methylsulfanylphenyl)-1-(4-fluorophenyl)cyclohexanecarbonitrile

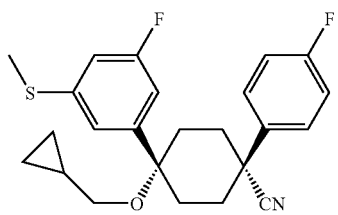

1.5 g of the compound of Example 298, 1.7 g of bromomethylcyclopropane and 301 mg of sodium hydride in 30 ml of anhydrous DMF were stirred at room temperature for 17 h. The reaction mixture was then poured onto 100 ml of a saturated aqueous sodium hydrogencarbonate solution and extracted three times with 30 ml each of EA. The combined organic phases were washed twice with 20 ml each of water, dried over magnesium sulfate, and the solvent was removed in vacuo. 1.6 g of the title compound were obtained as a viscous oil.

MS (ESI+): 414

EXAMPLE 300

1.6 g of the compound of Example 299 and 1.1 g of potassium hydroxide in 20 ml of ethylene glycol were stirred at 200° C. for 5 h. Subsequently, the mixture was cooled to room temperature, adjusted to pH=4 using aqueous sodium hydrogensulfate solution and extracted three times with 30 ml each of EA. The combined organic phases were dried over magnesium sulfate and the solvent was removed in vacuo. By chromatography on reversed phase silica gel, 170 mg of the compound of Example 300-1, 430 mg of the compound of Example 300-2 and 240 mg of the compound of Example 300-3 were obtained in the form of amorphous solids. 300-3 were obtained in the form of amorphous solids.

EXAMPLE 300-1

Cis-4-Cyclopropylmethoxy-4-(3-fluoro-5-methylsulfanylphenyl)-1-[4-(2-hydroxyethoxy)phenyl]cyclohexanecarboxylic Acid

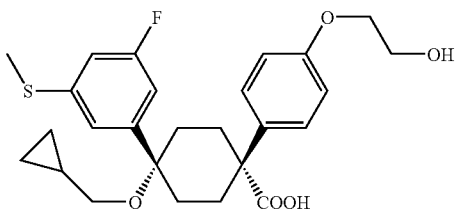

EXAMPLE 300-2

Cis-4-Cyclopropylmethoxy-1-(4-fluorophenyl)-4-[3-(2-hydroxyethoxy)-5-methylsulfanylphenyl]cyclohexanecarboxylic Acid

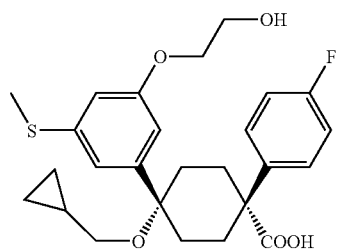

EXAMPLE 300-3

Cis-4-Cyclopropylmethoxy-4-(3-fluoro-5-methylsulfanylphenyl)-1-(4-fluorophenyl)cyclohexanecarboxylic Acid

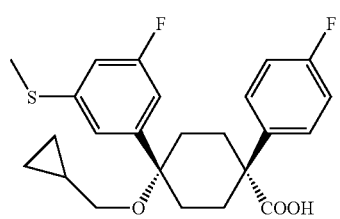

MS (ESI−): 431

EXAMPLE 301

Cis-4-Cyclopropylmethoxy-4-(3-fluoro-5-methanesulfonylphenyl)-1-(4-fluorophenyl)cyclohexanecarboxylic Acid

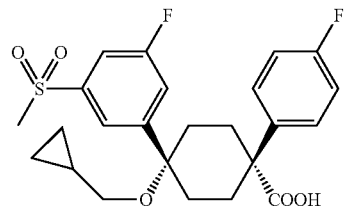

9.0 g of the compound of Example 300-3 were dissolved in 400 ml of THF and a solution of 40.5 g of potassium peroxomonosulfate in 400 ml of water was added at room temperature. The mixture was stirred at room temperature for 24 h, then treated with saturated aqueous sodium sulfite solution until oxidant was no longer detectable (Merkoquant®). Subsequently, it was treated with 200 ml of a 5% aqueous sodium hydrogensulfate solution and extracted three times with 300 ml each of EA. The combined organic phases were dried over magnesium sulfate and the solvent was removed in vacuo. Chromatography on reversed phase silica gel yielded 3.0 g of the title compound as an amorphous solid.

MS (ESI−): 463

TLC (EA/HEP 2:1): Rf 0.19

EXAMPLE 302

Cis-4-Cyclopropylmethoxy-4-(3-ethanesulfonyl-5-fluorophenyl)-1-(4-fluorophenyl)cyclohexanecarboxylic Acid

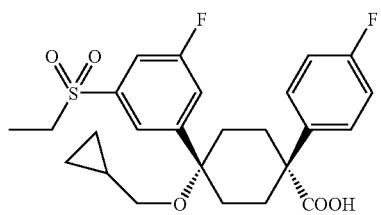

300 mg of the compound of Example 301 were dissolved in 15 ml of anhydrous THF and 0.58 ml of a 2.7 M solution of n-butyllithium in HEP was added dropwise at 0° C. The mixture was stirred at 0° C. for 1 h, then a solution of 183 mg of iodomethane in 2 ml of anhydrous THF was added and the mixture was stirred at 0° C. for 1 h and subsequently at room temperature for 22 h. The volatile constituents were removed in vacuo. Chromatography on reversed phase silica gel yielded 147 mg of the title compound as an amorphous solid.

MS (ESI−): 447

EXAMPLE 303

Cis-4-(3-Cyclopropanesulfonyl-5-fluorophenyl)-4-cyclopropylmethoxy-1-(4-fluorophenyl)cyclohexanecarboxylic Acid

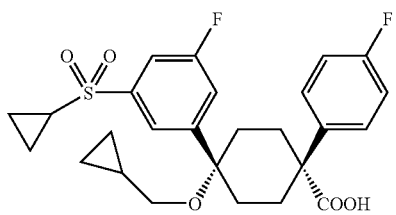

600 mg of the compound of Example 301 were dissolved in 60 ml of anhydrous THF and 2.1 ml of a 2 M solution of n-butyllithium in cyclohexane were added dropwise at 0° C. The mixture was stirred at 0° C. for 1 h, then a solution of 192 mg of 1,2-dichloroethane in 2 ml of anhydrous THF was added dropwise. The mixture was stirred at 0° C. for 1 h and subsequently at room temperature for 48 h. The volatile constituents were removed in vacuo. Chromatography on reversed phase silica gel yielded 40 mg of the title compound as an amorphous solid.

MS (ESI+): 491

EXAMPLE 304

By reaction of 600 mg of the compound of Example 301, 734 mg of iodomethane and 2.2 ml of a 2.7 M solution of n-butyllithium in HEP analogously to Example 302 and chromatographic separation of the crude product, 81 mg of the compound of Example 304-1, 41 mg of the compound of Example 304-2, 130 mg of the compound of Example 304-3 and 36 mg of the compound of Example 304-4 were obtained.

EXAMPLE 304-1

Cis-4-Cyclopropylmethoxy-1-(4-fluorophenyl)-4-[3-fluoro-5-(propane-2-sulfonyl)phenyl]cyclohexanecarboxylic Acid

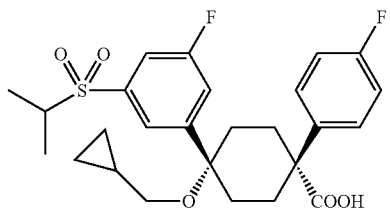

MS (ESI−): 491

EXAMPLE 304-2

Cis-4-Cyclopropylmethoxy-4-[3-fluoro-4-methyl-5-(2-methylpropane-2-sulfonyl)phenyl]-1-(4-fluorophenyl)cyclohexanecarboxylic Acid

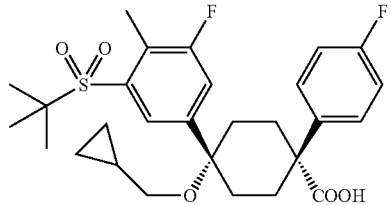

MS (ESI−): 519

EXAMPLE 304-3

Cis-4-Cyclopropylmethoxy-4-[3-fluoro-5-(2-methylpropane-2-sulfonyl)phenyl]-1-(4-fluorophenyl)cyclohexanecarboxylic Acid

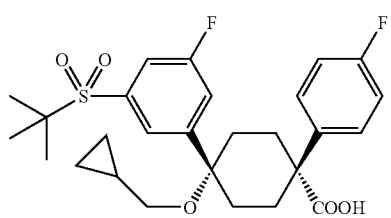

MS (ESI−): 505

EXAMPLE 304-4

Cis-4-Cyclopropylmethoxy-4-[3-fluoro-4-methyl-5-(propane-2-sulfonyl)phenyl]-1-(4-fluorophenyl)cyclohexanecarboxylic Acid

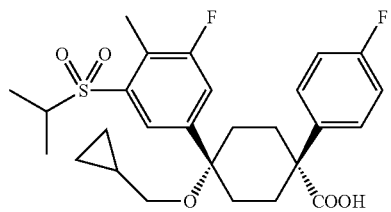

MS (ESI−): 505

EXAMPLE 305

4-(2-Cyclopropylethoxy)-4-(4-fluorophenyl)-1-phenylcyclohexanecarbonitrile

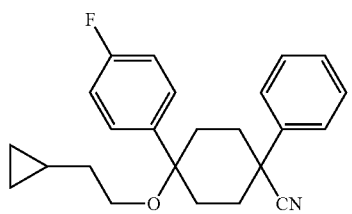

500 mg of the compound of Example 1, 760 mg of (2-bromoethyl)cyclopropane (Chorvat et al., J. Med. Chem. 28, 194-200 (1985)) and 122 mg of sodium hydride in 20 ml of anhydrous DMF were stirred at room temperature for 19 h. 760 mg of (2-bromoethyl)cyclopropane and 122 mg of sodium hydride were then added and the mixture was stirred at room temperature for 4 days. The reaction mixture was then treated with 100 ml of water and extracted three times with 50 ml each of EA. The combined organic phases were dried over magnesium sulfate and the solvent was removed in vacuo. 290 mg of the title compound were obtained as a pale yellow oil.
MS (ESI+): 364

EXAMPLE 306

4-(2-Cyclopropylethoxy)-4-(4-fluorophenyl)-1-phenylcyclohexanecarboxylic Acid

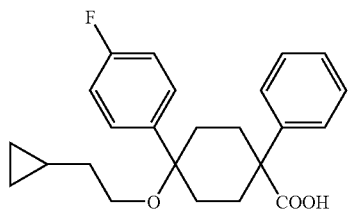

280 mg of the compound of Example 307 and 216 mg of potassium hydroxide in ethylene glycol were stirred at 200° C. for 3 h. Subsequently, the mixture was cooled to room temperature, adjusted to pH=5 using aqueous sodium hydrogensulfate solution and extracted three times with 30 ml each of EA. The combined organic phases were dried over magnesium sulfate and the solvent was removed in vacuo. Chromatography on reversed phase silica gel yielded 69 mg of the title compound as an amorphous solid.
MS (ESI+): 383

EXAMPLE 307

Cis-4-Hydroxy-1-phenyl-4-(6,7,8,9-tetrahydro-5H-[1,2,4]triazolo[4,3-a]azepin-3-yl)cyclohexanecarbonitrile and Trans-4-hydroxy-1-phenyl-4-(6,7,8,9-tetrahydro-5H-[1,2,4]triazolo[4,3-a]azepin-3-yl)cyclohexanecarbonitrile

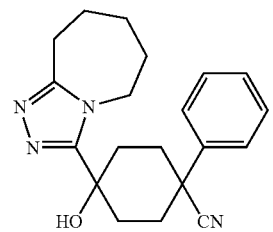

3.5 g of 6,7,8,9-tetrahydro-5H-[1,2,4]triazolo[4,3-a]azepine (Petersen et al., Chem. Ber. 90, 909-921 (1957)) were dissolved in 50 ml of anhydrous THF and 13.3 ml of a 2.7 M solution of n-butyllithium in HEP were added dropwise at 0° C. The mixture was stirred at 0° C. for 30 min, and subsequently a solution of 6.1 g of 4-oxo-1-phenylcyclohexanecarbonitrile in 40 ml of anhydrous THF was added dropwise at a temperature between −75° C. and −65° C. The mixture was subsequently stirred at −75° C. for 30 min, and then warmed to room temperature and stirred at room temperature for 8 h. The mixture was poured onto 250 ml of a saturated aqueous sodium hydrogencarbonate solution and extracted three times with 100 ml each of EA. The combined organic phases were dried over magnesium sulfate and the solvent was removed in vacuo. Chromatography on reversed phase silica gel yielded 2.8 g of the cis title compound and 1.6 g of the trans title compound in the form of amorphous solids.

EXAMPLE 307-1

Cis-4-Hydroxy-1-phenyl-4-(6,7,8,9-tetrahydro-5H-[1,2,4]triazolo[4,3-a]azepin-3-yl)cyclohexanecarbonitrile

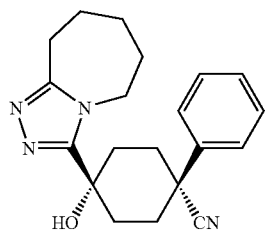

MS (ESI+): 337

EXAMPLE 307-2

Trans-4-Hydroxy-1-phenyl-4-(6,7,8,9-tetrahydro-5H-[1,2,4]triazolo[4,3-a]azepin-3-yl)cyclohexanecarbonitrile

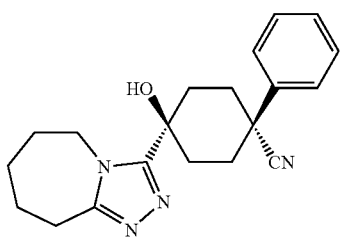

MS (ESI+): 337

EXAMPLE 308

Cis-4-Cyclopropylmethoxy-1-phenyl-4-(6,7,8,9-tetrahydro-5H-[1,2,4]triazolo[4,3-a]azepin-3-yl)cyclohexanecarbonitrile

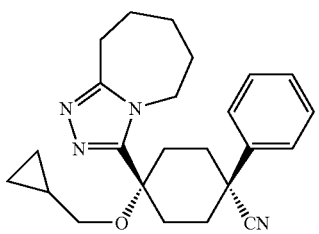

2.7 g of the compound of Example 307-1, 304 mg of sodium hydride and 1.6 ml of bromomethylcyclopropane were dissolved in 25 ml of anhydrous DMF and stirred at room temperature for 8 h. Subsequently, 149 mg of sodium hydride and 640 ml of bromomethylcyclopropane were added. The mixture was stirred at room temperature for 8 h and then allowed to stand at room temperature for 65 h. Subsequently, it was added to 100 ml of a saturated aqueous sodium hydrogencarbonate solution and extracted three times with 50 ml each of EA. The combined organic phases were dried over magnesium sulfate and the solvent was removed in vacuo. 2.1 g of the title compound were obtained as a viscous oil.

MS (ESI+): 391

EXAMPLE 309

Cis-4-Cyclopropyl methoxy-1-phenyl-4-(6,7,8,9-tetrahydro-5H-[1,2,4]triazolo[4,3-a]azepin-3-yl)cyclohexanecarboxylic Acid

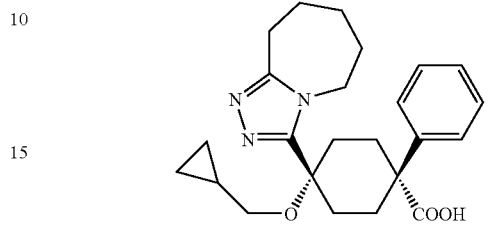

1.0 g of the compound of Example 308 and 720 mg of potassium hydroxide in 4 ml of ethylene glycol were stirred at 200° C. for 7.5 h. The reaction mixture was cooled to room temperature, adjusted to pH=4 using aqueous sodium hydrogensulfate solution and extracted three times with 25 ml each of EA. In the course of this, the product precipitated. It was filtered off with suction and dried in vacuo. 630 mg of the title compound were obtained in the form of pale yellow crystals. The cis configuration was confirmed by X-ray structural analysis.

MS (ESI+): 410

EXAMPLE 310

Trans-4-Cyclopropylmethoxy-1-phenyl-4-(6,7,8,9-tetrahydro-5H-[1,2,4]triazolo[4,3-a]azepin-3-yl)cyclohexanecarboxylic Acid

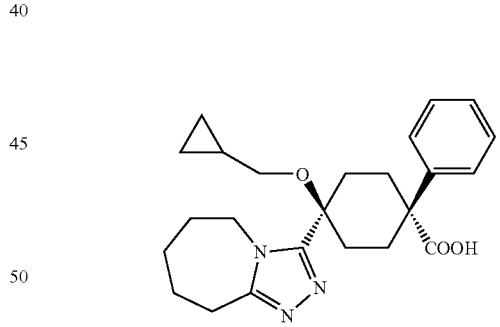

The compound of Example 307-2 was reacted analogously to Examples 308 and 309 via the intermediate stage of trans-4-cyclopropylmethoxy-1-phenyl-4-(6,7,8,9-tetrahydro-5H-[1,2,4]triazolo[4,3-a]azepin-3-yl)cyclohexanecarbonitrile. The obtained trans-4-cyclopropylmethoxy-1-phenyl-4-(6,7,8,9-tetrahydro-5H-[1,2,4]triazolo[4,3-a]azepin-3-yl)cyclohexanecarboxylic acid was purified by chromatography on reversed phase silica gel. 80 mg of the title compound were obtained.

MS (ESI−): 408

EXAMPLE 311

3-Bromo-5-phenyl-1H-pyrazole

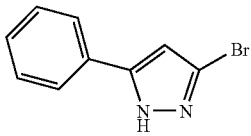

20 g of 3-amino-5-phenylpyrazole were suspended in 200 ml of a 24% aqueous hydrogen bromide solution and a solution of 9.5 g of sodium nitrite in 20 ml of water was added dropwise at 0° C. in the course of 10 min. The mixture was stirred at 0° C. for 10 min. Then the obtained suspension was added in portions to a suspension of 19.8 g of copper(I) bromide in 100 ml of a 24% aqueous hydrogen bromide solution. Subsequently, the mixture was stirred at room temperature for 2 h and then extracted three times with 300 ml each of EA. The combined organic phases were washed twice with 100 ml each of water and once with 100 ml of a saturated aqueous sodium carbonate solution. The organic phase was dried over magnesium sulfate and the solvent was removed in vacuo. Chromatography on silica gel with EA/HEP (1:5) yielded 5.7 g of the title compound as a colorless oil.

MS (ESI+): 222

EXAMPLE 312

3-Bromo-1-cyclopropylmethyl-5-phenyl-1H-pyrazole and 5-bromo-1-cyclopropylmethyl-3-phenyl-1H-pyrazole 5.7 g of 3-bromo-5-phenyl-1H-pyrazole were dissolved in 50 ml of anhydrous DMF, 0.74 g of sodium hydride and 4.1 g of bromomethylcyclopropane were added and the mixture was allowed to stand for 17 h at room temperature. The reaction mixture was then treated with 1 ml of water and the volatile constituents were removed in vacuo. Chromatography on reversed phase silica gel yielded 1.4 g of 3-bromo-1-cyclopropylmethyl-5-phenyl-1H-pyrazole and 2.7 g of 5-bromo-1-cyclopropylmethyl-3-phenyl-1H-pyrazole as viscous oils.

EXAMPLE 312-1

3-Bromo-1-cyclopropylmethyl-5-phenyl-1H-pyrazole

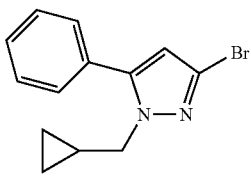

EXAMPLE 312-2

5-Bromo-1-cyclopropylmethyl-3-phenyl-1H-pyrazole

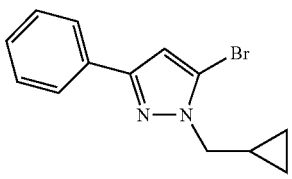

EXAMPLE 313

Cis-4-(2-Cyclopropylmethyl-5-phenyl-2H-pyrazol-3-yl)-4-hydroxy-1-phenylcyclohexanecarbonitrile and Trans-4-(2-cyclopropylmethyl-5-phenyl-2H-pyrazol-3-yl)-4-hydroxy-1-phenylcyclohexanecarbonitrile

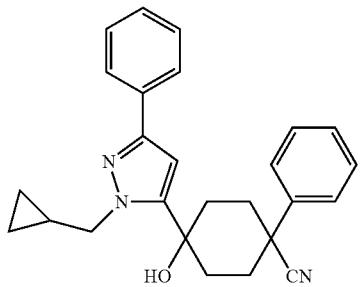

2.6 g of the compound of Example 312-2 were dissolved in 10 ml of anhydrous THF and 11.7 g of a 14% solution of isopropylmagnesium chloride x lithium chloride (1:1) in THF (Chemetall) were slowly added dropwise at room temperature. The mixture was stirred at room temperature for 2 h, then a solution of 4-oxo-1-phenylcyclohexanecarbonitrile in 15 ml of anhydrous THF was added at room temperature, and the mixture was stirred at room temperature for 18 h. Subsequently, the mixture was treated with 1 ml of water, filtered through 15 g of kieselguhr and washed with 100 ml of EA. The volatile constituents were removed in vacuo and the residue was chromatographed on reversed phase silica gel.

0.84 g of the cis title compound and 0.59 g of the trans title compound were obtained as viscous oils.

EXAMPLE 313-1

Cis-4-(2-Cyclopropylmethyl-5-phenyl-2H-pyrazol-3-yl)-4-hydroxy-1-phenylcyclohexanecarbonitrile

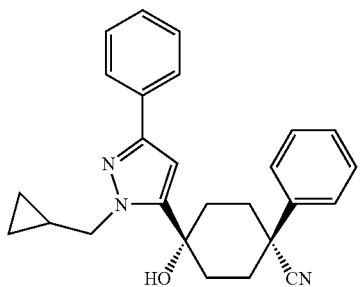

TLC (EA/HEP 1:1): Rf 0.45

EXAMPLE 313-2

Trans-4-(2-Cyclopropylmethyl-5-phenyl-2H-pyrazol-3-yl)-4-hydroxy-1-phenylcyclohexanecarbonitrile

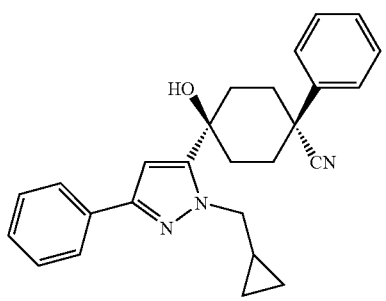

TLC (EA/HEP 1:1): Rf 0.45

EXAMPLE 314

Cis-4-Cyclopropylmethoxy-4-(2-cyclopropylmethyl-5-phenyl-2H-pyrazol-3-yl)-1-phenylcyclohexanecarbonitrile

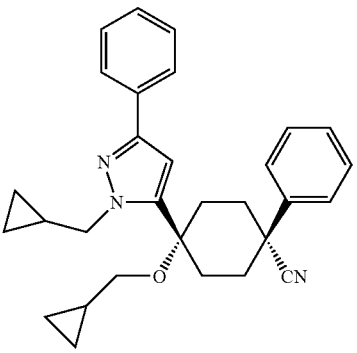

840 mg of the compound of Example 313-1, 150 mg of sodium hydride and 860 mg of bromomethylcyclopropane in 20 ml DMF were stirred at room temperature for 19 h. Subsequently, the reaction mixture was treated with 100 ml of water and extracted three times with 50 ml each of EA. The combined organic phases were dried over magnesium sulfate and the solvent was removed in vacuo. 820 mg of the title compound were obtained as a viscous oil.

TLC (EA/HEP 1:2): Rf 0.44

EXAMPLE 315

Trans-4-Cyclopropylmethoxy-4-(2-cyclopropylmethyl-5-phenyl-2H-pyrazol-3-yl)-1-phenylcyclohexanecarbonitrile

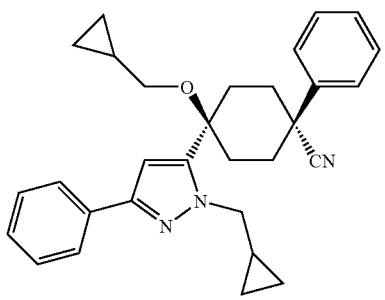

590 mg of the compound of Example 313-2, 110 mg of sodium hydride and 600 mg of bromomethylcyclopropane in 20 ml DMF were stirred at room temperature for 19 h. Subsequently, the reaction mixture was treated with 100 ml of water and extracted three times with 50 ml each of EA. The combined organic phases were dried over magnesium sulfate and the solvent was removed in vacuo. 500 mg of the title compound were obtained as a viscous oil.

TLC (EA/HEP 1:2): Rf 0.44

EXAMPLE 316

Cis-4-Cyclopropylmethoxy-4-(2-cyclopropylmethyl-5-phenyl-2H-pyrazol-3-yl)-1-phenylcyclohexanecarboxylic Acid

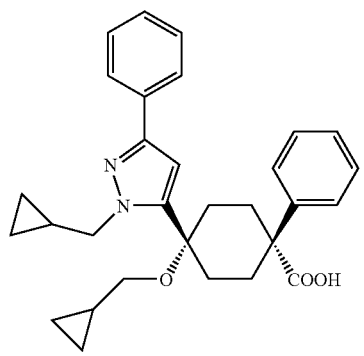

820 mg of the compound of Example 314 and 510 mg of potassium hydroxide in 5 ml of ethylene glycol were stirred at 200° C. for 3 h. The reaction mixture was treated with 50 ml of water, adjusted to pH=6 with aqueous sodium hydrogensulfate solution and extracted three times with 30 ml each of EA. The combined organic phases were dried over magnesium sulfate and the solvent was removed in vacuo. After chromatography on reversed phase silica gel, the product-containing fractions were concentrated to half of their volume on a rotary evaporator, treated with 50 ml of a saturated aqueous sodium chloride solution, adjusted to pH=6 with saturated aqueous sodium hydrogencarbonate solution and extracted three times with 50 ml each of EA. The combined organic phases were dried over magnesium sulfate and the solvent was removed in vacuo. 450 mg of the title compound were obtained as an amorphous solid. A sample was recrystallized from MOH and the cis configuration was confirmed by X-ray structural analysis.

TLC (EA/HEP 1:1): Rf 0.20

EXAMPLE 317

Trans-4-Cyclopropylmethoxy-4-(2-cyclopropylmethyl-5-phenyl-2H-pyrazol-3-yl)-1-phenylcyclohexanecarboxylic Acid

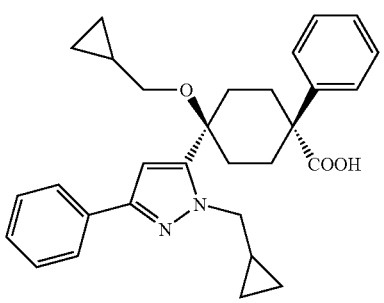

500 mg of the compound of Example 315 and 310 mg of potassium hydroxide in 5 ml of ethylene glycol were stirred at 200° C. for 3 h. The reaction mixture was treated with 50 ml of water, adjusted to pH=6 with aqueous sodium hydrogensulfate solution and extracted three times with 30 ml each of EA. The combined organic phases were dried over magnesium sulfate and the solvent was removed in vacuo. After chromatography on reversed phase silica gel, the product-containing fractions were concentrated to half of their volume on a rotary evaporator, treated with 50 ml of a saturated aqueous sodium chloride solution, adjusted to pH=6 with saturated aqueous sodium hydrogencarbonate solution and extracted three times with 50 ml each of EA. The combined organic phases were dried over magnesium sulfate and the solvent was removed in vacuo. 340 mg of the title compound were obtained as an amorphous solid. A sample was recrystallized from MOH and the trans configuration was confirmed by X-ray structural analysis.

TLC (EA/HEP 1:1): Rf 0.35

The compounds of Examples 318 and 319 were synthesized analogously to Examples 316 and 317.

EXAMPLE 318

Cis-4-Cyclopropylmethoxy-4-[2-cyclopropylmethyl-5-(4-methoxyphenyl)-2H-pyrazol-3-yl]-1-phenylcyclohexanecarboxylic Acid

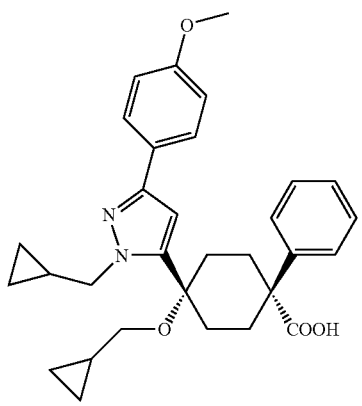

MS (ESI+): 501

EXAMPLE 319

Trans-4-Cyclopropylmethoxy-4-[2-cyclopropylmethyl-5-(4-methoxyphenyl)-2H-pyrazol-3-yl]-1-phenylcyclohexanecarboxylic Acid

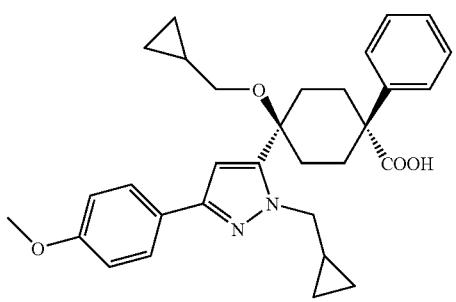

MS (ESI+): 501

EXAMPLE 320

Cis-4-(1-Cyclopropylmethyl-5-phenyl-1H-pyrazol-3-yl)-4-hydroxy-1-phenylcyclohexanecarbonitrile

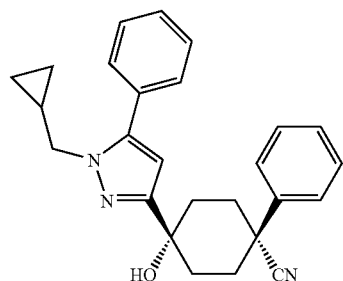

300 mg of the compound of Example 312-1 were dissolved in 15 ml of anhydrous diethyl ether and 0.52 ml of a 2.7 M solution of n-butyllithium in HEP was added dropwise at −70° C. The mixture was stirred at −75° C. for 45 min, a solution of 215 mg of 4-oxo-1-phenylcyclohexanecarbonitrile in 2 ml of THF was added and the mixture was warmed to room temperature. The volatile constituents were removed in vacuo and the residue was chromatographed on reversed phase silica gel. The product-containing fractions were concentrated, treated with 20 ml of a saturated aqueous sodium hydrogencarbonate solution and extracted three times with 50 ml each of EA. The combined organic phases were dried over magnesium sulfate and the solvent was removed in vacuo. 200 mg of the title compound were obtained as a colorless oil.

TLC (EA/HEP 1:1): Rf 0.39

EXAMPLE 321

Cis-4-Cyclopropylmethoxy-4-(1-cyclopropylmethyl-5-phenyl-1H-pyrazol-3-yl)-1-phenylcyclohexanecarbonitrile

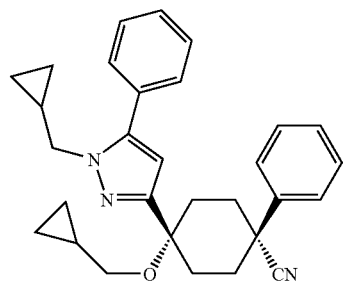

190 mg of the compound of Example 320, 190 mg of bromomethylcyclopropane and 34 mg of sodium hydride in 5 ml of anhydrous DMF were stirred at room temperature for 4 days. Subsequently, 190 mg of bromomethylcyclopropane and 34 mg of sodium hydride were added and the mixture was stirred at room temperature for a further 20 h. Then 20 ml of a saturated aqueous sodium hydrogencarbonate solution were slowly added and the mixture was extracted three times with 30 ml each of EA. The combined organic phases were dried over magnesium sulfate and the solvent was removed in vacuo. 130 mg of the title compound were obtained as a viscous oil.

TLC (EA/HEP 1:2): Rf 0.40

EXAMPLE 322

Cis-4-Cyclopropylmethoxy-4-(1-cyclopropylmethyl-5-phenyl-1H-pyrazol-3-yl)-1-phenylcyclohexanecarboxylic Acid

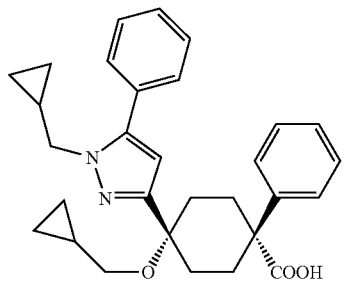

120 mg of the compound of Example 321 and 75 mg of potassium hydroxide in 3 ml of ethylene glycol were stirred at 200° C. for 3 h. Subsequently, the mixture was cooled to room temperature, 50 ml of water were added and the mixture was extracted three times with 50 ml each of EA. The combined organic phases were dried over magnesium sulfate and the solvent was removed in vacuo. The residue was chromatographed on reversed phase silica gel. The product-containing fractions were concentrated, treated with 50 ml of a saturated aqueous sodium chloride solution, adjusted to pH=6 with saturated aqueous sodium hydrogencarbonate solution and extracted three times with 50 ml each of EA. The combined organic phases were dried over magnesium sulfate and the solvent was removed in vacuo. The residue was chromatographed on silica gel using EA/HEP (1:1). 30 mg of the title compound were obtained as a colorless amorphous solid.

TLC (EA/HEP 1:1): Rf 0.21

EXAMPLE 323

Cis-4-Cyclopropylmethoxy-4-[1-cyclopropylmethyl-5-(4-methoxyphenyl)-1H-pyrazol-3-yl]-1-phenylcyclohexanecarboxylic Acid

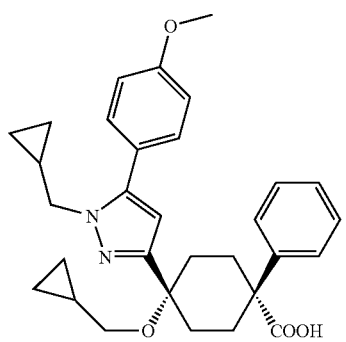

The title compound was synthesized analogously to Example 322.

TLC (EA/HEP 1:1): Rf 0.20

EXAMPLE 324

Cis-4-Hydroxy-1-phenyl-4-(5-phenylthiazol-2-yl)cyclohexanecarbonitrile and Trans-4-hydroxy-1-phenyl-4-(5-phenylthiazol-2-yl)cyclohexanecarbonitrile

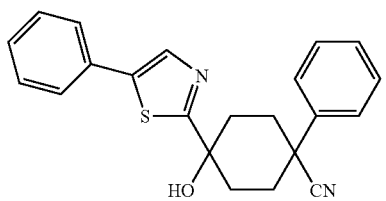

3.0 g of 5-phenylthiazole were dissolved in 50 ml of anhydrous THF and a 2 M solution of lithium diisopropylamide in THF/HEP/ethylbenzene (Aldrich) was added dropwise at −70° C. The mixture was stirred at −70° C. for 50 min, then a solution of 3.7 g of 4-oxo-1-phenylcyclohexanecarbonitrile in 30 ml of anhydrous THF was added dropwise at −65° C. to −70° C. Subsequently, the mixture was warmed to room temperature and stirred at room temperature for 17 h. The reaction mixture was poured onto 100 ml of a saturated aqueous sodium hydrogencarbonate solution and extracted three times with 50 ml each of EA. The combined organic phases were dried over magnesium sulfate and the solvent was removed in vacuo.

Chromatography on silica gel with EA/HEP (1:2) yielded 2.0 g of the cis title compound and 200 mg of the trans title compound.

EXAMPLE 324-1

Cis-4-Hydroxy-1-phenyl-4-(5-phenylthiazol-2-yl)cyclohexanecarbonitrile

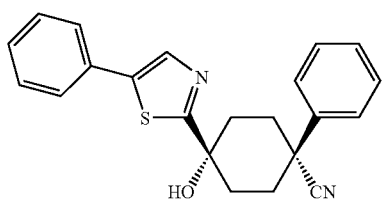

TLC (EA/HEP 1:2): Rf 0.46

EXAMPLE 324-2

Trans-4-Hydroxy-1-phenyl-4-(5-phenylthiazol-2-yl)cyclohexanecarbonitrile

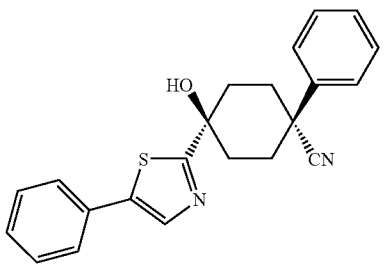

TLC (EA/HEP 1:2): Rf 0.35

EXAMPLE 325

Cis-4-Cyclopropylmethoxy-1-phenyl-4-(5-phenylthiazol-2-yl)cyclohexanecarbonitrile

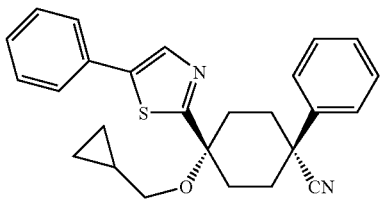

2.0 g of the compound of Example 324-1, 2.2 g of bromomethylcyclopropane and 400 mg of sodium hydride in 50 ml of anhydrous DMF were stirred at room temperature for 2 days. The reaction mixture was treated with 1 ml of water and chromatographed on reversed phase silica gel. The product-containing fractions were treated with 100 ml of a saturated aqueous sodium hydrogencarbonate solution and extracted three times with 30 ml each of EA. The combined organic phases were dried over magnesium sulfate and the solvent was removed in vacuo. 0.88 g of the title compound was obtained as a viscous oil.

TLC (EA/HEP 1:1): Rf 0.74

EXAMPLE 326

Cis-4-Cyclopropylmethoxy-1-phenyl-4-(5-phenylthiazol-2-yl)cyclohexanecarboxylic Acid

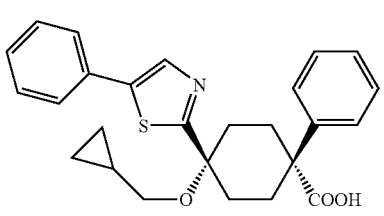

500 mg of the compound of Example 325 and 340 mg of potassium hydroxide in ethylene glycol were stirred at 200° C. for 3 h. Subsequently, the mixture was cooled to room temperature, 10 ml of water were added and the mixture was adjusted to pH=6 with aqueous sodium hydrogensulfate solution. The product was filtered off with suction, washed with water until neutral and dried in vacuo. 400 mg of the title compound were obtained as an amorphous solid.

TLC (EA/HEP 1:1): Rf 0.30
MS (ESI−): 432

EXAMPLE 327

Trans-4-Cyclopropylmethoxy-1-phenyl-4-(5-phenylthiazol-2-yl)cyclohexanecarboxylic Acid

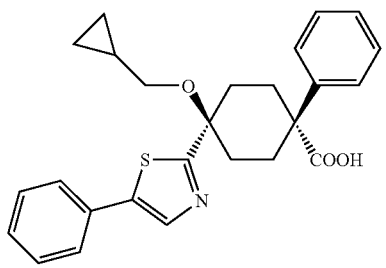

The preparation was carried out analogously to Examples 325 and 326 from 200 mg of the compound of Example 324-2 via intermediate stage of trans-4-cyclopropylmethoxy-1-phenyl-4-(5-phenylthiazol-2-yl)cyclohexanecarbonitrile. 5 mg of the title compound were obtained as an amorphous solid.

MS (ESI−): 432

EXAMPLE 328

8-(4-Phenylthiazol-2-yl)-1,4-dioxaspiro[4.5]decan-8-ol

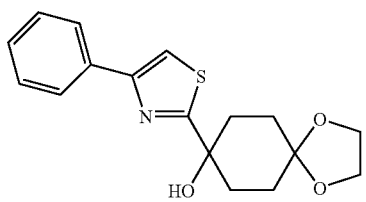

4.5 g of 4-phenylthiazole were dissolved in 80 ml of anhydrous THF and 18.1 ml of a 2 M solution of lithium diisopropylamide in THF/HEP/ethylbenzene (Aldrich) were added dropwise at −70° C. The mixture was stirred at −70° C. for 60 min, then a solution of 4.4 g of 1,4-dioxaspiro[4.5]decan-8-one in 50 ml of anhydrous THF was added dropwise at −65° C. to −70° C. Subsequently, the mixture was warmed to room temperature, poured onto 120 ml of a saturated aqueous sodium hydrogencarbonate solution and extracted three times with 80 ml each of EA. The combined organic phases were dried over magnesium sulfate and the solvent was removed in vacuo. 7.1 g of the title compound were obtained as a pale yellow oil.

MS (ESI+): 318

EXAMPLE 329

2-(8-Cyclopropylmethoxy-1,4-dioxaspiro[4.5]dec-8-yl)-4-phenylthiazole

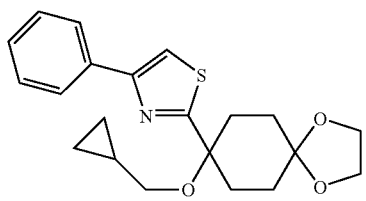

8.0 g of 8-(4-phenylthiazol-2-yl)-1,4-dioxa-spiro[4.5]decan-8-ol were dissolved in 100 ml of anhydrous DMF and treated with 1.1 g of sodium hydride. The mixture was stirred at room temperature for 15 min, then 6.0 g of bromomethylcyclopropane were added. The mixture was stirred at room temperature for 18 h, then poured onto 400 ml of a saturated aqueous sodium hydrogencarbonate solution and extracted three times with 300 ml each of EA. The combined organic phases were dried over magnesium sulfate and the solvent was removed in vacuo. 8.3 g of the title compound were obtained as a pale yellow oil.

MS (ESI+): 372

EXAMPLE 330

4-Cyclopropylmethoxy-4-(4-phenylthiazol-2-yl)cyclohexanone

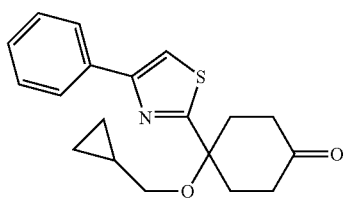

8.3 g of 2-(8-cyclopropylmethoxy-1,4-dioxaspiro[4.5]dec-8-yl)-4-phenylthiazole and 5.5 g of p-toluenesulfonic acid were dissolved in 137 ml of acetone and 14 ml of water. The mixture was stirred at room temperature for 4 days, then poured onto 100 ml of a saturated aqueous sodium hydrogencarbonate solution. The acetone was distilled off and the residue extracted three times with 100 ml each of EA. The combined organic phases were dried over magnesium sulfate and the solvent was removed in vacuo. 5.9 g of the title compound were obtained as an amorphous solid.

MS (ESI+): 328

EXAMPLE 331

Cis-4-Cyclopropylmethoxy-4-(4-phenylthiazol-2-yl)cyclohexanecarbonitrile and Trans-4-cyclopropylmethoxy-4-(4-phenylthiazol-2-yl)cyclohexanecarbonitrile

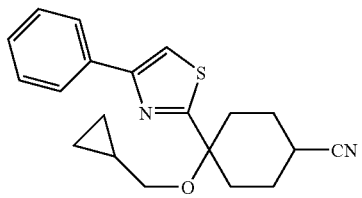

5.9 g of 4-cyclopropylmethoxy-4-(4-phenylthiazol-2-yl)cyclohexanone and 4.7 g of (p-toluenesulfonyl)methyl isocyanide were dissolved in 100 ml of anhydrous DME and 20 ml of anhydrous ethanol. 4.7 g of potassium tert-butylate were added at 0° C. and the mixture was stirred first at 0° C. for 2 h and then at room temperature for 2 h. Subsequently, the mixture was poured onto 200 ml of ice, diluted with 200 ml of water and extracted three times with 100 ml each of EA. The combined organic phases were dried over magnesium sulfate, the solvent was removed in vacuo and the residue was chromatographed on reversed phase silica gel. The product-containing fractions were concentrated, adjusted to pH=10 with aqueous sodium carbonate solution and extracted three times with 100 ml each of EA. The combined organic phases were dried over magnesium sulfate and the solvent was removed in vacuo. 3.0 g of the title compound (cis/trans mixture) were obtained as an amorphous solid.

MS (ESI+): 339

EXAMPLE 332

Cis-4-Cyclopropylmethoxy-1-phenyl-4-(4-phenylthiazol-2-yl)cyclohexanecarbonitrile and Trans-4-cyclopropylmethoxy-1-phenyl-4-(4-phenylthiazol-2-yl)cyclohexanecarbonitrile

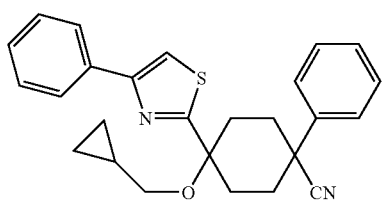

2.0 g of the compound of Example 331, 11.4 g of fluorobenzene and 2.4 g of bis(trimethylsilyl)sodium amide were stirred at room temperature for 24 h with exclusion of moisture. The reaction mixture was poured onto 100 ml of a saturated aqueous sodium hydrogencarbonate solution and extracted three times with 50 ml each of EA. The combined organic phases were dried over magnesium sulfate and the solvent was removed in vacuo. The residue was chromatographed on silica gel using EA/HEP (1:3). 240 mg of the title compound were obtained as a viscous oil.

TLC (EA/HEP 1:3): Rf 0.50

EXAMPLE 333

Cis-4-Cyclopropylmethoxy-1-phenyl-4-(4-phenylthiazol-2-yl)cyclohexanecarboxylic acid and Trans-4-cyclopropylmethoxy-1-phenyl-4-(4-phenylthiazol-2-yl)cyclohexanecarboxylic Acid

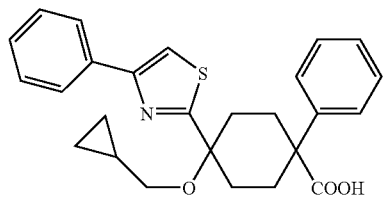

230 mg of the compound of Example 332 and 156 mg of potassium hydroxide in 5 ml of ethylene glycol were stirred at 200° C. for 24 h. The reaction mixture was poured onto 30 ml of water, adjusted to pH=3 with aqueous sodium hydrogensulfate solution and extracted three times with 30 ml each of EA. The combined organic phases were dried over magnesium sulfate and the solvent was removed in vacuo. Chromatography on reversed phase silica gel yielded 30 mg of the cis title compound and 130 mg of the trans title compound.

EXAMPLE 333-1

Cis-4-Cyclopropylmethoxy-1-phenyl-4-(4-phenylthiazol-2-yl)cyclohexanecarboxylic Acid

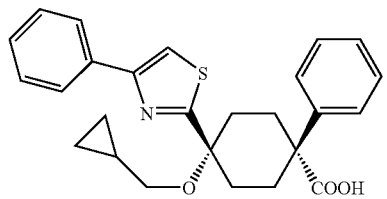

MS (ESI+): 434

EXAMPLE 333-2

Trans-4-Cyclopropylmethoxy-1-phenyl-4-(4-phenylthiazol-2-yl)cyclohexanecarboxylic Acid

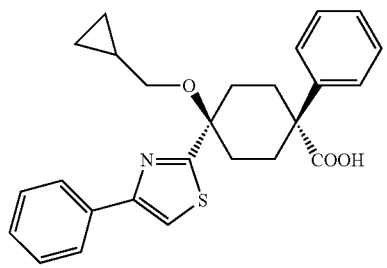

MS (ESI+): 434

EXAMPLE 334

Trans-4-Cyclopropylmethoxy-1-(4-fluorophenyl)-4-(5-fluoropyridin-2-yl)cyclohexanecarbonitrile

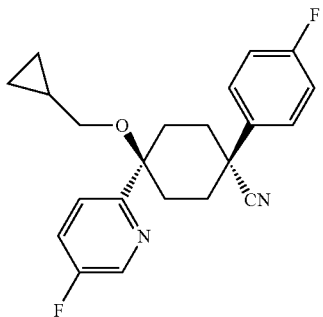

2 g of trans-1-(4-fluorophenyl)-4-(5-fluoropyridin-2-yl)-4-hydroxycyclohexanecarbonitrile and 4.3 g of bromomethylcyclopropane were dissolved in 20 ml of DMF, 0.61 g of sodium hydride (50% strength in mineral oil) were added and the reaction mixture was stirred for 18 h at room temperature. The mixture was then cooled to 0° C. and treated with a saturated aqueous ammonium chloride solution and extracted with EA. The combined organic phases were washed with brine and dried over sodium sulfate, and the solvent was removed in vacuo. Flash chromatography (silica gel; cyclohexane/EA, gradient from 100:0 to 70:30) yielded 2.33 g of the title compound as a white foam.

MS (ESI+): 369
HPLC (Method LC18): Rt 9.31 min

EXAMPLE 335

Trans-4-Cyclopropylmethoxy-1-(4-fluorophenyl)-4-(5-fluoropyridin-2-yl)cyclohexanecarboxamide

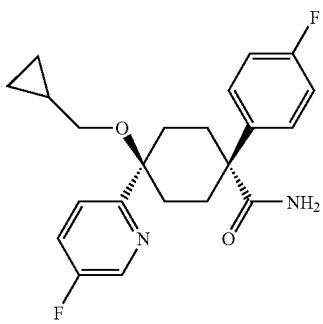

2.3 g of trans-4-cyclopropylmethoxy-1-(4-fluorophenyl)-4-(5-fluoropyridin-2-yl)cyclohexanecarbonitrile were dissolved in 60 ml of MOH. The mixture was heated to 60° C., and a solution of 0.7 g of potassium hydroxide in 2 ml of water was added, followed by 1.4 ml of hydrogen peroxide (30% strength in water). After one hour each, four further 1.4 ml portions of hydrogen peroxide (30% strength in water) were added. Subsequently, the reaction mixture was stirred for 12 h at 55° C. Then it was treated with water and extracted with EA. The combined organic phases were washed with brine and dried over sodium sulfate, and the solvent was removed in vacuo. Flash chromatography (silica gel; DCM/MOH, gradient from 100:0 to 95:5) yielded 1.4 g of the title compound as a white solid.

MS (ESI+): 387
HPLC (Method LC18): Rt 8.22 min

EXAMPLE 336

Trans-4-Cyclopropylmethoxy-1-(4-fluorophenyl)-4-(5-fluoropyridin-2-yl)cyclohexanecarboxylic Acid

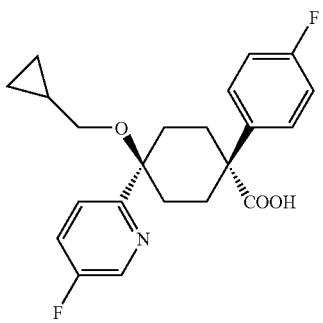

1.4 g of trans-4-cyclopropylmethoxy-1-(4-fluorophenyl)-4-(5-fluoropyridin-2-yl)cyclohexanecarboxamide were dissolved in 4 ml of DMF. Under nitrogen, the mixture was cooled to 0° C., and 1.38 g of nitrosylsulfuric acid were added. The green mixture was stirred for 1 h. 10 ml of water and EA were added. The aqueous layer was extracted with EA. The combined organic phases were washed with brine and dried over sodium sulfate, and the solvent was removed in vacuo. The residue was crystallized from a mixture of EA and pentane. 0.97 g of the title compound were obtained as a white solid.

MS (ESI+): 388
HPLC (Method LC18): Rt 8.96 min
$^1$H-NMR ($d_6$-DMSO; 200 MHz): 8.5 (d, 1H), 7.7 (m, 1H), 7.59 (m, 1H), 7.45 (m, 2H), 7.15 (m, 2H), 2.9 (d, 2H), 2.38 (m, 2H), 1.9 (m, 6H), 0.95 (m, 1H), 0.5 (m, 2H), 0.37 (m, 2H)
MP: 211° C.

EXAMPLE 337

Trans-1-(4-Fluorophenyl)-4-(5-fluoropyridin-2-yl)-4-(pyridin-2-yloxy)cyclohexanecarbonitrile

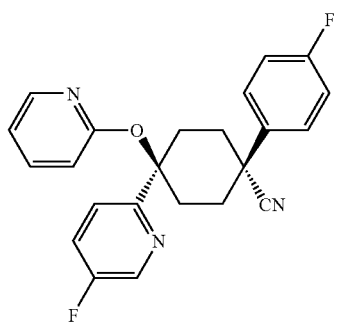

0.7 g of trans-1-(4-fluorophenyl)-4-(5-fluoropyridin-2-yl)-4-hydroxycyclohexanecarbonitrile and 1.7 g of 2-bromopyridine were dissolved in 7 ml of DMF, 0.21 g of sodium hydride (60% strength in mineral oil) were added, and the reaction mixture was stirred for 2 h at room temperature and then heated to 80° C. for 16 h. The mixture was then cooled to 0° C., treated with a saturated aqueous ammonium chloride solution and extracted with EA. The combined organic phases were washed with brine and dried over sodium sulfate, and the solvent was removed in vacuo. Flash chromatography (silica gel; cyclohexane/EA, gradient from 100:0 to 70:30) yielded 0.59 g of the title compound as a white solid.

EXAMPLE 338

Trans-1-(4-Fluorophenyl)-4-(5-fluoropyridin-2-yl)-4-(pyridin-2-yloxy)cyclohexanecarboxamide

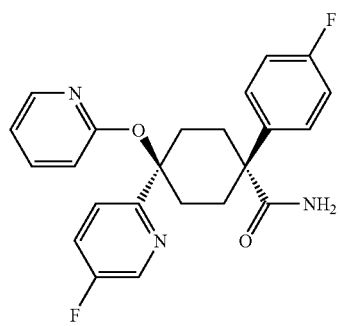

0.59 g of trans-1-(4-fluorophenyl)-4-(5-fluoropyridin-2-yl)-4-(pyridin-2-yloxy)cyclohexanecarbonitrile were dissolved in 15 ml of MOH and a solution of 0.17 g of potassium hydroxide in 0.5 ml of water was added. The mixture was heated to 55° C., and 1.7 ml of hydrogen peroxide (30% strength in water) was then added. The reaction mixture was stirred at 55° C. for 12 h. Then it was treated with water and extracted with EA. The combined organic phases were washed with brine and dried over sodium sulfate, and the solvent was removed in vacuo. The residue was triturated with DIP and pentane. 0.55 g of the title compound were obtained as a white solid.

EXAMPLE 339

Trans-1-(4-Fluorophenyl)-4-(5-fluoropyridin-2-yl)-4-(pyridin-2-yloxy)cyclohexanecarboxylic Acid

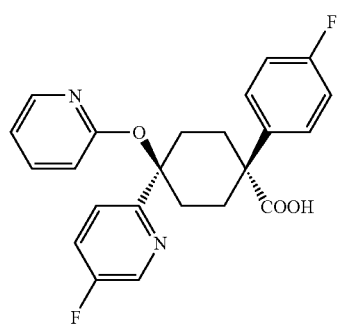

0.55 g of trans-1-(4-fluorophenyl)-4-(5-fluoropyridin-2-yl)-4-(pyridin-2-yloxy)cyclohexanecarboxamide were dissolved in 1.5 ml of DMF. Under nitrogen, the mixture was cooled to 0° C. and 0.58 g of nitrosylsulfuric acid were added. The green mixture was stirred for 1 h. 10 ml of water and EA were added. The aqueous layer was extracted with EA. The combined organic phases were washed with brine and dried over sodium sulfate, and the solvent was removed in vacuo. The residue was crystallized from a mixture of EA and pentane. 0.286 g of the title compound were obtained as a white solid.

MS (ESI+): 411

HPLC (Method LC18): Rt 8.49 min $^1$H-NMR ($d_6$-DMSO; 200 MHz): 8.45 (d, 1H), 7.8 (m, 2H), 7.7-7.3 (m, 5H), 7.13 (t, 2H), 6.82 (m, 2H), 2.5 (m, 4H), 2.1 (m, 2H), 1.9 (m, 2H)

MP: >300° C.

EXAMPLE 340

Trans-1-(4-Fluorophenyl)-4-(5-fluoropyridin-2-yl)-4-(pyrimidin-2-yloxy)cyclohexanecarbonitrile

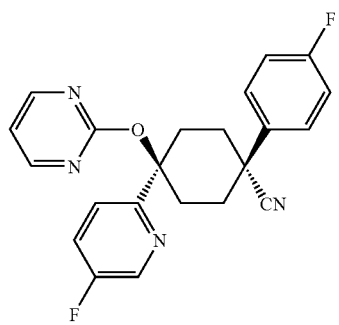

0.18 g of sodium hydride (60% strength in mineral oil) were washed with pentane under nitrogen and suspended in 9 ml of toluene. 0.94 g of trans-1-(4-fluorophenyl)-4-(5-fluoropyridin-2-yl)-4-hydroxycyclohexanecarbonitrile and 0.2 g of 15-C-5 crown ether were added. After stirring at 20° C. for 30 min, 0.38 g of 2-chloropyrimidine were added and the mixture was heated at 100° C. for 16 h. The mixture was then cooled to 0° C., treated with a saturated aqueous ammonium chloride solution and extracted with EA. The combined organic phases were washed with brine and dried over sodium sulfate. The solvent was removed in vacuo and the crude product was purified by flash chromatography (silica gel; cyclohexane/EA, gradient from 90:10 to 60:40). 0.6 g of the title compound were obtained as a white solid.

MS (ESI+): 415 (M+23)

HPLC (Method LC18): Rt 4.94 min

TLC (cyclohexane/EA 3:2): Rf 0.22

EXAMPLE 341

Trans-1-(4-Fluorophenyl)-4-(5-fluoropyridin-2-yl)-4-(pyrimidin-2-yloxy)cyclohexanecarboxamide

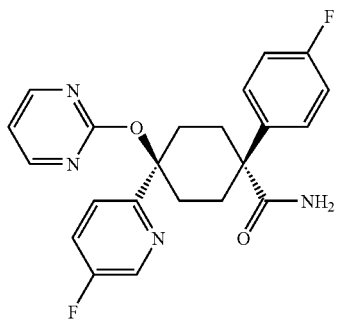

The title compound was prepared from trans-1-(4-fluorophenyl)-4-(5-fluoropyridin-2-yl)-4-(pyrimidin-2-yloxy)cyclohexanecarbonitrile analogously as described in Example 338.

MS (ESI+): 433 (M+23)

HPLC (Method LC18): Rt 5.71 min

EXAMPLE 342

Trans-1-(4-Fluorophenyl)-4-(5-fluoropyridin-2-yl)-4-(pyrimidin-2-yloxy)cyclohexanecarboxylic Acid

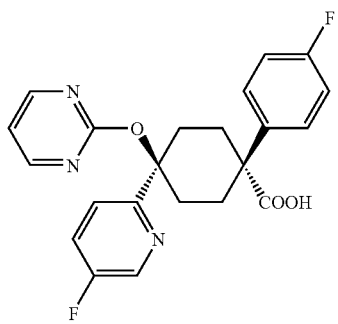

The title compound was prepared from trans-1-(4-fluorophenyl)-4-(5-fluoropyridin-2-yl)-4-(pyrimidin-2-yloxy)cyclohexanecarboxamide analogously as described in Example 339.

MS (ESI+): 434 (M+23)

HPLC (Method LC18): Rt 4.36 min $^1$H-NMR (d$_6$-DMSO; 200 MHz): 8.5 (d, 1H), 8.4 (d, 2H), 7.65-7.2 (m, 4H), 7.13 (t, 2H), 6.95 (t, 1H), 2.5 (m, 4H), 2.1 (m, 2H), 1.9 (m, 2H)

MP: 159° C.

EXAMPLE 343

Trans-1-(4-Fluorophenyl)-4-(5-fluoropyridin-2-yl)-4-phenoxycyclohexanecarbonitrile

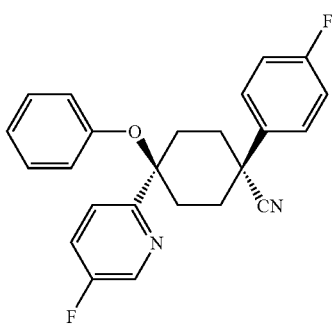

0.6 g of trans-1-(4-fluorophenyl)-4-(5-fluoropyridin-2-yl)-4-hydroxycyclohexanecarbonitrile and 0.36 g of cupric acetate hydrate were suspended in 10 ml of toluene. 4.3 g of triphenylbismuth diacetate were added, and the reaction mixture was heated to 110° C. for 2 h. The mixture was then cooled to 0° C., treated with 1 N hydrochloric acid and extracted with EA. The combined organic phases were washed with brine and dried over sodium sulfate and the solvent was removed in vacuo. Flash chromatography (silica gel; cyclohexane/EA, gradient from 100:0 to 80:20) yielded 0.65 g of the title compound as a white foam.

MS (ESI+): 391

HPLC (Method LC18): Rt 8.86 min

EXAMPLE 344

Trans-1-(4-Fluorophenyl)-4-(5-fluoropyridin-2-yl)-4-phenoxycyclohexanecarboxamide

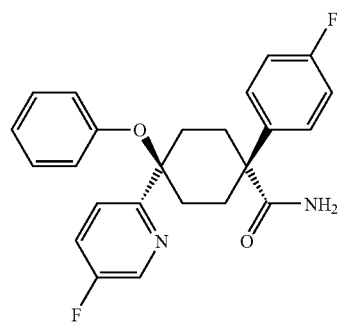

0.425 g of the title compound were obtained from 0.65 g of trans-1-(4-fluorophenyl)-4-(5-fluoropyridin-2-yl)-4-phenoxycyclohexanecarbonitrile analogously as described in Example 338.

EXAMPLE 345

Trans-1-(4-Fluorophenyl)-4-(5-fluoropyridin-2-yl)-4-phenoxycyclohexanecarboxylic Acid

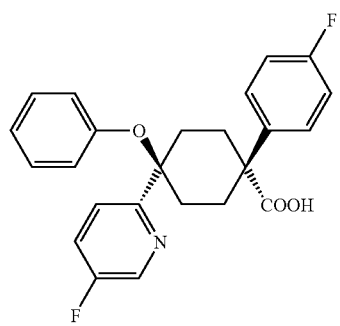

346 mg of the title compound were obtained from 425 mg of trans-1-(4-fluorophenyl)-4-(5-fluoropyridin-2-yl)-4-phenoxycyclohexanecarboxamide and 0.4 g of nitrosylsulfuric acid analogously as described in Example 339.

MS (ESI+): 410

HPLC (Method LC18): Rt 8.04 min $^1$H-NMR (d$_6$-DMSO; 200 MHz): 8.6 (d, 1H), 7.8-7.4 (m, 4H), 7.22-7.05 (m, 4H), 6.85 (t, 1H), 6.5 (d, 2H), 2.5-2.0 (m, 6H), 1.9 (m, 2H)

MP: 237° C.

EXAMPLE 346

2,4-Dibromo-1-cyclopropylmethyl-5-methyl-1H-imidazole and 2,5-dibromo-1-cyclopropylmethyl-4-methyl-1H-imidazole 1.65 g of sodium hydride (50% strength in mineral oil) were washed with pentane under a nitrogen atmosphere, suspended in 40 ml of DMF and cooled to 0° C. 9 g of 2,4-dibromo-5-methyl-1H-imidazole were added as a solution in 35 ml of DMF. Then 5.5 g of bromomethylcyclopropane were added and the mixture was stirred for 16 h at 20° C. 250 ml of water and EA were added and the aqueous layer was extracted with EA. The combined organic phases were washed with brine and dried over sodium sulfate. The solvent was removed in vacuo. Flash chromatography (silica gel; EA/toluene 1:19) of the residue yielded 5.5 g of 2,4-dibromo-1-cyclopropylmethyl-5-methyl-1H-imidazole (oil) and 4 g of 2,5-dibromo-1-cyclopropylmethyl-4-methyl-1H-imidazole (oil).

EXAMPLE 346-1

2,4-Dibromo-1-cyclopropylmethyl-5-methyl-1H-imidazole

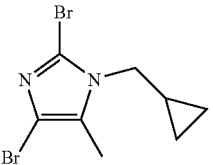

TLC (EA/toluene 1:9): Rf=0.5

EXAMPLE 346-2

2,5-Dibromo-1-cyclopropylmethyl-4-methyl-1H-imidazole

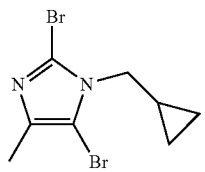

TLC (EA/toluene 1:9): Rf 0.36

EXAMPLE 347

Cis-4-(4-Bromo-1-cyclopropylmethyl-5-methyl-1H-imidazol-2-yl)-1-(4-fluorophenyl)-4-hydroxycyclohexanecarbonitrile and Trans-4-(4-bromo-1-cyclopropylmethyl-5-methyl-1H-imidazol-2-yl)-1-(4-fluorophenyl)-4-hydroxycyclohexanecarbonitrile

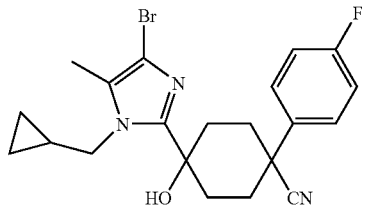

5.5 g of 2,4-dibromo-1-cyclopropylmethyl-5-methyl-1H-imidazole were dissolved in 20 ml of anhydrous THF and cooled to −70° C. under a nitrogen atmosphere. 12.9 ml of a 1.6 M solution of n-butyllithium in hexane were added dropwise. After 30 min a solution of 4 g of 1-(4-fluorophenyl)-4-oxocyclohexanecarbonitrile in 10 ml of THF was added. The reaction mixture was allowed to warm to room temperature during 4 h. 50 ml of water were added, and the mixture was extracted three times with 50 ml each of EA. The combined organic phases were washed with brine and dried over sodium sulfate. The solvent was removed in vacuo. Flash chromatography of the residue (240 g of silica gel; cyclohexane/EA, gradient from 80:20 to 70:30) yielded 5 g of the cis title compound (white solid) and 1.8 g of the trans title compound (white solid).

EXAMPLE 347-1

Cis-4-(4-Bromo-1-cyclopropylmethyl-5-methyl-1H-imidazol-2-yl)-1-(4-fluorophenyl)-4-hydroxycyclohexanecarbonitrile

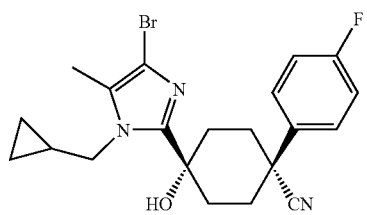

MS (ESI+): 433

HPLC (Method LC18): Rt 8.01 min

TLC (cyclohexane/EA 4:1): Rf 0.39

EXAMPLE 347-2

Trans-4-(4-Bromo-1-cyclopropylmethyl-5-methyl-1H-imidazol-2-yl)-1-(4-fluorophenyl)-4-hydroxycyclohexanecarbonitrile

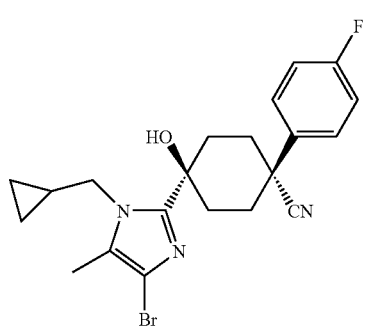

MS (ESI+): 433

HPLC (Method LC18): Rt 7.71 min

TLC (cyclohexane/EA 4:1): Rf 0.27

EXAMPLE 348

Cis-4-(4-Bromo-1-cyclopropylmethyl-5-methyl-1H-imidazol-2-yl)-4-cyclopropylmethoxy-1-(4-fluorophenyl)cyclohexanecarbonitrile

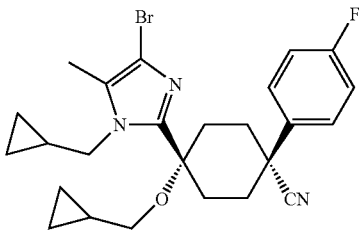

2.5 g of cis 4-(4-bromo-1-cyclopropylmethyl-5-methyl-1H-imidazol-2-yl)-1-(4-fluorophenyl)-4-hydroxycyclohexanecarbonitrile and 1.56 g of bromomethylcyclopropane were dissolved in 10 ml of a 4:1 mixture of dioxane and DMF, 0.46 g of sodium hydride (50% strength in mineral oil) were added, and the reaction mixture was stirred for 8 h at 60° C. The mixture was then cooled to 20° C., treated with a saturated aqueous ammonium chloride solution and extracted with EA. The combined organic phases were washed with brine and dried over sodium sulfate. The solvent was removed in vacuo. The crude product was purified by flash chromatography (silica gel; cyclohexane/EA 9:1). 2.7 g of the title compound were obtained as a white solid.

MS (ESI+): 488

HPLC (Method LC18): Rt 9.3 min

TLC (cyclohexane/EA 3:2): Rf 0.65

EXAMPLE 349

Cis 4-(4-Bromo-1-cyclopropylmethyl-5-methyl-1H-imidazol-2-yl)-4-cyclopropylmethoxy-1-(4-fluorophenyl)cyclohexanecarboxamide

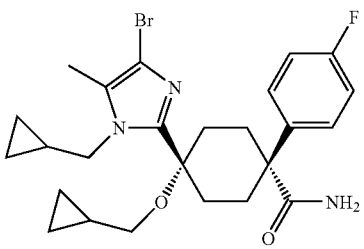

0.6 g of cis 4-(4-bromo-1-cyclopropylmethyl-5-methyl-1H-imidazol-2-yl)-4-cyclopropylmethoxy-1-(4-fluorophenyl)cyclohexanecarbonitrile were dissolved in 4 ml of MOH and heated to 50° C. A solution of 0.14 g of potassium hydroxide in 1 ml of water was then added, followed by 0.3 ml of hydrogen peroxide (30% strength in water). After one hour each, four further 0.3 ml portions of hydrogen peroxide (30% strength in water) were added. The reaction mixture was stirred for 12 h at 55° C. Then it was treated with water and extracted with DCM. The combined organic phases were washed with brine and dried over sodium sulfate. The solvent

EXAMPLE 350

Cis 4-(4-Bromo-1-cyclopropylmethyl-5-methyl-1H-imidazol-2-yl)-4-cyclopropylmethoxy-1-(4-fluorophenyl)cyclohexanecarboxylic Acid

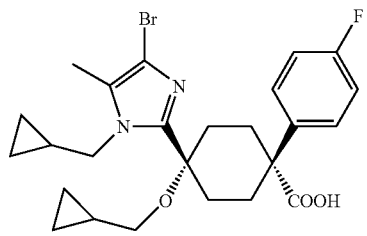

0.3 g of cis 4-(4-bromo-1-cyclopropylmethyl-5-methyl-1H-imidazol-2-yl)-4-cyclopropylmethoxy-1-(4-fluorophenyl)cyclohexanecarboxamide were dissolved in 2 ml of a 1:1 mixture of acetonitrile and DMF. The mixture was cooled to 0° C. under nitrogen, and 0.14 g of nitrosonium tetrafluoroborate were added. The green mixture was stirred for 1 h. 10 ml of water and 10 ml of DCM were added. The aqueous layer was extracted with DCM. The combined organic phases were washed with brine and dried over sodium sulfate. The solvent was removed in vacuo. The crude product was purified by flash chromatography (silica gel; DCM/MOH, gradient from 99:1 to 97:3). 0.11 g of the title compound were obtained as a white solid.

MS (ESI+): 505
HPLC (Method LC19): Rt 9.8 min
$^1$H-NMR ($d_6$-DMSO; 400 MHz): 7.4 (m, 2H), 7.12 (m, 2H), 4.1 (d, 2H), 2.78 (d, 2H), 2.28 (m, 2H), 2.1 (s, 3H), 2.02 (m, 4H), 1.87 (m, 2H), 0.9-0.8 (m, 2H), 0.58 (m, 2H), 0.36 (m, 4H), 0.0 (m, 2H)
MP: 210° C.

EXAMPLE 351

Cis-4-(5-Bromo-1-cyclopropylmethyl-4-methyl-1H-imidazol-2-yl)-1-(4-fluorophenyl)-4-hydroxycyclohexanecarbonitrile and Trans-4-(5-bromo-1-cyclopropylmethyl-4-methyl-1H-imidazol-2-yl)-1-(4-fluorophenyl)-4-hydroxycyclohexanecarbonitrile

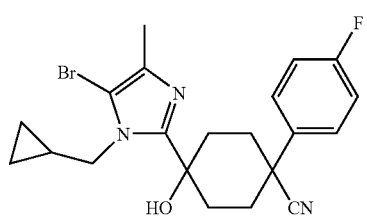

4 g of 2,5-dibromo-1-cyclopropylmethyl-4-methyl-1H-imidazole were dissolved in 15 ml of anhydrous THF and cooled to −70° C. under a nitrogen atmosphere. 9.4 ml of a 1.6 M solution of n-butyllithium in hexane were added dropwise. After 30 min a solution of 3 g of 1-(4-fluorophenyl)-4-oxo-cyclohexanecarbonitrile in 10 ml of THF was added. The reaction mixture was allowed to warm to room temperature during 4 h. 50 ml of water were added and the mixture was extracted three times with 50 ml each of EA. The combined organic phases were washed with brine and dried over sodium sulfate. The solvent was removed in vacuo. Flash chromatography of the residue (240 g of silica gel; cyclohexane/EA, gradient from 80:20 to 70:30) yielded 2.4 g of the cis title compound (white solid) and 1.1 g of the trans title compound (white solid).

EXAMPLE 351-1

Cis-4-(5-Bromo-1-cyclopropylmethyl-4-methyl-1H-imidazol-2-yl)-1-(4-fluorophenyl)-4-hydroxycyclohexanecarbonitrile

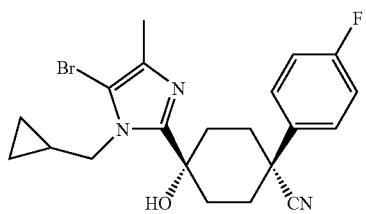

MS (ESI+): 433
HPLC (Method LC18): Rt 6.75 min
TLC (cyclohexane/EA 3:2): Rf 0.39

EXAMPLE 351-2

Trans-4-(5-Bromo-1-cyclopropylmethyl-4-methyl-1H-imidazol-2-yl)-1-(4-fluorophenyl)-4-hydroxycyclohexanecarbonitrile

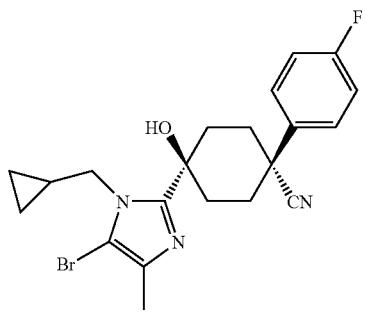

MS (ESI+): 433
HPLC (Method LC18): Rt 5.98 min
TLC (cyclohexane/EA 6:4): Rf. 0.27

EXAMPLE 352

Cis-4-(5-Bromo-1-cyclopropylmethyl-4-methyl-1H-imidazol-2-yl)-4-cyclopropylmethoxy-1-(4-fluorophenyl)cyclohexanecarbonitrile

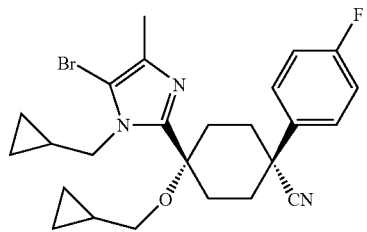

2.4 g of cis 4-(5-bromo-1-cyclopropylmethyl-4-methyl-1H-imidazol-2-yl)-1-(4-fluorophenyl)-4-hydroxycyclohexanecarbonitrile and 1.5 g of bromomethylcyclopropane were dissolved in 10 ml of a 4:1 mixture of dioxane and DMF, 0.46 g of sodium hydride (50% strength in mineral oil) were added, and the reaction mixture was stirred for 8 h at 60° C. The mixture was then cooled to 20° C., treated with a saturated aqueous ammonium chloride and extracted with EA. The combined organic phases were washed with brine and dried over sodium sulfate. The solvent was removed in vacuo. The crude product was purified by flash chromatography (silica gel; cyclohexane/EA 4:1). 2.2 g of the title compound were obtained as a white solid.

TLC (cyclohexane/EA 3:2): Rf=0.55

EXAMPLE 353

Cis 4-(5-Bromo-1-cyclopropylmethyl-4-methyl-1H-imidazol-2-yl)-4-cyclopropylmethoxy-1-(4-fluorophenyl)cyclohexanecarboxamide

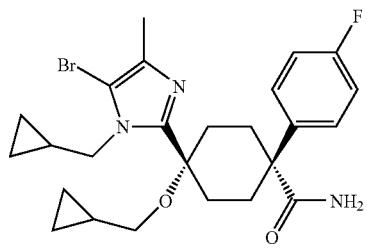

0.6 g of cis 4-(5-bromo-1-cyclopropylmethyl-4-methyl-1H-imidazol-2-yl)-4-cyclopropylmethoxy-1-(4-fluorophenyl)cyclohexanecarbonitrile were dissolved in 9 ml of MOH and heated to 50° C. A solution of 0.2 g of potassium hydroxide in 1 ml of water was then added, followed by 0.3 ml of hydrogen peroxide (30% strength in water). After one hour each, four further 0.3 ml portions of hydrogen peroxide (30% strength in water) were added. The reaction mixture was stirred for 12 h at 55° C. Then it was treated with water and extracted with DCM. The combined organic phases were washed with brine and dried over sodium sulfate. The solvent was removed in vacuo. The crude product was purified by crystallization from DIP/pentane. 520 mg of the title compound were obtained as a white solid.

MS (ESI+): 504

TLC (cyclohexane/EA 3:2): Rf 0.15

EXAMPLE 354

Cis-4-(5-Bromo-1-cyclopropylmethyl-4-methyl-1H-imidazol-2-yl)-4-cyclopropylmethoxy-1-(4-fluorophenyl)cyclohexanecarboxylic Acid

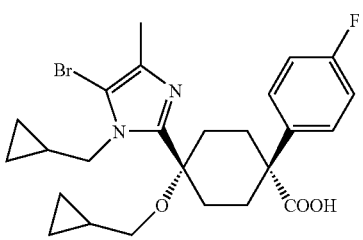

0.5 g of cis 4-(5-bromo-1-cyclopropylmethyl-4-methyl-1H-imidazol-2-yl)-4-cyclopropylmethoxy-1-(4-fluorophenyl)cyclohexanecarboxamide were dissolved in 2 ml of a 1:1 mixture of acetonitrile and DMF. The mixture was cooled to 0° C. under nitrogen, and 0.29 g of nitrosonium tetrafluoroborate are added. The green mixture was stirred for 1 h. 10 ml of water and 10 ml of DCM were added. The aqueous layer was extracted with DCM. The combined organic phases were washed with brine and dried over sodium sulfate. The solvent was removed in vacuo. The crude product was purified by flash chromatography (silica gel; DCM/MOH, gradient from 99:1 to 97:3). 0.25 g of the title compound were obtained as a white solid.

MS (ESI+): 505

HPLC (Method LC19): Rt 7.8 min $^1$H-NMR (d$_6$-DMSO; 400 MHz): 7.45 (m, 2H), 7.13 (m, 2H), 4.1 (d, 2H), 2.78 (d, 2H), 2.28 (m, 2H), 2.1 (m, 4H), 1.95 (s, 3H), 1.9 (m, 2H), 1.05 (m, 1H), 0.85 (m, 1H), 0.57 (m, 2H), 0.48 (m, 2H), 0.38 (m, 2H), 0.0 (m, 2H)

MP: 190° C.

EXAMPLE 355

Cis-4-Cyclopropylmethoxy-4-(1-cyclopropylmethyl-5-methyl-1H-imidazol-2-yl)-1-(4-fluorophenyl)cyclohexanecarbonitrile

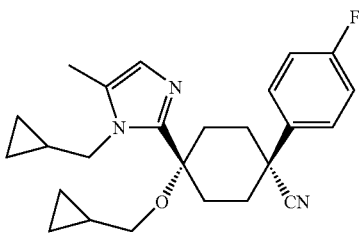

2.5 g of cis 4-(4-bromo-1-cyclopropylmethyl-5-methyl-1H-imidazol-2-yl)-4-cyclopropylmethoxy-1-(4-fluorophenyl)cyclohexanecarbonitrile were dissolved in 5 ml of anhydrous THF (5 ml) and cooled to −70° C. under a nitrogen atmosphere. 3.5 ml of a 1.6 M solution of n-butyllithium in hexane were added dropwise and the reaction mixture was stirred for 30 min. Then 50 ml of a saturated aqueous solution of ammonium chloride were added and the mixture was extracted three times with 50 ml each of EA. The combined organic phases were washed with brine and dried over sodium sulfate. The solvent was removed in vacuo. The crude product was purified by flash chromatography (silica gel; EA/cyclohexane 1:4). 1.5 g of the title compound were obtained as a white solid.

MS (ESI+): 408
HPLC (Method LC18): Rt 5.7 min
TLC (EA/HEP 2:3): Rf 0.27

EXAMPLE 356

Cis-4-Cyclopropylmethoxy-4-(1-cyclopropylmethyl-5-methyl-1H-imidazol-2-yl)-1-(4-fluorophenyl)cyclohexanecarboxamide

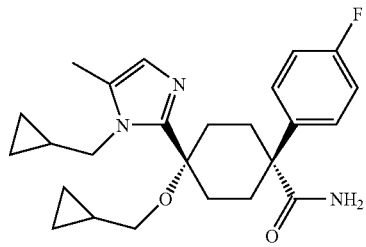

1.3 g of cis 4-cyclopropylmethoxy-4-(1-cyclopropylmethyl-5-methyl-1H-imidazol-2-yl)-1-(4-fluorophenyl)cyclohexanecarbonitrile were dissolved in 20 ml of MOH. The mixture was heated to 50° C. and a solution of 0.36 g of potassium hydroxide in 2 ml of water was added, followed by 0.6 ml of hydrogen peroxide (30% strength in water). After one hour each, four further 0.6 ml portions of hydrogen peroxide (30% strength in water) were added. The reaction mixture was stirred for 12 h at 50° C. It was then treated with water and extracted with DCM. The combined organic phases were washed with brine and dried over sodium sulfate. The solvent was removed in vacuo. The residue was crystallized from DIP. 1.2 g of the title compound were obtained as a white solid.

MS (ESI+): 426
HPLC (Method LC18): Rt 4.66 min

EXAMPLE 357

Cis-4-Cyclopropylmethoxy-4-(1-cyclopropylmethyl-5-methyl-1H-imidazol-2-yl)-1-(4-fluorophenyl)cyclohexanecarboxylic Acid

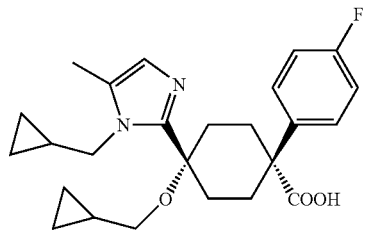

1.2 g of cis 4-cyclopropylmethoxy-4-(1-cyclopropylmethyl-5-methyl-1H-imidazol-2-yl)-1-(4-fluorophenyl)cyclohexanecarboxamide were dissolved in 5 ml of DMF. The mixture was cooled to 0° C. under nitrogen, and 0.66 g of nitrosonium tetrafluoroborate were added. The green mixture was stirred for 1 h. 10 ml of water and 10 ml of DCM were added. The aqueous layer was extracted with DCM. The combined organic phases were washed with brine and dried over sodium sulfate. The solvent was removed in vacuo. The crude product was purified by flash chromatography (silica gel; DCM MOH, gradient from 98:2 to 90:10). 0.65 g of the title compound were obtained as a white solid.

MS (ESI+): 427
HPLC (Method LC18): Rt 4.98 min
$^1$H-NMR (d$_6$-DMSO; 400 MHz): 7.42 (m, 2H), 7.1 (m, 2H), 6.48 (s, 1H), 4.1 (d, 2H), 2.78 (d, 2H), 2.32 (m, 2H), 2.2 (s, 3H), 2.1 (m, 4H), 1.9 (m, 2H), 0.9 (m, 2H), 0.6 (m, 2H), 0.4 (m, 4H), 0.0 (m, 2H)
MP: 187° C.

EXAMPLE 358

Cis-4-(4-Chloro-1-cyclopropylmethyl-5-methyl-1H-imidazol-2-yl)-4-cyclopropylmethoxy-1-(4-fluorophenyl)cyclohexanecarbonitrile

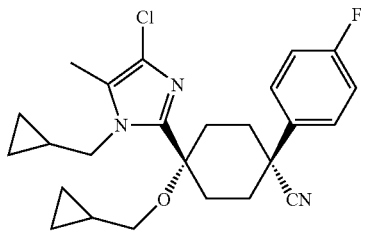

1.1 g of cis-4-(4-bromo-1-cyclopropylmethyl-5-methyl-1H-imidazol-2-yl)-4-cyclopropylmethoxy-1-(4-fluorophenyl)cyclohexanecarbonitrile were dissolved in 5 ml of anhydrous THF and cooled to −70° C. 1.4 ml of a 1.6 M solution of n-butyllithium in hexane were added, and the mixture was stirred at −70° C. for 30 min. Then a solution of 0.6 g of hexachloroethane in 5 ml of THF was added. The mixture was allowed to warm to room temperature over 1 h. A saturated aqueous solution of ammonium chloride was added, and the mixture was extracted three times with 50 ml each of EA. The combined organic phases were washed with brine and dried over sodium sulfate. The solvent was removed in vacuo. The crude product was purified by flash chromatography (silica gel; cyclohexane/EA 4:1). 0.79 g of the title compound were obtained as a white solid.

MS (ESI+): 442
TLC (cyclohexane/EA 3:2): Rf 0.6
HPLC (Method LC18): Rt 8.5 min

EXAMPLE 359

Cis-4-(4-Chloro-1-cyclopropylmethyl-5-methyl-1H-imidazol-2-yl)-4-cyclopropylmethoxy-1-(4-fluorophenyl)cyclohexanecarboxamide

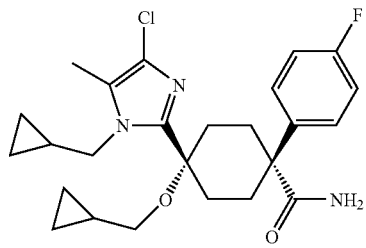

0.79 g of cis-4-(4-chloro-1-cyclopropylmethyl-5-methyl-1H-imidazol-2-yl)-4-cyclopropylmethoxy-1-(4-fluorophenyl)cyclohexanecarbonitrile were dissolved in 7 ml of MOH. The mixture was heated to 50° C. and a solution of 0.2 g of potassium hydroxide in 1 ml of water was added, followed by 0.3 ml of hydrogen peroxide (30% strength in water). After one hour each, four further 0.3 ml portions of hydrogen peroxide (30% strength in water) were added. The reaction mixture was stirred for 12 h at 55° C. It was then treated with water and extracted with DCM. The combined organic phases were washed with brine and dried over sodium sulfate. The solvent was removed in vacuo. The crude product was purified by flash chromatography (silica gel; DCM/MOH, gradient from 100:0 to 95:5). 805 mg of the title compound were obtained as a white solid.

MS (ESI+): 460
HPLC (Method LC18): Rt=7.4 min

EXAMPLE 360

Cis-4-(4-Chloro-1-cyclopropylmethyl-5-methyl-1H-imidazol-2-yl)-4-cyclopropylmethoxy-1-(4-fluorophenyl)cyclohexanecarboxylic Acid

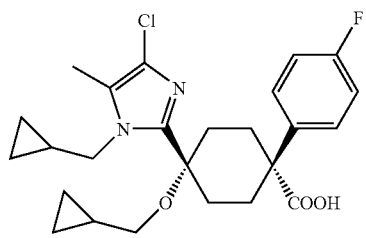

0.8 g of cis-4-(4-chloro-1-cyclopropylmethyl-5-methyl-1H-imidazol-2-yl)-4-cyclopropylmethoxy-1-(4-fluorophenyl)cyclohexanecarboxamide were dissolved in 2 ml of a 1:1 mixture of acetonitrile and DMF. The mixture is cooled to 0° C. under nitrogen, and 0.61 g of nitrosonium tetrafluoroborate were added. The green mixture is stirred for 1 h. 10 ml of water and 10 ml of DCM were added. The aqueous layer was extracted with DCM. The combined organic phases were washed with brine and dried over sodium sulfate. The solvent was removed in vacuo. The crude product was purified by flash chromatography (silica gel; DCM/MOH/conc. aqueous ammonia, gradient from 100:0:0 to 90:10:1). 0.489 g of the title compound were obtained as a white solid.

MS (ESI+): 461
HPLC (Method LC19): Rt 9.9 min
$^1$H-NMR (d$_6$-DMSO; 400 MHz): 7.4 (m, 2H), 7.10 (m, 2H), 4.05 (d, 2H), 2.75 (d, 2H), 2.25 (m, 2H), 2.1 (s, 3H), 2.02 (m, 4H), 1.87 (m, 2H), 0.9-0.8 (m, 2H), 0.58 (m, 2H), 0.36 (m, 4H), 0.0 (m, 2H)
MP: 185° C.

EXAMPLE 361

Cis-4-(5-Chloro-1-cyclopropylmethyl-4-methyl-1H-imidazol-2-yl)-4-cyclopropylmethoxy-1-(4-fluorophenyl)cyclohexanecarbonitrile

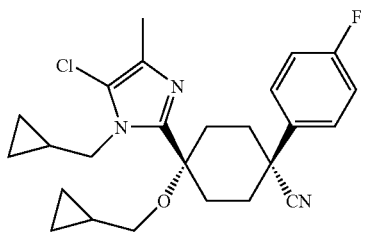

1.02 g of cis-4-(5-bromo-1-cyclopropylmethyl-4-methyl-1H-imidazol-2-yl)-4-cyclopropylmethoxy-1-(4-fluorophenyl)cyclohexanecarbonitrile were dissolved in 5 ml of anhydrous THF and cooled to −70° C. 1.3 ml of a 1.6 M solution of n-butyllithium in hexane were added and the mixture was stirred at −70° C. for 30 min. Then a solution of 0.54 g of hexachloroethane in 5 ml of THF was added. The mixture was allowed to warm to room temperature over 1 h. A saturated aqueous solution of ammonium chloride was added, and the mixture was extracted three times with 50 ml each of EA. The combined organic phases were washed with brine and dried over sodium sulfate. The solvent was removed in vacuo. The crude product was purified by flash chromatography (silica gel; cyclohexane/EA 4:1). 0.56 g of the title compound were obtained as a white solid.

MS (ESI+): 442
HPLC (Method LC18): Rt 8.9 min
TLC (cyclohexane/EA 3:2): Rf 0.66

EXAMPLE 362

Cis-4-(5-Chloro-1-cyclopropylmethyl-4-methyl-1H-imidazol-2-yl)-4-cyclopropylmethoxy-1-(4-fluorophenyl)cyclohexanecarboxamide

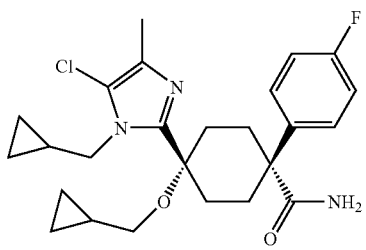

0.59 g of cis-4-(5-chloro-1-cyclopropylmethyl-4-methyl-1H-imidazol-2-yl)-4-cyclopropylmethoxy-1-(4-fluorophenyl)cyclohexanecarbonitrile were dissolved in 7 ml of MOH. The mixture was heated to 50° C. and a solution of 0.15 g of potassium hydroxide in 1 ml of water was added, followed by 0.3 ml of hydrogen peroxide (30% strength in water). After one hour each, four further 0.3 ml portions of hydrogen peroxide (30% strength in water) were added. The reaction mixture was stirred for 12 h at 55° C. It was then treated with water and extracted with DCM. The combined organic phases were washed with brine and dried over sodium sulfate. The solvent was removed in vacuo. The crude product was purified by flash chromatography (silica gel; DCM/MOH, gradient from 100:0 to 95:5). 605 mg of the title compound were obtained as a white solid.

MS (ESI+): 460
HPLC (Method LC18): Rt=7.7 min

EXAMPLE 363

Cis-4-(5-Chloro-1-cyclopropylmethyl-4-methyl-1H-imidazol-2-yl)-4-cyclopropylmethoxy-1-(4-fluorophenyl)cyclohexanecarboxylic Acid

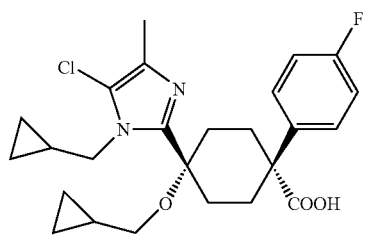

0.6 g of cis-4-(5-chloro-1-cyclopropylmethyl-4-methyl-1H-imidazol-2-yl)-4-cyclopropylmethoxy-1-(4-fluorophenyl)cyclohexanecarboxamide were dissolved in 2 ml of a 1:1 mixture of acetonitrile and DMF. The mixture was cooled to 0° C. under nitrogen, and 0.46 g of nitrosonium tetrafluoroborate were added. The green mixture was stirred for 1 h. 10 ml of water and 10 ml of DCM were added. The aqueous layer was extracted with DCM. The combined organic phases were washed with brine and dried over sodium sulfate. The solvent was removed in vacuo. The crude product was purified by flash chromatography (silica gel; DCM/MOH/conc. aqueous ammonia, gradient from 100:0:0 to 90:10:1). 0.323 g of the title compound were obtained as a white solid.

MS (ESI+): 461
HPLC (Method LC19): Rt 7.6 min $^1$H-NMR (d$_6$-DMSO; 400 MHz): 7.45 (m, 2H), 7.15 (m, 2H), 4.1 (d, 2H), 2.8 (d, 2H), 2.3 (m, 2H), 2.1 (m, 4H), 2.02 (s, 3H), 1.95 (m, 2H), 1.05 (m, 1H), 0.9 (m, 1H), 0.58 (m, 2H), 0.5-0.3 (m, 4H), 0.5 (m, 2H)

MP: 184° C.

Analogously to the preparation processes described above, the cis-4-Ar$^2$-4-(optionally substituted alkoxy)-1-(4-fluorophenyl)cyclohexanecarboxylic acids of the formula Ie and trans-4-Ar$^2$-4-(optionally substituted alkoxy)-1-(4-fluorophenyl)cyclohexanecarboxylic acids of the formula If listed in Table 13 were prepared.

TABLE 13

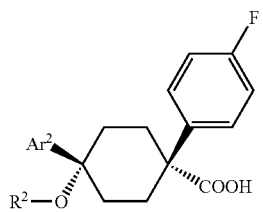

Ie

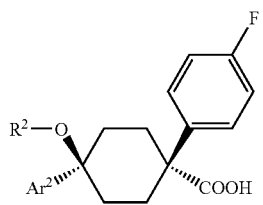

If

Example compounds of the formulae Ie and If

| Example | Ar$^2$ | R$^2$ | Formula configuration | MS (ESI+) | HPLC (Rt [min], Method) | MP |
|---|---|---|---|---|---|---|
| 364 | 1-cyclopropylmethyl-1H-imidazol-2-yl | cyclopropylmethyl | Ie cis | 413 | 6.85 LC19 | 160° C. |
| 365 (1) | 1-cyclopropylmethyl-4,5-dimethyl-1H-imidazol-2-yl | cyclopropylmethyl | Ie cis | 441 | 6.7 LC19 | 175° C. |

TABLE 13-continued

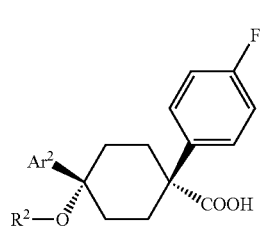

Ie

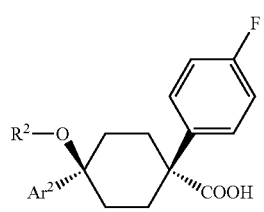

If

Example compounds of the formulae Ie and If

| Example | Ar² | R² | Formula configuration | MS (ESI+) | HPLC (Rt [min], Method) | MP |
|---|---|---|---|---|---|---|
| 366 | 1-cyclopropylmethyl-1H-benzoimidazol-2-yl | cyclopropyl-methyl | Ie cis | 463 | 4.89 LC19 | 246° C. |
| 367 | 1-cyclopropylmethyl-1H-benzoimidazol-2-yl | cyclopropyl-methyl | If trans | 463 | 6.9 LC19 | 302° C. |
| 368 | 1-cyclopropylmethyl-4-methyl-1H-imidazol-2-yl | cyclopropyl-methyl | Ie cis | 427 | 7.1 LC19 | 182-184° C. |
| 369 | 5-bromo-1-cyclopropylmethyl-4-methyl-1H-imidazol-2-yl | cyclopropyl-methyl | If trans | 507 | 8.8 LC19 | 227° C. |
| 370 | 1-cyclopropylmethyl-1H-imidazol-2-yl | 3-methyl-butyl | Ie cis | 429 | 7.0 LC19 | 205° C. |
| 371 | 1-cyclopropylmethyl-1H-imidazol-2-yl | 3-methyl-butyl | If trans | 429 | 9.5 LC19 | 193° C. |
| 372 | 1-cyclopropylmethyl-4,5-dimethyl-1H-imidazol-2-yl | 3-methyl-butyl | Ie cis | 457 | 8.0 LC19 | 215° C. |

(1) hydrochloride $^1$H-NMR data (d$_6$-DMSO; 400 MHz)

EXAMPLE 364

7.4 (m, 3H), 7.1 (m, 3H), 4.1 (d, 2H), 2.8 (d, 2H), 2.2 (m, 4H), 1.9 (m, 4H), 1.1 (m, 1H), 0.8 (m, 1H), 0.5 (m, 2H), 0.4 (m, 4H), 0.0 (m, 2H)

EXAMPLE 365

7.5 (m, 2H), 7.2 (m, 2H), 4.3 (d, 2H), 2.9 (d, 2H), 2.4 (m, 2H), 2.28 (s, 3H), 2.25 (m, 4H), 2.2 (s, 3H), 1.8 (m, 2H), 0.95 (m, 2H), 0.63 (m, 2H), 0.5 (m, 4H), 0.1 (m, 2H)

EXAMPLE 366

7.6 (m, 2H), 7.45 (m, 2H), 7.15 (m, 4H), 4.48 (d, 2H), 2.85 (d, 2H), 2.4 (m, 4H), 2.1 (m, 2H), 1.9 (m, 2H), 1.1 (m, 1H), 0.85 (m, 1H), 0.7 (m, 2H), 0.6 (m, 2H), 0.35 (m, 2H), 0.0 (m, 2H)

EXAMPLE 367

7.6-7.4 (m, 4H), 7.2-7.0 (m, 4H), 4.45 (d, 2H), 2.8 (d, 2H), 2.35 (m, 4H), 2.2 (m, 4H), 2.0 (m, 2H), 1.1 (m, 1H), 0.9 (m, 1H), 0.6 (m, 2H), 0.5 (m, 2H), 0.4 (m, 2H), 0.0 (m, 2H)

EXAMPLE 368

7.4 (m, 2H), 7.1 (m, 3H), 3.9 (d, 2H), 2.75 (d, 2H), 2.15 (m, 4H), 1.9 (s, 3H), 2.0-1.7 (m, 4H), 1.0 (m, 1H), 0.8 (m, 1H), 0.5 (m, 2H), 0.35 (m, 4H), 0.0 (m, 2H)

EXAMPLE 369

7.45 (m, 2H), 7.15 (m, 2H), 4.15 (d, 2H), 2.8 (d, 2H), 2.35 (m, 2H), 2.25 (m, 2H), 2.0 (s, 3H), 2.0-1.8 (m, 4H), 1.05 (m, 1H), 0.8 (m, 1H), 0.6 (m, 2H), 0.5 (m, 2H), 0.4 (m, 2H), 0.0 (m, 2H)

Analogously to the preparation processes described above, the cis-4-Ar²-4-(optionally substituted alkoxy)-1-phenylcyclohexanecarboxylic acids of the formula Ig and trans-4-Ar²-4-(optionally substituted alkoxy)-1-phenylcyclohexanecarboxylic acids of the formula Ih listed in Table 14 were prepared.

TABLE 14

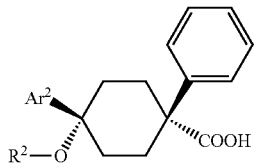

Ig

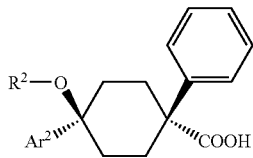

Ih

Example compounds of the formulae Ig and Ih

| Example | Ar² | R² | Formula, configuration | MS (ESI+) | HPLC (Rt [min], method) | MP |
|---|---|---|---|---|---|---|
| 373 | 4-bromo-1-cyclopropyl-methyl-5-methyl-1H-imidazol-2-yl | cyclopropyl-methyl | Ig cis | 487 | 10.0 LC19 | 183° C. |
| 374 | 4-bromo-1-cyclopropyl-methyl-5-methyl-1H-imidazol-2-yl | 3-methyl-butyl | Ig cis | 503 | 1.42 LC20 | 174° C. |
| 375 | 5-bromo-1-cyclopropyl-methyl-4-methyl-1H-imidazol-2-yl | 3-methyl-butyl | Ig cis | 503 | 1.14 LC20 | 192° C. |
| 376 | 1-cyclopropylmethyl-4,5-dimethyl-1H-imidazol-2-yl | 3-methyl-butyl | Ig cis | 439 | 7.1 LC19 | 212° C. |
| 377 | 1-cyclopropylmethyl-4,5-dimethyl-1H-imidazol-2-yl | cyclopropyl-methyl | Ig cis | 423 | 7.9 LC19 | 204° C. |
| 378 | 1-cyclopropylmethyl-5-trifluoromethyl-1H-imidazol-2-yl | cyclopropyl-methyl | Ig cis | 463 | 5.88 LC19 | 308° C. |
| 379 | 1-cyclopropylmethyl-5-trifluoromethyl-1H-imidazol-2-yl | cyclopropyl-methyl | Ih trans | 463 | 6.01 LC19 | 192 |
| 380 | 1-cyclopropylmethyl-4-trifluoromethyl-1H-imidazol-2-yl | cyclopropyl-methyl | Ig cis | 463 | 6.04 LC19 | 257° C. |
| 381 | 1-cyclopropylmethyl-4-trifluoromethyl-1H-imidazol-2-yl | cyclopropyl-methyl | Ih trans | 463 | 8.52 LC19 | 207° C. |
| 382 | 5-chloro-1-cyclopropyl-methyl-4-methyl-1H-imidazol-2-yl | cyclopropyl-methyl | Ig cis | 443 | 1.03 LC20 | 186° C. |
| 383 | 4-chloro-1-cyclopropylmethyl-5-methyl-1H-imidazol-2-yl | cyclopropyl-methyl | Ig cis | 443 | 2.17 LC20 | 188° C. |
| 384 | 5-chloro-1-cyclopropylmethyl-4-methyl-1H-imidazol-2-yl | 3-methyl-butyl | Ig cis | 461 | 1.14 LC20 | 259° C. |
| 385 | 5-chloro-1-cyclopropylmethyl-4-methyl-1H-imidazol-2-yl | 3-methyl-oxetan-3-ylmethyl | Ig cis | 474 | 1.07 LC20 | 162° C. |
| 386 | 5-chloro-1-cyclopropylmethyl-4-methyl-1H-imidazol-2-yl | 2-methoxy-ethyl | Ig cis | 447 | 4.28 LC21 | 149° C. |
| 387 | 1-cyclopropylmethyl-4,5-dichloro-1H-imidazol-2-yl | cyclopropyl-methyl | Ig cis | 463 | 1.50 LC20 | 218° C. |
| 388 | 5-chloro-4-methyl-1-n-propyl-1H-imidazol-2-yl | cyclopropyl-methyl | Ig cis | 431 | 1.04 LC20 | 130° C. |
| 389 | 5-chloro-4-methyl-1-n-propyl-1H-imidazol-2-yl | 3,3-dimethyl-butyl | Ig cis | 461 | 1.17 LC20 | 201° C. |
| 390 | 5-chloro-4-methyl-1-n-propyl-1H-imidazol-2-yl | 2-methoxy-ethyl | Ig cis | 435 | 0.94 LC20 | 152° C. |
| 391 | 5-chloro-1,4-dimethyl-1H-imidazol-2-yl | cyclopropyl-methyl | Ig cis | 403 | 1.16 LC20 | 203° C. |
| 392 | 5-chloro-1,4-dimethyl-1H-imidazol-2-yl | 3,3-dimethyl-butyl | Ig cis | 433 | 1.34 LC20 | 195° C. |

TABLE 14-continued

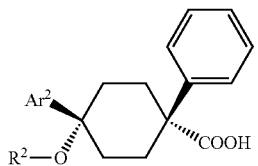

Ig

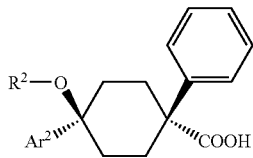

Ih

Example compounds of the formulae Ig and Ih

| Example | Ar² | R² | Formula, configuration | MS (ESI+) | HPLC (Rt [min], method) | MP |
|---|---|---|---|---|---|---|
| 393 | 5-chloro-4-tert-butyl-1-cyclopropylmethyl-1H-imidazol-2-yl | cyclopropyl-methyl | Ig cis | 486 | 5.46 LC21 | 204° C. |
| 394 | 5-chloro-1-cyclopropyl-methyl-4-isopropyl-1H-imidazol-2-yl | cyclopropyl-methyl | Ig cis | 472 | 1.18 LC20 | 131° C. |

EXAMPLE 395

5-Chloro-4-methyl-1H-imidazole

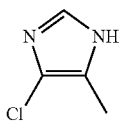

In a 500 ml three-necked flask 4-methyl-imidazole (40 g, 487 mmol) was dissolved in 40 ml water and cooled to 0° C. 400 ml of a 13% solution of sodium hypochlorite (1.5 eq.) were added slowly keeping the temperature below 10° C. The mixture was stirred for 1 h at 0° C. The solid was filtered off, washed with cold (0° C.) water and dried over phosphorus pentoxide. 12.6 g of the title compound were obtained.
TLC (MOH/DCM 1:19): Rf 0.44

EXAMPLE 396

5-Chloro-1-cyclopropylmethyl-4-methyl-1H-imidazole and 4-chloro-1-cyclopropylmethyl-5-methyl-1H-imidazole 4.7 g (118 mmol) of sodium hydride (60% strength in mineral oil) were washed with pentane under a nitrogen atmosphere, suspended in 100 ml of DMF and cooled to 0° C. A solution of 12.5 g (107 mmol) of 5-chloro-4-methyl-1H-imidazole in 100 ml of DMF was added. Then 5.5 g of bromomethylcyclopropane were added and the mixture was stirred for 16 h at 20° C. 250 ml of water and EA were added, the phases were separated and the aqueous layer was extracted with EA. The combined organic phases were washed with brine and dried over sodium sulfate. The solvent was removed in vacuo. Flash chromatography (silica gel; EA/HEP, gradient from 20:80 to 40:60) of the residue yielded 7.5 g of 4-chloro-1-cyclopropylmethyl-5-methyl-1H-imidazole as an oil and 3.6 g of 5-chloro-1-cyclopropylmethyl-4-methyl-1H-imidazole as an oil.

EXAMPLE 396-1

4-Chloro-1-cyclopropylmethyl-5-methyl-1H-imidazole

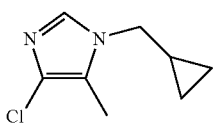

TLC (MOH/DCM 1:9): Rf=0.68

EXAMPLE 396-2

5-Chloro-1-cyclopropylmethyl-4-methyl-1H-imidazole

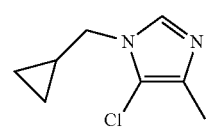

TLC (MOH/DCM 1:9): Rf=0.63

EXAMPLE 397

Cis-4-(5-Chloro-1-cyclopropylmethyl-4-methyl-1H-imidazol-2-yl)-1-phenyl-4-hydroxycyclohexanecarbonitrile and Trans-4-(5-chloro-1-cyclopropylmethyl-4-methyl-1H-imidazol-2-yl)-1-phenyl-4-hydroxycyclohexanecarbonitrile

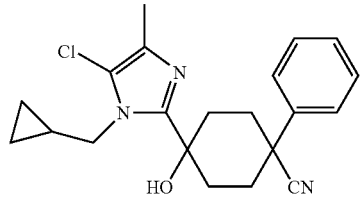

0.95 g of 5-chloro-1-cyclopropylmethyl-4-methyl-1H-imidazole were dissolved in 4 ml of anhydrous THF and cooled to −70° C. under a nitrogen atmosphere. 3.8 ml of a 1.6 M solution of n-butyllithium in hexane were added dropwise. After 30 min a solution of 1.1 g of 4-oxo-1-phenylcyclohexanecarbonitrile in 3 ml of THF was added. The reaction mixture was allowed to warm to room temperature during 4 h. 50 ml of water were added, and the mixture was extracted three times with 50 ml each of EA. The combined organic phases were washed with brine and dried over sodium sulfate. The solvent was removed in vacuo. Flash chromatography of the residue (40 g of silica gel; HEP/EA, gradient from 100:0 to 60:40) yielded 1.28 g of the cis title compound as a white solid and 0.5 g of the trans title compound as a white solid.

EXAMPLE 397-1

Cis-4-(5-Chloro-1-cyclopropylmethyl-4-methyl-1H-imidazol-2-yl)-1-phenyl-4-hydroxycyclohexanecarbonitrile

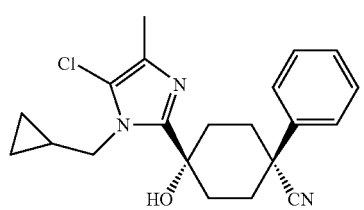

TLC (cyclohexane/EA 3:2): Rf 0.5

EXAMPLE 397-2

Trans-4-(5-Chloro-1-cyclopropylmethyl-4-methyl-1H-imidazol-2-yl)-1-phenyl-4-hydroxycyclohexanecarbonitrile

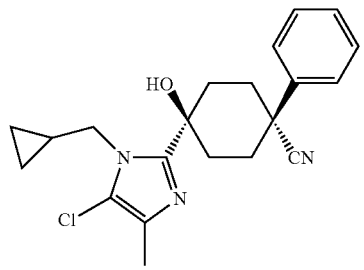

TLC (cyclohexane/EA 4:1): Rf 0.35

EXAMPLE 398

Cis-4-(5-Chloro-1-cyclopropylmethyl-4-methyl-1H-imidazol-2-yl)-4-phenoxy-1-phenyl-cyclohexanecarbonitrile

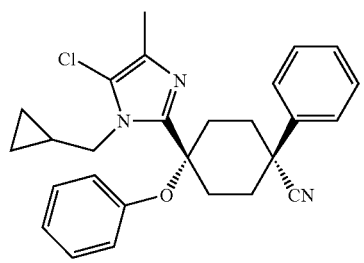

0.6 g of cis-4-(5-chloro-1-cyclopropylmethyl-4-methyl-1H-imidazol-2-yl)-1-phenyl-4-hydroxycyclohexanecarbonitrile and 0.134 g of copper were suspended in toluene. 3.6 g of triphenylbismuth diacetate were added and the reaction mixture was heated to 80° C. for 3 h. The mixture was then filtered over celite washed with EA (100 ml). The organic phase was washed with water and brine, dried over sodium sulfate and the solvent was removed in vacuo. The crude product was purified by flash chromatography (silica gel, DCM/MOH, gradient from 100:0 to 95:5) to yield 0.52 g of the title compound as a white foam.

TLC (DCM): Rf 0.75

EXAMPLE 399

Cis 4-(5-Chloro-1-cyclopropylmethyl-4-methyl-1H-imidazol-2-yl)-4-phenoxy-1-phenyl-cyclohexanecarboxamide

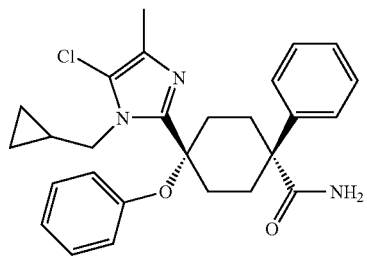

0.52 g of cis-4-(5-chloro-1-cyclopropylmethyl-4-methyl-1H-imidazol-2-yl)-4-phenoxy-1-phenylcyclohexanecarbonitrile were dissolved in 10 ml of MOH and heated to 50° C. A solution of 0.14 g of potassium hydroxide in 1 ml of water was added, followed by 0.3 ml of hydrogen peroxide (30% strength in water). After one hour each, four further 0.3 ml portions of hydrogen peroxide (30% strength in water) were added. The reaction mixture was stirred for 12 h at 55° C. Then it was treated with water and extracted with EA. The combined organic phases were washed with brine and dried over sodium sulfate. The solvent was removed in vacuo. The crude product was purified by flash chromatography (silica gel; DCM/MOH, gradient from 100:0 to 95:5). 0.466 g of the title compound were obtained as a white solid.

TLC (DCM/MOH 9:1): Rf 0.67

EXAMPLE 400

Cis 4-(5-Chloro-1-cyclopropylmethyl-4-methyl-1H-imidazol-2-yl)-4-phenoxy-1-phenylcyclohexanecarboxylic Acid

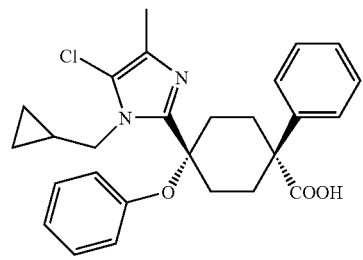

0.46 g of cis 4-(5-chloro-1-cyclopropylmethyl-4-methyl-1H-imidazol-2-yl)-4-phenoxy-1-phenylcyclohexanecarboxamide were dissolved in 2 ml of DMF. The mixture was cooled to 0° C. under nitrogen, and 0.35 g of nitrosonium tetrafluoroborate were added. The green mixture was stirred for 1 h. 10 ml of water and 10 ml of DCM were added. The aqueous layer was extracted with DCM. The combined organic phases were washed with brine and dried over sodium sulfate. The solvent was removed in vacuo. The crude product was purified by flash chromatography (silica gel; DCM/EA, gradient from 99:1 to 80:20). 0.19 g of the title compound were obtained as a white solid.

MS (ESI+): 465
HPLC (Method LC20): Rt 1.17 min $^1$H-NMR (d$_6$-DMSO; 400 MHz): 12.1 (b, 1H), 7.2 (d, 2H), 7.12 (t, 2H), 6.9 (m, 3H), 6.7 (m, 1H), 6.35 (d, 2H), 3.75 (d, 2H), 2.28-1.8 (b, 8H), 1,8 (s, 3H), 0.7 (m, 1H), 0.1 (m, 4H)
MP: 170° C.

EXAMPLE 401

Cis-4-(4-Bromo-1-cyclopropylmethyl-5-methyl-1H-imidazol-2-yl)-4-phenoxy-1-(4-fluorophenyl)cyclohexanecarbonitrile

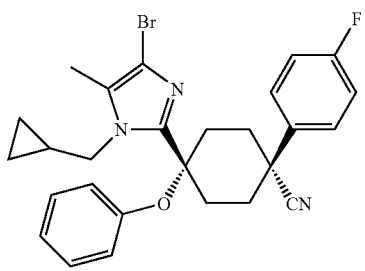

1.8 g of cis-4-(4-bromo-1-cyclopropylmethyl-5-methyl-1H-imidazol-2-yl)-1-(4-fluorophenyl)-4-hydroxycyclohexanecarbonitrile and 0.36 g of copper were suspended in 20 ml of toluene. 9.3 g of triphenylbismuth diacetate were added and the reaction mixture was heated to 80° C. for 3 h. The mixture was then cooled to 0° C. and treated with a 1 N solution of sodium hydroxide and extracted with EA. The combined organic phases were washed with brine and dried over sodium sulfate and the solvent was removed in vacuo. The crude product was purified by flash chromatography (silica gel, cyclohexane/EA, gradient from 100:0 to 80:20) to yield 2 g of the title compound as a white foam.

TLC (HEP/EA 3:2): Rf 0.75

EXAMPLE 402

Cis-4-(4-Bromo-1-cyclopropylmethyl-5-methyl-1H-imidazol-2-yl)-4-phenoxy-1-(4-fluorophenyl)cyclohexanecarboxamide

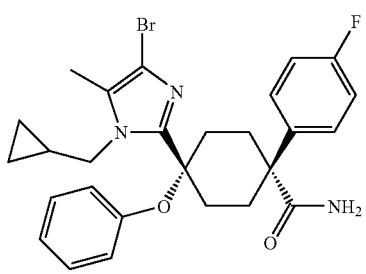

0.5 g of cis 4-(4-bromo-1-cyclopropylmethyl-5-methyl-1H-imidazol-2-yl)-4-phenoxy-1-(4-fluorophenyl)cyclohexanecarbonitrile were dissolved in 9 ml of MOH and heated to 50° C. A solution of 0.2 g of potassium hydroxide in 1 ml of water was then added, followed by 0.3 ml of hydrogen peroxide (30% strength in water). After one hour each, four further 0.3 ml portions of hydrogen peroxide (30% strength in water) were added. The reaction mixture was stirred for 12 h at 55° C. Then it was treated with water and extracted with DCM. The combined organic phases were washed with brine and dried over sodium sulfate. The solvent was removed in vacuo. The crude product was purified by flash chromatography (silica gel, HEP/EA, gradient from 100:0 to 60:40) to yield 0.36 g of the title compound as a white solid.

TLC (HEP/EA 3:2): Rf 0.10

EXAMPLE 403

Cis-4-(4-Bromo-1-cyclopropylmethyl-5-methyl-1H-imidazol-2-yl)-4-phenoxy-1-(4-fluorophenyl)cyclohexanecarboxylic Acid

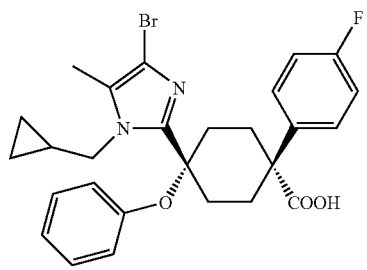

0.36 g of cis 4-(4-bromo-1-cyclopropylmethyl-5-methyl-1H-imidazol-2-yl)-4-phenoxy-1-(4-fluorophenyl)cyclohexanecarboxamide were dissolved in 2 ml of a 1:1 mixture of acetonitrile and DMF. The mixture was cooled to 0° C. under nitrogen, and 0.24 g of nitrosonium tetrafluoroborate were added. The green mixture was stirred for 1 h. 10 ml of water and 10 ml of DCM were added. The aqueous layer was extracted with DCM. The combined organic phases were washed with brine and dried over sodium sulfate. The solvent was removed in vacuo. The crude product was purified by flash chromatography (silica gel; DCM/MOH, gradient from 99:1 to 97:3). 0.075 g of the title compound were obtained as a white solid.

MS (ESI+): 527

HPLC (Method LC19): Rt 6.0 min $^1$H-NMR (d$_6$-DMSO; 400 MHz): 12.4 (b, 1H), 7.5 (m, 2H), 7.2 (t, 4H), 6.9 (m, 1H), 6.55 (d, 2H), 4.1 (d, 2H), 2.4-2.1 (b, 8H), 2.2 (s, 3H), 0.8 (m, 1H), 0.45 (m, 2H), 0.25 (m, 2H)

MP: 158° C.

Analogously to the preparation processes described above, the cis-4-Ar$^2$-4-phenoxy-1-(4-fluorophenyl)cyclohexanecarboxylic acids of the formula Ik and trans-4-Ar$^2$-4-phenoxy-1-(4-fluorophenyl)cyclohexanecarboxylic acids of the formula Im listed in Table 15 were prepared.

TABLE 15

Ik

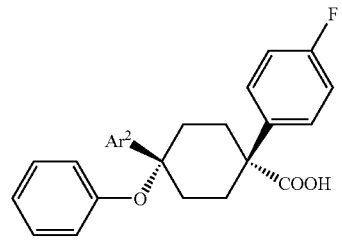

Im

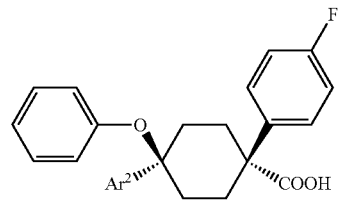

Example compounds of the formulae Ik and Im

| Example | Ar$^2$ | Formula, configuration | MS (ESI+) | HPLC (Rt [min], Method) | MP |
|---|---|---|---|---|---|
| 404 | 4-bromo-1-cyclopropylmethyl-5-methyl-1H-imidazol-2-yl | Im trans | 527 | 8.72 LC19 | 181° C. |
| 405 | 1-cyclopropylmethyl-1H-benzoimidazol-2-yl | Ik cis | 485 | 5.76 LC19 | 267° C. |
| 406 | 1-cyclopropylmethyl-1H-benzoimidazol-2-yl | Im trans | 485 | 5.57 LC19 | 255° C. |

Analogously to the preparation processes described above, the cis-1-Ar¹-4-Ar²-4-cyclopropylmethoxycyclohexanecarboxylic acids of the formula In listed in Table 16 were prepared.

TABLE 16

Example compounds of the formula In

| Example | Ar¹ | Ar² | MS (ESI+) | HPLC (Rt [min], Method) | MP |
|---|---|---|---|---|---|
| 407 | pyridin-3-yl | 5-chloro-1-cyclopropylmethyl-4-methyl-1H-imidazol-2-yl | 444 | 0.8 LC20 | 245° C. |
| 408 | 4-methane-sulfonylphenyl | 5-chloro-1-cyclopropylmethyl-4-methyl-1H-imidazol-2-yl | 522 | 0.96 LC20 | 156° C. |
| 409 | 3-trifluoromethoxy-phenyl | 5-chloro-1-cyclopropylmethyl-4-methyl-1H-imidazol-2-yl | 527 | 1.18 LC20 | 205° C. |
| 410 | 4-trifluoromethoxy-phenyl | 5-chloro-1-cyclopropylmethyl-4-methyl-1H-imidazol-2-yl | 527 | 1.16 LC20 | 106° C. |
| 411 | 6-methylpyridin-3-yl | 5-chloro-1-cyclopropylmethyl-4-methyl-1H-imidazol-2-yl | 495 | 3.35 LC21 | 120° C. |
| 412 | 4-methylphenyl | 1-cyclopropylmethyl-1H-benzoimidazol-2-yl | 459 | 1.05 LC20 | 163° C. |
| 413 | 3-methane-sulfonylphenyl | 1-cyclopropylmethyl-1H-benzoimidazol-2-yl | 523 | 0.95 LC20 | 229° C. |
| 414 | 3-trifluoromethoxy-phenyl | 1-cyclopropylmethyl-1H-benzoimidazol-2-yl | 529 | 5.26 LC21 | 222° C. |
| 415 | 6-methylpyridin-3-yl | 1-cyclopropylmethyl-1H-benzoimidazol-2-yl | 471 | 0.77 LC20 | 186° C. |

EXAMPLE 416

Cis-4-(4-Bromo-1-cyclopropylmethyl-5-methyl-1H-imidazol-2-yl)-4-cyclopropylmethoxy-1-(4-fluorophenyl)cyclohexanecarboxylic Acid Methyl Ester

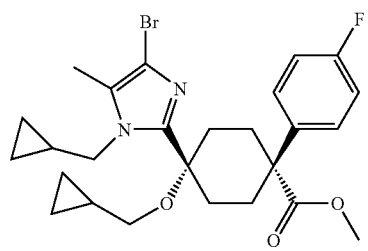

1.28 g (5 mmol) of cis 4-(4-bromo-1-cyclopropylmethyl-5-methyl-1H-imidazol-2-yl)-4-cyclopropylmethoxy-1-(4-fluorophenyl)cyclohexanecarboxylic acid and potassium carbonate (0.7 g, 5 mmol) were suspended in DMF (20 ml). Iodomethane (0.32 ml, 1 eq.) was added and the mixture was stirred for 18 h at 20° C. The reaction medium was poured into water and extract with EA. The combined organic phases were washed with brine and dried over sodium sulfate and the solvent was removed in vacuo. The crude product was purified by flash chromatography (silica gel, cyclohexane/EA, gradient from 100:0 to 70:30) to yield 0.541 g of the title compound as a white foam.
TLC (cyclohexane/EA 4:1): Rf 0.38

EXAMPLE 417

Cis-4-(4-Cyano-1-cyclopropylmethyl-5-methyl-1H-imidazol-2-yl)-4-cyclopropylmethoxy-1-(4-fluorophenyl)cyclohexanecarboxylic Acid Methyl Ester

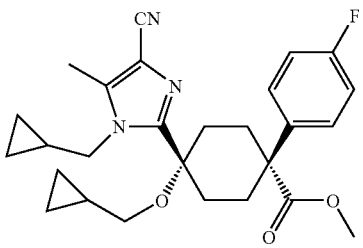

0.4 g (0.77 mmol) of cis 4-(4-bromo-1-cyclopropylmethyl-5-methyl-1H-imidazol-2-yl)-4-cyclopropylmethoxy-1-(4-fluorophenyl)cyclohexanecarboxylic acid methyl ester was dissolved in degassed toluene (8 ml) under nitrogen. Potassium iodide (25 mg, 0.15 mmol), sodium cyanide (45 mg, 0.93 mmol) and copper iodide (14.7 mg, 0.08 mmol) were then added, followed by N,N'-dimethyl-ethylenediamine (0.08 ml, 0.77 mmol). The reaction mixture was heated to 100° C. for 24 h. After cooling, the mixture was poured in water (10 ml) and EA (20 ml) and sodium hydroxide solution (1 N) were added. The mixture was stirred for 10 min. Then the aqueous layer was extracted with EA. The combined organic phases were dried over sodium sulfate and concentrated. The crude product was purified by flash chromatography (silica gel; cyclohexane/EA, gradient from 100:0 to 70:30). 0.3 g of the title compound were obtained as an oil.

TLC (cyclohexane/EA 4:1): Rf 0.23

EXAMPLE 418

Cis-4-(4-Cyano-1-cyclopropylmethyl-5-methyl-1H-imidazol-2-yl)-4-cyclopropylmethoxy-1-(4-fluorophenyl)cyclohexanecarboxylic Acid

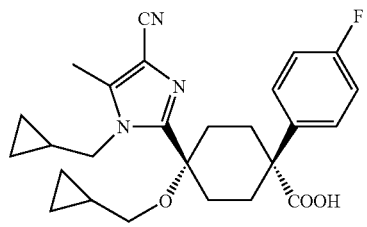

0.3 g (0.64 mmol) of cis 4-(4-cyano-1-cyclopropylmethyl-5-methyl-1H-imidazol-2-yl)-4-cyclopropylmethoxy-1-(4-fluorophenyl)cyclohexanecarboxylic acid methyl ester was dissolved in 3 ml of a 1:1:1 mixture of THF, MOH and water. A 1 N sodium hydroxide solution (1.29 ml) was added and the solution was heated to 60° C. for 3 h. The solvent was evaporated in vacuo and the residue taken up in water (10 ml). The aqueous layer was extracted with EA. The combined organic phases were washed with brine and dried over sodium sulfate. The solvent was removed in vacuo. The crude product was purified by flash chromatography (silica gel; DCM/MOH, gradient from 100:0 to 95:5). 0.16 g of the title compound were obtained as a white solid.

MS (ESI+): 452
HPLC (Method LC19): Rt 9.33 min
$^1$H-NMR ($d_6$-DMSO; 400 MHz): 12.3 (b, 1H), 7.4 (m, 2H), 7.12 (m, 2H), 4.15 (d, 2H), 2.78 (d, 2H), 2.32 (s, 3H), 2.28 (m, 2H), 2.02 (m, 4H), 1.87 (m, 2H), 0.9-0.8 (m, 2H), 0.58 (m, 2H), 0.36 (m, 4H), 0.0 (m, 2H)
MP: 245° C.

EXAMPLE 419

Cis-4-(5-Cyano-1-cyclopropylmethyl-4-methyl-1H-imidazol-2-yl)-4-cyclopropylmethoxy-1-phenylcyclohexanecarboxylic Acid

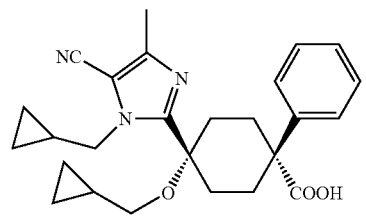

Analogously to the preparation of the compound of Example 418, the title compound was prepared starting from cis-4-(5-bromo-1-cyclopropylmethyl-4-methyl-1H-imidazol-2-yl)-4-cyclopropylmethoxy-1-phenylcyclohexanecarboxylic acid.

white solid.
MS (ESI+): 434
HPLC (Method LC20): Rt 1.26 min
$^1$H-NMR ($d_6$-DMSO; 400 MHz): 12.3 (b, 1H), 7.35 (d, 2H), 7.25 (t, 2H), 7.15 (m, 1H), 4.1 (d, 2H), 2.78 (d, 2H), 2.22 (m, 2H), 2.1 (s, 3H), 2.1 (m, 2H), 1.9 (m, 4H), 1.05 (m, 1H), 0.85 (m, 1H), 0.55 (m, 2H), 0.45 (m, 2H), 0.35 (m, 2H), 0.0 (m, 2H)
MP: 228° C.

EXAMPLE 420

Cis-4-Cyclopropylmethoxy-4-(1-cyclopropylmethyl-5-methyl-4-methylsulfanyl-1H-imidazol-2-yl)-1-phenylcyclohexanecarbonitrile

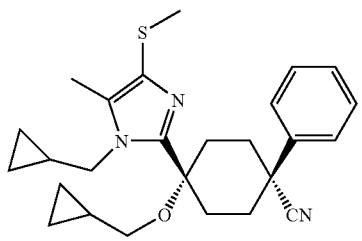

1.03 g of cis-4-(4-bromo-1-cyclopropylmethyl-5-methyl-1H-imidazol-2-yl)-4-cyclopropylmethoxy-1-phenylcyclohexanecarbonitrile were dissolved in 10 ml of anhydrous THF and cooled to −70° C. 1.1 ml of a 1.6 M solution of n-butyllithium in hexane was added, and the mixture was stirred at −70° C. for 30 min. Then a solution of 0.55 g of methanethiosulfonic acid S-methyl ester in 5 ml of THF was added. The mixture was allowed to warm to room temperature over 2 h. Water was added, and the mixture was extracted three times with 50 ml each of EA. The combined organic phases were washed with brine and dried over sodium sulfate. The solvent was removed in vacuo. The crude product was purified by flash chromatography (silica gel; cyclohexane/EA 9:1). 0.37 g of the title compound were obtained as a pale yellow solid.

TLC (cyclohexane/EA 4:1): Rf 0.5

EXAMPLE 421

Cis-4-Cyclopropylmethoxy-4-(1-cyclopropylmethyl-5-methyl-4-methanesulfonyl-1H-imidazol-2-yl)-1-phenylcyclohexanecarboxamide

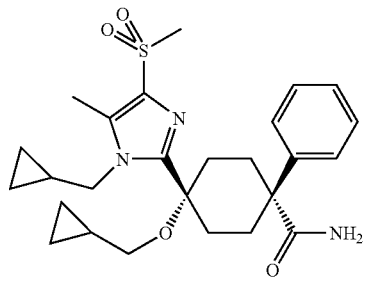

0.36 g of cis-4-cyclopropylmethoxy-4-(1-cyclopropylmethyl-5-methyl-4-methylsulfanyl-1H-imidazol-2-yl)-1-phenylcyclohexanecarbonitrile were dissolved in 7 ml of MOH. The mixture was heated to 50° C. and a solution of 0.1 g of potassium hydroxide in 1 ml of water was added, followed by 0.5 ml of hydrogen peroxide (30% strength in water). After one hour each, six further 0.5 ml portions of hydrogen peroxide (30% strength in water) were added. The reaction mixture was stirred for 12 h at 55° C. It was then treated with water and extracted with DCM. The combined organic phases were washed with brine and dried over sodium sulfate. The solvent was removed in vacuo. The crude product was purified by flash chromatography (silica gel; DCM/MOH, gradient from 100:0 to 95:5). 319 mg of the title compound were obtained as a white solid.

MS (ESI+): 486
HPLC (Method LC18): Rt=4.53 min
TLC (DCM/MOH 19:1): Rf 0.54

EXAMPLE 422

Cis-4-Cyclopropylmethoxy-4-(1-cyclopropylmethyl-5-methyl-4-methanesulfonyl-1H-imidazol-2-yl)-1-phenylcyclohexanecarboxylic Acid

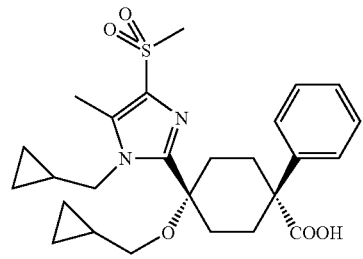

0.319 g of cis-4-cyclopropylmethoxy-4-(1-cyclopropylmethyl-5-methyl-4-methanesulfonyl-1H-imidazol-2-yl)-1-phenylcyclohexanecarboxamide were dissolved in 4 ml of DMF. The mixture was cooled to 0° C. under nitrogen, and 0.23 g of nitrosonium tetrafluoroborate were added. The green mixture was stirred for 1 h. 10 ml of water and 10 ml of DCM were added. The aqueous layer was extracted with DCM. The combined organic phases were washed with brine and dried over sodium sulfate. The solvent was removed in vacuo. The crude product was purified by flash chromatography (silica gel; DCM/MOH/conc. aqueous ammonia, gradient from 100:0:0 to 90:10:1). 0.277 g of the title compound were obtained as a white solid.

MS (ESI+): 487
HPLC (Method LC19): Rt 9.0 min
$^1$H-NMR (d$_6$-DMSO; 400 MHz): 12.3 (b, 1H), 7.35 (m, 2H), 7.25 (m, 2H), 7.15 (m, 1H), 4.15 (d, 2H), 2.8 (d, 2H), 2.55 (s, 3H), 2.5 (s, 3H), 2.25 (m, 2H), 2.02 (m, 4H), 1.9 (m, 2H), 0.9-0.8 (m, 2H), 0.55 (m, 2H), 0.36 (m, 4H), 0.0 (m, 2H)
MP: 242° C.

EXAMPLE 423

Cis-4-Cyclopropylmethoxy-4-(1-cyclopropylmethyl-4-methyl-5-methanesulfonyl-1H-imidazol-2-yl)-1-phenylcyclohexanecarboxylic Acid

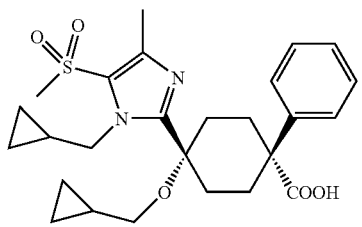

Analogously to the preparation of the compound of Example 422, the title compound was prepared starting from cis 4-(5-bromo-1-cyclopropylmethyl-4-methyl-1H-imidazol-2-yl)-4-cyclopropylmethoxy-1-phenylcyclohexanecarbonitrile and isolated in the form of the cis-4-cyclopropylmethoxy-4-(1-cyclopropylmethyl-4-methyl-5-methanesulfonyl-1H-imidazol-2-yl)-1-phenylcyclohexanecarboxylic acid methanesulfonic acid salt as a white solid.

MS (ESI+): 487
HPLC (Method LC20): Rt 1.11 min
$^1$H-NMR (d$_6$-DMSO; 400 MHz): 12.3 (b, 1H), 7.4 (m, 2H), 7.3 (m, 2H), 7.18 (m, 1H), 4.3 (d, 2H), 3.2 (s, 3H), 2.8 (d, 2H), 2.2 (s, 3H), 2.3-1.9 (m, 8H), 1.1 (m, 1H), 0.85 (m, 1H), 0.6 (m, 2H), 0.45 (m, 2H), 0.4 (m, 2H), 0.0 (m, 2H)
MP: 206° C.

EXAMPLE 424

Cis-4-Cyclopropylmethoxy-4-(1-cyclopropylmethyl-4-methyl-5-phenyl-1H-imidazol-2-yl)-1-phenylcyclohexanecarbonitrile

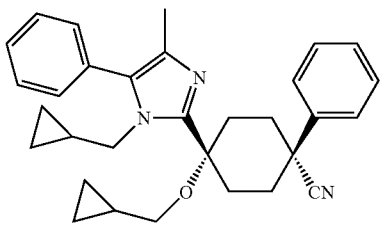

0.5 g of cis-4-(5-bromo-1-cyclopropylmethyl-4-methyl-1H-imidazol-2-yl)-4-cyclopropylmethoxy-1-phenylcyclohexanecarbonitrile were dissolved in 5 ml of degassed toluene. Trimethyl(phenyl)stannane (0.334 g, 1.3 eq.) and bis(triphenylphosphine)palladium(II) dichloride (15 mg, 20%) were added and the mixture was heated under reflux for 24 h. After cooling, a 5% w/w aqueous solution of potassium fluoride (25 ml) was added, and the mixture was stirred for 30 min. The aqueous layer was extracted three times with 25 ml each of DCM. The combined organic phases were washed with brine and dried over sodium sulfate. The solvent was removed in vacuo. The crude product was purified by flash chromatography (silica gel; cyclohexane/EA, gradient from 100:0 to 60:40). 0.18 g of the title compound was obtained as a white solid.

TLC (cyclohexane/EA 3:2): Rf 0.64

EXAMPLE 425

Cis-4-Cyclopropylmethoxy-4-(1-cyclopropylmethyl-4-methyl-5-phenyl-1H-imidazol-2-yl)-1-phenylcyclohexanecarboxamide

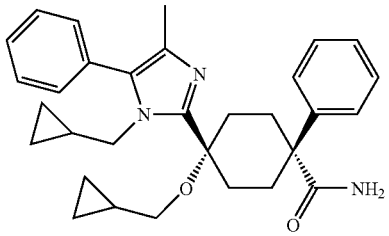

0.18 g of cis-4-cyclopropylmethoxy-4-(1-cyclopropylmethyl-4-methyl-5-phenyl-1H-imidazol-2-yl)-1-phenylcyclohexanecarbonitrile was hydrolyzed as described above using potassium hydroxide and hydrogen peroxide in MOH. The crude product was purified by flash chromatography (silica gel; DCM/MOH, gradient from 100:0 to 95:5). 162 mg of the title compound were obtained as a white solid.

TLC (DCM/MOH 9:1): Rf 0.34

EXAMPLE 426

Cis-4-Cyclopropylmethoxy-4-(1-cyclopropylmethyl-4-methyl-5-phenyl-1H-imidazol-2-yl)-1-phenylcyclohexanecarboxylic Acid

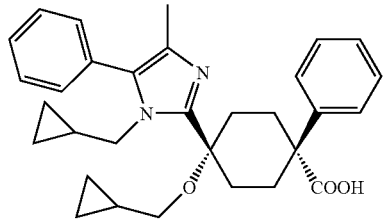

0.16 g of cis-4-cyclopropylmethoxy-4-(1-cyclopropylmethyl-4-methyl-5-phenyl-1H-imidazol-2-yl)-1-phenylcyclohexanecarboxamide were hydrolyzed as described above using nitrosonium tetrafluoroborate in DMF. The crude product was purified by flash chromatography (silica gel; DCM/MOH, gradient from 100:0 to 95:5). 0.16 g of the title compound were obtained as a white solid.

MS (ESI+): 485

HPLC (Method LC20): Rt 1.11 min $^1$H-NMR ($d_6$-DMSO; 400 MHz): 12.3 (b, 1H), 7.45 (m, 2H), 7.4-7.2 (m, 8H), 4.1 (d, 2H), 2.9 (d, 2H), 2.25 (m, 4H), 2.2 (m, 4H), 1.9 (s, 3H), 0.95 (m, 1H), 0.6 (m, 1H), 0.48 (m, 2H), 0.2 (m, 2H), 0.1 (m, 2H), −0.4 (m, 2H)

MP: 218° C.

EXAMPLE 427

Cis-4-Cyclopropylmethoxy-4-[1-cyclopropylmethyl-5-(4-fluorophenyl)-4-methyl-1H-imidazol-2-yl]-1-phenylcyclohexanecarboxylic Acid

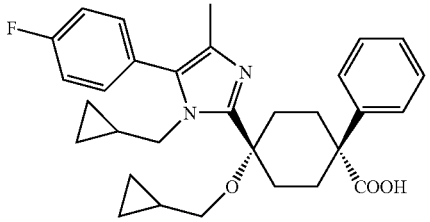

Analogously to the preparation processes described above, the title compound was prepared starting from cis-4-(5-bromo-1-cyclopropylmethyl-4-methyl-1H-imidazol-2-yl)-4-cyclopropylmethoxy-1-phenylcyclohexanecarbonitrile and tri(n-butyl)-(4-fluorophenyl)-stannane and obtained as a white solid.

MS (ESI+): 503

HPLC (Method LC18): Rt 3.87 min $^1$H-NMR ($d_6$-DMSO; 400 MHz): 12.1 (b, 1H), 7.4-7.2 (m, 9H), 4.0 (m, 2H), 2.8 (d, 2H), 2.20 (m, 4H), 1.9 (m, 4H), 1.8 (s, 3H), 0.85 (m, 1H), 0.5 (m, 1H), 0.35 (m, 2H), 0.1 (m, 4H), −0.6 (m, 2H)

MP: 199° C.

EXAMPLE 428

1-Cyclopropylmethyl-4-iodo-2-phenyl-1H-imidazole and 1-cyclopropylmethyl-5-iodo-2-phenyl-1H-imidazole 0.6 g of sodium hydride (60% strength in mineral oil) were washed with pentane under a nitrogen atmosphere, suspended in 20 ml of THF and cooled to 0° C. A solution of 3.4 g (12.5 mmol) of 4(5)-iodo-2-phenylimidazole in THF (10 ml) was added and the suspension stirred for 30 min. Then 2 g of bromomethylcyclopropane and 2.5 g of potassium iodide were added and the mixture was stirred for 16 h at 20° C. 250 ml of water and EA were added, the layers were separated and the aqueous layer was extracted with EA. The combined organic phases were washed with brine and dried over sodium sulfate. The solvent was removed in vacuo. Flash chromatography (silica gel; EA/cyclohexane, gradient from 10:90 to 40:60) of the residue yielded 2 g of 1-cyclopropylmethyl-4- iodo-2-phenyl-1H-imidazole as a white solid and 0.78 g of 1-cyclopropylmethyl-5-iodo-2-phenyl-1H-imidazole as an oil.

EXAMPLE 428-1

1-Cyclopropylmethyl-4-iodo-2-phenyl-1H-imidazole

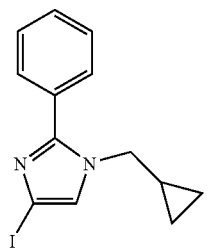

TLC (EA/HEP 2:3): Rf=0.5

EXAMPLE 428-2

1-Cyclopropylmethyl-5-iodo-2-phenyl-1H-imidazole

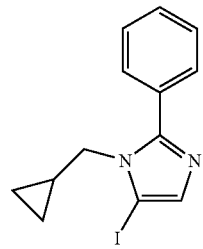

TLC (EA/HEP 2:3): Rf=0.3

EXAMPLE 429

Cis-4-(1-Cyclopropylmethyl-2-phenyl-1H-imidazol-4-yl)-1-(4-fluorophenyl)-4-hydroxycyclohexanecarbonitrile and Trans-4-(1-cyclopropylmethyl-2-phenyl-1H-imidazol-4-yl)-1-(4-fluorophenyl)-4-hydroxycyclohexanecarbonitrile

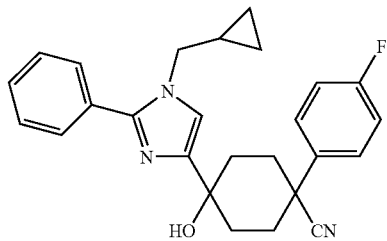

2 g of 1-cyclopropylmethyl-4-iodo-2-phenyl-1H-imidazole were dissolved in 10 ml of anhydrous THF and cooled to −70° C. under a nitrogen atmosphere. 4.24 ml of a 1.6 M solution of n-butyllithium in hexane were added dropwise. After 30 min a solution of 1.1 g of 1-(4-fluorophenyl)-4-oxocyclohexanecarbonitrile in 5 ml of THF was added. The reaction mixture was allowed to warm to room temperature during 18 h. 50 ml of water were added, and the mixture was extracted three times with 50 ml each of EA. The combined organic phases were washed with brine and dried over sodium sulfate. The solvent was removed in vacuo. Flash chromatography of the residue (80 g of silica gel; HEP/EA, gradient from 90:10 to 60:40) yielded 0.445 g of the trans title compound as a white solid and 1.4 g of the cis title compound as a white solid.

EXAMPLE 429-1

Trans-4-(1-Cyclopropylmethyl-2-phenyl-1H-imidazol-4-yl)-1-(4-fluorophenyl)-4-hydroxycyclohexanecarbonitrile

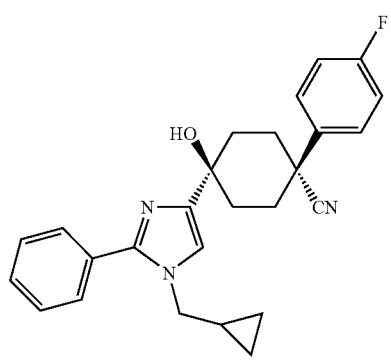

TLC (DCM/MOH 19:1): Rf 0.3

EXAMPLE 429-2

Cis-4-(1-Cyclopropylmethyl-2-phenyl-1H-imidazol-4-yl)-1-(4-fluorophenyl)-4-hydroxycyclohexanecarbonitrile

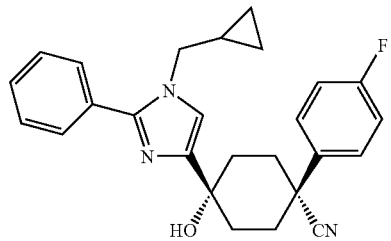

TLC (DCM/MOH 19:1): Rf 0.24

EXAMPLE 430

Trans-4-Cyclopropylmethoxy-4-(1-cyclopropylmethyl-2-phenyl-1H-imidazol-4-yl)-1-(4-fluorophenyl)cyclohexanecarbonitrile

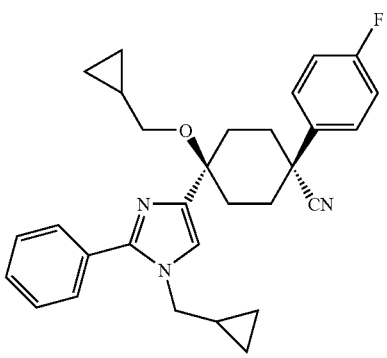

1.27 g of trans-4-(1-cyclopropylmethyl-2-phenyl-1H-imidazol-4-yl)-1-(4-fluorophenyl)-4-hydroxycyclohexanecarbonitrile and bromomethylcyclopropane (0.57 ml) were dissolved in a 3:1 mixture of dioxane and DMF (6 ml). 0.244 g of sodium hydride (60% in mineral oil) were added and the mixture was heated to 60° C. for 18 h. The mixture was then poured into 0.1 N aqueous hydrochloric acid and extracted three times with 50 ml each of EA. The combined organic layers were washed with brine and dried over sodium sulfate. The solvent was removed in vacuo. The crude product was purified by flash chromatography (silica gel, cyclohexane/EA, gradient from 100:0 to 60:40) to yield 1.22 g of the title compound as a white solid.

TLC (cyclohexane/EA 3:2): Rf 0.46

EXAMPLE 431

Trans-4-Cyclopropylmethoxy-4-(1-cyclopropylmethyl-2-phenyl-1H-imidazol-4-yl)-1-(4-fluorophenyl)cyclohexanecarboxamide

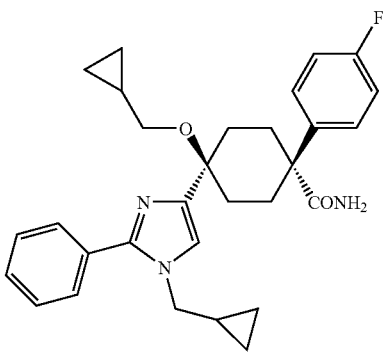

1.22 g of trans-4-cyclopropylmethoxy-4-(1-cyclopropylmethyl-2-phenyl-1H-imidazol-4-yl)-1-(4-fluorophenyl)cyclohexanecarbonitrile were dissolved in 26 ml of MOH and heated to 50° C. A solution of 0.29 g of potassium hydroxide in 1 ml of water was then added, followed by 1 ml of hydrogen peroxide (30% strength in water). After one hour each, four further 1 ml portions of hydrogen peroxide (30% strength in water) were added. The reaction mixture was stirred for 12 h at 50° C. Then it was treated with water and extracted with EA. The combined organic phases were washed with brine and dried over sodium sulfate. The solvent was removed in vacuo. The crude product was purified by flash chromatography (silica gel; DCM/MOH, gradient from 100:0 to 95:5). 1.25 g of the title compound were obtained as a white solid.

TLC (DCM/MOH 19:1): Rf 0.33

EXAMPLE 432

Trans-4-Cyclopropylmethoxy-4-(1-cyclopropylmethyl-2-phenyl-1H-imidazol-4-yl)-1-(4-fluorophenyl)cyclohexanecarboxylic Acid

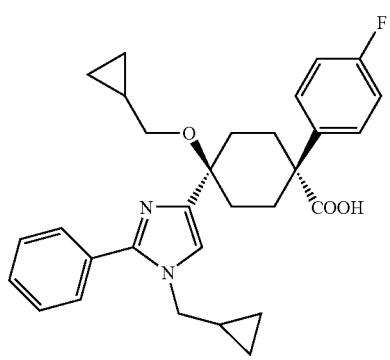

1.25 g of trans-4-cyclopropylmethoxy-4-(1-cyclopropylmethyl-2-phenyl-1H-imidazol-4-yl)-1-(4-fluorophenyl)cyclohexanecarboxamide were dissolved in 4 ml of DMF. The mixture was cooled to 0° C. under nitrogen, and 0.9 g of nitrosonium tetrafluoroborate was added. The green mixture was stirred for 1 h. 10 ml of water and 10 ml of DCM were added. The aqueous layer was extracted with DCM. The combined organic phases were washed with brine and dried over sodium sulfate. The solvent was removed in vacuo. The crude product was purified by flash chromatography (silica gel; DCM/EA, gradient from 99:1 to 80:20). 1.02 g of the title compound was obtained as a white solid.

MS (ESI+): 489

HPLC (Method LC19): Rt 8.0 min $^1$H-NMR ($d_6$-DMSO; 400 MHz): 12.4 (b, 1H), 7.6 (d, 2H), 7.45 (m, 5H), 7.3 (s, 1H), 7.2 (t, 2H), 3.9 (d, 2H), 3.0 (d, 2H), 2.35 (m, 2H), 2.2 (m, 2H), 1.87 (m, 4H), 1.1 (m, 1H), 0.8 (m, 1H), 0.5 (m, 2H), 0.36 (m, 2H), 0.25 (m, 2H), 0.0 (m, 2H)

MP: 209° C.

EXAMPLE 433

Cis-4-Cyclopropylmethoxy-4-(1-cyclopropylmethyl-2-phenyl-1H-imidazol-4-yl)-1-(4-fluorophenyl)cyclohexanecarboxylic Acid

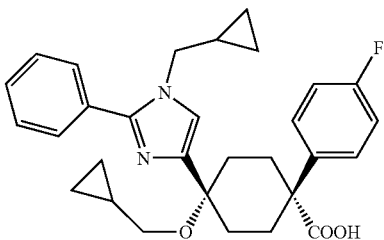

Analogously to the preparation of the compound of Example 432, the title compound was prepared starting from cis-4-cyclopropylmethoxy-4-(1-cyclopropylmethyl-2-phenyl-1H-imidazol-4-yl)-1-(4-fluorophenyl)cyclohexanecarbonitrile and obtained as a white solid.

MS (ESI+): 489

HPLC (Method LC19): Rt 7.5 min $^1$H-NMR (d$_6$-DMSO; 400 MHz): 12.4 (b, 1H), 7.6 (d, 2H), 7.45 (m, 5H), 7.3 (s, 1H), 7.2 (t, 2H), 3.9 (d, 2H), 3.0 (d, 2H), 2.4 (m, 2H), 2.2 (m, 2H), 1.87 (m, 4H), 1.1 (m, 1H), 0.8 (m, 1H), 0.45 (m, 2H), 0.35 (m, 2H), 0.2 (m, 2H), 0.0 (m, 2H)

MP: 198° C.

EXAMPLE 434

Cis-4-Hydroxy-1-phenyl-4-trimethylsilanylethynyl-cyclohexanecarbonitrile

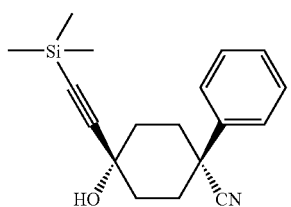

Ethynyl(trimethyl)silane (3.6 g, 37 mmol) was dissolved in THF (50 ml). The solution is cooled to −70° C. under nitrogen and a 1.6 M solution of n-butyllithium in hexane (14.8 ml, 37 mmol) was added. After stirring for 1 h at −70° C., a solution of 6.7 g of 4-oxo-1-phenylcyclohexanecarbonitrile in 50 ml of THF was added. The reaction mixture was stirred for 2 h at −70° C. Then a saturated aqueous solution ammonium chloride was added (20 ml) and the mixture was allowed to warm to room temperature. 50 ml of water were added, and the mixture was extracted three times with 100 ml each of EA. The combined organic phases were washed with brine and dried over sodium sulfate. The solvent was removed in vacuo. 8 g of the title compound were obtained as a white solid.

TLC (HEP/EA 3:2): Rf 0.46

EXAMPLE 435

Cis-4-Ethynyl-4-hydroxy-1-phenylcyclohexanecarbonitrile

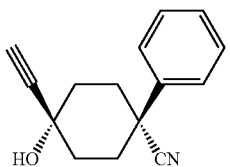

8 g of cis-4-hydroxy-1-phenyl-4-trimethylsilanylethynyl-cyclohexanecarbonitrile were dissolved in 50 ml of THF. The solution was cooled to 0° C. under nitrogen and acetic acid (4.6 ml, 4 eq.) was added followed by a 1 M solution of tetra(n-butyl)ammonium fluoride in THF (31 ml). The reaction mixture was stirred at 20° C. for 16 h. Then a saturated aqueous solution of sodium hydrogencarbonate (50 ml) was added and the mixture was extracted three times with 100 ml each of EA. The combined organic phases were washed with brine and dried over sodium sulfate. The solvent was removed in vacuo. 6 g of the title compound were obtained as a white solid.

TLC (HEP/EA 3:2): Rf 0.27

EXAMPLE 436

Cis-4-Cyclopropylmethoxy-4-ethynyl-1-phenylcyclohexanecarbonitrile

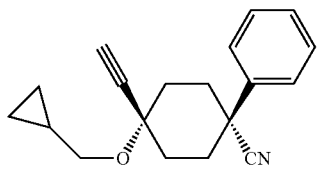

6 g of cis-4-ethynyl-4-hydroxy-1-phenylcyclohexanecarbonitrile and 3.1 ml of bromomethylcyclopropane were dissolved in dry DMF. The mixture was cooled to 0° C. and 1.5 g of sodium hydride (60% strength in mineral oil) were added portionwise. The mixture was stirred between 0° C. and 20° C. for 24 h. The mixture was then poured in 100 ml of a 0.1 N aqueous hydrochloric acid and extracted three times with 100 ml each of with EA. The combined organic layers were washed with brine, dried over sodium sulfate and evaporated in vacuo. The crude product was purified by flash chromatography (silica gel, cyclohexane/EA 4:1) to yield 4.5 g of the title compound as a white solid.

TLC (cyclohexane/EA 3:2): Rf 0.64

EXAMPLE 437

N-[2-(cis-4-Cyano-1-cyclopropylmethoxy-4-phenyl-cyclohexylethynyl)-phenyl]-methanesulfonamide

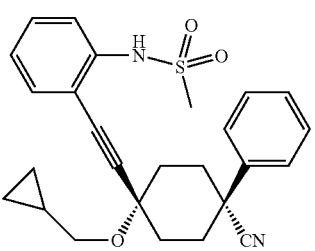

2.5 g of cis-4-cyclopropylmethoxy-4-ethynyl-1-phenylcyclohexanecarbonitrile and N-(2-iodo-phenyl)-methanesulfonamide (2.65 g) were dissolved in 50 ml of degassed THF. Copper(I) iodide (0.17 g) and N,N-diisopropyl-ethylamine (1.56 ml) were then added followed by 0.314 g of tetrakis(triphenylphosphine)palladium(0). The solution was refluxed for 3 h. The mixture was poured in water (50 ml) and extracted three times with 50 ml each of EA. The combined organic phases were washed with brine and dried over sodium sulfate. The solvent was removed in vacuo. The crude product was purified by flash chromatography (silica gel, cyclohexane/EA 17:3) to yield 3 g of the title compound as a white solid.

TLC (HEP/EA 3:2): Rf 0.32

EXAMPLE 438

Cis-4-Cyclopropylmethoxy-4-(1-methanesulfonyl-1H-indol-2-yl)-1-phenylcyclohexanecarbonitrile

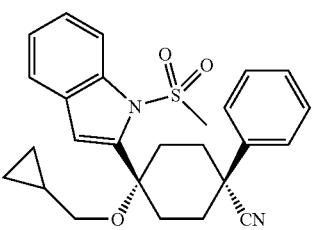

3 g of N-[2-(cis-4-cyano-1-cyclopropylmethoxy-4-phenylcyclohexylethynyl)-phenyl]-methanesulfonamide, copper(I) iodide (0.124 g) and triethylamine (0.94 ml) were dissolved in dry DMF (22 ml). The solution was heated at 90° C. for 3 h. The mixture was poured in water (50 ml) and extracted three times with 50 ml each of EA. The combined organic phases were washed with brine and dried over sodium sulfate. The solvent was removed in vacuo. The crude product was purified by flash chromatography (silica gel, cyclohexane/EA 9:1) to yield 2.5 g of the title compound as a white solid.

TLC (HEP/EA 3:2): Rf 0.51

EXAMPLE 439

Cis-4-Cyclopropylmethoxy-4-(1-methanesulfonyl-1H-indol-2-yl)-1-phenylcyclohexanecarboxamide

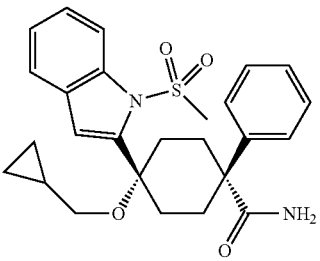

1.4 g of cis-4-cyclopropylmethoxy-4-(1-methanesulfonyl-1H-indol-2-yl)-1-phenylcyclohexanecarbonitrile were dissolved in 35 ml of MOH and heated to 50° C. A solution of 0.33 g of potassium hydroxide in 2 ml of water was added, followed by 2 ml of hydrogen peroxide (30% strength in water). After one hour each, four further 2 ml portions of hydrogen peroxide (30% strength in water) were added. The reaction mixture was stirred for 12 h at 50° C. Then it was treated with water and extracted with EA. The combined organic phases were washed with brine and dried over sodium sulfate. The solvent was removed in vacuo. The crude product was purified by flash chromatography (silica gel; DCM/EA, gradient from 95:5 to 80:20). 0.99 g of the title compound was obtained as a white solid.

TLC (HEP/EA 3:2): Rf 0.16

EXAMPLE 440

Cis-4-Cyclopropylmethoxy-4-(1-methanesulfonyl-1H-indol-2-yl)-1-phenylcyclohexanecarboxylic Acid

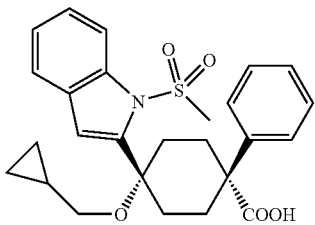

0.56 g of cis-4-cyclopropylmethoxy-4-(1-methanesulfonyl-1H-indol-2-yl)-1-phenylcyclohexanecarboxamide were dissolved in 4 ml of DMF. The mixture was cooled to 0° C. under nitrogen, and 0.266 g of nitrosylsulfuric acid were added. The green mixture was stirred for 1 h. 10 ml of water and 10 ml of DCM were added and he phases were separated. The aqueous layer was extracted with DCM. The combined organic phases were washed with brine and dried over sodium sulfate. The solvent was removed in vacuo. The crude product was purified by flash chromatography (silica gel; DCM/MOH, gradient from 99:1 to 97:3). 0.38 g of the title compound were obtained as a white solid.

MS (ESI+): 466

HPLC (Method LC21): Rt 5.52 min $^1$H-NMR (d$_6$-DMSO; 400 MHz): 12.2 (b, 1H), 7.8 (d, 1H), 7.35 (d, 1H), 7.2 (m, 2H), 7.15-7.0 (m, 5H), 6.75 (s, 1H), 3,0 (s, 3H), 2.95 (d, 2H), 2.28 (m, 2H), 2.1 (m, 4H), 1.7 (m, 2H), 0.8 (m, 1H), 0.25 (m, 2H), 0.0 (m, 2H)

MP: 152° C.

EXAMPLE 441

3-Methylsulfanyl-2-nitrophenylamine

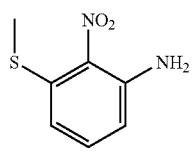

20 g of 3-chloro-2-nitroaniline are dissolved in 230 ml of dry DMF. The mixture was cooled to 0° C. and sodium methanethiolate (10 g) was added portionwise. The mixture was stirred for 2 h at 20° C. The solvent was evaporated in vacuo and the residue taken up in water and EA (200 ml each). The aqueous layer was extracted with EA, and the combined organic phases were washed with brine and dried over sodium sulfate. The solvent was removed in vacuo. The crude product was purified by flash chromatography (300 g silica gel; cyclohexane/EA, gradient from 100:0 to 50:50). 8.3 g of the title compound were obtained as a red solid.

TLC (HEP/EA 4:1): Rf 0.28

EXAMPLE 442

4-Methylsulfanyl-1H-benzoimidazole

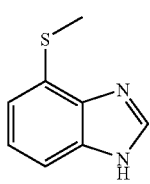

6 g of 3-methylsulfanyl-2-nitrophenylamine were dissolved in 150 ml of glacial acetic acid and 60 ml of trimethyl orthoformate. Zinc powder (7 g) was added and the mixture was stirred for 2 h at 60° C. The solids were removed by filtration, the solvent was evaporated in vacuo and the residue was taken up in water and EA (200 ml each) and made basic with potassium carbonate. The precipitate was filtered off and the filtrate was extracted with EA, the combined organic phases were washed with brine, dried over sodium sulfate and the solvent removed in vacuo. The crude product was purified by flash chromatography (200 g silica gel; DCM/MOH, gradient from 100:0 to 90:10). 2 g of the title compound were obtained as an off-white solid.

TLC (DCM/MOH 9:1): Rf 0.46

EXAMPLE 443

1-Cyclopropylmethyl-4-methylsulfanyl-1H-benzoimidazole and 1-cyclopropylmethyl-7-methylsulfanyl-1H-benzoimidazole 2 g of 4-methylsulfanyl-1H-benzoimidazole were dissolved in 20 ml of dry DMF. 0.6 g of sodium hydride (60% strength in mineral oil) were added portionwise at 0° C. After stirring for 1 h at 20° C., the mixture was cooled to 0° C. and bromomethylcyclopropane (1.5 ml) was added. The reaction mixture was stirred for 18 h at 20° C. The solvent was evaporated in vacuo and the residue was taken up in water and EA (100 ml each). The phases were separated, the aqueous phase was extracted with EA, and the combined organic phases were washed with brine and dried over sodium sulfate. The solvent was removed in vacuo. The crude product was purified by flash chromatography (100 g silica gel; DCM/EA, gradient from 100:0 to 80:20) to yield 1.2 g of 1-cyclopropylmethyl-4-methylsulfanyl-1H-benzoimidazole and 0.8 g of 1-cyclopropylmethyl-7-methylsulfanyl-1H-benzoimidazole.

EXAMPLE 443-1

1-Cyclopropylmethyl-4-methylsulfanyl-1H-benzoimidazole

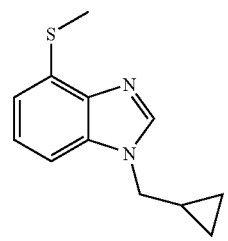

TLC (DCM/MOH 9:1): Rf 0.70

EXAMPLE 443-2

1-Cyclopropylmethyl-7-methylsulfanyl-1H-benzoimidazole

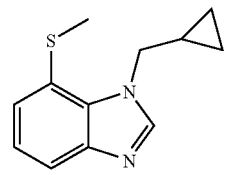

TLC (DCM/MOH 9:1): Rf 0.59

EXAMPLE 444

Cis-4-(1-Cyclopropylmethyl-4-methylsulfanyl-1H-benzoimidazol-2-yl)-4-hydroxy-1-phenylcyclohexanecarbonitrile and Trans-4-(1-cyclopropylmethyl-4-methylsulfanyl-1H-benzoimidazol-2-yl)-4-hydroxy-1-phenylcyclohexanecarbonitrile

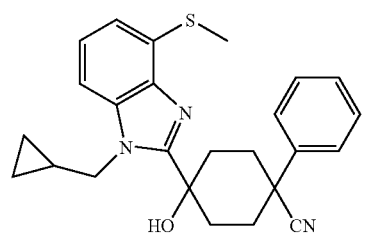

1.8 g of 1-cyclopropylmethyl-4-methylsulfanyl-1H-benzoimidazole were dissolved in 15 ml of anhydrous THF and cooled to −70° C. under a nitrogen atmosphere. 3.63 ml of a 2.5 M solution of n-butyllithium in hexane were added dropwise. After 1 h a solution of 1.6 g of 4-oxo-1-phenylcyclohexanecarbonitrile in 5 ml of THF was added. The reaction mixture was allowed to warm to room temperature during 18 h. 50 ml of water were added, and the mixture was extracted three times with 50 ml each of EA. The combined organic phases were washed with brine and dried over sodium sulfate. The solvent was removed in vacuo. Flash chromatography of the residue (120 g of silica gel; DCM/EA, gradient from 100:0 to 90:10) yielded 0.833 g of the trans title compound as a white solid and 1.4 g of the cis title compound as a white solid.

EXAMPLE 444-1

Trans-4-(1-Cyclopropylmethyl-4-methylsulfanyl-1H-benzoimidazol-2-yl)-4-hydroxy-1-phenylcyclohexanecarbonitrile

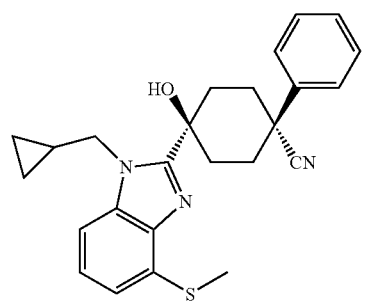

TLC (cyclohexane/EA 3:2): Rf 0.74

EXAMPLE 444-2

Cis-4-(1-Cyclopropylmethyl-4-methylsulfanyl-1H-benzoimidazol-2-yl)-4-hydroxy-1-phenylcyclohexanecarbonitrile

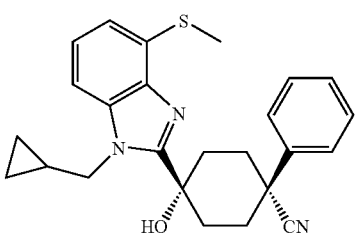

TLC (cyclohexane/EA 3:2): Rf 0.66

EXAMPLE 445

Cis-4-Cyclopropylmethoxy-4-(1-cyclopropylmethyl-4-methylsulfanyl-1H-benzoimidazol-2-yl)-1-phenyl-cyclohexanecarbonitrile

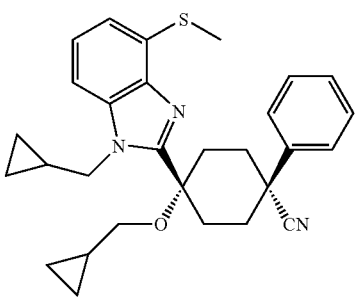

Analogously to the processes described above, starting from 1.4 g of cis-4-(1-cyclopropylmethyl-4-methylsulfanyl-1H-benzoimidazol-2-yl)-4-hydroxy-1-phenylcyclohexanecarbonitrile, 1.4 g of the title compound were obtained as a white solid.

TLC (cyclohexane/EA 3:2): Rf 0.67

EXAMPLE 446

Cis-4-Cyclopropylmethoxy-4-(1-cyclopropylmethyl-4-methanesulfonyl-1H-benzoimidazol-2-yl)-1-phenylcyclohexanecarboxamide

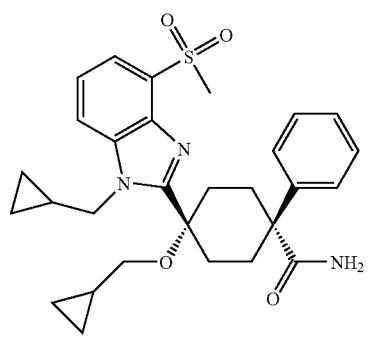

1.4 g of cis-4-cyclopropylmethoxy-4-(1-cyclopropylmethyl-4-methylsulfanyl-1H-benzoimidazol-2-yl)-1-phenylcyclohexanecarbonitrile were dissolved in 5:1 mixture of MOH and 1-methylpyrrolidin-2-one (30 ml). The mixture was heated to 50° C. A solution of 0.34 g of potassium hydroxide in 2 ml of water was then added, followed by 1 ml of hydrogen peroxide (30% strength in water). After one hour each, 7 further 1 ml portions of hydrogen peroxide (30% strength in water) were added. The reaction mixture was stirred for 12 h at 50° C. Then it was treated with water and extracted with EA. The combined organic phases were washed with brine and dried over sodium sulfate. The solvent was removed in vacuo. The crude product was purified by flash chromatography (silica gel; DCM/MOH, gradient from 100:0 to 95:5). 0.425 g of the title compound were obtained as a white solid.

TLC (DCM/MOH 19:1): Rf 0.34

EXAMPLE 447

Cis-4-Cyclopropylmethoxy-4-(1-cyclopropylmethyl-4-methanesulfonyl-1H-benzoimidazol-2-yl)-1-phenylcyclohexanecarboxylic Acid

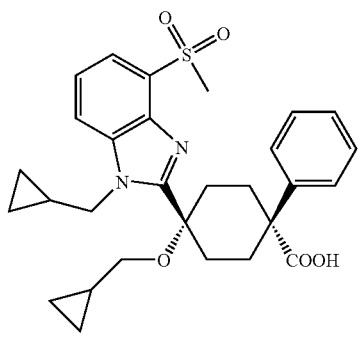

Analogously to the processes described above, 0.46 g of cis-4-(1-cyclopropylmethyl-4-methanesulfonyl-1H-benzoimidazol-2-yl)-4-hydroxy-1-phenylcyclohexanecarboxamide was hydrolyzed using nitrosonium tetrafluoroborate to yield 0.395 g of the title compound as a white solid.

TLC (DCM/MOH 19:1): Rf 0.30
MS (ESI+): 523
HPLC (Method LC20): Rt 1.24 min
$^1$H-NMR (d$_6$-DMSO; 400 MHz): 12.4 (b, 1H), 7.95 (d, 1H), 7.6 (d, 1H), 7.35 (m, 3H), 7.2 (t, 2H), 7.15 (m, 1H), 4.5 (d, 2H), 3.3 (s, 3H), 2.9 (d, 2H), 2.35-2.15 (m, 6H), 2.05 (m, 2H), 1.1 (m, 1H), 0.9 (m, 1H), 0.55 (m, 4H), 0.35 (m, 2H), 0.0 (m, 2H)
MP: 227° C.

Analogously to the preparation processes described above, the cis-4-Ar$^2$-4-cyclopropylmethoxy-1-phenylcyclohexanecarboxylic acids of the formula Ip and trans-4-Ar$^2$-4-cyclopropylmethoxy-1-phenylcyclohexanecarboxylic acids of the formula Iq listed in Table 17 were prepared.

TABLE 17

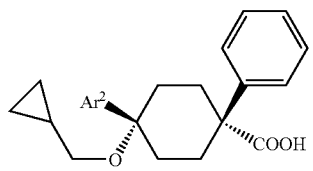

Ip

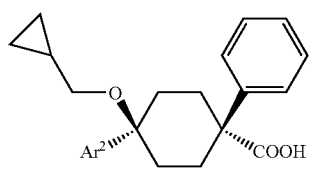

Iq

Example compounds of the formulae Ip and Iq

| Example | Ar$^2$ | Formula, configuration | MS (ESI+) | HPLC (Rt [min], Method) | MP |
|---|---|---|---|---|---|
| 448 | 3-cyclopropylmethyl-3H-imidazo[4,5-b]pyridin-2-yl | Ip cis | 446 | 1.21 LC20 | 243° C. |
| 449 (1) | 1-cyclopropylmethyl-4,5,6,7-tetrahydro-1H-benzoimidazol-2-yl | Ip cis | 449 | 5.34 LC21 | 97° C. |

TABLE 17-continued

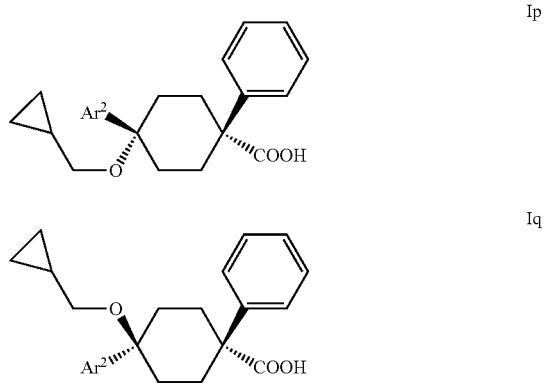

Example compounds of the formulae Ip and Iq

| Example | Ar² | Formula, configuration | MS (ESI+) | HPLC (Rt [min], Method) | MP |
|---|---|---|---|---|---|
| 450 (2) | 5-chloro-1-cyclopropylmethyl-1H-benzoimidazol-2-yl | Ip cis | 479 | 1.26 LC20 | 218° C. |
| 451 | 5-chloro-1-cyclopropylmethyl-1H-benzoimidazol-2-yl | Iq trans | 479 | 1.28 LC20 | 161° C. |
| 452 | 1-cyclopropylmethyl-5-fluoro-1H-benzoimidazol-2-yl | Ip cis | 463 | 1.13 LC20 | 243° C. |
| 453 | 1-cyclopropylmethyl-5-fluoro-1H-benzoimidazol-2-yl | Iq trans | 463 | 1.2 LC20 | 246° C. |
| 454 | 1-cyclopropylmethyl-5-methane-sulfonyl-1H-benzoimidazol-2-yl | Ip cis | 523 | 1.11 LC20 | 310° C. |
| 455 | 1-cyclopropylmethyl-7-methane-sulfonyl-1H-benzoimidazol-2-yl | Ip CIS | 523 | 1.2 LC20 | 165° C. |

(1) tetrafluoroboric acid salt
(2) hydrochloride

EXAMPLE 456

3-Methylsulfanylbenzamide

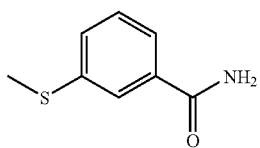

10 g of 3-methylsulfanylbenzoic acid and 0.05 ml of DMF were suspended in 50 ml of DCM. 9 ml of thionyl chloride were added and the mixture was heated under reflux for 4 h. The volatiles were removed in vacuo and the residue was taken up in 30 ml of toluene and transferred to a pressure bottle. 180 ml of a 0.5 M solution of ammonia in dioxane were added, the bottle was sealed and the mixture was heated to 120° C. for 5 h. The solvent was removed in vacuo and the residue taken in water and EA. The phases were separated and the aqueous layer was extracted with EA. The combined organic phases were washed with brine and dried over sodium sulfate. The solvent was removed in vacuo. 8.6 g of the title compound were obtained as a brown solid.

TLC (DCM/MOH 9:1): Rf=0.36

EXAMPLE 457

N-[1-Dimethylaminomethylidene]-3-methylsulfanyl-benzamide

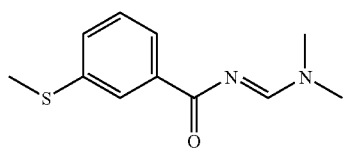

8.5 g of 3-methylsulfanylbenzamide and 18 ml of dimethylformamide dimethyl acetal were heated at 120° C. while the formed methanol was eliminated by distillation. After heating for 3 h, the volatiles were removed in vacuo. The crude product was purified by flash chromatography (300 g silica gel; DCM/MOH, gradient from 100:0 to 95:5). 8 g of the title compound were obtained as an oil.

TLC (DCM/MOH 9:1): Rf=0.81

EXAMPLE 458

3-(3-Methylsulfanylphenyl)-1H-[1,2,4]triazole

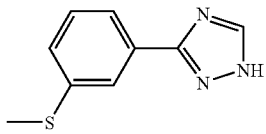

8 g of N-[1-dimethylaminomethylidene]-3-methylsulfanyl-benzamide were dissolved in 80 ml of glacial acetic acid. 2 ml of hydrazine hydrate were added and the mixture was heated to 90° C. for 2 h. The solvent was removed in vacuo. The crude product was purified by flash chromatography (300 g of silica gel; DCM/MOH, gradient from 100:0 to 95:5). 4.5 g of the title compound were obtained as an oil.

TLC (DCM/MOH 9:1): Rf=0.32

EXAMPLE 459

1-Cyclopropylmethyl-3-(3-methylsulfanylphenyl)-1H-[1,2,4]triazole and 1-cyclopropylmethyl-5-(3-methylsulfanylphenyl)-1H-[1,2,4]triazole 4.5 g of 3-(3-methylsulfanylphenyl)-1H-[1,2,4]triazole were dissolved in 40 ml of dry DMF. 1 g of sodium hydride (60% strength in mineral oil) was added portionwise at 0° C. After stirring at 20° C. for 1 h, bromomethylcyclopropane (2.4 ml) was added. The reaction mixture was stirred for 18 h at 20° C. The solvent was removed in vacuo and the residue was taken up in water and EA (100 ml each). The phases were separated and the aqueous phase was extracted with EA. The combined organic phases were washed with brine and dried over sodium sulfate. The solvent was removed in vacuo. The crude product was purified by flash chromatography (240 g of silica gel; HEP/EA, gradient from 100:0 to 60:40) to yield 1.7 g of 1-cyclopropylmethyl-3-(3-methylsulfanyl-phenyl)-1H-[1, 2, 4]triazole and 1.9 g of 1-cyclopropylmethyl-5-(3-methylsulfanyl-phenyl)-1H-[1, 2, 4]triazole.

EXAMPLE 459-1

1-Cyclopropylmethyl-3-(3-methylsulfanylphenyl)-1H-[1,2,4]triazole

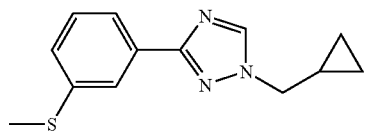

TLC (HEP/EA 3:2): Rf 0.27

EXAMPLE 459-2

1-Cyclopropylmethyl-5-(3-methylsulfanylphenyl)-1H-[1,2,4]triazole

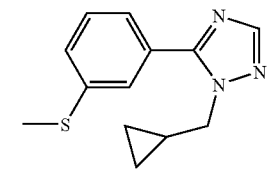

TLC (HEP/EA 3:2): Rf 0.20

EXAMPLE 460

Cis-4-[2-Cyclopropylmethyl-5-(3-methylsulfanylphenyl)-2H-[1,2,4]triazol-3-yl]-4-hydroxy-1-phenylcyclohexanecarbonitrile and Trans-4-[2-cyclopropylmethyl-5-(3-methylsulfanylphenyl)-2H-[1,2,4]triazol-3-yl]-4-hydroxy-1-phenylcyclohexanecarbonitrile

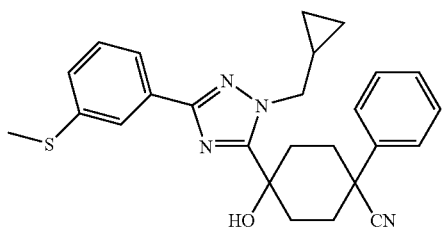

1.7 g of 1-cyclopropylmethyl-3-(3-methylsulfanylphenyl)-1H-[1,2,4]triazole were dissolved in 15 ml of anhydrous THF and cooled to −70° C. under a nitrogen atmosphere. 3.05 ml of a 2.5 M solution of n-butyllithium in hexane were added dropwise. After 30 min a solution of 1.1 g of 4-oxo-1-phenylcyclohexanecarbonitrile in 5 ml of THF was added. The reaction mixture was allowed to warm to room temperature during 18 h. 50 ml of water were added, and the mixture was extracted three times with 50 ml each of EA. The combined organic phases were washed with brine and dried over sodium sulfate. The solvent was removed in vacuo. Flash chromatography of the residue (120 g of silica gel; HEP/EA, gradient from 90:10 to 60:40) yielded 1.6 g of the cis title compound as a white solid and 0.58 g of the trans title compound as a white solid.

EXAMPLE 460-1

Cis-4-[2-Cyclopropylmethyl-5-(3-methylsulfanylphenyl)-2H-[1,2,4]triazol-3-yl]-4-hydroxy-1-phenylcyclohexanecarbonitrile

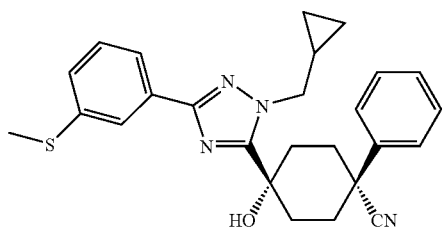

TLC (HEP/EA 3:2): Rf 0.58

EXAMPLE 460-2

Trans-4-[2-Cyclopropylmethyl-5-(3-methylsulfanylphenyl)-2H-[1,2,4]triazol-3-yl]-4-hydroxy-1-phenylcyclohexanecarbonitrile

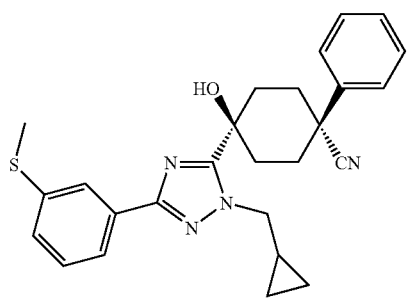

TLC (HEP/EA 3:2): Rf 0.52

EXAMPLE 461

Trans-4-[2-Cyclopropylmethyl-5-(3-methylsulfanylphenyl)-2H-[1,2,4]triazol-3-yl]-4-phenoxy-1-phenylcyclohexanecarbonitrile

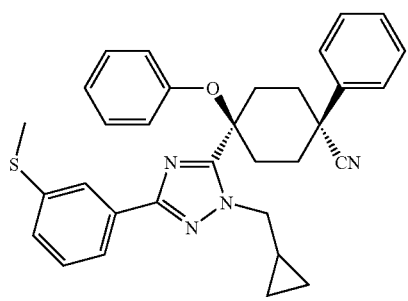

0.58 g of trans-4-[2-cyclopropylmethyl-5-(3-methylsulfanylphenyl)-2H-[1,2,4]triazol-3-yl]-4-hydroxy-1-phenylcyclohexanecarbonitrile and 0.11 g of copper were suspended in toluene (5 ml). 2.9 g of triphenylbismuth diacetate were added and the reaction mixture was heated to 80° C. for 18 h. The mixture was then filtered over celite and the solid washed with EA (100 ml). The combined solutions were washed with water and brine and dried over sodium sulfate. The solvent was removed in vacuo. The crude product was purified by flash chromatography (silica gel, HEP/EA, gradient from 100:0 to 90:10) to yield 0.535 g of the title compound as a white solid.

TLC (HEP/EA 3:2): Rf 0.9

EXAMPLE 462

Trans-4-[2-Cyclopropylmethyl-5-(3-methanesulfonylphenyl)-2H-[1,2,4]triazol-3-yl]-4-phenoxy-1-phenylcyclohexanecarboxamide

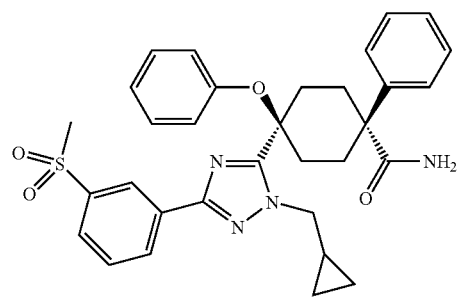

0.535 g of trans-4-[2-cyclopropylmethyl-5-(3-methylsulfanylphenyl)-2H-[1,2,4]triazol-3-yl]-4-phenoxy-1-phenylcyclohexanecarbonitrile were dissolved in 10 ml of MOH and heated to 50° C. A solution of 0.115 g of potassium hydroxide in 1 ml of water was then added, followed by 1 ml of hydrogen peroxide (30% strength in water). After one hour each, four further 1 ml portions of hydrogen peroxide (30% strength in water) were added. The reaction mixture was stirred for 12 h at 50° C. Then it was treated with water and extracted with EA. The combined organic phases were washed with brine and dried over sodium sulfate. The solvent was removed in vacuo. The crude product was purified by flash chromatography (silica gel; DCM/MOH, gradient from 100:0 to 95:5). 0.47 g of the title compound were obtained as a white solid.

TLC (DCM/MOH 9:1): Rf 0.70

EXAMPLE 463

Trans-4-[2-Cyclopropylmethyl-5-(3-methanesulfonylphenyl)-2H-[1,2,4]triazol-3-yl]-4-phenoxy-1-phenylcyclohexanecarboxylic Acid

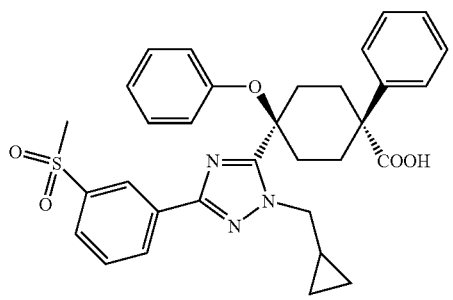

0.47 g of trans-4-[2-cyclopropylmethyl-5-(3-methanesulfonylphenyl)-2H-[1,2,4]triazol-3-yl]-4-phenoxy-1-phenylcyclohexanecarboxamide were dissolved in 4 ml of DMF. The mixture was cooled to 0° C. under nitrogen, and 0.3 g of nitrosonium tetrafluoroborate were added. The green mixture was stirred for 1 h. 10 ml of water and 10 ml of DCM were added. The aqueous layer was extracted with DCM. The combined organic phases were washed with brine and dried over sodium sulfate. The solvent was removed in vacuo. The crude product was purified by flash chromatography (silica gel; DCM/MOH, gradient from 100:0 to 95:5). 0.3 g of the title compound were obtained as a white solid.

MS (ESI+): 572
HPLC (Method LC20): Rt 1.45 min
$^{1}$H-NMR ($d_6$-DMSO; 400 MHz): 12.7 (b, 1H), 8.5 (s, 1H), 8.4 (d, 1H), 8.05 (d, 1H), 7.8 (t, 1H), 7.5 (d, 2H), 7.4 (t, 2H), 7.3 (m, 1H), 7.25 (t, 2H), 6.95 (t, 1H), 6.6 (d, 2H), 4.25 (d, 2H), 3.3 (s, 3H), 2.6-2.45 (m, 4H), 2.25 (m, 2H), 2.0 (m, 2H), 1.2 (m, 1H), 0.5 (m, 2H), 0.25 (m, 2H)
MP: 198° C.

Analogously to the preparation processes described above, the cis 4-Ar$^2$-4-phenoxy-1-(optionally substituted phenyl) cyclohexanecarboxylic acids of formula Ir and the trans-4-Ar$^2$-4-phenoxy-1-(optionally substituted phenyl)cyclohexanecarboxylic acids of formula Is listed in Table 18 were prepared.

TABLE 18

Example compounds of the formulae Ir and Is

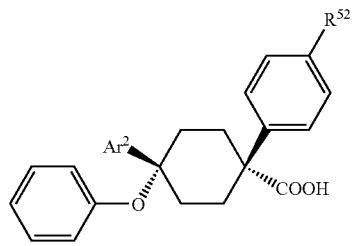

Ir

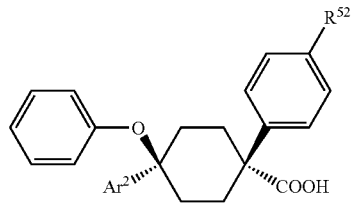

Is

| Example | Ar$^2$ | R$^{52}$ | Formula, configuration | MS (ESI+) | HPLC (Rt [min], Method) | MP |
|---|---|---|---|---|---|---|
| 464 | 1-cyclopropylmethyl-5-phenyl-1H-[1,2,4]triazol-3-yl | F | Is trans | 512 | 11.6 LC19 | 180° C. |
| 465 | 1-cyclopropylmethyl-5-phenyl-1H-[1,2,4]triazol-3-yl | F | Ir cis | 512 | 11.8 LC19 | 221° C. |
| 466 | 2-cyclopropylmethyl-5-phenyl-2H-[1,2,4]triazol-3-yl | H | Is trans | 494 | 1.55 LC20 | 220° C. |
| 467 | 2-cyclopropylmethyl-5-(4-methanesulfonylphenyl)-2H-[1,2,4]triazol-3-yl | H | Is trans | 572 | 1.45 LC20 | 265° C. |
| 468 | 1-cyclopropylmethyl-5-(4-methanesulfonylphenyl)-1H-[1,2,4]triazol-3-yl | H | Ir cis | 572 | 1.18 LC20 | 199° C. |
| 469 | 1-cyclopropylmethyl-5-(3-methanesulfonylphenyl)-1H-[1,2,4]triazol-3-yl | H | Ir cis | 572 | 1.15 LC20 | 102° C. |
| 470 | 4-phenylthiazol-2-yl | H | Ir cis | 456 | 1.49 LC20 | 103° C. |

EXAMPLE 471

Cis-4-(1-Cyclopropylmethyl-5-phenyl-1H-[1,2,4]triazol-3-yl)-4-hydroxy-1-phenylcyclohexanecarbonitrile and Trans-4-(1-cyclopropylmethyl-5-phenyl-1H-[1,2,4]triazol-3-yl)-4-hydroxy-1-phenylcyclohexanecarbonitrile

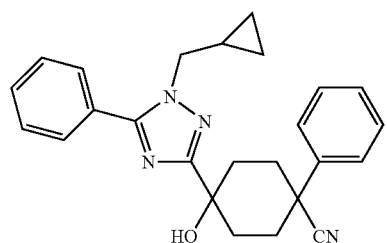

5 g of 1-cyclopropylmethyl-5-phenyl-1H-[1,2,4]triazole were dissolved in 50 ml of anhydrous THF and cooled to −70° C. under a nitrogen atmosphere. 17.3 ml of a 1.6 M solution of n-butyllithium in hexane were added dropwise. After 30 min a solution of 5 g of 4-oxo-1-phenylcyclohexanecarbonitrile in 25 ml of THF was added. The reaction mixture was allowed to warm to room temperature during 18 h. 50 ml of water were added, and the mixture was extracted three times with 50 ml each of EA. The combined organic phases were washed with brine and dried over sodium sulfate. The solvent was removed in vacuo. Flash chromatography of the residue (400 g of silica gel; DCM/MOH, gradient from 97:3 to 95:5) yielded 2.38 g of the trans title compound as a pale yellow solid and 3 g of the cis title compound as a beige solid.

EXAMPLE 471-1

Trans-4-(1-Cyclopropylmethyl-5-phenyl-1H-[1,2,4]triazol-3-yl)-4-hydroxy-1-phenylcyclohexanecarbonitrile

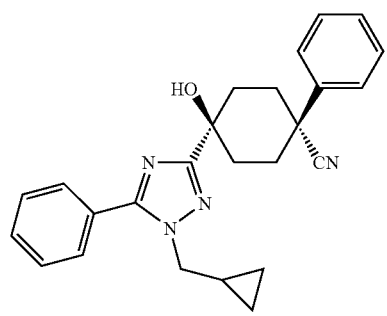

TLC (DCM/MOH 19:1): Rf 0.3

EXAMPLE 471-2

Cis-4-(1-Cyclopropylmethyl-5-phenyl-1H-[1,2,4]triazol-3-yl)-4-hydroxy-1-phenylcyclohexanecarbonitrile

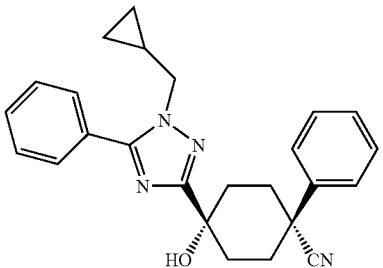

TLC (DCM/MOH 19:1): Rf 0.28

EXAMPLE 472

Cis-4-(1-Cyclopropylmethyl-5-phenyl-1H-[1,2,4]triazol-3-yl)-1-phenyl-4-(4-trifluoromethylphenoxy)cyclohexanecarbonitrile

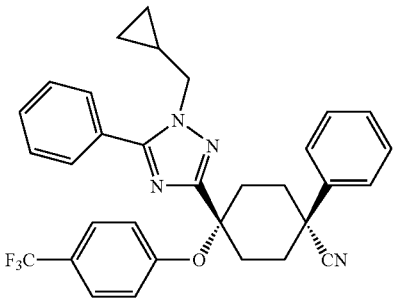

1.6 g of cis-4-(1-cyclopropylmethyl-5-phenyl-1H-[1,2,4]triazol-3-yl)-4-hydroxy-1-phenylcyclohexanecarbonitrile were dissolved in dry DMF (13 ml). 0.25 g of sodium hydride (60% strength in mineral oil) were added and the mixture was stirred for 30 min at 70° C. 1-Fluoro-4-trifluoromethylbenzene (1.05 ml) was added and the reaction mixture was stirred at 110° C. for 18 h. The mixture was then poured in ice and made neutral with 1 N aqueous hydrochloric acid. The aqueous layer was extracted three times with 50 ml each of EA and the combined organic phases were washed with water and brine and dried over sodium sulfate. The solvent was removed in vacuo. The crude product was purified by flash chromatography (silica gel, HEP/EA, gradient from 100:0 to 70:30). 1.24 g of the title compound were obtained as foam.

TLC (HEP/EA 7:3): Rf 0.55

EXAMPLE 473

Cis-4-(1-Cyclopropylmethyl-5-phenyl-1H-[1,2,4]triazol-3-yl)-1-phenyl-4-(4-trifluoromethylphenoxy)cyclohexanecarboxamide

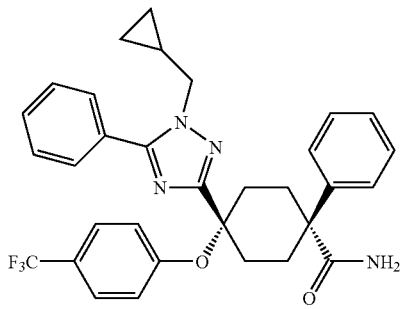

1.24 g of cis-4-(1-cyclopropylmethyl-5-phenyl-1H-[1,2,4]triazol-3-yl)-1-phenyl-4-(4-trifluoromethylphenoxy)-cyclohexanecarbonitrile were hydrolyzed using potassium hydroxide and hydrogen peroxide analogously as described above. The crude product was purified by crystallization using a DCM/MOH/diethyl ether/pentane mixture. 1.1 g of the title compound were obtained as a white solid.

TLC (cyclohexane/EA 3:2): Rf 0.25

EXAMPLE 474

Cis-4-(1-Cyclopropylmethyl-5-phenyl-1H-[1,2,4]triazol-3-yl)-1-phenyl-4-(4-trifluoromethylphenoxy)cyclohexanecarboxylic Acid

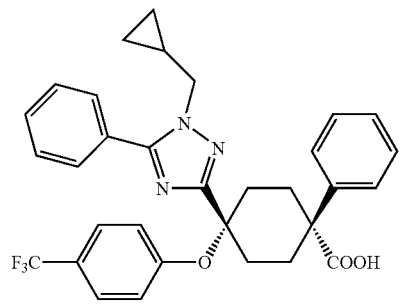

As described in the processes above, 1 g of cis-4-(1-cyclopropylmethyl-5-phenyl-1H-[1,2,4]triazol-3-yl)-1-phenyl-4-(4-trifluoromethylphenoxy)cyclohexanecarboxamide was hydrolyzed using nitrosonium tetrafluoroborate to yield 0.9 g of the title compound as a white solid.

TLC (DCM/MOH 19:1): Rf 0.30
MS (ESI+): 562
HPLC (Method LC20): Rt 1.47 min
$^1$H-NMR (d$_6$-DMSO; 400 MHz): 12.5 (b, 1H), 7.6 (m, 2H), 7.45 (m, 5H), 7.35 (m, 2H), 7.25 (m, 2H), 7.15 (m, 1H), 6.85 (d, 2H), 4.0 (d, 2H), 2.6 (m, 4H), 2.1 (m, 2H), 1.8 (m, 2H), 0.95 (m, 1H), 0.25 (m, 2H), 0.0 (m, 2H)
MP: 85° C.

Analogously to the preparation processes described above, the cis-4-(1-cyclopropylmethyl-5-phenyl-1H-[1,2,4]triazol-3-yl)-4-(substituted phenoxy)-1-phenylcyclohexanecarboxylic acids of formula It listed in Table 19 were prepared.

TABLE 19

It

| Example | R² | MS (ESI+) | HPLC (Rt [min], Method) | MP |
|---|---|---|---|---|
| 475 | 3-fluorophenyl | 512 | 1.39 LC20 | 118° C. |
| 476 | 4-methanesulfonylphenyl | 572 | 1.23 LC20 | 139° C. |
| 477 | 3-trifluoromethylphenyl | 562 | 1.47 LC20 | 121° C. |
| 478 | 3-methanesulfonylphenyl | 572 | 1.24 LC20 | 109° C. |

EXAMPLE 479

1-Bromo-3-fluoro-2-methyl-5-methylsulfanylbenzene 7.5 ml of a 2 M solution of lithium diisopropylamide in THF/HEP/ethylbenzene (Aldrich) were dissolved in 30 ml of anhydrous THF and cooled to −73° C. A solution of 3.0 g of 1-bromo-3-fluoro-5-methylsulfanylbenzene in 10 ml of anhydrous THF added at a temperature between −73° C. and −67° C. Stirring was continued for 90 min at −75° C., then 1.0 ml of iodomethane was added at this temperature. The mixture was then warmed up to room temperature, 100 ml of a saturated aqueous solution of sodium chloride were added and the mixture was extracted twice with 100 ml each of EA.

The extracts were dried and concentrated in vacuo to yield 2.0 g of the title compound as a slight yellow oil that was used without further purification.

EXAMPLE 480

Cis-4-Cyclopropylmethoxy-4-(3-fluoro-2-methyl-5-methanesulfonylphenyl)-1-phenylcyclohexanecarboxylic Acid

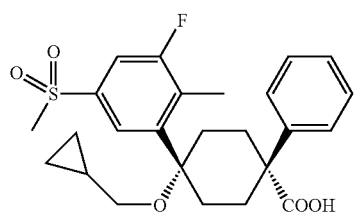

The synthesis of the title compound was carried out analogously to the synthesis of the compound of Example 301, using 1-bromo-3-fluoro-2-methyl-5-methylsulfanylbenzene as starting material.

TLC (EA/HEP 1:1): Rf 0.25

EXAMPLE 481

Cis-4-Cyclopropylmethoxy-4-(3-fluoro-4-methyl-5-methylsulfanylphenyl)-1-phenylcyclohexanecarbonitrile

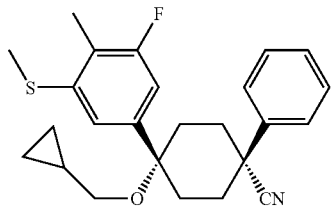

1.4 g of cis-4-cyclopropylmethoxy-4-(3-fluoro-5-methylsulfanylphenyl)-1-phenylcyclohexanecarbonitrile (prepared analogously to the preparation of the compound of Example 299) were dissolved in 200 ml of anhydrous THF and cooled to −75° C. At that temperature, 2.3 ml of a 1.7 M solution of tert-butyllithium in n-pentane was added. Stirring was continued for 1 h at −75° C. Then 0.34 ml of iodomethane were added at −75° C. and the mixture was allowed to warm up to room temperature. 300 ml of a saturated aqueous solution of sodium hydrogencarbonate were added and the mixture was extracted twice with 100 ml each of EA. The combined organic layers was dried with magnesium sulfate and evaporated. Chromatography of the residue on reversed phase silica gel yielded 0.30 g of the title compound as a colorless oil.

TLC (EA/HEP 1:2): Rf 0.50

EXAMPLE 482

Cis-4-Cyclopropylmethoxy-4-(3-fluoro-5-methanesulfonyl-4-methylphenyl)-1-phenylcyclohexanecarboxylic Acid

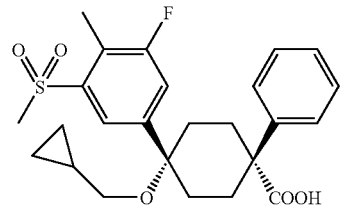

From the compound of Example 481, the title compound was prepared according to the procedure described in Example 301.

MS (ESI−): 919 (2M-1)

EXAMPLE 483

Cis-4-Hydroxy-1-phenyl-4-(4-phenylpyridin-2-yl)cyclohexanecarbonitrile and Trans-4-hydroxy-1-phenyl-4-(4-phenylpyridin-2-yl)cyclohexanecarbonitrile

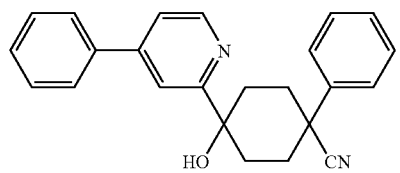

51.5 ml of a 2.7 M solution of n-butyllithium in HEP were added to a solution of 4.6 g 2-dimethylamino-ethanol in 300 ml of anhydrous HEP at 0° C. Stirring was continued for 30 min at 0° C. Then, 2.0 g of 4-phenylpyridine were added portionwise at 0° C. Stirring was continued for 1 h at 0° C. The mixture was then cooled to −75° C. and 12.3 g of 4-oxo-1-phenylcyclohexanecarbonitrile were added portionwise at −75° C. Stirring was continued for 30 min at −75° C. and then for 2 h at 0° C. The mixture was warmed up to room temperature and poured into 300 ml of water. The organic layer was separated and the aqueous layer extracted with 100 ml of EA. The combined organic layers were dried over magnesium sulfate and the volatiles were removed in vacuo. Chromatography of the residue on reversed phase silica gel yielded 1.5 g of the title compound (cis/trans mixture) as a colorless oil.

MS (ESI+): 355

EXAMPLE 484

Cis-4-Cyclopropylmethoxy-1-phenyl-4-(4-phenylpyridin-2-yl)cyclohexanecarbonitrile and Trans-4-cyclopropylmethoxy-1-phenyl-4-(4-phenylpyridin-2-yl)cyclohexanecarbonitrile

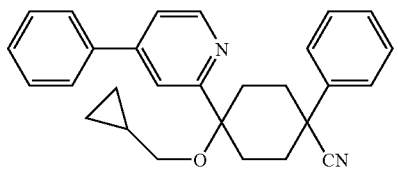

1.5 g of the compound of Example 483, 1.7 g of bromomethylcyclopropane and 0.3 g sodium hydride were stirred in 50 ml of anhydrous DMF for 2 days at room temperature. The reaction mixture was poured into 200 ml of a saturated aqueous solution of sodium hydrogencarbonate and extracted three times with 100 ml each of EA. The combined organic layers were dried with magnesium sulfate and evaporated in vacuo. Chromatography of the residue (cis/trans mixture) on reversed phase silica gel yielded 290 mg of cis title compound as a colorless oil and 100 mg of trans title compound as a colorless oil.

EXAMPLE 484-1

Cis-4-Cyclopropylmethoxy-1-phenyl-4-(4-phenylpyridin-2-yl)cyclohexanecarbonitrile

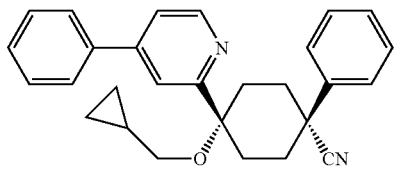

MS (ESI+): 409
TLC (EA/HEP 1:5): Rf 0.17

EXAMPLE 484-2

Trans-4-Cyclopropylmethoxy-1-phenyl-4-(4-phenylpyridin-2-yl)cyclohexanecarbonitrile

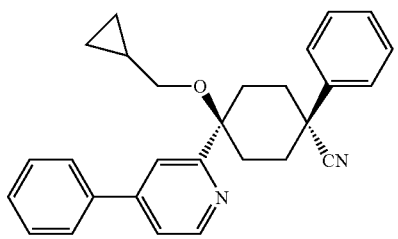

MS (ESI+): 409
TLC (EA/HEP 1:5): Rf 0.17

EXAMPLE 485

Cis-4-Cyclopropylmethoxy-1-phenyl-4-(4-phenylpyridin-2-yl)cyclohexanecarboxylic Acid

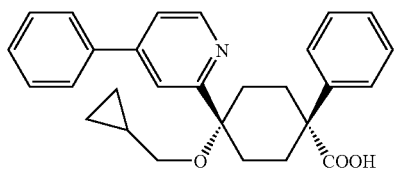

From the compound of Example 484-1, the title compound was prepared according to the procedure described in Example 326.
MS (ESI+): 428
TLC (EA): Rf 0.63

EXAMPLE 486

Trans-4-Cyclopropylmethoxy-1-phenyl-4-(4-phenylpyridin-2-yl)cyclohexanecarboxylic Acid

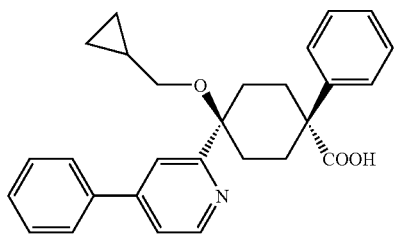

From the compound of Example 484-2, the title compound was prepared according to the procedure described in Example 326.
MS (ESI+): 428
TLC (EA): Rf 0.62

EXAMPLE 487

Cis-4-Hydroxy-1-phenyl-4-(2-phenylpyridin-4-yl)cyclohexanecarbonitrile and Trans-4-hydroxy-1-phenyl-4-(2-phenylpyridin-4-yl)cyclohexanecarbonitrile

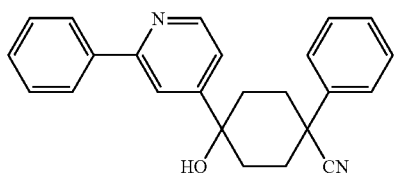

3.0 g of 4-bromo-2-phenylpyridine (Comins et al., J. Org. Chem. 50, 4410-4411 (1985)) were dissolved in 100 ml of anhydrous diethyl ether and 5.2 ml of a 2.7 M solution of n-butyllithium in HEP were added at −70° C. Stirring was continued for 10 min, then a solution of 2.6 g of 4-oxo-1-phenylcyclohexanecarbonitrile in 20 ml of anhydrous THF was added between −60° C. and −70° C. The reaction mixture was warmed up to room temperature, 100 ml of a saturated aqueous solution of sodium hydrogencarbonate were added and the mixture extracted with 50 ml of EA. The organic layer was dried with magnesium sulfate and the volatiles were removed in vacuo to give 4.2 g of the title compound as a pale yellow oil.

MS (ESI+): 355
TLC (EA/HEP 1:2): Rf 0.22

EXAMPLE 488

Cis-4-Cyclopropylmethoxy-1-phenyl-4-(2-phenylpyridin-4-yl)cyclohexanecarboxylic Acid

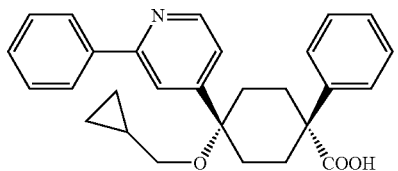

The preparation of the title compound was carried out analogously to the preparation of the compound of Example 485.

MS (ESI+): 428
TLC (EA): Rf 0.40

EXAMPLE 489

Trans-4-Cyclopropylmethoxy-1-phenyl-4-(2-phenylpyridin-4-yl)cyclohexanecarboxylic Acid

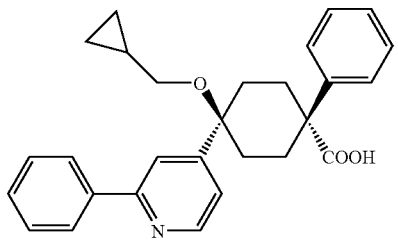

The preparation of the title compound was carried out analogously to the preparation of the compound of Example 486.

MS (ESI+): 428
TLC (EA): Rf 0.30

EXAMPLE 490

Cis-Cyclopropylmethyl-1H-imidazol-2-yl)-4-hydroxy-1-phenylcyclohexanecarbonitrile and Trans-cyclopropylmethyl-1H-imidazol-2-yl)-4-hydroxy-1-phenylcyclohexanecarbonitrile

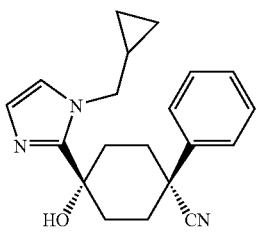

5.0 g of 1-cyclopropylmethyl-1H-imidazole were dissolved in 100 ml of anhydrous THF and 32.2 ml of a 1.4 M solution of sec-butyllithium in cyclohexane added at a temperature between −73° C. and −65° C. Stirring was continued for 1 h at −72° C., then a solution of 8.6 g of 4-oxo-1-phenylcyclohexanecarbonitrile in 75 ml of anhydrous THF was added between −60° C. and −70° C. Stirring was continued for 2 h at −72° C. The reaction mixture was then warmed up to room temperature and poured into 150 ml of a saturated aqueous solution of sodium hydrogencarbonate. The mixture was extracted twice with 100 ml each of EA. The combined organic layers were dried with magnesium sulfate and the volatiles removed in vacuo. Chromatography (silica gel, EA/HEP 2:1) of the residue (cis/trans mixture) yielded 2.0 g of cis title compound and 1.5 g of the trans title compound.

EXAMPLE 490-1

Cis-Cyclopropylmethyl-1H-imidazol-2-yl)-4-hydroxy-1-phenylcyclohexanecarbonitrile

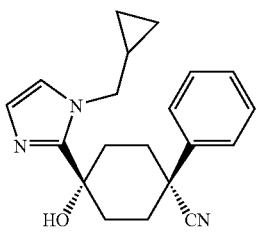

MS (ESI+): 322
TLC (EA/HEP 2:1): Rf 0.30

EXAMPLE 490-2

Trans-Cyclopropylmethyl-1H-imidazol-2-yl)-4-hydroxy-1-phenylcyclohexanecarbonitrile

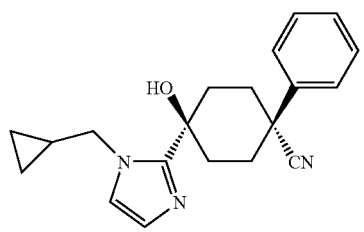

MS (ESI+): 322
TLC (EA/HEP 2:1): Rf 0.15

EXAMPLE 491

Cis-4-Cyclopropylmethoxy-4-(1-cyclopropylmethyl-1H-imidazol-2-yl)-1-phenylcyclohexanecarbonitrile

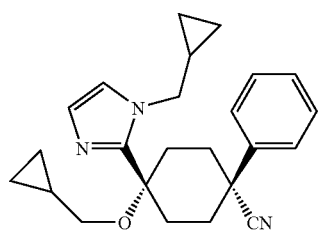

2.4 g of the compound of Example 490-1 were dissolved in 50 ml of anhydrous DMF and 0.37 g of sodium hydride added at room temperature. Stirring was continued for 30 min at room temperature, then 1.4 ml of bromomethylcyclopropane were added. Stirring was continued for 3 h at room temperature. The mixture was then poured into 100 ml of a saturated aqueous solution of sodium hydrogencarbonate and extracted twice with 75 ml each of MTB. The combined organic layers were dried over magnesium sulfate and the volatiles were removed in vacuo. 2.7 g of the title compound were obtained as a pale yellow oil that was used without further purification.

EXAMPLE 492

Cis-Cyclopropylmethoxy-4-(1-cyclopropylmethyl-1H-imidazol-2-yl)-1-phenylcyclohexanecarboxylic Acid

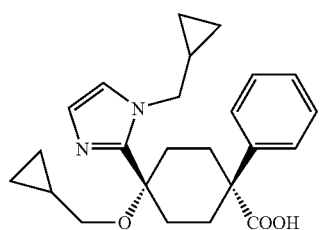

2.7 g of the compound of Example 491 and 2.0 g of potassium hydroxide were stirred in 25 ml of ethylene glycol for 3.5 h at 200° C. The reaction mixture was cooled to room temperature and poured into 100 ml of water. The pH was adjusted to 5 with an aqueous solution of sodium hydrogensulfate. The mixture was extracted three times with 100 ml each of EA. The combined organic layers were dried with magnesium sulfate and the volatiles were removed in vacuo. Chromatography of the residue on silica gel yielded 1.9 g of the title compound as a colorless solid.
MS (ESI$^+$): 395

EXAMPLE 493

Trans-Cyclopropylmethoxy-4-(1-cyclopropylmethyl-1H-imidazol-2-yl)-1-phenylcyclohexanecarboxylic Acid

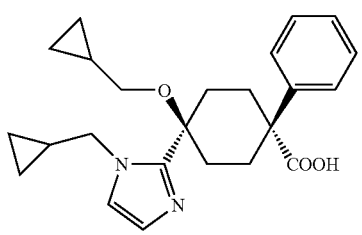

The title compound was prepared from the compound of Example 490-2 analogously to the preparation of the compound of Example 492.
MS (ESI+): 395

EXAMPLE 494

Cis-4-(1-Cyclopropylmethyl-1H-imidazol-2-yl)-1-phenyl-4-(3-phenyloxetan-3-ylmethoxy)cyclohexanecarbonitrile

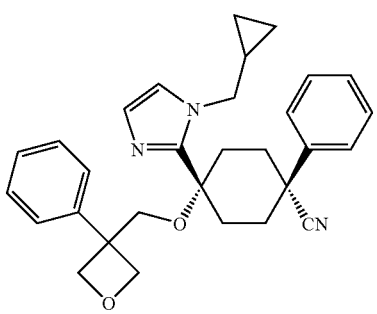

300 mg of the compound of Example 490-1, 300 mg of toluene-4-sulfonic acid 3-phenyloxetan-3-ylmethyl ester (Kanoh et al., Tetrahedron 58, 7065-7074 (2002)), and 33.6 mg of sodium hydride were stirred in 5 ml of anhydrous 1-methylpyrrolidin-2-one for 5 h at 40° C. The reaction mixture was then poured into 50 ml of water and extracted three times with 50 ml each of EA. The combined organic layers were washed twice with 10 ml each of water and with 10 ml of a saturated aqueous solution of sodium chloride, dried over magnesium sulfate and evaporated in vacuo. Chromatography of the residue on reversed phase silica gel yielded 230 mg of the title compound as a white foam.

MS (ESI+): 468

EXAMPLE 495

Cis-4-(1-Cyclopropylmethyl-1H-imidazol-2-yl)-1-phenyl-4-(2-phenylallyloxy)cyclohexanecarboxylic Acid

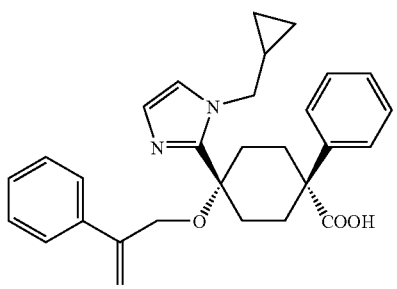

220 mg of the compound of Example 494 and 79 mg of potassium hydroxide were stirred in 2 ml of ethylene glycol for 8 h at 200° C. The reaction mixture was poured into 30 ml of water and the pH was adjusted to 5-6 with a saturated aqueous hydrogensulfate solution. The solution was then extracted three times with 30 ml each of EA. The combined organic layer was dried with magnesium sulfate and the volatiles were removed in vacuo. Chromatography of the residue on reversed phase silica gel yielded 55 mg of the title compound as an amorphous solid.

MS (ESI+): 457

EXAMPLE 496

Cis-4-(1-Cyclopropylmethyl-1H-imidazol-2-yl)-1-phenyl-4-(3-phenyloxetan-3-ylmethoxy)cyclohexanecarboxamide

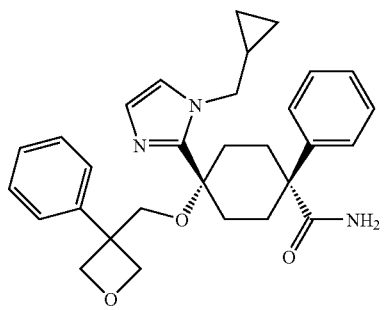

100 mg of the compound of Example 494 were dissolved in 8 ml of ethanol and 50 µl of water. 1 mg of [PtH(P(CH$_3$)$_2$OH)(P(CH$_3$)$_2$O)$_2$H] (Ghaffar et al., Tetrahedron Lett. 36, 8657-8660 (1995)) was added and the mixture was stirred at 78° C. for 9 h. 30 ml of a saturated aqueous solution of sodium carbonate was added and the mixture was extracted three times with 20 ml each of EA. The combined organic layers were dried with magnesium sulfate and the volatiles removed in vacuo to give 80 mg of the title compound as an amorphous solid.

MS (ESI+): 486

EXAMPLE 497

4-(1-Cyclopropylmethyl-1H-imidazol-2-yl)-1-phenyl-4-(3-phenyloxetan-3-ylmethoxy)cyclohexanecarboxylic Acid

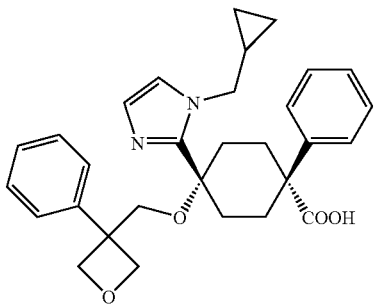

750 mg of the compound of Example 496 were dissolved in 30 ml of acetonitrile. 5.5 ml of a 0.53 M solution of dinitrogen tetroxide in tetrachloromethane were added at −20° C. The reaction mixture was warmed to room temperature and then poured on 30 g of ice. The pH was adjusted to 5-6 using saturated aqueous solution of sodium hydrogencarbonate. The mixture was extracted three times with 50 ml each of EA. The combined organic layer were dried with magnesium sulfate and the volatiles removed in vacuo. Chromatography of the residue on reversed phase silica gel yielded 250 mg of the title compound as an amorphous solid.

MS (ESI+): 487

EXAMPLE 498

4-(4-Fluorophenyl)-1-phenyl-4-(3-phenyloxetan-3-ylmethoxy)cyclohexanecarbonitrile

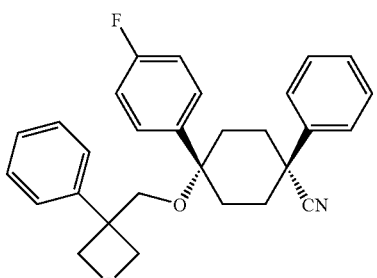

The preparation of the title compound was carried out analogously to the preparation of the compound of Example 494.

MS (ESI+): 442

EXAMPLE 499

4-(4-Fluorophenyl)-1-phenyl-4-(3-phenyloxetan-3-ylmethoxy)cyclohexanecarboxylic Acid

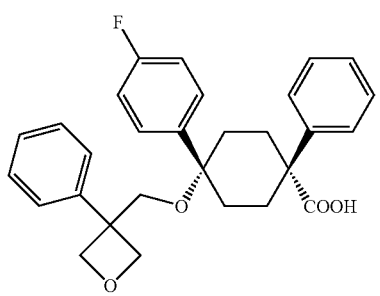

170 mg of the compound of Example 498 and 65 mg of potassium hydroxide were stirred in 2 ml of ethylene glycol for 8 h at 200° C. The mixture was poured into 30 ml of water and the pH adjusted to 5-6 with a saturated aqueous solution of sodium hydrogensulfate. The mixture was extracted three times with 30 ml each of EA. The combined organic layers were dried with magnesium sulfate and the volatiles removed in vacuo. Chromatography of the residue on reversed phase silica gel yielded 11 mg of the title compound as a colorless amorphous solid.

MS (ESI−): 919 (2M−1)

Pharmacological Investigations

1) Action on the SUR2A/Kir6.2 potassium channel (myocardial action) The action of the compounds on the ion transport through the myocardial ATP-sensitive potassium channel (SUR2A/Kir6.2) was determined in the rubidium efflux test system described below on human embryonic kidney cells HEK293 which were transfected with the components SUR2A and Kir6.2 (cf. Weyermann et al., Naunyn-Schmiedeberg's Arch. Pharmacol. 369, 374-381 (2004)).

The HEK293 cells were cultured at 37° C. in a humidified air atmosphere with 7% carbon dioxide in minimal essential medium with Earle's salts and L-glutamine (MEM, Gibco), which was supplemented with 10% fetal calf serum and zeozin (0.36 mg/ml) and geneticin (0.75 mg/ml). The transfection of the cells and the preparation of a cell line with stable expression of Kir6.2 from the mouse (accession number AF037313) and SUR2A from the rat (accession number D83598/L40624) were carried out as described in Giblin et al., J. Biol. Chem. 274, 22652-22659 (1999).

60 000 transfected cells per well were inoculated into a poly-D-lysine-coated 96-well microtiter plate (Greiner #650 201). After incubation for 24 h at 37° C., the cells were washed three times with buffer 1 (150 mM NaCl, 2 mM $CaCl_2$, 0.8 mM $NaH_2PO_4$, 1 mM $MgCl_2$, 5 mM glucose, 25 mM HEPES, pH=7.4). Subsequently, the buffer solution was replaced by 100 μl of rubidium loading buffer (buffer 1 with 5.4 mM RbCl) and the cells were incubated for a further 3 h at 37° C. The rubidium loading buffer was then removed by washing the cells three times with 200 μl each of potassium chloride wash buffer (buffer 1 with 5.4 mM KCl). After addition of the test substances (70 μl; dissolved in potassium chloride wash buffer with addition of DMSO), the KATP channels of the cells were opened by addition of 70 μl of rilmakalim (2 μM) (cf. Krause et al., Pflügers Arch. 429, 625-635 (1995)) and the cells were incubated at 37° C. for 25 min. Subsequently, the cell supernatants were transferred to a new 96-well microtiter plate and the cells were lyzed by addition of 200 μl of lysis buffer (buffer 1 with 1% Triton X-100). The concentrations of $Rb^+$ in the cell supernatant and in the cell lyzate were measured by means of atomic absorption spectroscopy using an Al 1200 apparatus (Aurora Instruments Ltd.).

The $Rb^+$ efflux rate was calculated as $[Rb^+_{SN}]/[Rb^+_{total}]$, wherein $[Rb^+_{SN}]$ is the amount of $Rb^+$ in the cell supernatant and $[Rb^+_{total}]$ is the sum of the amounts of $Rb^+$ in the cell supernatant and cell lyzate. $IC_{50}$ values for the inhibition of the rubidium efflux were calculated with the aid of the Hill equation.

Numerous compounds of the formula I were investigated in the assay described and proved to be inhibitors of rubidium efflux and thus inhibitors of the myocardial ATP-sensitive potassium channel (SUR2A/Kir6.2) which prolong the action potential and show an antiarrhythmic action. In general, the investigated compounds showed $IC_{50}$ values of less than about 30 μM. Preferred compounds, including the compounds of Examples 92, 93, 95, 98, 100, 101, 102, 103, 104, 105, 119, 120, 123, 124, 125, 131, 135, 136, 137, 141, 148, 150, 152, 161, 163, 167, 168, 169, 172, 173, 174, 175, 182, 234, 235, 236, 237, 238, 239, 242, 243, 244, 247, 248, 249, 250, 251, 253, 254, 255, 258, 263, 267, 270, 275, 279, 280, 296-2, 301, 304-1, 304-2, 304-3, 304-4, 306, 319, 333-1, 333-2, 339, 345, 350, 354, 357, 360, 363, 364, 365, 366, 368, 369, 370, 372, 373, 374, 375, 376, 377, 378, 379, 380, 381, 382, 383, 384, 385, 387, 388, 389, 390, 391, 392, 393, 394, 400, 403, 404, 406, 407, 408, 409, 410, 411, 412, 415, 418, 419, 422, 426, 427, 432, 440, 448, 449, 450, 451, 452, 453, 455, 463, 466, 467, 474, 480, 482, 485, 486, 488, 489, 492, 493, 495, 497, 499 showed $IC_{50}$ values of less than about 1 μM.

2) Action on the SUR2B/Kir6.2 Potassium Channel (Vascular Action)

The action of the compounds on the ion transport through the vascular ATP-sensitive potassium channel (SUR2B/Kir6.2) was determined analogously to 1) in a rubidium efflux test system on human embryonic kidney cells HEK293 which were transfected with the components SUR2B and Kir6.2.

Analogously to 1), HEK293 cells were cultured at 37° C. in a humidified air atmosphere with 7% carbon dioxide in minimal essential medium with Earle's salts and L-glutamine (MEM, Gibco), which was supplemented with 10% fetal calf serum and zeozin (0.36 mg /ml) and geneticin (0.75 mg/ml). The transfection of the cells and the preparation of a cell line with stable expression of Kir6.2 from the mouse (accession number AF037313) and SUR2B from the rat (accession number AB045281) were carried out as described in Giblin et al., J. Biol. Chem. 274, 22652-22659 (1999). 80 000 transfected cells per well were inoculated into a poly-D-lysine-coated 96-well microtiter plate (Greiner #650 201). The further conducting of the test and the evaluation were carried out as described under 1), but the incubation time after addition of the rubidium loading buffer was only 90 min and the incubation time after addition of the test substances was only 15 min.

Various compounds of the formula I were investigated in the assay described and showed, in comparison to the action on the cardiac ATP-sensitive potassium channel (SUR2A/Kir6.2), only a slight inhibition of the rubidium efflux and thus only a slight inhibition of the vascular ATP-sensitive potassium channel (SUR2B/Kir6.2) and only a slight inhibition of coronary vasodilatation.

3) Action on the SUR1/Kir6.2 Potassium Channel (Hypoglycemic Action)

The target organ of blood sugar-lowering sulfonylureas such as glibenclamide is the β-cell of the pancreas, where they block ATP-sensitive potassium channels and, by influencing the electrical potential of the cell membrane, bring about a release of the blood sugar-lowering hormone insulin. In molecular biology terms, pancreatic ATP-sensitive potassium channels are composed of the sulfonylurea receptor SUR1 and the inwardly rectifying potassium channel Kir6.2. A hypoglycemic compound such as, for example, glibenclamide causes, by binding to the sulfonylurea receptor, a depolarization of the cell membrane, which leads to an increased influx of calcium ions and, as a consequence thereof, to insulin release. The action of the compounds on the pancreatic ATP-sensitive potassium channel (SUR1/Kir6.2) and thus the extent of the depolarization of the cell membrane of the β-cell caused by them was determined in the FLIPR test system described below on CHO (Chinese hamster ovary) cells which were transfected with the components SUR1 and Kir6.2.

The CHO cells were cultured at 37° C. in a humidified air atmosphere with 7% carbon dioxide in Iscove medium (Biochrom, catalog number 31095-029) with 2 mM L-glutamine, which was supplemented with 10% fetal calf serum and zeozin (0.35 mg/ml) and geneticin (0.4 mg/ml). The transfection of the cells and the preparation of a cell line with stable expression of human Kir6.2 (accession number BC064497) and human SUR1 (accession number AF087138) were carried out as described in Giblin et al., J. Biol. Chem. 274, 22652-22659 (1999).

60 000 transfected cells per well were inoculated into a poly-D-lysine-coated 96-well microtiter plate (Costar #3904). After incubation for 24 h at 37° C., the cells were washed twice with assay buffer (120 mM NaCl, 2 mM $CaCl_2$, 1 mM $MgCl_2$, 2 mM KCl, 5 mM glucose, 20 mM HEPES, pH 7.4). After washing the cells, the volume in each well of the microtiter plate was 100 µl. After addition of 100 µl of the membrane potential-sensitive stain from the membrane potential assay kit R-8034 (Molecular Devices Corporation, Sunnyvale, Calif., USA; the lyophilizate was taken up in 100 ml of assay buffer and diluted in a ratio of 1:5 in assay buffer for the experiment), the cells were first incubated for 30 min at 37° C. in the $CO_2$ incubator, then for 15 min at room temperature, and subsequently transferred to the FLIPR apparatus. After 35 seconds the addition of the KATP channel opener diaxozide (30 µM), and after 135 seconds the addition of the test substances (dissolved in assay buffer with addition of DMSO), was carried out in the apparatus. After this, the fluorescence signal was recorded for a further 17.75 min. In each experiment, positive controls (glibenclamide in a concentration of 10 µM, which corresponds to 100% inhibition) and negative controls (assay buffer with the amount of DMSO corresponding to the test substances, which corresponds to 0% inhibition) were tested in the same microtiter plate as the test substances.

The measured value used for the determination of the inhibition was obtained by subtraction of the fluorescence shortly before substance addition (t=130 seconds) from the fluorescence at the end of the experiment (t=20 min). The percentage inhibition by the test substance was determined using the following equation:

$$\text{Percentage inhibition} = \frac{(\text{measured value of test substance}) - (\text{measured value of negative control})}{(\text{measured value of positive control}) - (\text{measured value of negative control})}$$

$IC_{50}$ values for the inhibition were calculated with the aid of the Hill equation.

Various compounds of the formula I were investigated in the described assay and in comparison to the action on the cardiac ATP-sensitive potassium channel (SUR2A/Kir6.2) showed only a slight depolarization of the cell membrane and thus only a slight inhibition of the pancreatic ATP-sensitive potassium channel (SUR1/Kir6.2) and only a slight hypoglycemic action.

4) Action on the Action Potential Duration on the Papillary Muscle of the Guinea Pig ATP deficiency states, such as are observed during ischemia of the heart muscle cell, lead to a shortening of the action potential duration. They are regarded as one of the causes of reentry arrhythmias, which can cause sudden cardiac death. The opening of ATP-sensitive potassium channels by the lowering of the ATP level (ATP=adenosine triphosphate) is regarded as causal for this. The action of the compounds on the action potential can be determined on the papillary muscle of the guinea pig using a standard microelectrode technique according to the following procedure in which the action potential duration is shortened by hypoxia.

Guinea pigs of both sexes are killed by a blow to the head, the heart is removed, and the papillary muscles are detached and suspended in an organ bath. The organ bath is irrigated with Ringer's solution (136 mM NaCl, 3.3 mM KCl, 2.5 mM $CaCl_2$, 1.2 mM $KH_2PO_4$, 1.1 mM $MgSO_4$, 5.0 mM glucose, 10.0 mM 1-(2-hydroxyethyl)piperazine-4-(2-ethanesulfonic acid) (HEPES), pH adjusted to 7.4 with NaOH) and aerated with 100% oxygen at a temperature of 37° C. The muscle is stimulated by means of an electrode with square-wave pulses of 1 V and 1 millisecond duration and a frequency of 1 Hz. The action potential is derived and recorded by means of an intracellularly inserted glass microelectrode, which is filled with 3 M potassium chloride solution. The action potential is amplified using an amplifier from Hugo Sachs (March-Hugstetten, Germany) and stored and evaluated by means of a computer. The duration of the action potential is determined at a degree of repolarization of 90% ($APD_{90}$). The action potential shortening is caused after an equilibration time of 30 min by rinsing the papillary muscle with a hypoxic solution. In this process, the glucose is removed, the HEPES buffer is replaced by PIPES buffer (piperazine-1,4-bis(2-ethanesulfonic acid)), the pH is adjusted to 6.5 and aeration with 100% nitrogen is carried out. After a period of 60 min, this leads to a marked shortening of the $APD_{90}$. After this time, the test substance is added in the form of a stock solution, so that the desired concentration of the substance is present in the bath solution. After a further 60 min, the relengthening of the action potential is recorded.

5) Action on the Coronary Flow Under Hypoxic Conditions in the Guinea Pig Heart

As is known, an oxygen deficiency in coronary vessels leads to a reflectory dilatation of the vessels, in order to compensate the oxygen deficiency. The vascular KATP channel (SUR2B/Kir6.2) plays an important role in this process. Its opening leads to hyperpolarization of the cell membrane of the smooth muscle cell and as a consequence to a decreased calcium influx which results in a dilatation of the vessel. Blockade of the vascular KATP channel inhibits the dilation of the vessel and thus the adaptation of the coronary flow under hypoxic conditions. The action of the compounds on the coronary flow can be determined according to the procedure described below in the isolated perfused guinea pig heart according to Langendorff.

Guinea pigs of both sexes are killed by a blow to the head. The heart is quickly removed and cannulated in the aorta.

After the cannulation, the heart is suspended in the perfusion solution in a Langendorff apparatus and a latex balloon is inserted into the left ventricle. The coronary flow is recorded using a flow transducer, type E, from Hellige (Freiburg, Germany). The heart is perfused with a constant pressure of 55 mm Hg. Hypoxia is induced by changing the aeration from 95% oxygen/5% carbon dioxide (=normoxia) to 20% oxygen/75% nitrogen/5% carbon dioxide. In the control, i.e. without addition of a test substance to the perfusate, the coronary flow markedly increases under hypoxic conditions. The test substance is added to the perfusate 10 min before beginning the hypoxia, and then the coronary flow is determined under hypoxic conditions in the presence of the substance.

The invention claimed is:

1. A compound of the formula I,

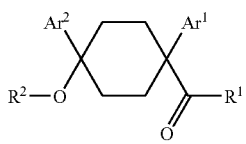

in which
Ar$^1$ and Ar$^2$, which are independent of one another and can be identical or different, are phenyl, naphthyl or heteroaryl, which are all optionally substituted by 1, 2, 3 or 4 identical or different substituents from the series consisting of halogen, cyano, $(C_1-C_5)$-alkyl, $(C_2-C_5)$-alkenyl, $(C_3-C_8)$-cycloalkyl-$C_vH_{2v}$—, Ar$^3$, $(C_1-C_5)$-alkyl-O—, HO—$(C_1-C_5)$-alkyl-O—, —O—$(C_1-C_3)$-alkyl-O—, $(C_3-C_8)$-cycloalkyl-S(O)$_f$—, $(C_1-C_5)$-alkyl-S(O)$_k$— and R$^{11}$R$^{12}$N—S(O)$_2$—, wherein all alkyl groups, alkenyl groups and cycloalkyl groups in Ar$^1$ and Ar$^2$ are optionally substituted by one or more fluorine substituents;
Ar$^3$ and Ar$^5$, which are independent of one another and can be identical or different, are phenyl or monocyclic heteroaryl, which are all optionally substituted by 1, 2 or 3 identical or different substituents from the series consisting of halogen, cyano, $(C_1-C_5)$-alkyl, $(C_1-C_5)$-alkyl-O—, —O—$(C_1-C_3)$-alkyl-O—, $(C_1-C_5)$-alkyl-S(O)$_m$— and R$^{13}$R$^{14}$N—S(O)$_2$—, wherein all alkyl groups in Ar$^3$ and Ar$^5$ are optionally substituted by one or more fluorine substituents;
Ar$^4$ is phenyl or heteroaryl, which are all optionally substituted by 1, 2, 3 or 4 identical or different substituents from the series consisting of halogen, cyano, $(C_1-C_5)$-alkyl, $(C_2-C_5)$-alkenyl, $(C_3-C_8)$-cycloalkyl-$C_wH_{2w}$—, Ar$^5$, $(C_1-C_5)$-alkyl-O—, HO—$(C_1-C_5)$-alkyl-O—, —O—$(C_1-C_3)$-alkyl-O—, $(C_1-C_5)$-alkyl-S(O)$_n$— and R$^{15}$R$^{16}$N—S(O)$_2$—, wherein all alkyl groups, alkenyl groups and cycloalkyl groups in Ar$^4$ are optionally substituted by one or more fluorine substituents;
R$^1$ is R$^3$—, R$^4$—O— or R$^5$R$^6$N—;
R$^2$ is hydrogen, $(C_1-C_8)$-alkyl, $(C_2-C_8)$-alkenyl, $(C_3-C_8)$-alkynyl, phenyl-$(C_2-C_8)$-alkenyl-, Ar$^4$, R$^{17}$—O—$(C_1-C_8)$-alkyl-, R$^{18}$R$^{19}$N—$(C_1-C_8)$-alkyl-, Het-$C_uH_{2u}$— or $(C_3-C_8)$-cycloalkyl-$C_uH_{2u}$—, wherein the phenyl group in phenyl-$(C_2-C_8)$-alkenyl- is optionally substituted by 1, 2 or 3 identical or different substituents from the series consisting of halogen, cyano, $(C_1-C_5)$-alkyl, $(C_1-C_5)$-alkyl-O— and $(C_1-C_5)$-alkyl-S(O)$_g$—, and wherein all alkyl groups, alkenyl groups, alkynyl groups and cycloalkyl groups in R$^2$ are optionally substituted by one or more fluorine substituents;
R$^3$, R$^4$, R$^5$ and R$^6$, which are all independent of one another and can be identical or different, are hydrogen, $(C_1-C_8)$-alkyl or $(C_3-C_8)$-cycloalkyl-$C_pH_{2p}$—, wherein all alkyl groups and cycloalkyl groups in R$^3$, R$^4$, R$^5$ and R$^6$ are optionally substituted by one or more fluorine substituents;
R$^{11}$, R$^{12}$, R$^{13}$, R$^{14}$, R$^{15}$, R$^{16}$, R$^{17}$, R$^{18}$ and R$^{19}$, which are all independent of one another and can be identical or different, are hydrogen, $(C_1-C_8)$-alkyl or $(C_3-C_8)$-cycloalkyl-$C_qH_{2q}$—, wherein all alkyl groups and cycloalkyl groups in R$^{11}$, R$^{12}$, R$^{13}$, R$^{14}$, R$^{15}$, R$^{16}$, R$^{17}$, R$^{18}$ and R$^{19}$ are optionally substituted by one or more fluorine substituents;
Het is a residue of a monocyclic 4-membered to 7-membered saturated ring which contains 1 or 2 identical or different ring heteroatoms from the series consisting of nitrogen, oxygen and sulfur, which is bonded via a ring carbon atom and which is optionally substituted by 1, 2, 3 or 4 identical or different substituents from the series consisting of phenyl and $(C_1-C_5)$-alkyl, wherein phenyl groups in Het are optionally substituted by 1, 2 or 3 identical or different substituents from the series consisting of halogen, cyano, $(C_1-C_5)$-alkyl, $(C_1-C_5)$-alkyl-O— and $(C_1-C_5)$-alkyl-S(O)$_h$—, and wherein Het and all alkyl groups in Het are optionally substituted by one or more fluorine substituents;
heteroaryl is a residue of a monocyclic 5-membered or 6-membered or of a bicyclic 8-membered, 9-membered or 10-membered aromatic ring system which contains 1, 2 or 3 identical or different ring heteroatoms from the series consisting of nitrogen, oxygen and sulfur;
f, g, h, k, m and n, which are all independent of one another and can be identical or different, are 0, 1 or 2;
p, q, v and w, which are all independent of one another and can be identical or different, are 0, 1, 2, 3 or 4;
u is 0, 1, 2, 3, 4, 5 or 6;
wherein all cycloalkyl groups, independently of any other substituents, are optionally substituted by one or more identical or different $(C_1-C_4)$-alkyl substituents;
in any of its stereoisomeric forms or a mixture of stereoisomeric forms in any ratio, or a physiologically acceptable salt thereof;
provided that Ar$^1$ and Ar$^2$ cannot both be unsubstituted phenyl if simultaneously R$^1$ is hydroxy and R$^2$ is hydrogen.

2. A compound of the formula I as claimed in claim 1, in which Ar$^1$ is phenyl or heteroaryl, which are all optionally substituted by 1, 2, 3 or 4 identical or different substituents from the series consisting of halogen, cyano, $(C_1-C_5)$-alkyl, $(C_2-C_5)$-alkenyl, $(C_3-C_8)$-cycloalkyl-$C_vH_{2v}$—, Ar$^3$, $(C_1-C_5)$-alkyl-O—, HO—$(C_1-C_5)$-alkyl-O—, —O—$(C_1-C_3)$-alkyl-O—, $(C_3-C_8)$-cycloalkyl-S(O)$_f$—, $(C_1-C_5)$-alkyl-S(O)$_k$— and R$^{11}$R$^{12}$N—S(O)$_2$—, wherein all alkyl groups, alkenyl groups and cycloalkyl groups in Ar$^1$ are optionally substituted by one or more fluorine substituents, in any of its stereoisomeric forms or a mixture of stereoisomeric forms in any ratio, or a physiologically acceptable salt thereof.

3. A compound of the formula I as claimed in claim 1, in which Ar$^1$ is phenyl or pyridinyl which are all optionally substituted by 1, 2, 3 or 4 identical or different substituents from the series consisting of halogen, cyano, $(C_1-C_5)$-alkyl, $(C_2-C_5)$-alkenyl, $(C_3-C_8)$-cycloalkyl-$C_vH_{2v}$—, Ar$^3$, $(C_1-C_5)$-alkyl-O—, HO—$(C_1-C_5)$-alkyl-O—, —O—$(C_1-C_3)$-alkyl-O—, $(C_3-C_8)$-cycloalkyl-S(O)$_f$—, $(C_1-C_5)$-alkyl-S(O)$_k$— and R$^{11}$R$^{12}$N—S(O)$_2$—, wherein all alkyl groups, alkenyl groups and cycloalkyl groups in Ar$^1$ are optionally substituted by one or more fluorine substituents, in any of its stereoisomeric forms or a mixture of stereoisomeric forms in any ratio, or a physiologically acceptable salt thereof.

4. A compound of the formula I as claimed in claim 1, in which Ar$^2$ is phenyl or heteroaryl, which are all optionally substituted by 1, 2, 3 or 4 identical or different substituents from the series consisting of halogen, cyano, $(C_1-C_5)$-alkyl, $(C_2-C_5)$-alkenyl, $(C_3-C_8)$-cycloalkyl-$C_vH_{2v}$—, $Ar^3$, $(C_1-C_5)$-alkyl-O—, HO—$(C_1-C_5)$-alkyl-O—, —O—$(C_1-C_3)$-alkyl-O—, $(C_3-C_8)$-cycloalkyl-$S(O)_f$—, $(C_1-C_5)$-alkyl-$S(O)_k$— and $R^{11}R^{12}N$—$S(O)_2$—, wherein all alkyl groups, alkenyl groups and cycloalkyl groups in $Ar^2$ are optionally substituted by one or more fluorine substituents, in any of its stereoisomeric forms or a mixture of stereoisomeric forms in any ratio, or a physiologically acceptable salt thereof.

5. A compound of the formula I as claimed in claim 1, in which $R^2$ is hydrogen, $(C_1-C_8)$-alkyl, $(C_2-C_8)$-alkenyl, $Ar^4$, $R^{17}$—O—$(C_1-C_8)$-alkyl-, $R^{18}R^{19}N$—$(C_1-C_8)$-alkyl-, Het-$C_uH_{2u}$— or $(C_3-C_8)$-cycloalkyl-$C_uH_{2u}$—, wherein all alkyl groups, alkenyl groups and cycloalkyl groups in $R^2$ are optionally substituted by one or more fluorine substituents, in any of its stereoisomeric forms or a mixture of stereoisomeric forms in any ratio, or a physiologically acceptable salt thereof.

6. A compound of the formula I as claimed in claim 1, in which $R^2$ is $(C_1-C_8)$-alkyl, $Ar^4$, Het-$C_uH_{2u}$— or $(C_3-C_8)$-cycloalkyl-$C_uH_{2u}$—, wherein all alkyl groups and cycloalkyl groups in $R^2$ are optionally substituted by one or more fluorine substituents, in any of its stereoisomeric forms or a mixture of stereoisomeric forms in any ratio, or a physiologically acceptable salt thereof.

7. A compound of the formula I as claimed in claim 1, in which $R^1$ is $R^4$—O— or $R^5R^6N$—, in any of its stereoisomeric forms or a mixture of stereoisomeric forms in any ratio, or a physiologically acceptable salt thereof.

8. A compound of the formula I as claimed in claim 1, in which $R^1$ is $R^4$—O— and $R^4$ is hydrogen, in any of its stereoisomeric forms or a mixture of stereoisomeric forms in any ratio, or a physiologically acceptable salt thereof.

9. A compound of the formula I as claimed in claim 1, in which $Ar^1$ and $Ar^2$, which are independent of one another and can be identical or different, are phenyl, naphthyl or heteroaryl, which are all optionally substituted by 1, 2 or 3 identical or different substituents from the series consisting of halogen, cyano, $(C_1-C_5)$-alkyl, $(C_3-C_6)$-cycloalkyl-$C_vH_{2v}$—, $Ar^3$, $(C_1-C_5)$-alkyl-O—, —O—$(C_1-C_3)$-alkyl-O—, $(C_3-C_6)$-cycloalkyl-$S(O)_f$— and $(C_1-C_5)$-alkyl-$S(O)_k$—, wherein all alkyl groups and cycloalkyl groups in $Ar^1$ and $Ar^2$ are optionally substituted by one or more fluorine substituents;

$Ar^3$ and $Ar^5$, which are independent of one another and can be identical or different, are phenyl or monocyclic heteroaryl, which are all optionally substituted by 1 or 2 identical or different substituents from the series consisting of halogen, $(C_1-C_5)$-alkyl and $(C_1-C_5)$-alkyl-O—, wherein all alkyl groups in $Ar^3$ and $Ar^5$ are optionally substituted by one or more fluorine substituents;

$Ar^4$ is phenyl or monocyclic heteroaryl, which are all optionally substituted by 1, 2 or 3 identical or different substituents from the series consisting of halogen, cyano, $(C_1-C_5)$-alkyl, $Ar^5$, $(C_1-C_5)$-alkyl-O—, HO—$(C_1-C_5)$-alkyl-O—, —O—$(C_1-C_3)$-alkyl-O— and $(C_1-C_5)$-alkyl-$S(O)_n$—, wherein all alkyl groups in $Ar^4$ are optionally substituted by one or more fluorine substituents;

$R^1$ is $R^4$—O— or $R^5R^6N$—;

$R^2$ is hydrogen, $(C_1-C_6)$-alkyl, $Ar^4$, $R^{17}$—O—$(C_1-C_6)$-alkyl-, $R^{18}R^{19}N$—$(C_1-C_6)$-alkyl-, Het-$C_uH_{2u}$— or $(C_3-C_7)$-cycloalkyl-$C_uH_{2u}$—, wherein all alkyl groups and cycloalkyl groups in $R^2$ are optionally substituted by one or more fluorine substituents;

$R^4$, $R^5$ and $R^6$, which are all independent of one another and can be identical or different, are hydrogen, $(C_1-C_5)$-alkyl or $(C_3-C_7)$-cycloalkyl-$C_pH_{2p}$—, wherein all alkyl groups and cycloalkyl groups in $R^4$, $R^5$ and $R^6$ are optionally substituted by one or more fluorine substituents;

$R^{17}$, $R^{18}$ and $R^{19}$, which are all independent of one another and can be identical or different, are hydrogen, $(C_1-C_5)$-alkyl or $(C_3-C_7)$-cycloalkyl-$C_qH_{2q}$—, wherein all alkyl groups and cycloalkyl groups in $R^{17}$, $R^{18}$ and $R^{19}$ are optionally substituted by one or more fluorine substituents;

Het is a residue of a monocyclic 4-membered to 7-membered saturated ring which contains 1 ring heteroatom from the series consisting of nitrogen, oxygen and sulfur, which is bonded via a ring carbon atom and which is optionally substituted by 1, 2 or 3 identical or different substituents from the series consisting of phenyl and $(C_1-C_5)$-alkyl, wherein phenyl groups in Het are optionally substituted by 1 or 2 identical or different substituents from the series consisting of halogen, $(C_1-C_5)$-alkyl and $(C_1-C_5)$-alkyl-O—, and wherein Het and all alkyl groups in Het are optionally substituted by one or more fluorine substituents;

heteroaryl is a residue of a monocyclic 5-membered or 6-membered or of a bicyclic 9-membered or 10-membered aromatic ring system which contains 1, 2 or 3 identical or different ring heteroatoms from the series consisting of nitrogen, oxygen and sulfur;

f, k and n, which are all independent of one another and can be identical or different, are 0, 1 or 2;

p, q and v, which are all independent of one another and can be identical or different, are 0, 1 or 2;

u is 0, 1, 2 or 3;

wherein all cycloalkyl groups, independently of any other substituents, are optionally substituted by one or more identical or different $(C_1-C_4)$-alkyl substituents;

in any of its stereoisomeric forms or a mixture of stereoisomeric forms in any ratio, or a physiologically acceptable salt thereof;

provided that $Ar^1$ and $Ar^2$ cannot both be unsubstituted phenyl if simultaneously $R^1$ is hydroxy and $R^2$ is hydrogen.

10. A process for the preparation of a compound of the formula I as claimed in claim 1, in which $R^1$ is $R^4$—O— and $R^4$ is hydrogen, or of a physiologically acceptable salt thereof, which comprises the hydrolysis of the nitrile group in a compound of the formula X.

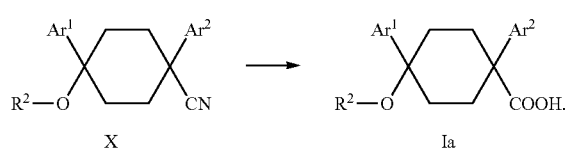

11. A pharmaceutical composition comprising at least one compound according to claim 1 or claim 9, or a physiologically acceptable salt thereof, and a pharmaceutically acceptable carrier.

12. A method of treating a subject in need thereof, said method comprising administering to said subject a therapeutically effective amount of a compound according to claim 1 or claim 9, or a physiologically acceptable salt thereof, wherein said subject is afflicted with ventricular fibrillation.

* * * * *